United States Patent
Huang et al.

(10) Patent No.: US 10,131,648 B2
(45) Date of Patent: Nov. 20, 2018

(54) SUBSTITUTED BENZOTHIOPHENYL DERIVATIVES AS GPR40 AGONISTS FOR THE TREATMENT OF TYPE II DIABETES

(71) Applicant: Janssen Pharmaceutica NV, Beerse (BE)

(72) Inventors: Hui Huang, Blue Bell, PA (US); Gee-Hong Kuo, Scotch Plains, NJ (US); Mark R. Player, Phoenixville, PA (US); Shyh-Ming Yang, Doylestown, PA (US); Yue-Mei Zhang, Wellesley, MA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/697,867

(22) Filed: Sep. 7, 2017

(65) Prior Publication Data

US 2017/0362196 A1  Dec. 21, 2017

Related U.S. Application Data

(62) Division of application No. 14/877,972, filed on Oct. 8, 2015, now Pat. No. 9,790,198.

(60) Provisional application No. 62/061,330, filed on Oct. 8, 2014.

(51) Int. Cl.
| | | |
|---|---|---|
| C07D 409/10 | (2006.01) | |
| C07D 333/54 | (2006.01) | |
| C07D 333/56 | (2006.01) | |
| C07D 409/04 | (2006.01) | |
| C07D 409/12 | (2006.01) | |
| C07D 409/14 | (2006.01) | |
| C07D 495/10 | (2006.01) | |
| A61K 31/381 | (2006.01) | |
| A61K 31/4436 | (2006.01) | |
| C07D 233/56 | (2006.01) | |
| C07D 409/02 | (2006.01) | |

(52) U.S. Cl.
CPC .......... *C07D 333/54* (2013.01); *A61K 31/381* (2013.01); *A61K 31/4436* (2013.01); *C07D 233/56* (2013.01); *C07D 333/56* (2013.01); *C07D 409/02* (2013.01); *C07D 409/04* (2013.01); *C07D 409/10* (2013.01); *C07D 409/12* (2013.01); *C07D 409/14* (2013.01); *C07D 495/10* (2013.01)

(58) Field of Classification Search
CPC .................................................. C07D 409/10
USPC ........................................ 546/202; 514/324
See application file for complete search history.

(56) References Cited

U.S. PATENT DOCUMENTS

| | | |
|---|---|---|
| 7,384,965 B2 | 6/2008 | Conner et al. |
| 7,598,266 B2 | 10/2009 | Conner et al. |
| 7,816,367 B2 | 10/2010 | Akerman et al. |
| 2007/0093476 A1 | 4/2007 | Debnath et al. |
| 2007/0142384 A1 | 6/2007 | Akerman et al. |
| 2007/0213364 A1 | 9/2007 | Yasuma et al. |
| 2009/0012093 A1 | 1/2009 | Fukatsu et al. |
| 2015/0291584 A1 | 10/2015 | Lee et al. |

FOREIGN PATENT DOCUMENTS

| | | |
|---|---|---|
| EP | 1559422 A1 | 8/2005 |
| EP | 1731505 A1 | 12/2006 |
| WO | WO 2001/66098 A2 | 9/2001 |
| WO | WO 2004/063155 A1 | 7/2004 |
| WO | WO 2005/086661 A2 | 9/2005 |
| WO | WO 2014/073904 A1 | 5/2014 |

OTHER PUBLICATIONS

Brisco et al., "The Orphan G Protein-coupled Receptor GPR40 is Activated by Medium and Long Chain Fatty Acids.", J. Biol. Chem., 2003, pp. 11303-11311, vol. 278.
Edfalk et al., "Gpr40 is Expressed in Enteroendrocrine Cells and Mediates Free Fatty Acid Stimulation of Incertin Secretion.", Diabetes, 2008, pp. 2280-2287, vol. 57.
Itoh et al., "Free fatty acids regulate insulin secretion form pancreatic β cells through GPR40.", Nature, 2003, pp. 173-176, vol. 422.
Kotarsky et al., "A human cell surface receptor activated by free fatty acids and thiasolidinedione drugs.", Biochem Biophys Res Commun., 2003, pp. 406-410, vol. 31.

(Continued)

*Primary Examiner* — Patricia L Morris

(57) ABSTRACT

Disclosed are compounds, compositions and methods for treating of disorders that are affected by the modulation of the GPR40 receptor. Such compounds are represented by Formula (I) as follows:

Formula (I)

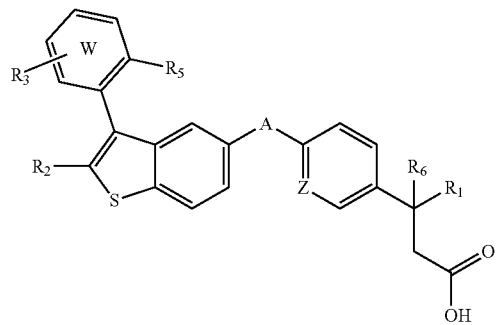

wherein $R_1$, $R_2$, $R_3$, $R_5$, $R_6$, W, and A are defined herein.

14 Claims, No Drawings

(56) References Cited

OTHER PUBLICATIONS

Mitsunobu, O., "The Use of Diethyl Azodicarboxylate and Triphenylphosphine in Synthesis and Transformation of Natural Products.", Synthesis, 1981, pp. 1-28.
Murai et al., "Palladium-Catalyzed Direct Hydroxymethylation of Aryl Halides and Triflates with Potassium Acetoxymethyltrifluoroborate.", Org. Lett., 2012, pp. 1278-1281, vol. 14.
International Search Report of the International Searching Authority relating to corresponding International Patent Application No. PCT/US2015/054581, filed Oct. 8, 2015, dated Jan. 18, 2016.
Written Opinion of the International Searching Authority relating to corresponding International Patent Application No. PCT/US2015/054581, filed Oct. 8, 2015, dated Jan. 18, 2016.

SUBSTITUTED BENZOTHIOPHENYL DERIVATIVES AS GPR40 AGONISTS FOR THE TREATMENT OF TYPE II DIABETES

CROSS-REFERENCE TO RELATED APPLICATIONS

This Application is a divisional application of U.S. application Ser. No. 14/877,972, filed Oct. 8, 2015, which claims priority to U.S. Provisional Patent Application No. 62/061,330, filed Oct. 8, 2014 which are hereby incorporated by reference in their entireties.

FIELD OF THE INVENTION

The present invention relates to novel compounds which are GPR40 agonists and are useful for the treatment of disorders that are affected by the modulation of the GPR40 receptor. The invention also relates to pharmaceutical compositions comprising one or more of such compounds, to processes to prepare such compounds and compositions, and to the use of such compounds or pharmaceutical compositions for the treatment of various diseases, syndromes and disorders, including Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema, that are related to GPR40 modulation.

BACKGROUND OF THE INVENTION

According to WHO 2013 estimates, diabetes continues to present an increasing health risk to the global population, affecting 347 million individuals worldwide. There are two main types of diabetes. Type 1 diabetes, which affects ~10% of diabetic patients, is characterized by a depletion of pancreatic insulin supply, resulting from an autoimmune destruction of the insulin-producing beta-cells. Treatment requires the administration of exogenous insulin in order to meet energy demands. Type 2 diabetes, which affects the vast majority (~90%) of the diabetic population, occurs when the body cannot effectively utilize the insulin that is being produced. A number of factors may contribute to an impaired insulin response, including decreases in insulin production, insulin secretion or insulin sensitivity. In the initial stages of Type 2 diabetes, most patients' beta cells undergo a compensatory expansion of functional mass and insulin output. As the disease progresses, this compensatory response eventually fails and pharmaceutical intervention is required in order to adequately regulate glucose levels. However, with further disease progression, the effectiveness of initially prescribed therapeutics generally declines, thus requiring additional agents to be incorporated into the treatment regimen, each of which carries its own side-effect liability or risk.

Agents that reduce hepatic glucose production, the so-called biguanides, such as metformin or phenformin, are generally preferred as the first-line of treatment for newly-diagnosed patients. Glitazones, such as rosiglitazone and pioglitazone function as insulin sensitizers (i.e., enhance insulin action) through the activation of peroxisome proliferator-activated receptor-γ (PPAR-γ). These agents can provide the benefit of enhanced insulin action in tissues such as muscle, liver and adipose, but their use is frequently accompanied by increased weight and edema. In addition, rosiglitazone has recently been linked to heart attacks and its use has subsequently been more restricted. The insulin secretagogue sulfonylureas (such as tolbutamide, chlorpropamide, glipizide or glyburide) enhance insulin secretion from functional beta cells and are often combined with biguanide or glitazone therapy. However, because their effects on stimulating insulin release are independent of glucose levels, the sulfonylureas bear the risk of inducing incidences of hypoglycemia. Weight gain is also a common side-effect from this compound class.

More recently, agents capable of inducing insulin secretion from beta cells in a glucose-dependent fashion have been developed, based upon the mechanisms of incretin peptide hormones (ex., GLP-1, GIP). Importantly, because of their glucose-dependent mechanisms of action, these agents are able to provide glucose control while avoiding the risk of hypoglycemia. The direct GLP-1 receptor agonists, Exendin-4 (Byetta®) and Liraglutide (Victoza®), which were engineered to provide enhanced metabolic stabilities in vivo, have been developed as marketed biological therapeutics. Dipeptidyl-peptidase-4 (DPP-4) inhibitors (the so-called, "gliptins" such as sitagliptin, saxagliptin, linagliptin, vildagliptin, anagliptin or alogliptin) inhibit the metabolic degradation of endogenous incretins and thereby provide indirect increases in insulin secretion in response to elevations in circulating glucose levels.

Most recently, the recognition of GPR40 as a receptor whose activation enhances glucose-dependent insulin secretion has led to the search for selective agonists for this putative therapeutic target. GPR40, also known as free fatty acid receptor 1 (FFR1), is one of a family of G-protein coupled receptors that, through receptor deorphanization studies, was shown to be endogenously activated by medium- to long-chain saturated and unsaturated fatty acids (~$C_{12-20}$) (Brisco, et al., 2003, J Biol Chem, 278: 11303-11311; Itoh, et al., 2003, Nature, 422: 173-176; Kotarsky et al., 2003, Biochem Biophys Res Commun, 301: 406-410). In humans and rodents, although present in brain and enteroendocrine cells, its expression is particularly high in pancreatic beta cells. Operating primarily through $G\alpha_{q/11}$ signaling, GPR40 activation of the beta cell leads to an increase in intracellular calcium levels, which in the presence of glucose, ultimately results in augmented insulin secretion. In enteroendocrine cells, GPR40 activation by fatty acids leads to stimulation of incretin secretion (Edfalk, et al., 2008, Diabetes, 57: 2280-2287). Thus, in addition to directly promoting GSIS from islet beta cells, GPR40 activation in enteroendocrine cells provides an indirect means of stimulating GSIS through the actions of released incretins.

Because of the hyperglycemic dependency of GPR40-mediated effects on insulin secretion, selective activation of this receptor provides a unique potential therapeutic mechanism by which to treat the diabetic state with minimal risk of hypoglycemic incidents. Given the relatively restricted tissue expression pattern of GPR40, selective GPR40 agonists may offer the additional advantage of providing an improved safety profile relative to the aforementioned therapeutic agents. Thus, GPR40 agonists of the present invention may provide therapeutic benefit for the treatment of diabetes (particularly Type 2 diabetes) and its associated conditions, including Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema, that are related to GPR40 modulation.

SUMMARY OF THE INVENTION

The present invention is directed to compounds of Formula (I)

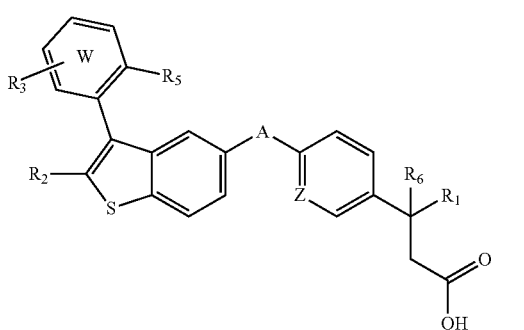

Formula (I)

wherein
ring W is phenyl or pyridyl;
A is —CH$_2$O— or —OCH$_2$—;
Z is CH or N;
R$_6$ is hydrogen;
R$_1$ is selected from hydrogen or methylacetylenyl; or R$_1$ and R$_6$ are taken together to form a spirofused 3-hydroxycyclobutyl or a spirofused 3-oxocyclobutyl;
R$_2$ is selected from hydrogen or methyl;
R$_3$ is hydrogen, chloro, or a substituent selected from the group consisting of C$_{1-3}$alkyl, hydroxy, 1,1-dioxothian-4-yl, 1,1-dioxido-3,6-dihydro-2H-thiopyran-4-yl, 1,1-dioxo-1,4-thiazinane-4-ylcarbonyl, C$_{1-3}$alkylsulfonyl, C$_{1-3}$alkylsulfonylamino, 1,1-dioxido-1-thia-6-azaspiro[3.3]heptan-6-yl, piperidin-4-yl, piperidin-4-ylmethyl, and —OR$_4$;
  wherein R$_4$ is
  i) C$_{1-8}$alkyl optionally independently substituted with one or two C$_{1-3}$alkoxy or hydroxy substituents;
  ii) C$_{3-7}$cycloalkyl;
  iii) 4-hydroxy-1,1-dioxo-thian-4-ylmethyl;
  iv) 1,1-dioxothian-4-yl;
  v) 1,1-dioxidotetrahydro-2H-thiopyran-4-ylmethyl;
  vi) tetrahydro-2H-pyran-4-yl;
  vii) C$_{1-3}$alkylsulfonylpropyl;
  viii) 2-(1-hydroxycyclopropyl)ethyl;
  ix) 3-methyloxetan-3-yl-methyl;
  x) (3-methyl-1,1-dioxidothietan-3-yl)methyl;
  xi) (1-C$_{3-6}$cycloalkyl-1-ol)methyl;
  xii) 4-hydroxy-tetrahydropyran-4-ylmethyl;
  xiii) 2-(C$_{3-7}$cycloalkyl)-2-hydroxyethyl;
  xiv) tetrahydro-2H-pyran-4-ylmethyl;
  or
  xv) tetrahydrofuran-3-yl;
R$_5$ is methyl, methoxy, bromo, chloro, C$_{1-6}$alkoxy-C$_{1-6}$alkoxyl, C$_{1-6}$alkylsulfonyl, or trifluoromethyl;
or an enantiomer, diastereomer, or pharmaceutically acceptable salt forms thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I), or a pharmaceutically acceptable salt form thereof.

Also provided are processes for making a pharmaceutical composition comprising, consisting of, and/or consisting essentially of admixing a compound of Formula (I), and a pharmaceutically acceptable carrier, a pharmaceutically acceptable excipient, and/or a pharmaceutically acceptable diluent.

The present invention further provides methods for treating or ameliorating a disease, syndrome, or condition in a subject, including a mammal and/or human in which the disease, syndrome, or condition is affected by the agonism of GPR40, such as Type II diabetes mellitus, using a compound of Formula (I).

The present invention also is also directed to the use of any of the compounds described herein in the preparation of a medicament wherein the medicament is prepared for treating a disease or condition that is affected by the agonism of GPR40, selected from the group consisting of Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema, in a subject in need thereof.

The present invention is also directed to the preparation of substituted benzothiophenyl derivatives that act as selective agonists of the GPR40 receptor.

Exemplifying the invention are methods of treating a disorder modulated by GPR40 selected from the group consisting of Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema, comprising administering to a subject in need thereof a therapeutically effective amount of any of the compounds or pharmaceutical compositions described above.

In another embodiment, the present invention is directed to a compound of Formula (I) for use in the treatment of a disorder affected by the agonism of GPR40 selected from the group consisting of Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema.

In another embodiment, the present invention is directed to a composition comprising a compound of Formula (I) for the treatment of a disorder affected by the agonism of GPR40 selected from the group consisting of Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., C$_{1-8}$) refer independently to the number of carbon atoms in an alkyl moiety or to the alkyl portion of a larger alkyl-containing substituent. In substituent groups with multiple alkyl groups such as, ($C_{1-6}$ alkyl)$_2$amino-, the $C_{1-6}$alkyl groups of the dialkylamino may be the same or different.

The term "alkoxy" refers to an -O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl. The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "carboxy" refers to the group —C(=O)OH.

The term "formyl" refers to the group —C(=O)H.

The term "oxo" or "oxido" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

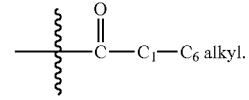

The substituent "—CH$_2$O—" is oriented such that the oxygen atom is covalently bound to the Z-containing ring. Likewise, the substituent "—OCH$_2$—" is oriented such that the methylene group is covalently bound to the Z-containing ring.

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "GPR40 agonist" is intended to encompass a compound that interacts with GPR40 to substantially increase its catalytic activity, thereby increasing the concentrations of its substrate(s). The term "GPR40-modulated" is used to refer to the condition of being affected by the modulation of the GPR40 receptor, including but not limited to, the state of being mediated by the GPR40 receptor, for the treatment of a disease or condition such as Type II diabetes or impaired glucose tolerance.

As used herein, unless otherwise noted, the term "disorder modulated by the GPR40 receptor" shall mean any disease, disorder or condition characterized in that at least one of its characteristic symptoms is alleviated or eliminated upon treatment with a GPR40 receptor agonist. Suitably examples include, but are not limited to Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema; more preferably, Type II diabetes mellitus and impaired glucose tolerance.

As used herein unless otherwise noted, the term "cardiovascular risk factors" shall mean any cardiovascular disease, disorder or condition in which obesity or diabetes (preferably, Type II diabetes) has a role in the initiation or exacerbation of said disorder or condition. Suitable examples include, but are not limited to, hypertension, atherosclerosis and cardiac fibrosis.

As used herein, unless otherwise noted, the term "affect" or "affected" (when referring to a disease, syndrome, condition or disorder that is affected by agonism of GPR40) includes a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of the instant invention are useful in methods for treating or ameliorating a disease, a syndrome, a condition or a disorder that is affected by the agonism of GPR40 receptor. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

In particular, the compounds of Formula (I), or an enantiomer, diastereomer, solvate or pharmaceutically acceptable salt form thereof are useful for treating or ameliorating diseases, syndromes, conditions, or disorders such as Type II diabetes mellitus, obesity, obesity-related disorders, impaired glucose tolerance, insulin resistance, metabolic syndrome, other cardiovascular risk factors such as hypertension and cardiovascular risk factors related to unmanaged cholesterol and/or lipid levels, osteoporosis, inflammation, and eczema.

More particularly, the compounds of Formula (I), or an enantiomer, diastereomer, solvate or pharmaceutically acceptable salt form thereof, are useful for treating or ameliorating Type II diabetes mellitus or impaired glucose tolerance, comprising administering to a subject in need thereof a therapeutically effective amount of a compound of Formula (I), or an enantiomer, diastereomer, solvate or pharmaceutically acceptable salt form thereof as herein defined.

Embodiments of the present invention include a compound of Formula (I)

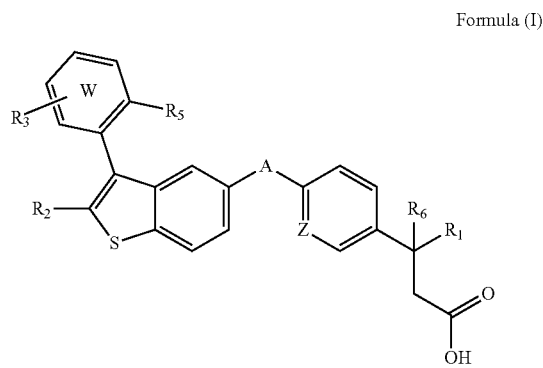

Formula (I)

wherein
a) ring W is phenyl;
b) ring W is pyridyl;
c) A is —CH$_2$O—;
d) A is —OCH$_2$—;
e) Z is CH, R$_6$ is hydrogen and R$_1$ is (S)-methylacetylenyl; or R$_1$ and R$_6$ are taken together to form a spirofused 3-hydroxycyclobutyl or a spirofused 3-oxocyclobutyl;
f) Z is N, R$_6$ is hydrogen and R$_1$ is (R)-methylacetylenyl; or R$_1$ and R$_6$ are taken together to form a spirofused 3-hydroxycyclobutyl or a spirofused 3-oxocyclobutyl;
g) R$_2$ is hydrogen;
h) R$_3$ is hydrogen, chloro, or a substituent selected from the group consisting of C$_{1-3}$alkyl, hydroxy, 1,1-dioxothian-4-yl, 1,1-dioxido-3,6-dihydro-2H-thiopyran-4-yl, 1,1-dioxo-1,4-thiazinane-4-ylcarbonyl, C$_{1-3}$alkylsulfonyl, C$_{1-3}$alkylsulfonylamino, 1,1-dioxido-1-thia-6-azaspiro[3.3]heptan-6-yl, piperidin-4-yl, piperidin-4-ylmethyl, and —OR$_4$;
wherein R$_4$ is
i) C$_{1-8}$alkyl optionally independently substituted with one or two C$_{1-3}$alkoxy or hydroxy substituents;

ii) $C_{3-7}$cycloalkyl;
iii) 4-hydroxy-1,1-dioxo-thian-4-ylmethyl;
iv) 1,1-dioxothian-4-yl;
v) 1,1-dioxidotetrahydro-2H-thiopyran-4-ylmethyl;
vi) tetrahydro-2H-pyran-4-yl;
vii) $C_{1-3}$alkylsulfonylpropyl;
viii) 2-(1-hydroxycyclopropyl)ethyl;
ix) 3-methyloxetan-3-yl-methyl;
x) (3-methyl-1,1-dioxidothietan-3-yl)methyl;
xi) tetrahydro-2H-pyran-4-ylmethyl;
or
xii) tetrahydrofuran-3-yl;
i) $R_3$ is hydrogen or a substituent that is —$OR_4$;
wherein $R_4$ is
i) $C_{1-4}$alkyl optionally independently substituted with one or two hydroxy or $C_{1-3}$alkoxy substituents;
ii) (4-hydroxy-1,1-dioxo-thian-4-yl)methyl;
iii) 1,1-dioxidotetrahydro-2H-thiopyran-4-ylmethyl;
iv) tetrahydro-2H-pyran-4-yl;
v) $C_{1-3}$alkylsulfonylpropyl;
vi) tetrahydro-2H-pyran-4-ylmethyl;
or
vii) tetrahydrofuran-3-yl;
j) $R_3$ is selected from the group consisting of hydrogen; methyl; hydroxy; chloro; (4-hydroxy-1,1-dioxo-thian-4-yl)methoxy; 4-(3-methylsulfonylpropoxy; 1,1-dioxo-1,4-thiazinane-4-carbonyl; 1,1-dioxido-3,6-dihydro-2H-thiopyran-4-yl; 1,1-dioxothian-4-yl; (1,1-dioxothian-4-yl)oxy; (1-hydroxycyclopropyl)ethoxy; 3-hydroxy-3-methylbutoxy; 2,3-dihydroxypropoxy; (3-methyloxetan-3-yl)methoxy; (tetrahydro-2H-pyran-4-yl)oxy; 2-methoxyethoxy; (1,1-dioxidotetrahydro-2H-thiopyran-4-yl)methoxy; (3-methyl-1,1-dioxidothietan-3-yl)methoxy; (3-(methylsulfonyl)propoxy; 1,1-dioxidotetrahydro-2H-thiopyran-4-yl; 2-ethoxyethoxy; 1,1-dioxidotetrahydro-2H-thiopyran-4-yl)oxy; (tetrahydro-2H-pyran-4-yl)oxy; 1,1-dioxido-1-thia-6-azaspiro[3.3]heptan-6-yl; methylsulfonyl; methylsulfonamido; piperidin-4-yl; piperidin-4-ylmethyl; and tetrahydro-2H-pyran-4-yl)oxy;
k) $R_5$ is methyl, methoxy, 2-methoxyethoxy, methanesulfonyl, chloro, or trifluoromethyl;

and any combination of embodiments a) through k) above, provided that it is understood that combinations in which different embodiments of the same substituent would be combined are excluded; or an enantiomer, diastereomer, or pharmaceutically acceptable salt form thereof.

Embodiments of the present invention include a compound of Formula (I)

Formula (I)

wherein
ring W is phenyl or pyridyl;
A is —$CH_2O$— or —$OCH_2$—;
Z is CH or N;
$R_6$ is hydrogen;
$R_1$ is selected from hydrogen or methylacetylenyl; or $R_1$ and $R_6$ are taken together to form a spirofused 3-hydroxycyclobutyl or a spirofused 3-oxocyclobutyl;
$R_2$ is hydrogen;
$R_3$ is hydrogen, chloro, or a substituent selected from the group consisting of $C_{1-3}$alkyl, hydroxy, 1,1-dioxothian-4-yl, 1,1-dioxido-3,6-dihydro-2H-thiopyran-4-yl, 1,1-dioxo-1,4-thiazinane-4-ylcarbonyl, $C_{1-3}$alkylsulfonyl, $C_{1-3}$alkylsulfonylamino, 1,1-dioxido-1-thia-6-azaspiro[3.3]heptan-6-yl, piperidin-4-yl, piperidin-4-ylmethyl, and —$OR_4$;
wherein $R_4$ is
i) $C_{1-8}$alkyl optionally independently substituted with one or two $C_{1-3}$alkoxy or hydroxy substituents;
ii) $C_{3-7}$cycloalkyl;
iii) 4-hydroxy-1,1-dioxo-thian-4-ylmethyl;
iv) 1,1-dioxothian-4-yl;
v) 1,1-dioxidotetrahydro-2H-thiopyran-4-ylmethyl;
vi) tetrahydro-2H-pyran-4-yl;
vii) $C_{1-3}$alkylsulfonylpropyl;
viii) 2-(1-hydroxycyclopropyl)ethyl;
ix) 3-methyloxetan-3-yl-methyl;
x) (3-methyl-1,1-dioxidothietan-3-yl)methyl;
xi) tetrahydro-2H-pyran-4-ylmethyl;
or
xii) tetrahydrofuran-3-yl;
$R_5$ is methyl, methoxy, 2-methoxyethoxy, methanesulfonyl, chloro, or trifluoromethyl;
or an enantiomer, diastereomer, or pharmaceutically acceptable salt form thereof.

Embodiments of the present invention include a compound of Formula (I)

Formula (I)

wherein
ring W is phenyl or pyridyl;
A is —$CH_2O$— or —$OCH_2$—;
when Z is CH, $R_6$ is hydrogen and $R_1$ is (S)-methylacetylenyl; or $R_1$ and $R_6$ are taken together to form a spirofused 3-hydroxycyclobutyl or a spirofused 3-oxocyclobutyl;
or, when Z is N, $R_6$ is hydrogen and $R_1$ is (R)-methylacetylenyl; or $R_1$ and $R_6$ are taken together to form a spirofused 3-hydroxycyclobutyl or a spirofused 3-oxocyclobutyl;
$R_2$ is hydrogen;
$R_3$ is hydrogen, chloro, or a substituent selected from the group consisting of $C_{1-3}$alkyl, hydroxy, 1,1-dioxothian-4-yl, 1,1-dioxido-3,6-dihydro-2H-thiopyran-4-yl, 1,1-dioxo-1,4-thiazinane-4-ylcarbonyl, $C_{1-3}$alkylsulfonyl, $C_{1-3}$alkylsulfonylamino, 1,1-dioxido-1-thia-6-azaspiro[3.3]heptan-6-yl, piperidin-4-yl, piperidin-4-ylmethyl, and —OR$_4$;
  wherein R$_4$ is
    i) C$_{1-8}$alkyl optionally independently substituted with one or two C$_{1-3}$alkoxy or hydroxy substituents;
    ii) C$_{3-7}$cycloalkyl;
    iii) 4-hydroxy-1,1-dioxo-thian-4-ylmethyl;
    iv) 1,1-dioxothian-4-yl;
    v) 1,1-dioxidotetrahydro-2H-thiopyran-4-ylmethyl;
    vi) tetrahydro-2H-pyran-4-yl;
    vii) C$_{1-3}$alkylsulfonylpropyl;
    viii) 2-(1-hydroxycyclopropyl)ethyl;
    ix) 3-methyloxetan-3-yl-methyl;
    x) (3-methyl-1,1-dioxidothietan-3-yl)methyl;
    xi) tetrahydro-2H-pyran-4-ylmethyl; or
    xii) tetrahydrofuran-3-yl;
  R$_5$ is methyl, methoxy, 2-methoxyethoxy, methanesulfonyl, chloro, or trifluoromethyl;
  or an enantiomer, diastereomer, or pharmaceutically acceptable salt form thereof.

Embodiments of the present invention include a compound of Formula (I)

Formula (I)

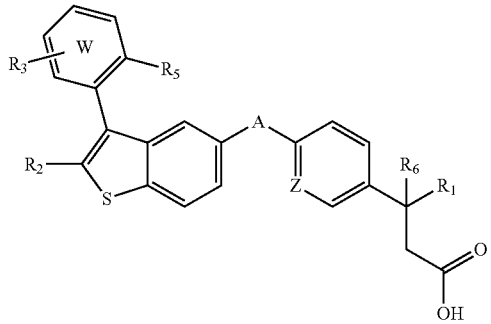

wherein
  ring W is pyridyl;
  A is —CH$_2$O— or —OCH$_2$—;
  Z is CH, R$_6$ is hydrogen and R$_1$ is (S)-methylacetylenyl; or R$_1$ and R$_6$ are taken together to form a spirofused 3-hydroxycyclobutyl or a spirofused 3-oxocyclobutyl; or
  Z is N, R$_6$ is hydrogen and R$_1$ is (R)-methylacetylenyl; or R$_1$ and R$_6$ are taken together to form a spirofused 3-hydroxycyclobutyl or a spirofused 3-oxocyclobutyl;
  R$_2$ is hydrogen;
  R$_3$ is hydrogen or a substituent that is —OR$_4$;
  wherein R$_4$ is
    i) C$_{1-4}$alkyl optionally independently substituted with one or two hydroxy or C$_{1-3}$alkoxy substituents;
    ii) (4-hydroxy-1,1-dioxo-thian-4-yl)methyl;
    iii) 1,1-dioxidotetrahydro-2H-thiopyran-4-ylmethyl;
    iv) tetrahydro-2H-pyran-4-yl;
    v) C$_{1-3}$alkylsulfonylpropyl;
    vi) tetrahydro-2H-pyran-4-ylmethyl; or
    vii) tetrahydrofuran-3-yl;
  R$_5$ is methyl, methoxy, 2-methoxyethoxy, methanesulfonyl, chloro, or trifluoromethyl;
  or an enantiomer, diastereomer, or pharmaceutically acceptable salt form thereof.

Embodiments of the present invention include a compound of Formula (I)

Formula (I)

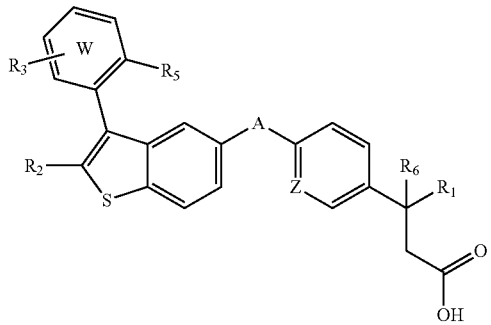

wherein
  ring W is phenyl;
  A is —CH$_2$O— or —OCH$_2$—;
  when Z is CH, R$_6$ is hydrogen and R$_1$ is (S)-methylacetylenyl; or R$_1$ and R$_6$ are taken together to form a spirofused 3-hydroxycyclobutyl or a spirofused 3-oxocyclobutyl; or
  when Z is N, R$_6$ is hydrogen and R$_1$ is (R)-methylacetylenyl; or R$_1$ and R$_6$ are taken together to form a spirofused 3-hydroxycyclobutyl or a spirofused 3-oxocyclobutyl;
  R$_2$ is hydrogen;
  R$_3$ is hydrogen or a substituent that is piperidin-4-yl, piperidin-4-ylmethyl, or —OR$_4$;
  wherein R$_4$ is
    i) C$_{1-4}$alkyl optionally independently substituted with one or two hydroxy or C$_{1-3}$alkoxy substituents;
    ii) (4-hydroxy-1,1-dioxo-thian-4-yl)methyl;
    iii) 1,1-dioxidotetrahydro-2H-thiopyran-4-ylmethyl;
    iv) tetrahydro-2H-pyran-4-yl;
    v) C$_{1-3}$alkylsulfonylpropyl;
    vi) tetrahydro-2H-pyran-4-ylmethyl; or
    vii) tetrahydrofuran-3-yl;
  R$_5$ is methyl, methoxy, 2-methoxyethoxy, methanesulfonyl, chloro, or trifluoromethyl;
  or an enantiomer, diastereomer, or pharmaceutically acceptable salt form thereof.

Embodiments of the present invention include a compound of Formula (I)

Formula (I)

wherein
  ring W is phenyl or pyridyl;
  A is —CH$_2$O—;
  when Z is CH, R$_6$ is hydrogen and R$_1$ is (S)-methylacetylenyl; or R$_1$ and R$_6$ are taken together to form a spirofused 3-hydroxycyclobutyl or a spirofused 3-oxocyclobutyl; or
  when Z is N, R$_6$ is hydrogen and R$_1$ is (R)-methylacetylenyl; or R$_1$ and R$_6$ are taken together to form a spirofused 3-hydroxycyclobutyl or a spirofused 3-oxocyclobutyl;

R₂ is hydrogen;
R₃ is hydrogen or a substituent that is —OR₄;
wherein R₄ is
  i) $C_{1-4}$alkyl optionally independently substituted with one or two hydroxyl or $C_{1-3}$alkoxy substituents;
  ii) (4-hydroxy-1,1-dioxo-thian-4-yl)methyl;
  iii) 1,1-dioxidotetrahydro-2H-thiopyran-4-ylmethyl;
  iv) tetrahydro-2H-pyran-4-yl;
  v) $C_{1-3}$alkylsulfonylpropyl;
  vi) tetrahydro-2H-pyran-4-ylmethyl; or
  vii) tetrahydrofuran-3-yl;
R₅ is methyl, methoxy, 2-methoxyethoxy, methanesulfonyl, chloro, or trifluoromethyl;
or an enantiomer, diastereomer, or pharmaceutically acceptable salt form thereof.

Embodiments of the present invention include a compound of Formula (I)

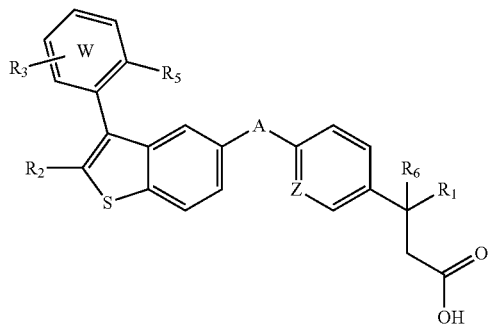

Formula (I)

wherein
ring W is phenyl or pyridyl;
A is —CH₂O— or —OCH₂—;
Z is CH or N
R₆ is hydrogen;
R₁ is selected from hydrogen or methylacetylenyl; or R₁ and R₆ are taken together to form a spirofused 3-hydroxycyclobutyl or a spirofused 3-oxocyclobutyl;
R₂ is selected from hydrogen or methyl;
R₃ is selected from the group consisting of hydrogen; methyl; methoxy; hydroxy; chloro; (4-hydroxy-1,1-dioxo-thian-4-yl)methoxy; 4-(3-methylsulfonylpropoxy; 1,1-dioxo-1,4-thiazinane-4-carbonyl; 1,1-dioxido-3,6-dihydro-2H-thiopyran-4-yl; 1,1-dioxothian-4-yl; (1,1-dioxothian-4-yl)oxy; (1-hydroxycyclopropyl)ethoxy; 3-hydroxy-3-methylbutoxy; 2,3-dihydroxypropoxy; (3-methyloxetan-3-yl)methoxy; (tetrahydro-2H-pyran-4-yl)oxy; 2-methoxyethoxy; (1,1-dioxidotetrahydro-2H-thiopyran-4-yl)methoxy; (3-methyl-1,1-dioxidothietan-3-yl)methoxy; (3-(methylsulfonyl)propoxy; 1,1-dioxidotetrahydro-2H-thiopyran-4-yl; 2-ethoxyethoxy; 1,1-dioxidotetrahydro-2H-thiopyran-4-yl)oxy; (tetrahydro-2H-pyran-4-yl)oxy; 1,1-dioxido-1-thia-6-azaspiro[3.3]heptan-6-yl; methylsulfonyl; methylsulfonamido; 3-hydroxy-3-methylbutoxy; tetrahydro-2H-pyran-4-yl)methoxy; tetrahydrofuran-3-yloxy; piperidin-4-yl; piperidin-4-ylmethyl; and tetrahydro-2H-pyran-4-yl)oxy;
R₅ is methyl, methoxy, 2-methoxyethoxy, methanesulfonyl, chloro, or trifluoromethyl;
or an enantiomer, diastereomer, or pharmaceutically acceptable salt form thereof.

Embodiments of the present invention include a compound of Formula (I)

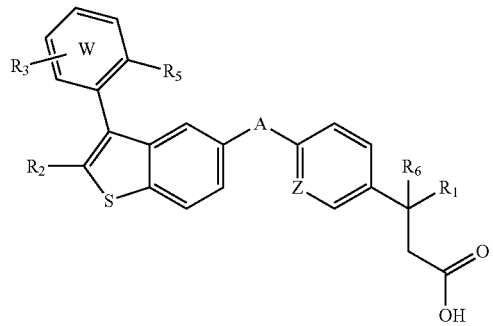

Formula (I)

wherein
ring W is phenyl or pyridyl;
A is —CH₂O— or —OCH₂—;
when Z is CH, R₆ is hydrogen and R₁ is (S)-methylacetylenyl; or R₁ and R₆ are taken together to form a spirofused 3-hydroxycyclobutyl or a spirofused 3-oxocyclobutyl; or
when Z is N, R₆ is hydrogen and R₁ is (R)-methylacetylenyl; or R₁ and R₆ are taken together to form a spirofused 3-hydroxycyclobutyl or a spirofused 3-oxocyclobutyl;
R₂ is selected from hydrogen or methyl;
R₃ is selected from the group consisting of hydrogen; methyl; methoxy; hydroxy; chloro; (4-hydroxy-1,1-dioxo-thian-4-yl)methoxy; 4-(3-methylsulfonylpropoxy; 1,1-dioxo-1,4-thiazinane-4-carbonyl; 1,1-dioxido-3,6-dihydro-2H-thiopyran-4-yl; 1,1-dioxothian-4-yl; (1,1-dioxothian-4-yl)oxy; (1-hydroxycyclopropyl)ethoxy; 3-hydroxy-3-methylbutoxy; 2,3-dihydroxypropoxy; (3-methyloxetan-3-yl)methoxy; (tetrahydro-2H-pyran-4-yl)oxy; 2-methoxyethoxy; (1,1-dioxidotetrahydro-2H-thiopyran-4-yl)methoxy; (3-methyl-1,1-dioxidothietan-3-yl)methoxy; (3-(methylsulfonyl)propoxy; 1,1-dioxidotetrahydro-2H-thiopyran-4-yl; 2-ethoxyethoxy; 1,1-dioxidotetrahydro-2H-thiopyran-4-yl)oxy; (tetrahydro-2H-pyran-4-yl)oxy; 1,1-dioxido-1-thia-6-azaspiro[3.3]heptan-6-yl; methylsulfonyl; methylsulfonamido; 3-hydroxy-3-methylbutoxy; tetrahydro-2H-pyran-4-yl)methoxy; tetrahydrofuran-3-yloxy; piperidin-4-yl; piperidin-4-ylmethyl; and tetrahydro-2H-pyran-4-yl)oxy;
R₅ is methyl, methoxy, 2-methoxyethoxy, methanesulfonyl, chloro, or trifluoromethyl;
or an enantiomer, diastereomer, or pharmaceutically acceptable salt form thereof.

Additional embodiments of the present invention include a compound of Formula (I)

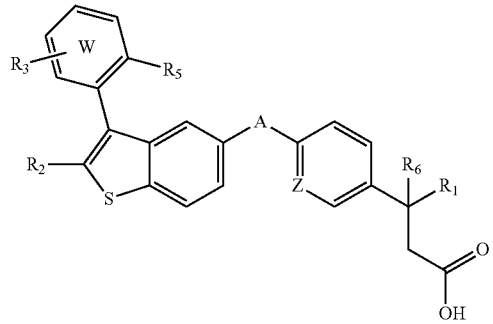

Formula (I)

wherein
ring W is phenyl;
A is —CH$_2$O—;
Z is CH;
R$_6$ is hydrogen;
R$_1$ is methylacetylenyl;
R$_2$ is hydrogen;
R$_3$ is hydrogen;
R$_5$ is methyl;
or an enantiomer, diastereomer, or pharmaceutically acceptable salt form thereof.

Additional embodiments of the present invention include a compound of Formula (I)

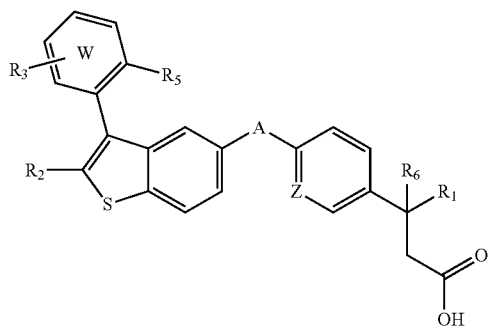

Formula (I)

wherein
ring W is phenyl;
A is —CH$_2$O—;
Z is CH;
R$_6$ is hydrogen;
R$_1$ is (S)-methylacetylenyl;
R$_2$ is hydrogen;
R$_3$ is hydrogen;
R$_5$ is methyl;
or pharmaceutically acceptable salt forms thereof.

A further embodiment of the present invention is directed to the compound of Formula (I) that is 3-(4-((3-(2-methylphenyl)benzo[b]thiophen-5-yl)methoxy)phenyl)hex-4-ynoic acid, Cpd 97

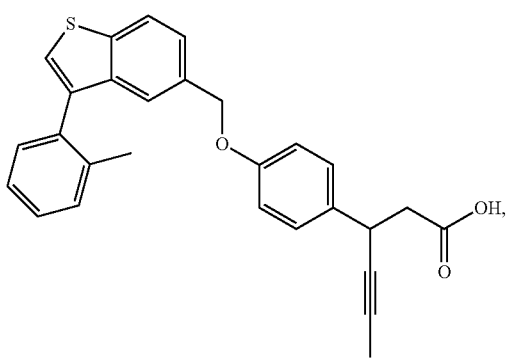 [SMILES: CC#CC(CC(=O)O)c1ccc(OCc2ccc3scc(-c4ccccc4C)c3c2)cc1]

or a pharmaceutically acceptable salt form thereof.

A further embodiment of the present invention is directed to the compound of Formula (I) that is (3S)-3-[4-[[3-(2-methylphenyl)benzo[b]thiophen-5-yl]methoxy]phenyl]hex-4-ynoic acid, Cpd 2

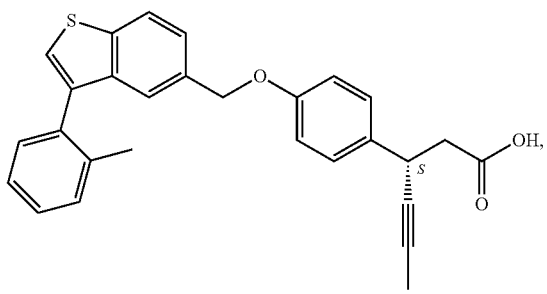

or an enantiomer, diastereomer, or pharmaceutically acceptable salt form thereof.

A further embodiment of the present invention is directed to the compound of Formula (I) that is 3-(4-((3-(2-methylphenyl)benzo[b]thiophen-5-yl)methoxy)phenyl) hex-4-ynoic acid, Cpd 97

A further embodiment of the present invention is directed to the compound of Formula (I) that is (3S)-3-[4-[[3-(2-methylphenyl)benzo[b]thiophen-5-yl]methoxy]phenyl]hex-4-ynoic acid, Cpd 2

Additional embodiments of the present invention include compounds of Formula (I) as herein defined, or an enantiomer, diastereomer, solvate, or a pharmaceutically acceptable salt form thereof, as exemplified in the listing in Table 1, below.

TABLE 1

| Structure | Cpd No. | Cpd Name |
|---|---|---|
| 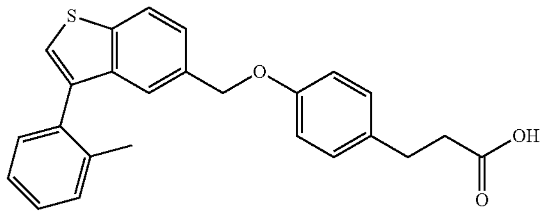 [SMILES: Cc1ccccc1-c1csc2ccc(COc3ccc(CCC(=O)O)cc3)cc12] | 1 | 3-[4-[[3-(2-Methylphenyl)benzo[b]thiophen-5-yl]methoxy]phenyl] propanoic acid |
| 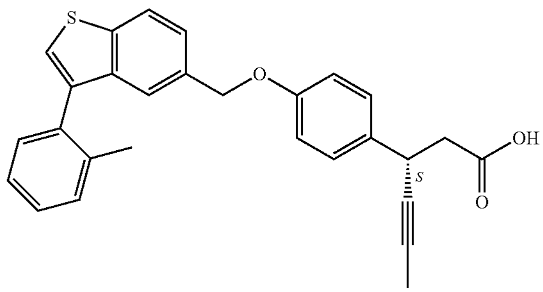 | 2 | (3S)-3-[4-[[3-(2-Methylphenyl)benzo[b]thiophen-5-yl]methoxy]phenyl] hex-4-ynoic acid |
| 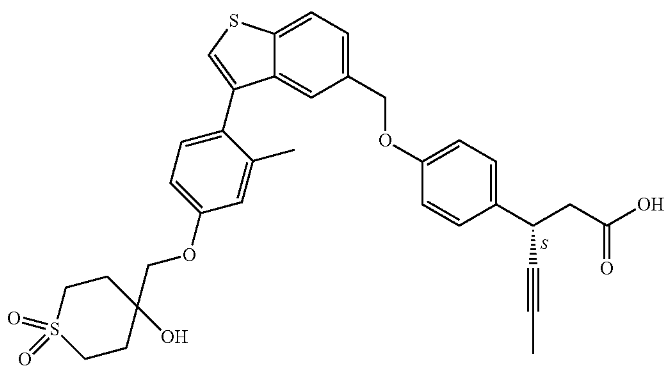 | 3 | (3S)-3-[4-[[3-[4-[(4-Hydroxy-1,1-dioxo-thian-4-yl)methoxy]-2-methyl-phenyl]benzo[b]thiophen-5-yl]methoxy]phenyl] hex-4-ynoic acid |
| 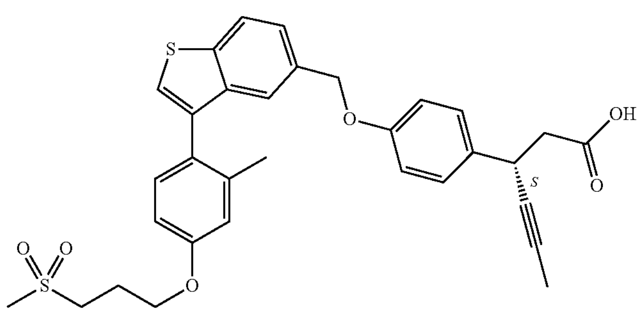 | 4 | (3S)-3-[4-[[3-[2-Methyl-4-(3-methylsulfonylpropoxy)phenyl]benzo[b]thiophen-5-yl]methoxy]phenyl] hex-4-ynoic acid |
| 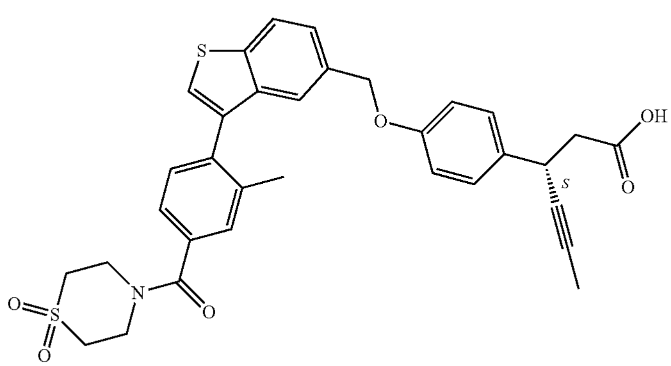 | 5 | (3S)-3-[4-[[3-[4-(1,1-Dioxo-1,4-thiazinane-4-carbonyl)-2-methyl-phenyl]benzo[b]thiophen-5-yl]methoxy]phenyl] hex-4-ynoic acid |

TABLE 1-continued

| Structure | Cpd No. | Cpd Name |
|---|---|---|
| 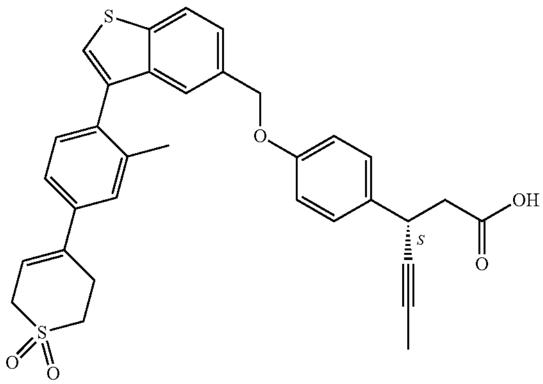 | 6 | (3S)-3-[4-[[3-[4-(1,1-Dioxo-3,6-dihydro-2H-thiopyran-4-yl)-2-methyl-phenyl]benzo[b]thiophen-5-yl]methoxy]phenyl] hex-4-ynoic acid |
| 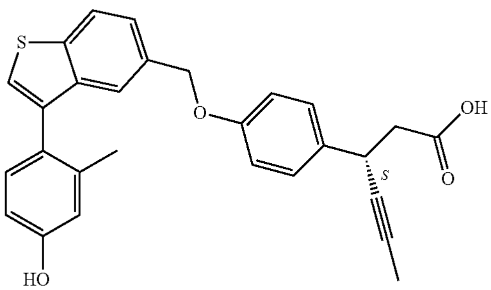 | 7 | (3S)-3-[4-[[3-[3-(4-Hydroxy-2-methyl-phenyl)benzo[b]thiophen-5-yl]methoxy]phenyl] hex-4-ynoic acid |
| 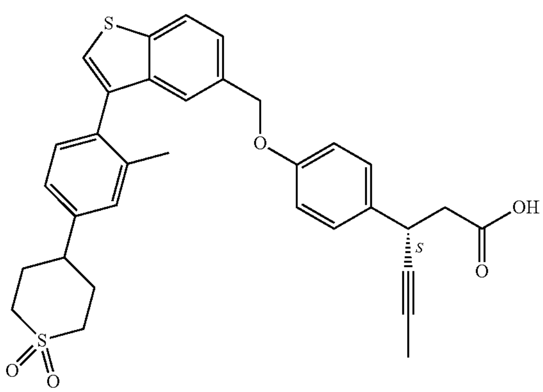 | 8 | (3S)-3-[4-[[3-[4-(1,1-Dioxothian-4-yl)-2-methyl-phenyl]benzo[b]thiophen-5-yl]methoxy]phenyl] hex-4-ynoic acid |
| 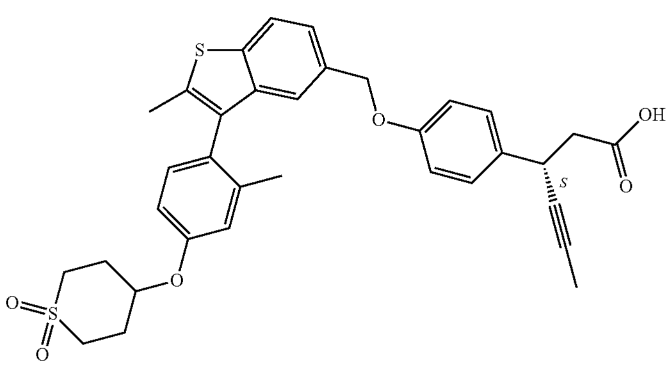 | 9 | (3S)-3-[4-[[3-[4-(1,1-Dioxothian-4-yl)oxy-2-methyl-phenyl]-2-methyl-benzo[b]thiophen-5-yl]methoxy]phenyl] hex-4-ynoic acid |

TABLE 1-continued

| Structure | Cpd No. | Cpd Name |
|---|---|---|
| 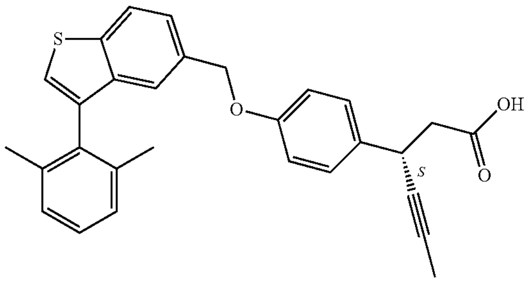 | 10 | (3S)-3-[4-[[3-(2,6-Dimethylphenyl)benzo[b]thiophen-5-yl]methoxy]phenyl]hex-4-ynoic acid |
| 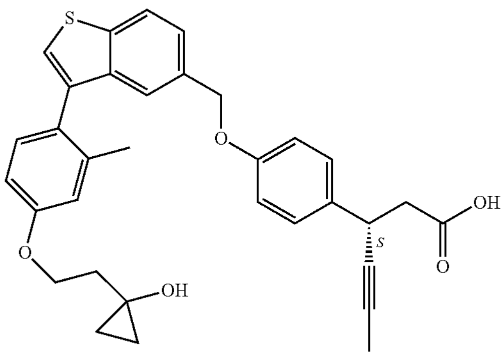 | 11 | (3S)-3-(4-((3-(4-(2-(1-Hydroxycyclopropyl)ethoxy)-2-methylphenyl)benzo[b]thiophen-5-yl)methoxy)phenyl)hex-4-ynoic acid |
| 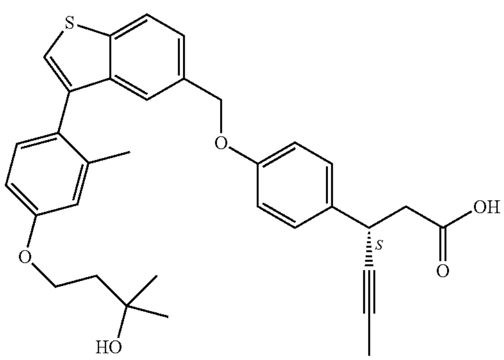 | 12 | (3S)-3-(4-((3-(4-(3-Hydroxy-3-methylbutoxy)-2-methylphenyl)benzo[b]thiophen-5-yl)methoxy)phenyl)hex-4-ynoic acid |
| 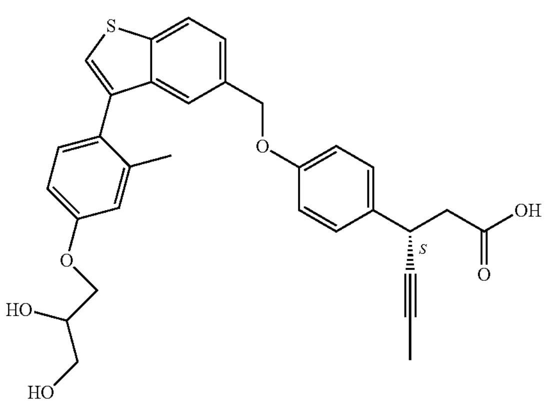 | 13 | (3S)-3-(4-((3-(4-(2,3-Dihydroxypropoxy)-2-methylphenyl)benzo[b]thiophen-5-yl)methoxy)phenyl)hex-4-ynoic acid |

TABLE 1-continued

| Structure | Cpd No. | Cpd Name |
|---|---|---|
| 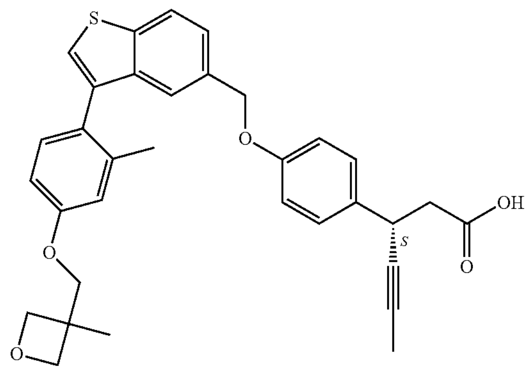 | 14 | (3S)-3-(4-((3-(2-Methyl-4-((3-methyloxetan-3-yl)methoxy)phenyl)benzo[b]thiophen-5-yl)methoxy)phenyl)hex-4-ynoic acid |
| 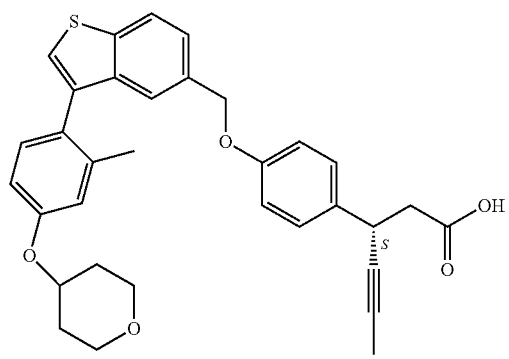 | 15 | (3S)-3-(4-((3-(2-Methyl-4-((tetrahydro-2H-pyran-4-yl)oxy)phenyl)benzo[b]thiophen-5-yl)methoxy)phenyl)hex-4-ynoic acid |
| 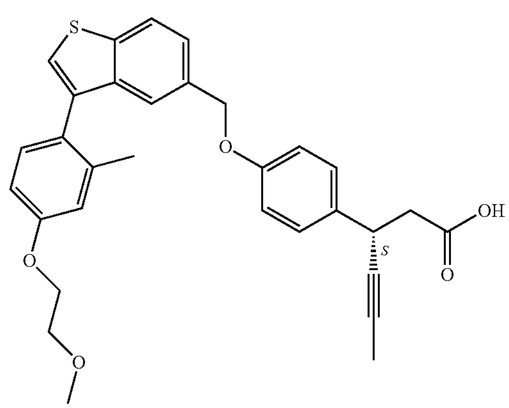 | 16 | (3S)-3-(4-((3-(4-(2-Methoxyethoxy)-2-methylphenyl)benzo[b]thiophen-5-yl)methoxy)phenyl)hex-4-ynoic acid |
| 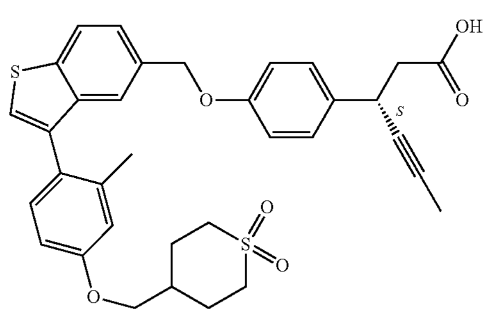 | 17 | (3S)-3-(4-((3-(4-((1,1-Dioxidotetrahydro-2H-thiopyran-4-yl)methoxy)-2-methylphenyl)benzo[b]thiophen-5-yl)methoxy)phenyl)hex-4-ynoic acid |

TABLE 1-continued

| Structure | Cpd No. | Cpd Name |
|---|---|---|
| 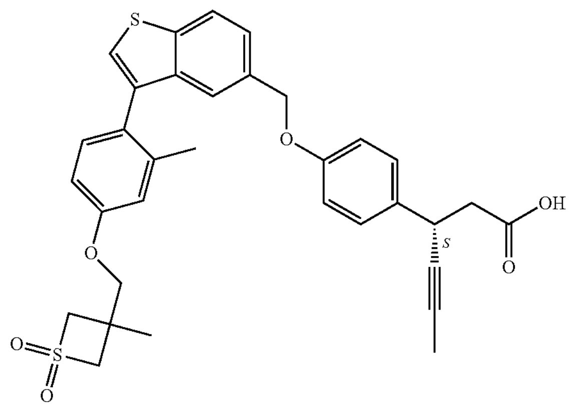 | 18 | (3S)-3-(4-((3-(2-Methyl-4-((3-methyl-1,1-dioxidothietan-3-yl)methoxy)phenyl)benzo[b]thiophen-5-yl)methoxy)phenyl)hex-4-ynoic acid |
| 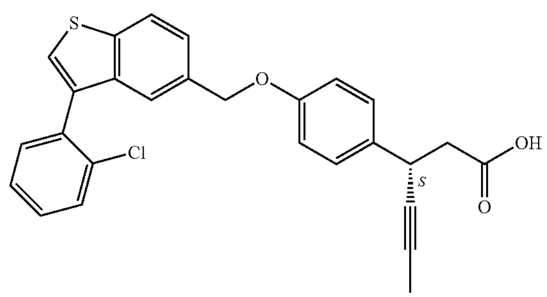 | 19 | (3S)-3-(4-((3-(2-Chlorophenyl)benzo[b]thiophen-5-yl)methoxy)phenyl)hex-4-ynoic acid |
| 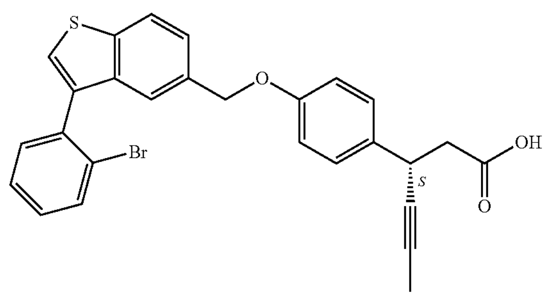 | 20 | (3S)-3-(4-((3-(2-Bromophenyl)benzo[b]thiophen-5-yl)methoxy)phenyl)hex-4-ynoic acid |
| 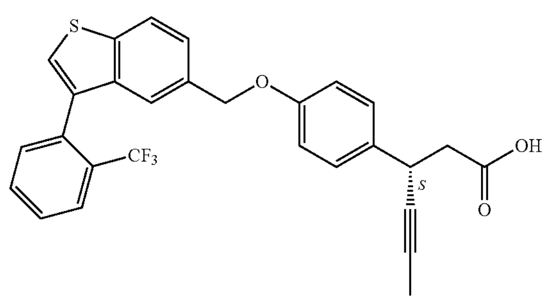 | 21 | (3S)-3-(4-((3-(2-(Trifluoromethyl)phenyl)benzo[b]thiophen-5-yl)methoxy)phenyl)hex-4-ynoic acid |
| 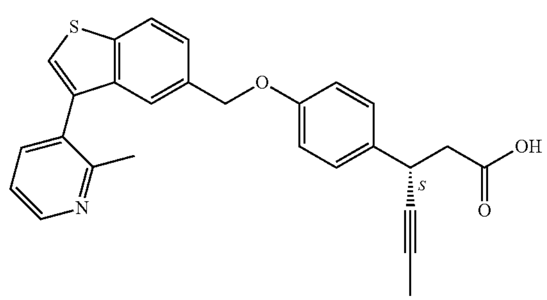 | 22 | (3S)-3-(4-((3-(2-Methylpyridin-3-yl)benzo[b]thiophen-5-yl)methoxy)phenyl)hex-4-ynoic acid |

TABLE 1-continued

| Structure | Cpd No. | Cpd Name |
|---|---|---|
| 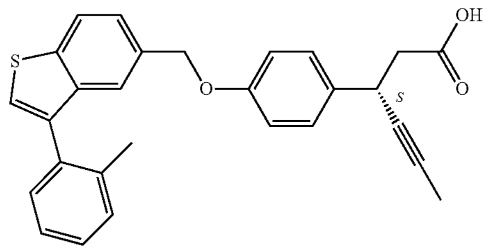 | 23 | (3S)-3-(4-(((3-(2-Methylphenyl)benzo[b]thiophen-5-yl)oxy)methyl)phenyl)hex-4-ynoic acid |
| 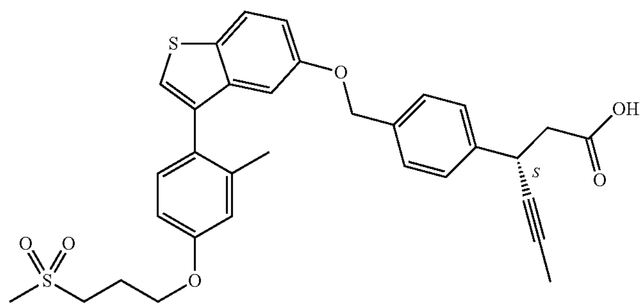 | 24 | (3S)-3-(4-(((3-(2-Methyl-4-(3-(methylsulfonyl)propoxy)phenyl)benzo[b]thiophen-5-yl)oxy)methyl)phenyl)hex-4-ynoic acid |
| 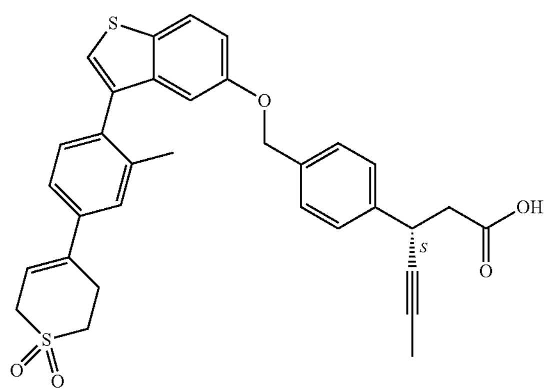 | 25 | (3S)-3-(4-(((3-(4-(1,1-Dioxido-3,6-dihydro-2H-thiopyran-4-yl)-2-methylphenyl)benzo[b]thiophen-5-yl)oxy)methyl)phenyl)hex-4-ynoic acid |
| 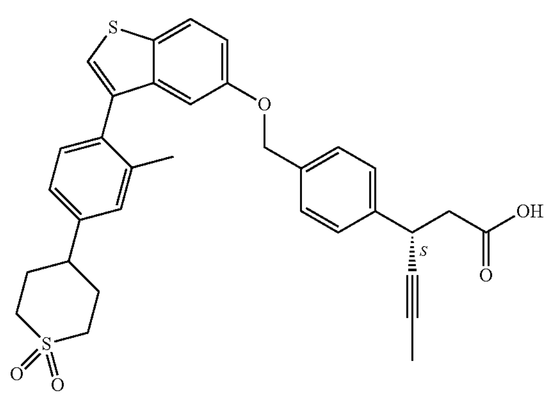 | 26 | (3S)-3-(4-(((3-(4-(1,1-Dioxidotetrahydro-2H-thiopyran-4-yl)-2-methylphenyl)benzo[b]thiophen-5-yl)oxy)methyl)phenyl)hex-4-ynoic acid |

TABLE 1-continued

| Structure | Cpd No. | Cpd Name |
|---|---|---|
| 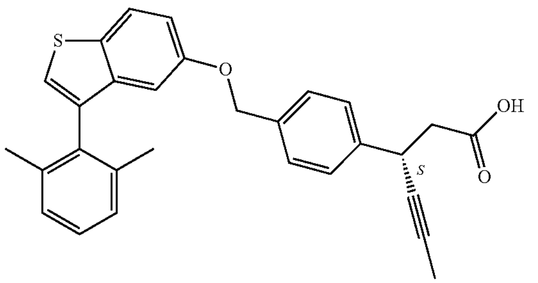 | 27 | (3S)-3-(4-(((3-(2,6-Dimethylphenyl)benzo[b]thiophen-5-yl)oxy)methyl)phenyl) hex-4-ynoic acid |
| 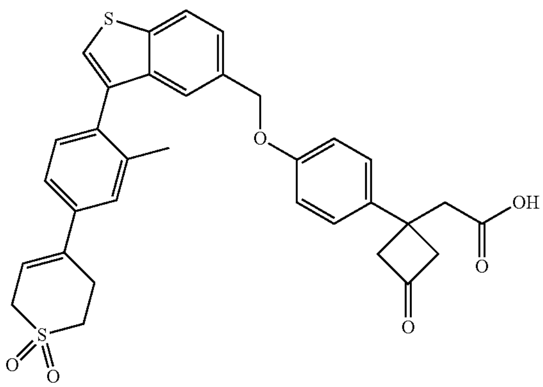 [SMILES: Cc1cc(C2=CCS(=O)(=O)CC2)ccc1-c1csc2ccc(COc3ccc(C4(CC(=O)O)CC(=O)C4)cc3)cc12] | 28 | 2-(1-(4-((3-(4-(1,1-Dioxido-3,6-dihydro-2H-thiopyran-4-yl)-2-methylphenyl)benzo[b]thiophen-5-yl)methoxy)phenyl)-3-oxocyclobutyl)acetic acid |
| 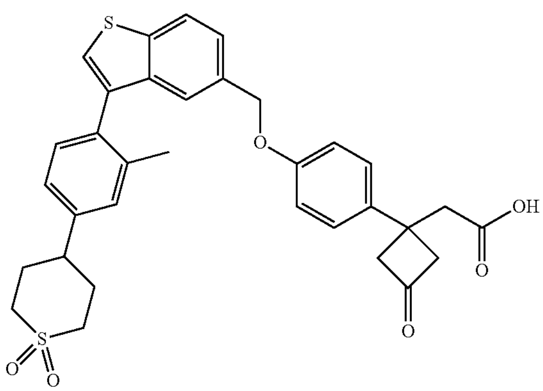 [SMILES: Cc1cc(C2CCS(=O)(=O)CC2)ccc1-c1csc2ccc(COc3ccc(C4(CC(=O)O)CC(=O)C4)cc3)cc12] | 29 | 2-(1-(4-((3-(4-(1,1-Dioxidotetrahydro-2H-thiopyran-4-yl)-2-methylphenyl)benzo[b]thiophen-5-yl)methoxy)phenyl)-3-oxocyclobutyl)acetic acid |
| 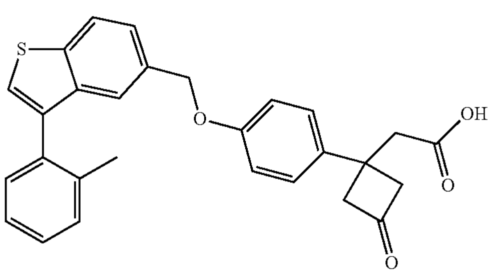 [SMILES: Cc1ccccc1-c1csc2ccc(COc3ccc(C4(CC(=O)O)CC(=O)C4)cc3)cc12] | 30 | 2-(3-Oxo-1-(4-((3-(2-methylphenyl) benzo[b]thiophen-5-yl)methoxy)phenyl)cyclobutyl) acetic acid |
| 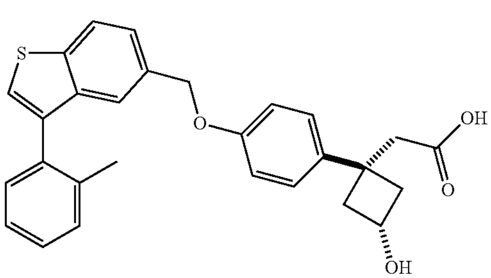 | 31 | 2-((1r,3r)-3-Hydroxy-1-(4-((3-(2-methylphenyl) benzo[b]thiophen-5-yl)methoxy)phenyl)cyclobutyl) acetic acid |

TABLE 1-continued

| Structure | Cpd No. | Cpd Name |
|---|---|---|
| 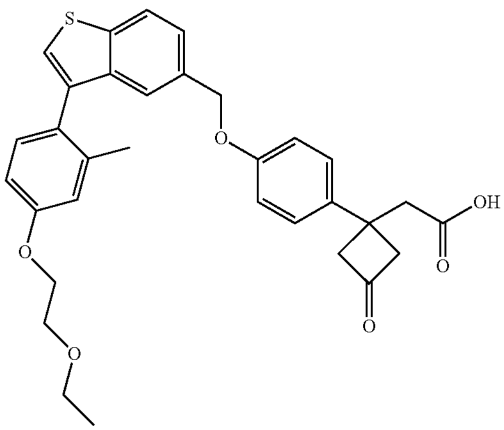 [SMILES: CCOCCOc1ccc(-c2csc3ccc(COc4ccc(C5(CC(=O)O)CC(=O)C5)cc4)cc23)c(C)c1] | 32 | 2-(1-(4-((3-(4-(2-Ethoxyethoxy)-2-methylphenyl)benzo[b]thiophen-5-yl)methoxy)phenyl)-3-oxocyclobutyl)acetic acid |
| 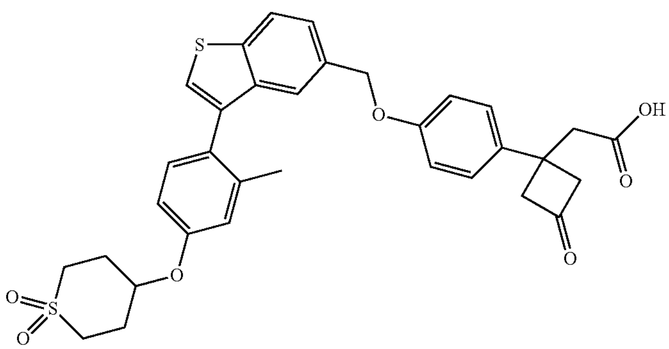 [SMILES: Cc1cc(OC2CCS(=O)(=O)CC2)ccc1-c1csc2ccc(COc3ccc(C4(CC(=O)O)CC(=O)C4)cc3)cc12] | 33 | 2-(1-(4-((3-(4-((1,1-Dioxidotetrahydro-2H-thiopyran-4-yl)oxy)-2-methylphenyl)benzo[b]thiophen-5-yl)methoxy)phenyl)-3-oxocyclobutyl)acetic acid |
| 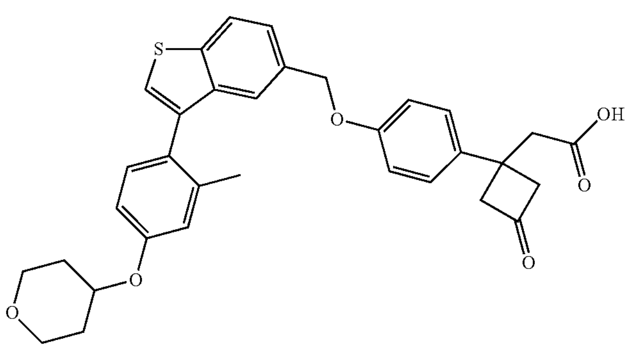 [SMILES: Cc1cc(OC2CCOCC2)ccc1-c1csc2ccc(COc3ccc(C4(CC(=O)O)CC(=O)C4)cc3)cc12] | 34 | 2-(1-(4-((3-(2-Methyl-4-((tetrahydro-2H-pyran-4-yl)oxy)phenyl)benzo[b]thiophen-5-yl)methoxy)phenyl)-3-oxocyclobutyl)acetic acid |
| 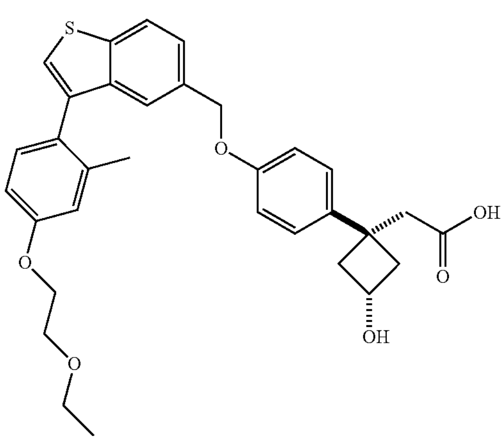 | 35 | 2-((1r,3r)-3-Hydroxy-1-(4-((3-(4-(2-ethoxyethoxy)-2-methylphenyl)benzo[b]thiophen-5-yl)methoxy)phenyl)cyclobutyl)acetic acid |

TABLE 1-continued

| Structure | Cpd No. | Cpd Name |
|---|---|---|
| 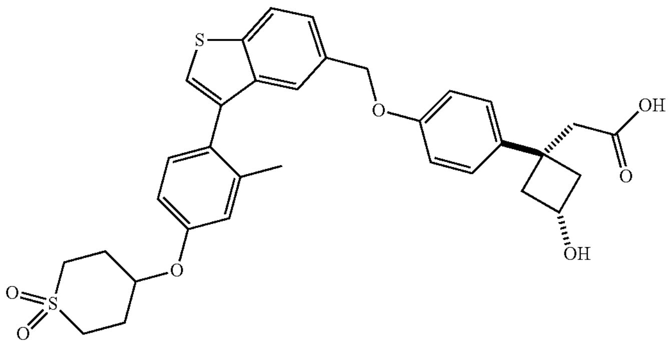 | 36 | 2-((1r,3r)-1-(4-((3-(4-((1,1-Dioxidotetrahydro-2H-thiopyran-4-yl)oxy)-2-methylphenyl)benzo[b]thiophen-5-yl)methoxy)phenyl)-3-hydroxycyclobutyl)acetic acid |
| 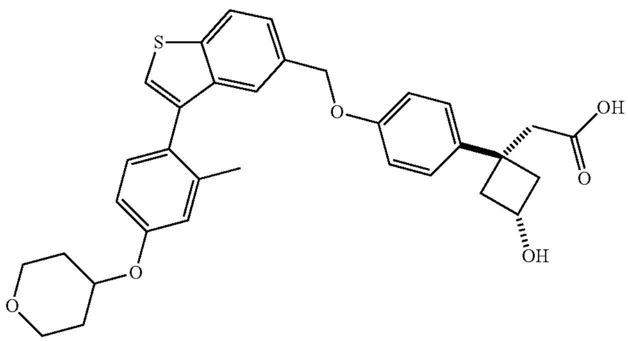 | 37 | 2-((1r,3r)-3-Hydroxy-1-(4-((3-(2-methyl-4-((tetrahydro-2H-pyran-4-yl)oxy)phenyl)benzo[b]thiophen-5-yl)methoxy)phenyl)cyclobutyl)acetic acid |
| 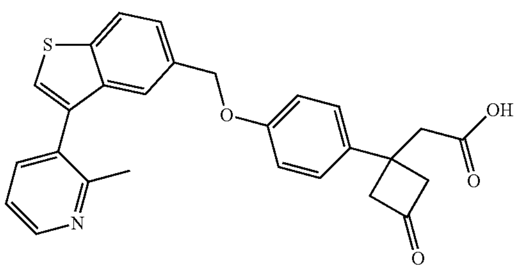 [SMILES: Cc1ncccc1-c1csc2ccc(COc3ccc(C4(CC(=O)O)CC(=O)C4)cc3)cc12] | 38 | 2-(1-(4-((3-(2-Methylpyridin-3-yl)benzo[b]thiophen-5-yl)methoxy)phenyl)-3-oxocyclobutyl)acetic acid |
| 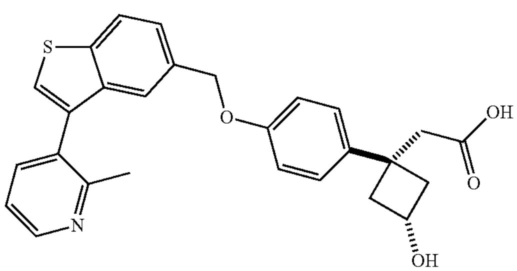 | 39 | 2-((1r,3r)-3-Hydroxy-1-(4-((3-(2-methylpyridin-3-yl)benzo[b]thiophen-5-yl)methoxy)phenyl)cyclobutyl)acetic acid |
| 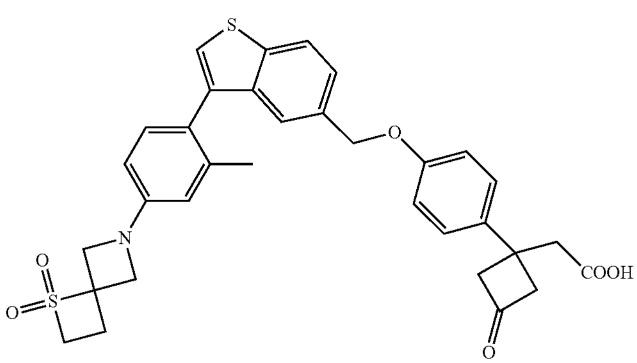 [SMILES: Cc1cc(N2CC3(CCS3(=O)=O)C2)ccc1-c1csc2ccc(COc3ccc(C4(CC(=O)O)CC(=O)C4)cc3)cc12] | 40 | 2-(1-(4-((3-(4-(1,1-Dioxido-1-thia-6-azaspiro[3.3]heptan-6-yl)-2-methylphenyl)benzo[b]thiophen-5-yl)methoxy)phenyl)-3-oxocyclobutyl)acetic acid |

TABLE 1-continued

| Structure | Cpd No. | Cpd Name |
|---|---|---|
| 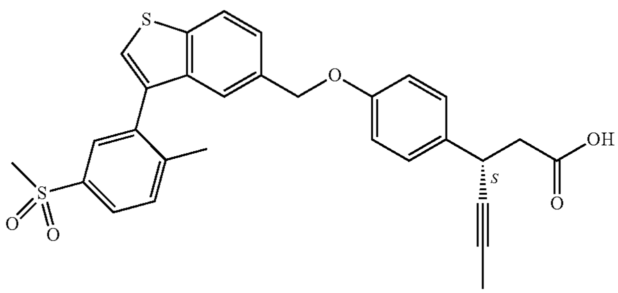 | 41 | (3S)-3-(4-((3-(2-Methyl-5-(methylsulfonyl)phenyl)benzo[b]thiophen-5-yl)methoxy)phenyl)hex-4-ynoic acid |
| 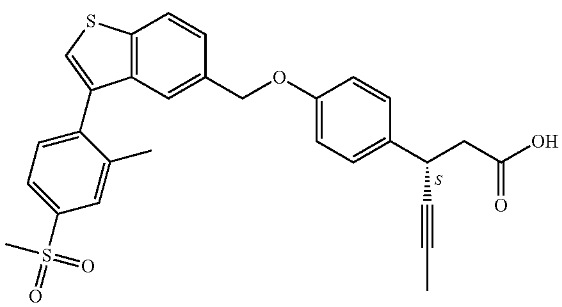 | 42 | (3S)-3-(4-((3-(2-Methyl-4-(methylsulfonyl)phenyl)benzo[b]thiophen-5-yl)methoxy)phenyl)hex-4-ynoic acid |
| 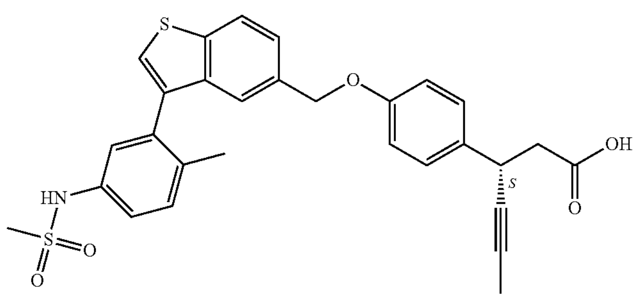 | 43 | (3S)-3-(4-((3-(2-Methyl-5-(methylsulfonamido)phenyl)benzo[b]thiophen-5-yl)methoxy)phenyl)hex-4-ynoic acid |
| 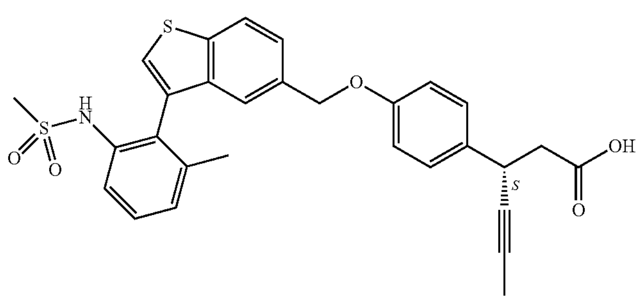 | 44 | (3S)-3-(4-((3-(2-Methyl-6-(methylsulfonamido)phenyl)benzo[b]thiophen-5-yl)methoxy)phenyl)hex-4-ynoic acid |
| 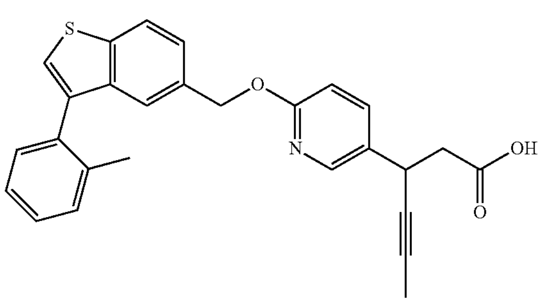 [SMILES: CC#CC(CC(=O)O)c1ccc(OCc2ccc3scc(-c4ccccc4C)c3c2)nc1] | 45 | 3-(6-((3-(2-Methylphenyl)benzo[b]thiophen-5-yl)methoxy)pyridin-3-yl)hex-4-ynoic acid |

TABLE 1-continued

| Structure | Cpd No. | Cpd Name |
|---|---|---|
| 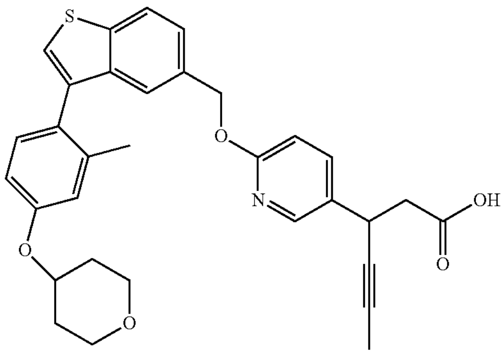 [SMILES: CC#CC(CC(=O)O)c1ccc(OCc2ccc3scc(-c4ccc(OC5CCOCC5)cc4C)c3c2)nc1] | 46 | 3-(6-((3-(2-Methyl-4-((tetrahydro-2H-pyran-4-yl)oxy)phenyl)benzo[b]thiophen-5-yl)methoxy)pyridin-3-yl) hex-4-ynoic acid |
| 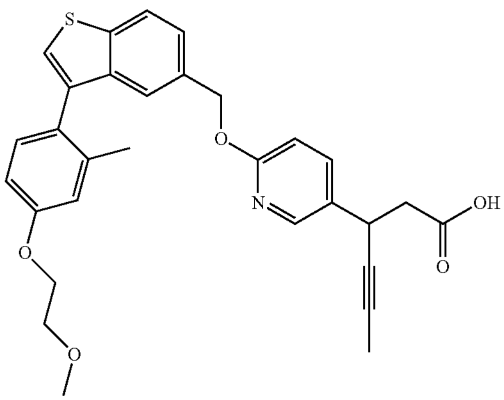 [SMILES: CC#CC(CC(=O)O)c1ccc(OCc2ccc3scc(-c4ccc(OCCOC)cc4C)c3c2)nc1] | 47 | 3-(6-((3-(4-(2-Methoxyethoxy)-2-methylphenyl) benzo[b]thiophen-5-yl)methoxy)pyridin-3-yl) hex-4-ynoic acid |
| 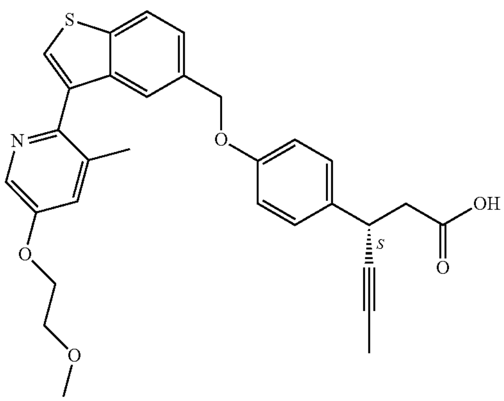 | 48 | (3S)-3-(4-((3-(5-(2-Methoxyethoxy)-3-methylpyridin-2-yl)benzo[b]thiophen-5-yl)methoxy)phenyl) hex-4-ynoic acid |
| 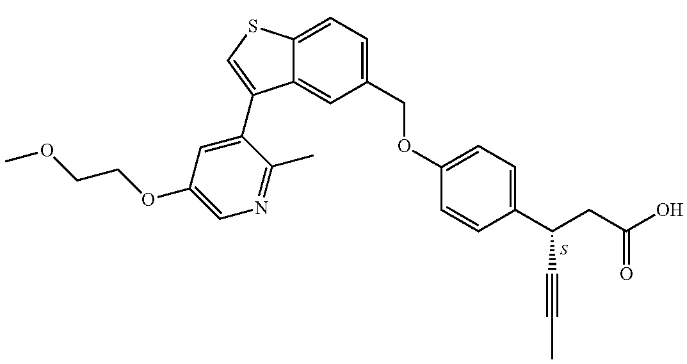 | 49 | (3S)-3-(4-((3-(5-(2-Methoxyethoxy)-2-methylpyridin-3-yl)benzo[b]thiophen-5-yl)methoxy)phenyl) hex-4-ynoic acid |

TABLE 1-continued

| Structure | Cpd No. | Cpd Name |
|---|---|---|
| 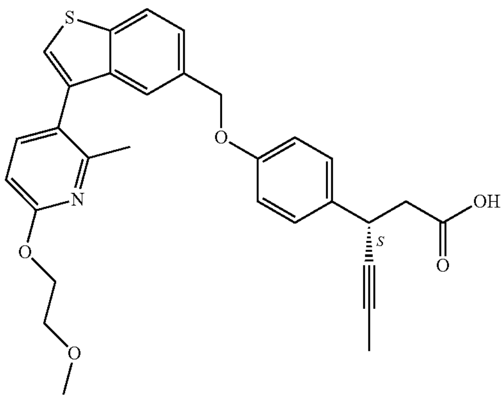 | 50 | (3S)-3-(4-((3-(6-(2-Methoxyethoxy)-2-methylpyridin-3-yl)benzo[b]thiophen-5-yl)methoxy)phenyl) hex-4-ynoic acid |
| 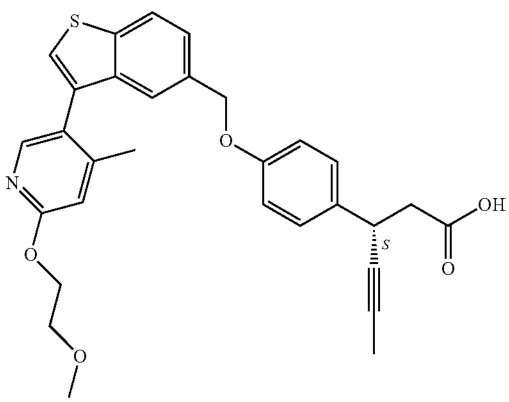 | 51 | (3S)-3-(4-((3-(6-(2-Methoxyethoxy)-4-methylpyridin-3-yl)benzo[b]thiophen-5-yl)methoxy)phenyl) hex-4-ynoic acid |
| 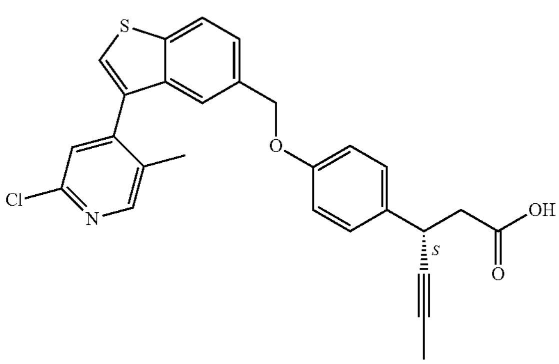 | 52 | (3S)-3-(4-((3-(2-Chloro-5-methylpyridin-4-yl)benzo[b]thiophen-5-yl)methoxy)phenyl) hex-4-ynoic acid |
| 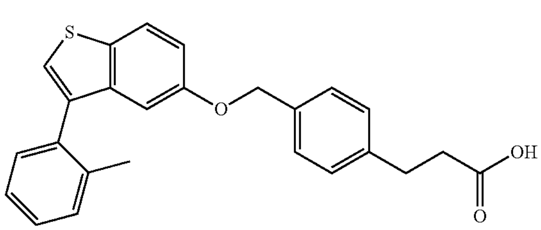 [SMILES: Cc1ccccc1-c1csc2ccc(OCc3ccc(CCC(=O)O)cc3)cc12] | 53 | 3-(4-(((3-(2-Methylphenyl)benzo[b]thiophen-5-yl)oxy)methyl)phenyl) propanoic acid |

TABLE 1-continued

| Structure | Cpd No. | Cpd Name |
|---|---|---|
| 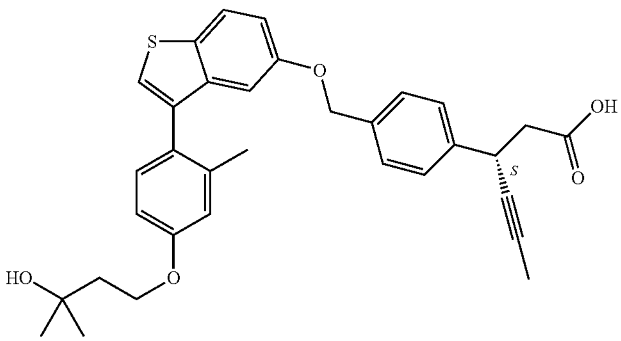 | 54 | (3S)-3-[4-[([3-[4-(3-Hydroxy-3-methylbutoxy)-2-methylphenyl]-1-benzothiophen-5-yl]oxy)methyl]phenyl] hex-4-ynoic acid |
| 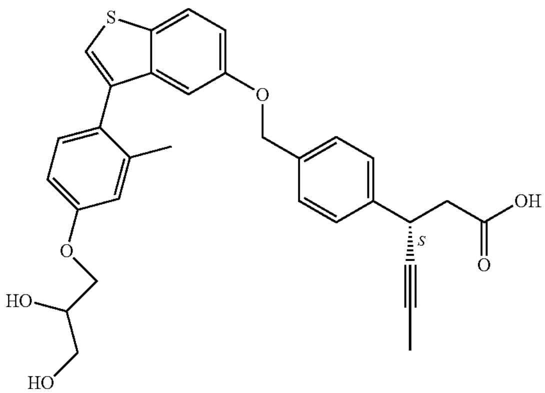 | 55 | (3S)-3-[4-[([3-[4-(2,3-Dihydroxypropoxy)-2-methylphenyl]-1-benzothiophen-5-yl]oxy)methyl]phenyl] hex-4-ynoic acid |
| 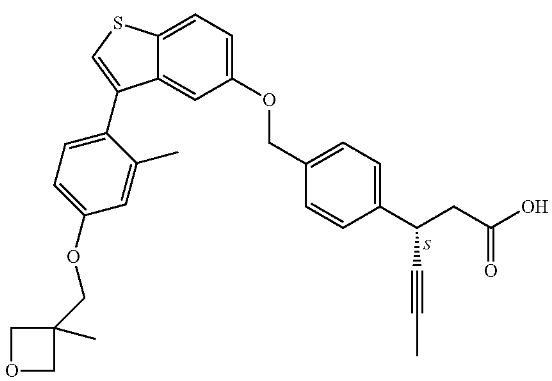 | 56 | (3S)-3-(4-[[(3-[2-Methyl-4-[(3-methyloxetan-3-yl)methoxy]phenyl]-1-benzothiophen-5-yl)oxy]methyl]phenyl) hex-4-ynoic acid |
| 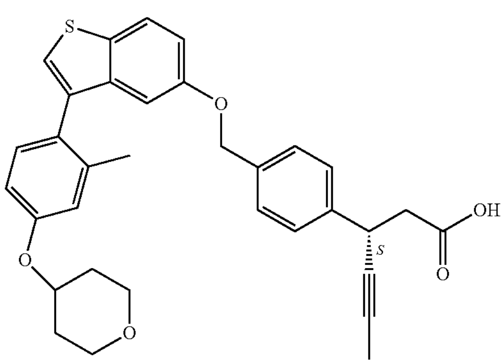 | 57 | (3S)-3-[4-[([3-[2-Methyl-4-(oxan-4-yloxy)phenyl]-1-benzothiophen-5-yl]oxy)methyl]phenyl] hex-4-ynoic acid |

TABLE 1-continued

| Structure | Cpd No. | Cpd Name |
|---|---|---|
| 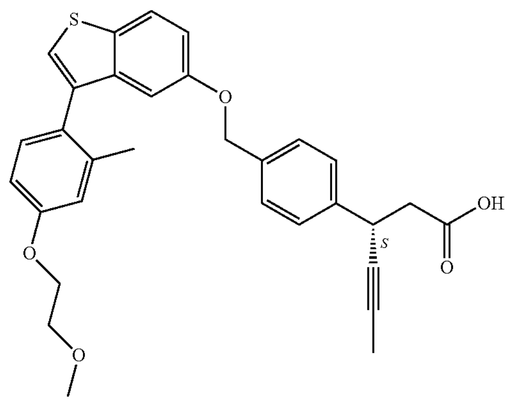 | 58 | (3S)-3-[4-[([3-[4-(2-Methoxyethoxy)-2-methylphenyl]-1-benzothiophen-5-yl]oxy)methyl]phenyl] hex-4-ynoic acid |
| 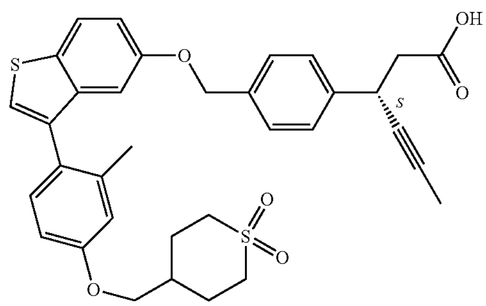 | 59 | (3S)-3-{4-[((3-{4-[(1,1-Dioxo-tetrahydro-2H-thiopyran-4-yl)methoxy]-2-methylphenyl}-1-benzothiophen-5-yl)oxy)methyl]phenyl} hex-4-ynoic acid |
| 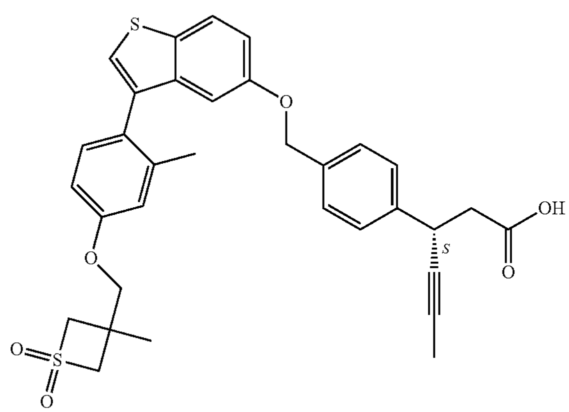 | 60 | (3S)-3-(4-(((3-(2-Methyl-4-((3-methyl-1,1-dioxidothietan-3-yl)methoxy)phenyl)benzo[b]thiophen-5-yl)oxy)methyl)phenyl) hex-4-ynoic acid |
| 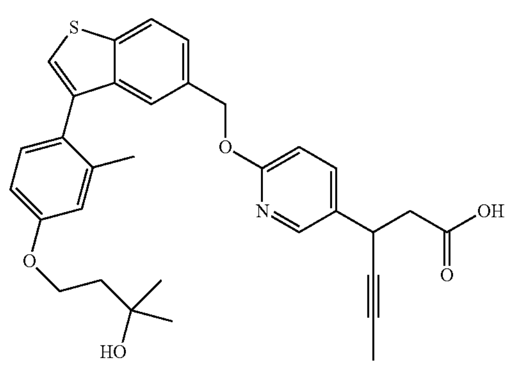 [SMILES: CC#CC(CC(=O)O)c1ccc(OCc2ccc3scc(-c4ccc(OCCC(C)(C)O)cc4C)c3c2)nc1] | 61 | 3-[6-([3-[4-(3-Hydroxy-3-methylbutoxy)-2-methylphenyl]-1-benzothiophen-5-yl]methoxy)pyridin-3-yl] hex-4-ynoic acid |

TABLE 1-continued

| Structure | Cpd No. | Cpd Name |
|---|---|---|
| 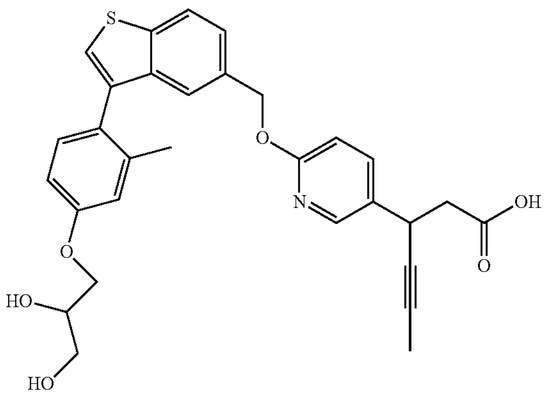 [SMILES: CC#CC(CC(=O)O)c1ccc(OCc2ccc3scc(-c4ccc(OCC(O)CO)cc4C)c3c2)nc1] | 62 | 3-(6-((3-(4-(2,3-Dihydroxypropoxy)-2-phenyl)benzo[b]thiophen-5-yl)methoxy)pyridin-3-yl)hex-4-ynoic acid |
| 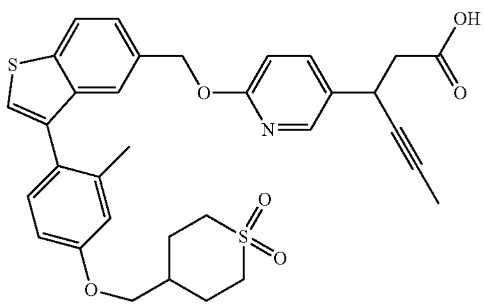 [SMILES: CC#CC(CC(=O)O)c1ccc(OCc2ccc3scc(-c4ccc(OCC5CCS(=O)(=O)CC5)cc4C)c3c2)nc1] | 63 | 3-(6-((3-(4-((1,1-Dioxidotetrahydro-2H-thiopyran-4-yl)methoxy)-2-methylphenyl)benzo[b]thiophen-5-yl)methoxy)pyridin-3-yl)hex-4-ynoic acid |
| 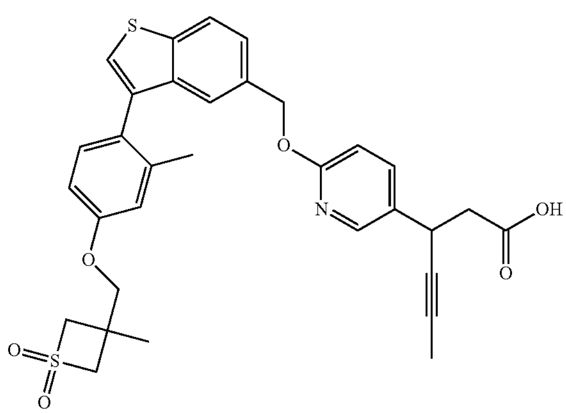 [SMILES: CC#CC(CC(=O)O)c1ccc(OCc2ccc3scc(-c4ccc(OCC5(C)CS(=O)(=O)C5)cc4C)c3c2)nc1] | 64 | 3-(6-((3-(2-Methyl-4-((3-methyl-1,1-dioxidothietan-3-yl)methoxy)phenyl)benzo[b]thiophen-5-yl)methoxy)pyridin-3-yl)hex-4-ynoic acid |
| 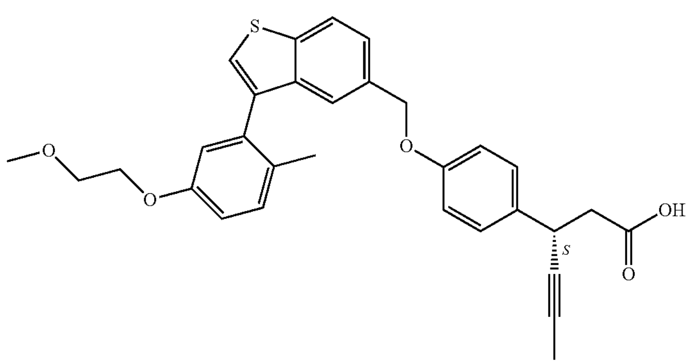 | 65 | (3S)-3-[4-(([3-[5-(2-Methoxyethoxy)-2-methylphenyl]-1-benzothiophen-5-yl]methoxy)phenyl]hex-4-ynoic acid |

TABLE 1-continued
| Structure | Cpd No. | Cpd Name |
|---|---|---|
| 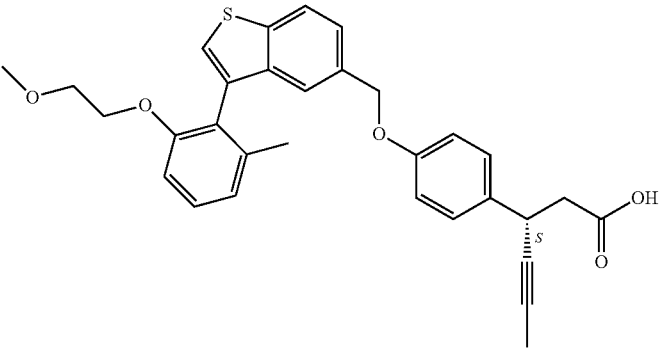 | 66 | (3S)-3-[4-([3-[2-(2-Methoxyethoxy)-6-methylphenyl]-1-benzothiophen-5-yl]methoxy)phenyl]hex-4-ynoic acid |
| 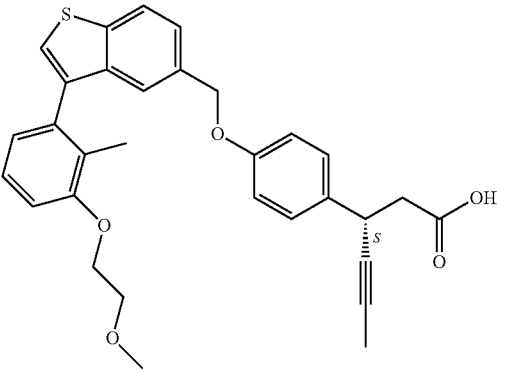 | 67 | (3S)-3-[4-([3-[3-(2-Methoxyethoxy)-2-methylphenyl]-1-benzothiophen-5-yl]methoxy)phenyl]hex-4-ynoic acid |
| 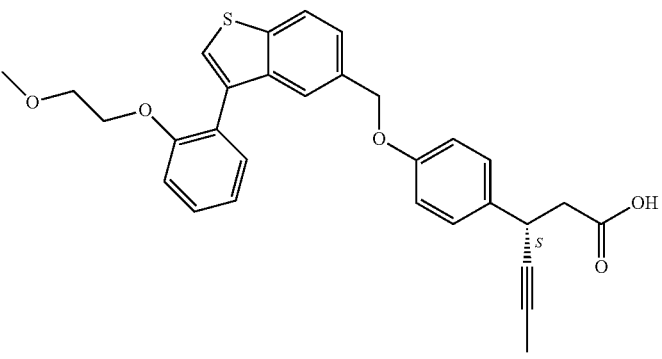 | 68 | (3S)-3-[4-([3-[2-(2-Methoxyethoxy)phenyl]-1-benzothiophen-5-yl]methoxy)phenyl]hex-4-ynoic acid |
| 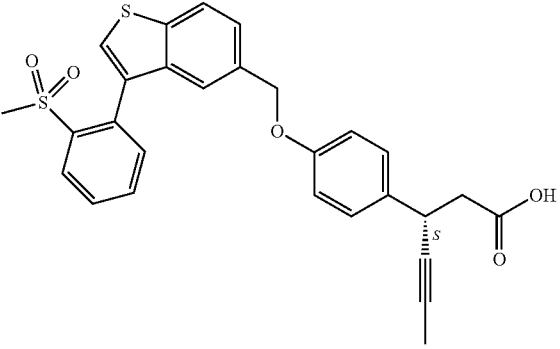 | 69 | (3S)-3-[4-[[3-(2-Methanesulfonylphenyl)-1-benzothiophen-6-yl]methoxy]phenyl)hex-4-ynoic acid |

TABLE 1-continued

| Structure | Cpd No. | Cpd Name |
|---|---|---|
| 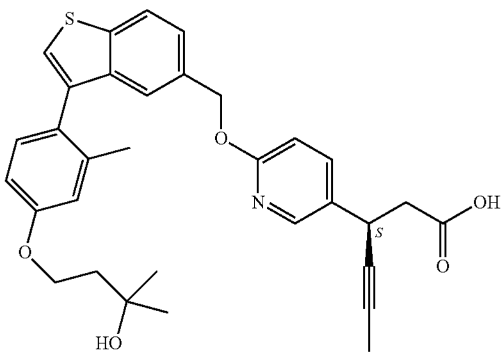 | 70 | (3S)-3-(6-((3-(4-(3-Hydroxy-3-methylbutoxy)-2-methylphenyl)benzo[b]thiophen-5-yl)methoxy)pyridin-3-yl)hex-4-ynoic acid |
| 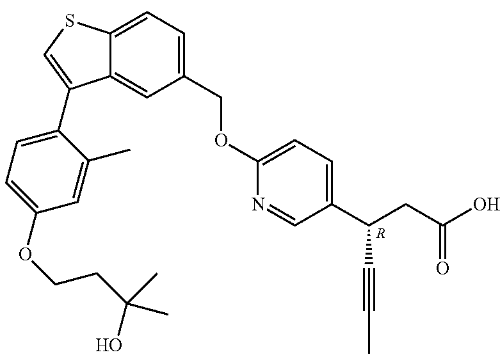 | 71 | (3R)-3-(6-((3-(4-(3-Hydroxy-3-methylbutoxy)-2-methylphenyl)benzo[b]thiophen-5-yl)methoxy)pyridin-3-yl)hex-4-ynoic acid |
| 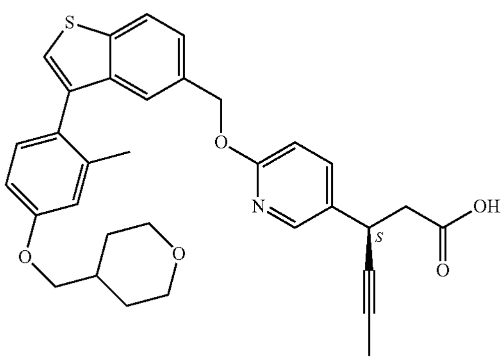 | 72 | (3S)-3-(6-((3-(2-Methyl-4-((tetrahydro-2H-pyran-4-yl)methoxy)phenyl)benzo[b]thiophen-5-yl)methoxy)pyridin-3-yl)hex-4-ynoic acid |
| 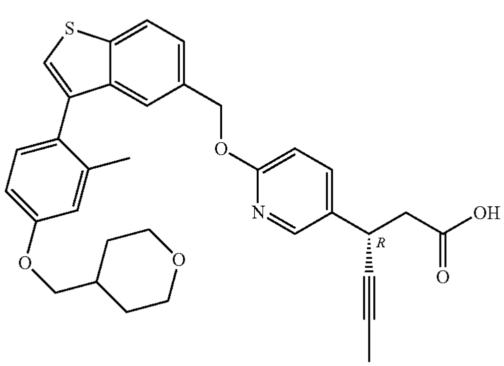 | 73 | (3R)-3-(6-((3-(2-Methyl-4-((tetrahydro-2H-pyran-4-yl)methoxy)phenyl)benzo[b]thiophen-5-yl)methoxy)pyridin-3-yl)hex-4-ynoic acid |

TABLE 1-continued

| Structure | Cpd No. | Cpd Name |
|---|---|---|
| 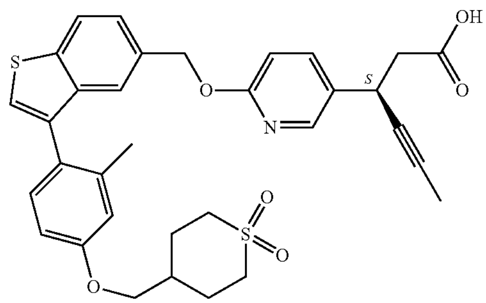 | 74 | (3S)-3-(6-((3-(4-((1,1-Dioxidotetrahydro-2H-thiopyran-4-yl)methoxy)-2-methylphenyl)benzo[b]thiophen-5-yl)methoxy)pyridin-3-yl) hex-4-ynoic acid |
| 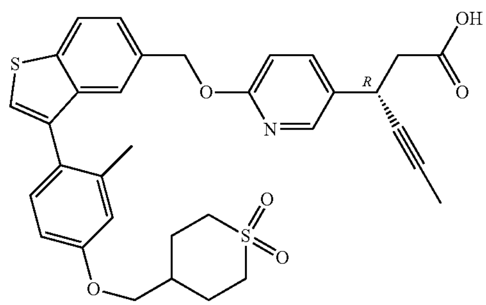 | 75 | (3R)-3-(6-((3-(4-((1,1-Dioxidotetrahydro-2H-thiopyran-4-yl)methoxy)-2-methylphenyl)benzo[b]thiophen-5-yl)methoxy)pyridin-3-yl) hex-4-ynoic acid |
| 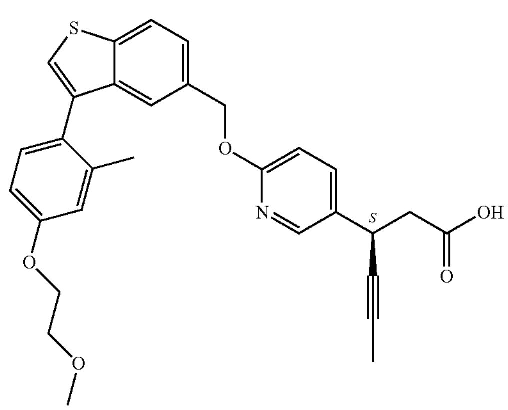 | 76 | (3S)-3-(6-((3-(4-(2-Methoxyethoxy)-2-methylphenyl) benzo[b]thiophen-5-yl)methoxy)pyridin-3-yl) hex-4-ynoic acid |
| 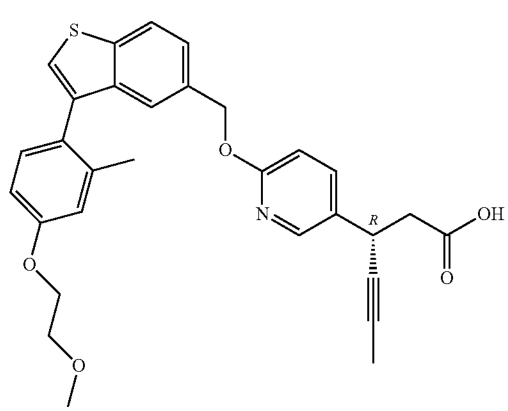 | 77 | (3R)-3-(6-((3-(4-(2-Methoxyethoxy)-2-methylphenyl) benzo[b]thiophen-5-yl)methoxy)pyridin-3-yl) hex-4-ynoic acid |

TABLE 1-continued

| Structure | Cpd No. | Cpd Name |
|---|---|---|
| 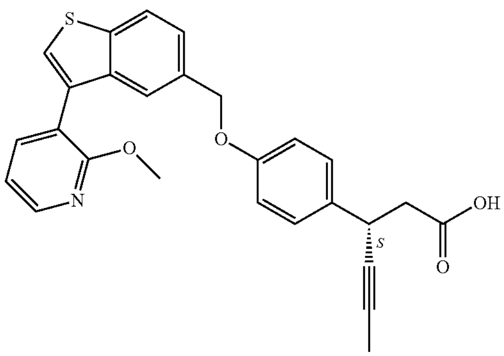 | 78 | (3S)-3-(4-((3-(2-Methoxypyridin-3-yl)benzo[b]thiophen-5-yl)methoxy)phenyl)hex-4-ynoic acid |
| 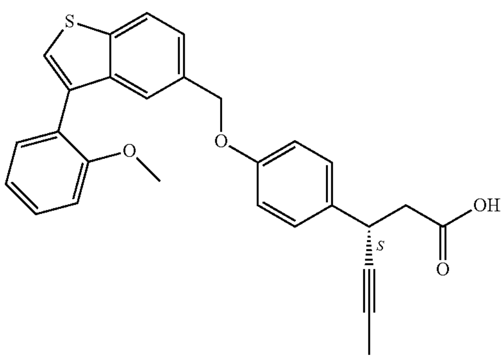 | 79 | (3S)-3-(4-((3-(2-Methoxyphenyl)benzo[b]thiophen-5-yl)methoxy)phenyl)hex-4-ynoic acid |
| 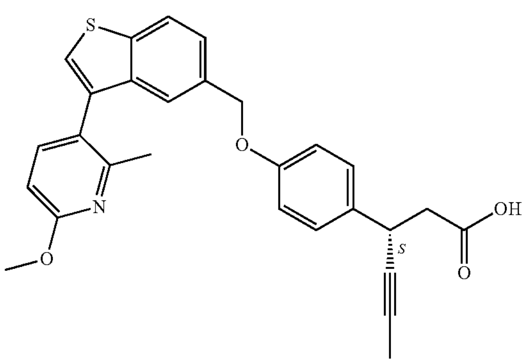 | 80 | (3S)-3-(4-((3-(6-Methoxy-2-methylpyridin-3-yl)benzo[b]thiophen-5-yl)methoxy)phenyl)hex-4-ynoic acid |
| 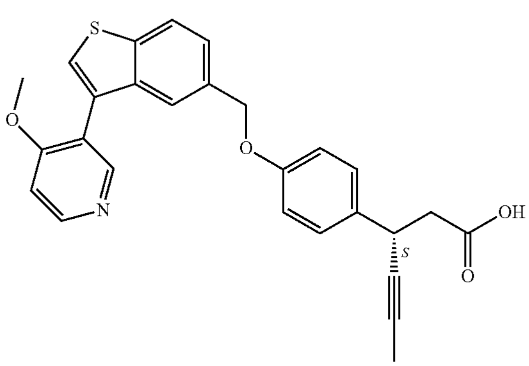 | 81 | (3S)-3-(4-((3-(4-Methoxypyridin-3-yl)benzo[b]thiophen-5-yl)methoxy)phenyl)hex-4-ynoic acid |

TABLE 1-continued

| Structure | Cpd No. | Cpd Name |
|---|---|---|
| 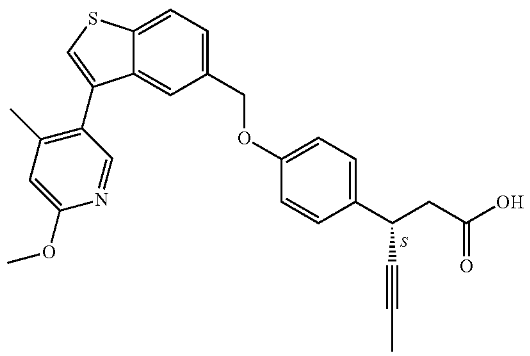 | 82 | (3S)-3-(4-((3-(6-Methoxy-4-methylpyridin-3-yl)benzo[b]thiophen-5-yl)methoxy)phenyl)hex-4-ynoic acid |
| 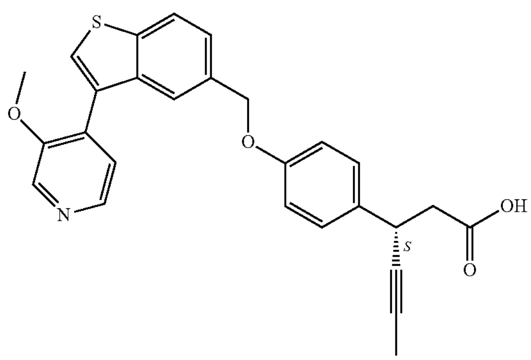 | 83 | (3S)-3-(4-((3-(3-Methoxypyridin-4-yl)benzo[b]thiophen-5-yl)methoxy)phenyl)hex-4-ynoic acid |
| 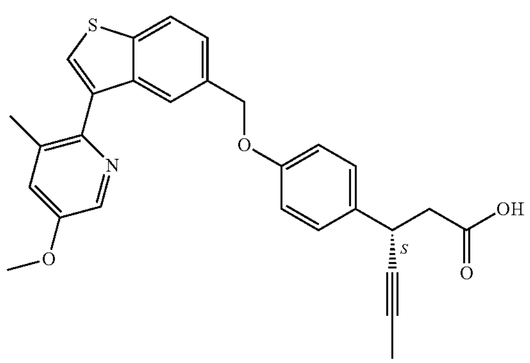 | 84 | (3S)-3-(4-((3-(5-Methoxy-3-methylpyridin-2-yl)benzo[b]thiophen-5-yl)methoxy)phenyl)hex-4-ynoic acid |
| 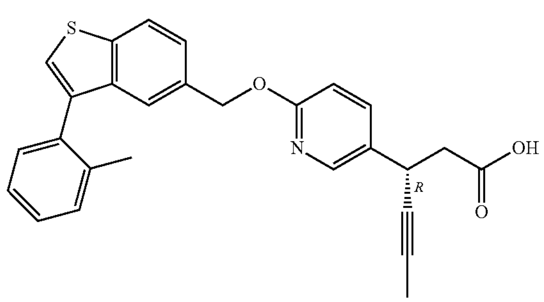 | 85 | (3R)-3-[6-[[3-(2-Methylphenyl)benzo[b]thiophen-5-yl]methoxy]pyridin-3-yl]hex-4-ynoic acid |

TABLE 1-continued

| Structure | Cpd No. | Cpd Name |
|---|---|---|
| 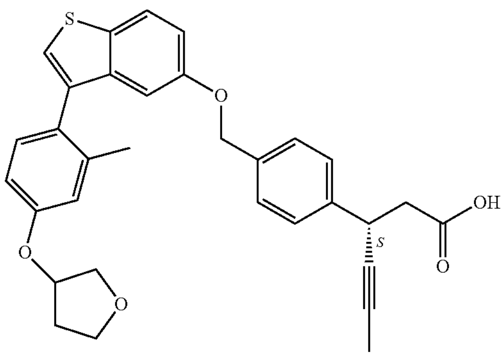 | 86 | (3S)-3-[4-[([3-[2-Methyl-4-(tetrahydrofuran-3-yloxy)phenyl]-1-benzothiophen-5-yl]oxy)methyl]phenyl] hex-4-ynoic acid |
| 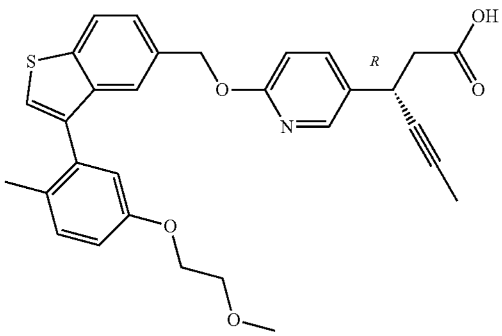 | 87 | (3R)-3-(6-((3-(5-(2-Methoxyethoxy)-2-methylphenyl) benzo[b]thiophen-5-yl)methoxy)pyridin-3-yl) hex-4-ynoic acid |
| 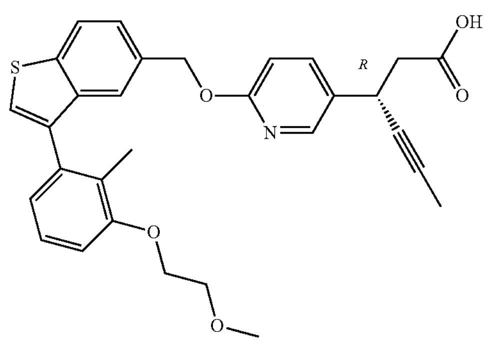 | 88 | (3R)-3-(6-((3-(3-(2-Methoxyethoxy)-2-methylphenyl) benzo[b]thiophen-5-yl)methoxy)pyridin-3-yl) hex-4-ynoic acid |
| 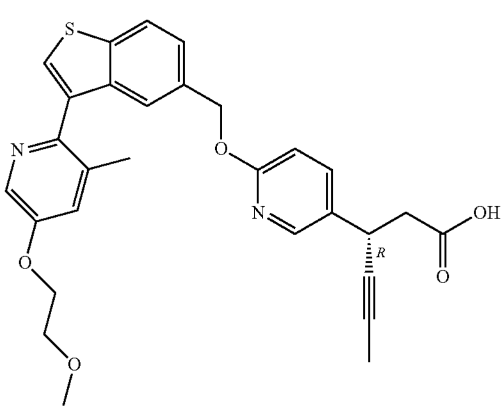 | 89 | (3R)-3-(6-((3-(5-(2-Methoxyethoxy)-3-methylpyridin-2-yl)benzo[b]thiophen-5-yl)methoxy)pyridin-3-yl) hex-4-ynoic acid |

TABLE 1-continued

| Structure | Cpd No. | Cpd Name |
|---|---|---|
| 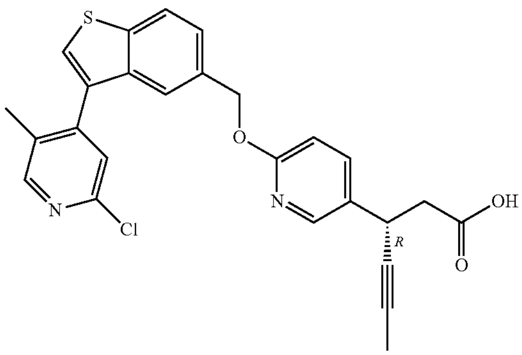 | 90 | (3R)-3-(6-((3-(2-Chloro-5-methylpyridin-4-yl)benzo[b]thiophen-5-yl)methoxy)pyridin-3-yl)hex-4-ynoic acid |
| 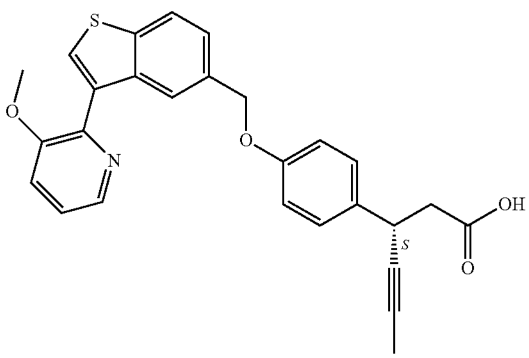 | 91 | (3S)-3-(4-((3-(3-Methoxypyridin-2-yl)benzo[b]thiophen-5-yl)methoxy)phenyl)hex-4-ynoic acid |
| 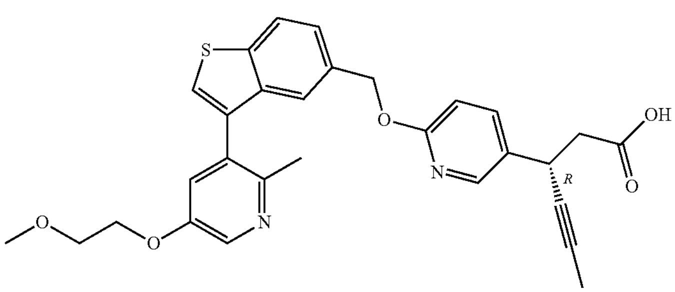 | 92 | (3R)-3-(6-((3-(5-(2-Methoxyethoxy)-2-methylpyridin-3-yl)benzo[b]thiophen-5-yl)methoxy)pyridine-3-yl)hex-4-ynoic acid |
| 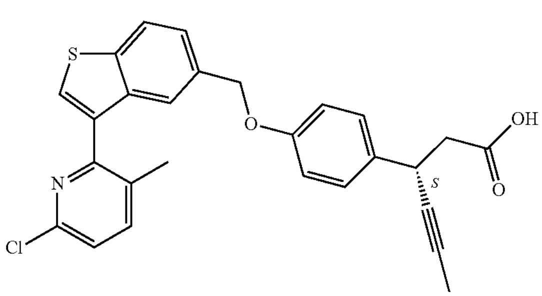 | 93 | (3S)-3-(4-((3-(6-Chloro-3-methylpyridin-2-yl)benzo[b]thiophen-5-yl)methoxy)phenyl)hex-4-ynoic acid |

TABLE 1-continued

| Structure | Cpd No. | Cpd Name |
|---|---|---|
| 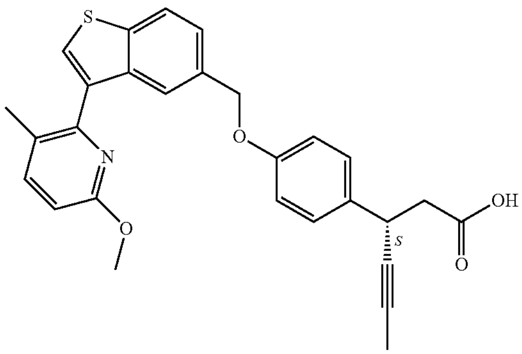 | 94 | (3S)-3-(4-((3-(6-Methoxy-3-methylpyridin-2-yl)benzo[b]thiophen-5-yl)methoxy)phenyl)hex-4-ynoic acid |
| 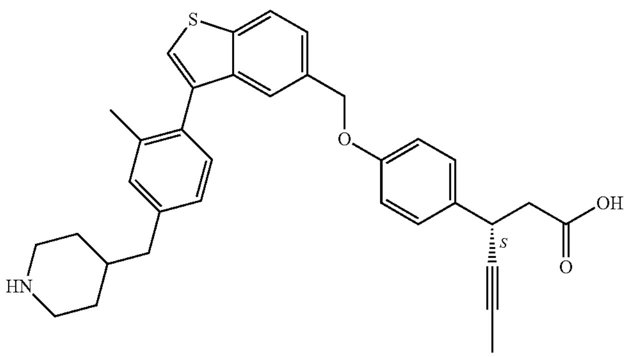 | 95 | (3S)-3-(4-((3-(2-Methyl-4-(piperidin-4-ylmethyl)phenyl)benzo[b]thiophen-5-yl)methoxy)phenyl)hex-4-ynoic acid |
| 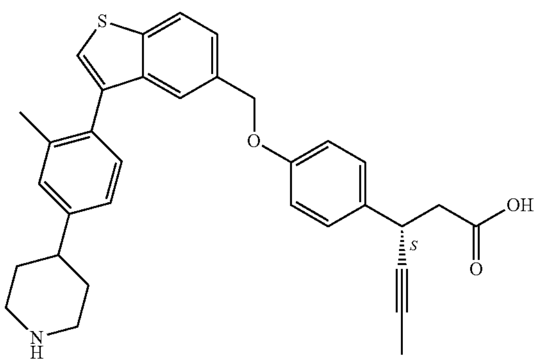 | 96 | (3S)-3-(4-((3-(2-Methyl-4-(piperidin-4-yl)phenyl)benzo[b]thiophen-5-yl)methoxy)phenyl)hex-4-ynoic acid |
| 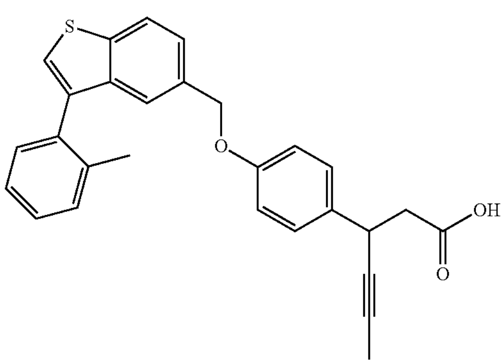 [SMILES: CC#CC(CC(=O)O)c1ccc(OCc2ccc3scc(-c4ccccc4C)c3c2)cc1] | 97 | 3-(4-((3-(2-Methylphenyl)benzo[b]thiophen-5-yl)methoxy)phenyl)hex-4-ynoic acid |

| Structure | Cpd No. | Cpd Name |
|---|---|---|
| 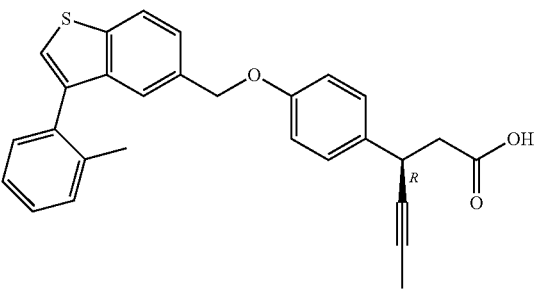 | 98 | (3R)-3-[4-[[3-(2-Methylphenyl)benzo[b]thiophen-5-yl]methoxy]phenyl]hex-4-ynoic acid |

In a further embodiment, the invention is directed to a compound of Formula (I)

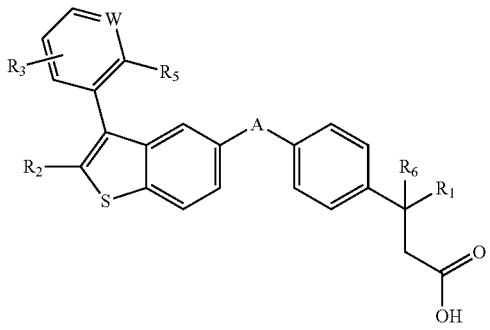

Formula (I)

selected from the group consisting of

Cpd 1, 3-[4-[[3-(2-Methylphenyl)benzo[b]thiophen-5-yl]methoxy]phenyl]propanoic acid;

Cpd 2, (3S)-3-[4-[[3-(2-Methylphenyl)benzo[b]thiophen-5-yl]methoxy]phenyl]hex-4-ynoic acid;

Cpd 3, (3S)-3-[4-[[3-[4-[(4-Hydroxy-1,1-dioxo-thian-4-yl)methoxy]-2-methyl-phenyl]benzo[b]thiophen-5-yl]methoxy]phenyl]hex-4-ynoic acid;

Cpd 4, (3S)-3-[4-[[3-[2-Methyl-4-(3-methylsulfonylpropoxy)phenyl]benzo[b]thiophen-5-yl]methoxy]phenyl]hex-4-ynoic acid;

Cpd 5, (3S)-3-[4-[[3-[4-(1,1-Dioxo-1,4-thiazinane-4-carbonyl)-2-methyl-phenyl]benzo[b]thiophen-5-yl]methoxy]phenyl]hex-4-ynoic acid;

Cpd 6, (3S)-3-[4-[[3-[4-(1,1-Dioxo-3,6-dihydro-2H-thiopyran-4-yl)-2-methyl-phenyl]benzo[b]thiophen-5-yl]methoxy]phenyl]hex-4-ynoic acid;

Cpd 7, (3S)-3-[4-[[3-(4-Hydroxy-2-methyl-phenyl)benzo[b]thiophen-5-yl]methoxy]phenyl]hex-4-ynoic acid;

Cpd 8, (3S)-3-[4-[[3-[4-(1,1-Dioxothian-4-yl)-2-methylphenyl]benzo[b]thiophen-5-yl]methoxy]phenyl]hex-4-ynoic acid;

Cpd 9, (3S)-3-[4-[[3-[4-(1,1-Dioxothian-4-yl)oxy-2-methyl-phenyl]-2-methyl-benzo[b]thiophen-5-yl]methoxy]phenyl]hex-4-ynoic acid;

Cpd 10, (3S)-3-[4-[[3-(2,6-Dimethylphenyl)benzo[b]thiophen-5-yl]methoxy]phenyl]hex-4-ynoic acid;

Cpd 11, (3S)-3-(4-((3-(4-(2-(1-Hydroxycyclopropyl)ethoxy)-2-methylphenyl)benzo[b]thiophen-5-yl)methoxy)phenyl)hex-4-ynoic acid;

Cpd 12, (3S)-3-(4-((3-(4-(3-Hydroxy-3-methylbutoxy)-2-methylphenyl)benzo[b]thiophen-5-yl)methoxy)phenyl)hex-4-ynoic acid;

Cpd 13, (3S)-3-(4-((3-(4-(2,3-Dihydroxypropoxy)-2-methylphenyl)benzo[b]thiophen-5-yl)methoxy)phenyl)hex-4-ynoic acid;

Cpd 14, (3S)-3-(4-((3-(2-Methyl-4-((3-methyloxetan-3-yl)methoxy)phenyl)benzo[b]thiophen-5-yl)methoxy)phenyl)hex-4-ynoic acid;

Cpd 15, (3S)-3-(4-((3-(2-Methyl-4-((tetrahydro-2H-pyran-4-yl)oxy)phenyl)benzo[b]thiophen-5-yl)methoxy)phenyl)hex-4-ynoic acid;

Cpd 16, (3S)-3-(4-((3-(4-(2-Methoxyethoxy)-2-methylphenyl)benzo[b]thiophen-5-yl)methoxy)phenyl)hex-4-ynoic acid;

Cpd 17, (3S)-3-(4-((3-(4-((1,1-Dioxidotetrahydro-2H-thiopyran-4-yl)methoxy)-2-methylphenyl)benzo[b]thiophen-5-yl)methoxy)phenyl)hex-4-ynoic acid;

Cpd 18, (3S)-3-(4-((3-(2-Methyl-4-((3-methyl-1,1-dioxidothietan-3-yl)methoxy)phenyl)benzo[b]thiophen-5-yl)methoxy)phenyl)hex-4-ynoic acid;

Cpd 19, (3S)-3-(4-((3-(2-Chlorophenyl)benzo[b]thiophen-5-yl)methoxy)phenyl)hex-4-ynoic acid;

Cpd 20, (3S)-3-(4-((3-(2-Bromophenyl)benzo[b]thiophen-5-yl)methoxy)phenyl)hex-4-ynoic acid;

Cpd 21, (3S)-3-(4-((3-(2-(Trifluoromethyl)phenyl)benzo[b]thiophen-5-yl)methoxy)phenyl)hex-4-ynoic acid;

Cpd 22, (3S)-3-(4-((3-(2-Methylpyridin-3-yl)benzo[b]thiophen-5-yl)methoxy)phenyl)hex-4-ynoic acid;

Cpd 23, (3S)-3-(4-(((3-(2-Methylphenyl)benzo[b]thiophen-5-yl)oxy)methyl)phenyl)hex-4-ynoic acid;

Cpd 24, (3S)-3-(4-(((3-(2-Methyl-4-(3-(methylsulfonyl)propoxy)phenyl)benzo[b]thiophen-5-yl)oxy)methyl)phenyl)hex-4-ynoic acid;

Cpd 25, (3S)-3-(4-(((3-(4-(1,1-Dioxido-3,6-dihydro-2H-thiopyran-4-yl)-2-methylphenyl)benzo[b]thiophen-5-yl)oxy)methyl)phenyl)hex-4-ynoic acid;

Cpd 26, (3S)-3-(4-(((3-(4-(1,1-Dioxidotetrahydro-2H-thiopyran-4-yl)-2-methylphenyl)benzo[b]thiophen-5-yl)oxy)methyl)phenyl)hex-4-ynoic acid;

Cpd 27, (3S)-3-(4-(((3-(2,6-Dimethylphenyl)benzo[b]thiophen-5-yl)oxy)methyl)phenyl)hex-4-ynoic acid;

Cpd 28, 2-(1-(4-((3-(4-(1,1-Dioxido-3,6-dihydro-2H-thiopyran-4-yl)-2-methylphenyl)benzo[b]thiophen-5-yl)methoxy)phenyl)-3-oxocyclobutyl)acetic acid;

Cpd 29, 2-(1-(4-((3-(4-(1,1-Dioxidotetrahydro-2H-thiopyran-4-yl)-2-methylphenyl)benzo[b]thiophen-5-yl)methoxy)phenyl)-3-oxocyclobutyl)acetic acid;

Cpd 30, 2-(3-Oxo-1-(4-((3-(2-methylphenyl)benzo[b]thiophen-5-yl)methoxy)phenyl)cyclobutyl)acetic acid;

Cpd 31, 2-((1r,3r-3-Hydroxy-1-(4-((3-(2-methylphenyl)benzo[b]thiophen-5-yl)methoxy)phenyl)cyclobutyl)acetic acid;

Cpd 32, 2-(1-(4-((3-(4-(2-Ethoxyethoxy)-2-methylphenyl)benzo[b]thiophen-5-yl)methoxy)phenyl)-3-oxocyclobutyl)acetic acid;

Cpd 33, 2-(1-(4-((3-(4-((1,1-Dioxidotetrahydro-2H-thiopyran-4-yl)oxy)-2-methylphenyl)benzo[b]thiophen-5-yl)methoxy)phenyl)-3-oxocyclobutyl)acetic acid;

Cpd 34, 2-(1-(4-((3-(2-Methyl-4-((tetrahydro-2H-pyran-4-yl)oxy)phenyl)benzo[b]thiophen-5-yl)methoxy)phenyl)-3-oxocyclobutyl)acetic acid;

Cpd 35, 2-((1r,3r-3-Hydroxy-1-(4-((3-(4-(2-ethoxyethoxy)-2-methylphenyl)benzo[b]thiophen-5-yl)methoxy)phenyl)cyclobutyl)acetic acid;

Cpd 36, 2-((1r,3r)-1-(4-((3-(4-((1,1-Dioxidotetrahydro-2H-thiopyran-4-yl)oxy)-2-methylphenyl)benzo[b]thiophen-5-yl)methoxy)phenyl)-3-hydroxycyclobutyl)acetic acid;

Cpd 37, 2-((1r,3r)-3-Hydroxy-1-(4-((3-(2-methyl-4-((tetrahydro-2H-pyran-4-yl)oxy)phenyl)benzo[b]thiophen-5-yl)methoxy)phenyl)cyclobutyl)acetic acid;

Cpd 38, 2-(1-(4-((3-(2-Methylpyridin-3-yl)benzo[b]thiophen-5-yl)methoxy)phenyl)-3-oxocyclobutyl)acetic acid;

Cpd 39, 2-((1r,3r-3-Hydroxy-1-(4-((3-(2-methylpyridin-3-yl)benzo[b]thiophen-5-yl)methoxy)phenyl)cyclobutyl)acetic acid;

Cpd 40, 2-(1-(4-((3-(4-(1,1-Dioxido-1-thia-6-azaspiro[3.3]heptan-6-yl)-2-methylphenyl)benzo[b]thiophen-5-yl)methoxy)phenyl)-3-oxocyclobutyl)acetic acid;

Cpd 41, (3S)-3-(4-((3-(2-Methyl-5-(methylsulfonyl)phenyl)benzo[b]thiophen-5-yl)methoxy)phenyl)hex-4-ynoic acid;

Cpd 42, (3S)-3-(4-((3-(2-Methyl-4-(methylsulfonyl)phenyl)benzo[b]thiophen-5-yl)methoxy)phenyl)hex-4-ynoic acid;

Cpd 43, (3S)-3-(4-((3-(2-Methyl-5-(methylsulfonamido)phenyl)benzo[b]thiophen-5-yl)methoxy)phenyl)hex-4-ynoic acid;

Cpd 44, (3S)-3-(4-((3-(2-Methyl-6-(methylsulfonamido)phenyl)benzo[b]thiophen-5-yl)methoxy)phenyl)hex-4-ynoic acid;

Cpd 45, 3-(6-((3-(2-Methylphenyl)benzo[b]thiophen-5-yl)methoxy)pyridin-3-yl)hex-4-ynoic acid;

Cpd 46, 3-(6-((3-(2-Methyl-4-((tetrahydro-2H-pyran-4-yl)oxy)phenyl)benzo[b]thiophen-5-yl)methoxy)pyridin-3-yl)hex-4-ynoic acid;

Cpd 47, 3-(6-((3-(4-(2-Methoxyethoxy)-2-methylphenyl)benzo[b]thiophen-5-yl)methoxy)pyridin-3-yl)hex-4-ynoic acid;

Cpd 48, (3S)-3-(4-((3-(5-(2-Methoxyethoxy)-3-methylpyridin-2-yl)benzo[b]thiophen-5-yl)methoxy)phenyl)hex-4-ynoic acid;

Cpd 49, (3S)-3-(4-((3-(5-(2-Methoxyethoxy)-2-methylpyridin-3-yl)benzo[b]thiophen-5-yl)methoxy)phenyl)hex-4-ynoic acid;

Cpd 50, (3S)-3-(4-((3-(6-(2-Methoxyethoxy)-2-methylpyridin-3-yl)benzo[b]thiophen-5-yl)methoxy)phenyl)hex-4-ynoic acid;

Cpd 51, (3S)-3-(4-((3-(6-(2-Methoxyethoxy)-4-methylpyridin-3-yl)benzo[b]thiophen-5-yl)methoxy)phenyl)hex-4-ynoic acid;

Cpd 52, (3S)-3-(4-((3-(2-Chloro-5-methylpyridin-4-yl)benzo[b]thiophen-5-yl)methoxy)phenyl)hex-4-ynoic acid;

Cpd 53, 3-(4-(((3-(2-Methylphenyl)benzo[b]thiophen-5-yl)oxy)methyl)phenyl)propanoic acid;

Cpd 54, (3S)-3-[4-[([3-[4-(3-Hydroxy-3-methylbutoxy)-2-methylphenyl]-1-benzothiophen-5-yl]oxy)methyl]phenyl]hex-4-ynoic acid;

Cpd 55, (3S)-3-[4-[([3-[4-(2,3-Dihydroxypropoxy)-2-methylphenyl]-1-benzothiophen-5-yl]oxy)methyl]phenyl]hex-4-ynoic acid;

Cpd 56, (3S)-3-(4-[[(3-[2-Methyl-4-[(3-methyloxetan-3-yl)methoxy]phenyl]-1-benzothiophen-5-yl)oxy]methyl]phenyl]hex-4-ynoic acid;

Cpd 57, (3S)-3-[4-[([3-[2-Methyl-4-(oxan-4-yloxy)phenyl]-1-benzothiophen-5-yl]oxy)methyl]phenyl]hex-4-ynoic acid;

Cpd 58, (3S)-3-[4-[([3-[4-(2-Methoxyethoxy)-2-methylphenyl]-1-benzothiophen-5-yl]oxy)methyl]phenyl]hex-4-ynoic acid;

Cpd 59, (3S)-3-{4-[((3-{4-[(1,1-Dioxo-tetrahydro-2H-thiopyran-4-yl)methoxy]-2-methylphenyl}-1-benzothiophen-5-yl)oxy)methyl]phenyl}hex-4-ynoic acid;

Cpd 60, (3S)-3-(4-(((3-(2-Methyl-4-((3-methyl-1,1-dioxidothietan-3-yl)methoxy)phenyl)benzo[b]thiophen-5-yl)oxy)methyl)phenyl)hex-4-ynoic acid;

Cpd 61, 3-[(6-([3-[4-(3-Hydroxy-3-methylbutoxy)-2-methylphenyl]-1-benzothiophen-5-yl]methoxy)pyridin-3-yl]hex-4-ynoic acid;

Cpd 62, 3-(6-((3-(4-(2,3-Dihydroxypropoxy)-2-methylphenyl)benzo[b]thiophen-5-yl)methoxy)pyridin-3-yl)hex-4-ynoic acid;

Cpd 63, 3-(6-((3-(4-((1,1-Dioxidotetrahydro-2H-thiopyran-4-yl)methoxy)-2-methylphenyl)benzo[b]thiophen-5-yl)methoxy)pyridin-3-yl)hex-4-ynoic acid;

Cpd 64, 3-(6-((3-(2-Methyl-4-((3-methyl-1,1-dioxidothietan-3-yl)methoxy)phenyl)benzo[b]thiophen-5-yl)methoxy)pyridin-3-yl)hex-4-ynoic acid;

Cpd 65, (3S)-3-[4-([3-[5-(2-Methoxyethoxy)-2-methylphenyl]-1-benzothiophen-5-yl]methoxy)phenyl]hex-4-ynoic acid;

Cpd 66, (3S)-3-[4-([3-[2-(2-Methoxyethoxy)-6-methylphenyl]-1-benzothiophen-5-yl]methoxy)phenyl]hex-4-ynoic acid;

Cpd 67, (3S)-3-[4-([3-[3-(2-Methoxyethoxy)-2-methylphenyl]-1-benzothiophen-5-yl]methoxy)phenyl]hex-4-ynoic acid;

Cpd 68, (3S)-3-[4-([3-[2-(2-Methoxyethoxy)phenyl]-1-benzothiophen-5-yl]methoxy)phenyl]hex-4-ynoic acid;

Cpd 69, (3S)-3-(4-[[3-(2-Methanesulfonylphenyl)-1-benzothiophen-6-yl]methoxy]phenyl)hex-4-ynoic acid;

Cpd 70, (3S)-3-(6-((3-(4-(3-Hydroxy-3-methylbutoxy)-2-methylphenyl)benzo[b]thiophen-5-yl)methoxy)pyridin-3-yl)hex-4-ynoic acid Cpd 71, (3R)-3-(6-((3-(4-(3-Hydroxy-3-methylbutoxy)-2-methylphenyl)benzo[b]thiophen-5-yl)methoxy)pyridin-3-yl)hex-4-ynoic acid Cpd 72, (3S)-3-(6-((3-(2-Methyl-4-((tetrahydro-2H-pyran-4-yl)methoxy)phenyl)benzo[b]thiophen-5-yl)methoxy)pyridin-3-yl)hex-4-ynoic acid Cpd 73, (3R)-3-(6-((3-(2-Methyl-4-((tetrahydro-2H-pyran-4-yl)methoxy)phenyl)benzo[b]thiophen-5-yl)methoxy)pyridin-3-yl)hex-4-ynoic acid Cpd 74, (3S)-3-(6-((3-(4-((1,1-Dioxidotetrahydro-2H-thiopyran-4-yl)methoxy)-2-methylphenyl)benzo[b]thiophen-5-yl)methoxy)pyridin-3-yl)hex-4-ynoic acid;

Cpd 75, (3R)-3-(6-((3-(4-((1,1-Dioxidotetrahydro-2H-thiopyran-4-yl)methoxy)-2-methylphenyl)benzo[b]thiophen-5-yl)methoxy)pyridin-3-yl)hex-4-ynoic acid;

Cpd 76, (3S)-3-(6-((3-(4-(2-Methoxyethoxy)-2-methylphenyl)benzo[b]thiophen-5-yl)methoxy)pyridin-3-yl)hex-4-ynoic acid;

Cpd 77, (3R)-3-(6-((3-(4-(2-Methoxyethoxy)-2-methylphenyl)benzo[b]thiophen-5-yl)methoxy)pyridin-3-yl)hex-4-ynoic acid;

Cpd 78, (3S)-3-(4-((3-(2-Methoxypyridin-3-yl)benzo[b]thiophen-5-yl)methoxy)phenyl)hex-4-ynoic acid;

Cpd 79, (3S)-3-(4-((3-(2-Methoxyphenyl)benzo[b]thiophen-5-yl)methoxy)phenyl)hex-4-ynoic acid;

Cpd 80, (3S)-3-(4-((3-(6-Methoxy-2-methylpyridin-3-yl)benzo[b]thiophen-5-yl)methoxy)phenyl)hex-4-ynoic acid;

Cpd 81, (3S)-3-(4-((3-(4-Methoxypyridin-3-yl)benzo[b]thiophen-5-yl)methoxy)phenyl)hex-4-ynoic acid;

Cpd 82, (3S)-3-(4-((3-(6-Methoxy-4-methylpyridin-3-yl)benzo[b]thiophen-5-yl)methoxy)phenyl)hex-4-ynoic acid;

Cpd 83, (3S)-3-(4-((3-(3-Methoxypyridin-4-yl)benzo[b]thiophen-5-yl)methoxy)phenyl)hex-4-ynoic acid;

Cpd 84, (3S)-3-(4-((3-(5-Methoxy-3-methylpyridin-2-yl)benzo[b]thiophen-5-yl)methoxy)phenyl)hex-4-ynoic acid;

Cpd 85, (3R)-3-[6-[[3-(2-Methylphenyl)benzo[b]thiophen-5-yl]methoxy]pyridin-3-yl]hex-4-ynoic acid;

Cpd 86, (3S)-3-[4-[([3-[2-Methyl-4-(tetrahydrofuran-3-yloxy)phenyl]-1-benzothiophen-5-yl]oxy)methyl]phenyl]hex-4-ynoic acid;

Cpd 87, (3R)-3-(6-((3-(5-(2-Methoxyethoxy)-2-methylphenyl)benzo[b]thiophen-5-yl)methoxy)pyridin-3-yl)hex-4-ynoic acid;

Cpd 88, (3R)-3-(6-((3-(3-(2-Methoxyethoxy)-2-methylphenyl)benzo[b]thiophen-5-yl)methoxy)pyridin-3-yl)hex-4-ynoic acid;

Cpd 89, (3R)-3-(6-((3-(5-(2-Methoxyethoxy)-3-methylpyridin-2-yl)benzo[b]thiophen-5-yl)methoxy)pyridin-3-yl)hex-4-ynoic acid;

Cpd 90, (3R)-3-(6-((3-(2-Chloro-5-methylpyridin-4-yl)benzo[b]thiophen-5-yl)methoxy)pyridin-3-yl)hex-4-ynoic acid;

Cpd 91, (3S)-3-(4-((3-(3-Methoxypyridin-2-yl)benzo[b]thiophen-5-yl)methoxy)phenyl)hex-4-ynoic acid;

Cpd 92, (3R)-3-(6-((3-(5-(2-Methoxyethoxy)-2-methylpyridin-3-yl)benzo[b]thiophen-5-yl)methoxy)pyridine-3-yl)hex-4-ynoic acid;

Cpd 93, (3S)-3-(4-((3-(6-Chloro-3-methylpyridin-2-yl)benzo[b]thiophen-5-yl)methoxy)phenyl)hex-4-ynoic acid;

Cpd 94, (3S)-3-(4-((3-(6-Methoxy-3-methylpyridin-2-yl)benzo[b]thiophen-5-yl)methoxy)phenyl)hex-4-ynoic acid;

Cpd 95, (3S)-3-(4-((3-(2-Methyl-4-(piperidin-4-ylmethyl)phenyl)benzo[b]-thiophen-5-yl)methoxy)phenyl)hex-4-ynoic acid;

Cpd 96, (3S)-3-(4-((3-(2-Methyl-4-(piperidin-4-yl)phenyl)benzo[b]thiophen-5-yl)methoxy)phenyl)hex-4-ynoic acid;

Cpd 97, 3-(4-((3-(2-Methylphenyl)benzo[b]thiophen-5-yl)methoxy)phenyl)hex-4-ynoic acid;

Cpd 98, (3R)-3-[4-[[3-(2-Methylphenyl)benzo[b]thiophen-5-yl]methoxy]phenyl]hex-4-ynoic acid;

or a pharmaceutically acceptable salt form thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salt forms thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I).

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

One embodiment of the present invention is directed to a pharmaceutical composition comprising 3-(4-((3-(2-Methylphenyl)benzo[b]thiophen-5-yl)methoxy)phenyl)hex-4-ynoic acid (compound 97) and at least one of a pharmaceutically acceptable carrier, a pharmaceutically acceptable excipient, and a pharmaceutically acceptable diluent.

Another embodiment of the present invention is directed to a pharmaceutical composition comprising (3S)-3-[4-[[3-(2-Methylphenyl)benzo[b]thiophen-5-yl]methoxy]phenyl]hex-4-ynoic acid (compound 2) and at least one of a pharmaceutically acceptable carrier, a pharmaceutically acceptable excipient, and a pharmaceutically acceptable diluent.

As GPR40 agonists, the compounds of Formula (I) are useful in methods for treating or preventing a disease, a syndrome, a condition or a disorder in a subject, including an animal, a mammal and a human in which the disease, the syndrome, the condition or the disorder is affected by the modulation, including agonism, of the GPR40 receptor. Such methods comprise, consist of and/or consist essentially of administering to a subject, including an animal, a mammal, and a human, in need of such treatment or prevention, a therapeutically effective amount of a compound, salt or solvate of Formula (I).

In another embodiment, the present invention is directed to a compound of Formula (I) for use in the treatment of a disorder affected by the agonism of GPR40 receptor selected from the group consisting of Type 2 diabetes mellitus, obesity, obesity related disorders, impaired glucose tolerance, insulin resistance, metabolic syndrome, other cardiovascular risk factors such as hypertension and cholesterol/lipids, osteoporosis, inflammation and eczema; preferably, Type II diabetes mellitus, metabolic syndrome, and impaired glucose tolerance; more preferably, Type II diabetes mellitus or impaired glucose tolerance.

In another embodiment, the present invention is directed to a compound of Formula (I) for use in the treatment of Type 2 diabetes mellitus.

In another embodiment, the present invention is directed to a compound of Formula (I) for use in the treatment of obesity.

In another embodiment, the present invention is directed to a compound of Formula (I) for use in the treatment of metabolic syndrome.

In another embodiment, the present invention is directed to a compound of Formula (I) for use in the treatment of insulin resistance.

In another embodiment, the present invention is directed to a compound of Formula (I) for use in the treatment of impaired glucose tolerance.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. The various starting materials used in the schemes and examples are commercially available or may be prepared by methods well within the skill of persons versed in the art. The variables are as defined herein.

Abbreviations used in the instant specification, particularly the schemes and examples, are as follows:
- ADDP azodicarboxylic acid dipiperidide
- aq aqueous
- 9-BBN 9-borabicyclo[3,3,1]nonane
- BINAP 2,2'-bis[1,1-diphenylphosphino]-1,1'-binaphthalene
- Boc tert-butoxycarbonyl
- CDI 1,1'-carbonyldiimidazole
- CyJohnPhos (2-biphenyl)dicyclohexylphosphine
- DBAD di-tert-butyl azodicarboxylate
- DCE 1,2-dichloroethane
- DCM dichloromethane
- DEA diethylamine
- DEAD diethyl azodicarboxylate
- DIAD diisopropyl azodicarboxylate
- DIBAL-H diisobutylaluminum hydride
- DIEA diisopropylethylamine
- DME ethylene glycol dimethyl ether
- DMF dimethylformamide
- DMSO methyl sulfoxide
- EDC N-(3-dimethylaminopropyl)-N'-ethylcarbodiimide
- EDCI 1-(3-dimethylaminopropyl)-3-ethylcarbodiimide hydrochloride
- Et ethyl
- EtOAc ethyl acetate
- h hour(s)
- HATU O-(7-azabenzotriazol-1-yl)-N,N,N',N'-tetramethyluronium hexafluorophosphate
- HBTU 2-(1H-Benzotriazole-1-yl)-1,1,3,3-tetramethyluronium hexafluorophosphate)
- HCl hydrochloric acid
- HPLC high performance liquid chromatography
- LAH lithium aluminum hydride
- LCAP liquid chromatography area percent
- LCMS high pressure liquid chroatography with mass spectrometer
- mCPBA 3-chloroperbenzoic acid
- Me methyl
- MeCN acetonitrile
- MeOH methyl alcohol
- mg milligram
- MOM methoxymethyl
- MTBE methyl t-butyl ether
- NBS N-bromosuccinimide
- NCS N-chlorosuccinimide
- NIS N-iodosuccinimide
- NMP N-methyl-2-pyrrolidone
- N,N-DMA N,N-dimethylacetamide
- PCC pyridinium chlorochromate
- PDC pyridinium dichromate
- $PdCl_2(dppf).CH_2Cl_2$ 1,1'-bis(diphenylphosphino)ferrocene-palladium(II)dichloride dichloromethane complex)
- $Pd_2(dba)_3$ tris(dibenzylideneacetone)dipalladium(0)
- PPTS pyridine p-toluenesulfonate
- $P(o\text{-tol})_3$ tri(o-tolyl)phosphine
- rt room temperature
- RuPhos 2-dicyclohexylphosphino-2',6'-diisopropoxybiphenyl
- satd. saturated
- SPhos 2-dicyclohexylphosphino-2',6'-dimethoxybiphenyl
- TBTU O-benzotriazol-1-yl-N,N,N',N'-tetramethyluronium hexafluorophosphate
- $Tf_2O$ triflic anhydride
- TFA trifluoroacetic acid
- THF tetrahydrofuran
- THP tetrahydropyranyl Scheme A illustrates a method for the preparation of certain compounds of Formula (I) of the present invention wherein A is —$CH_2O$—.

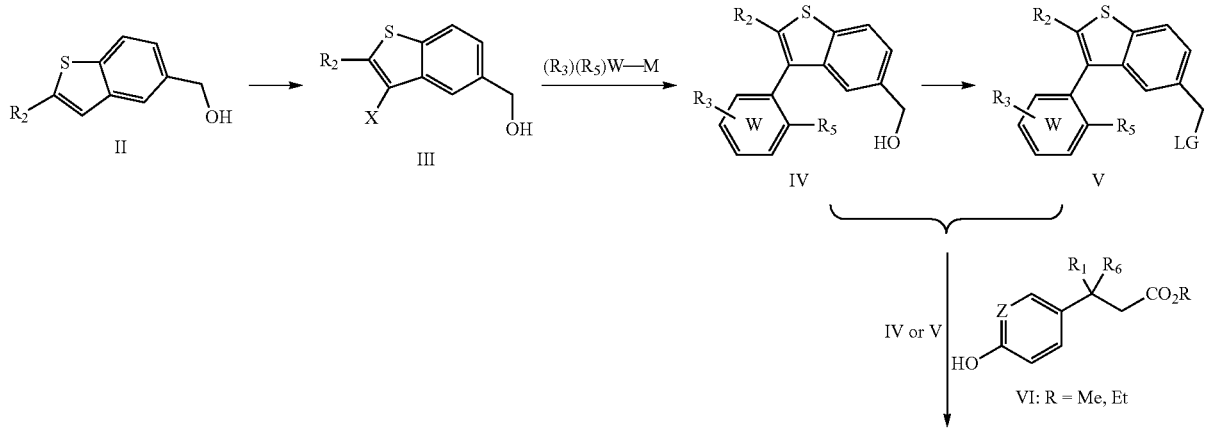

Scheme A

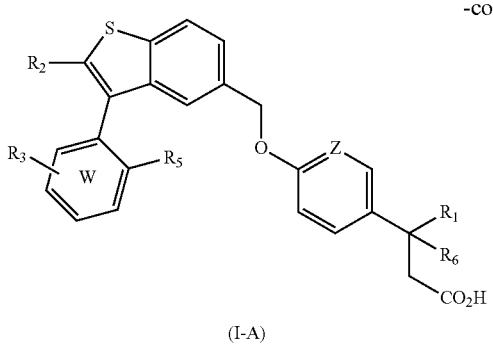

(I-A)

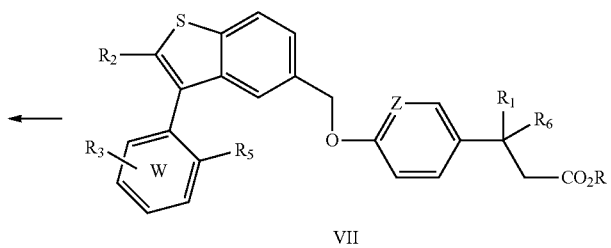

VII

Certain compounds of Formula (I-A) may be synthesized as outlined by the general synthetic route illustrated in Scheme A. Treatment of 5-hydroxymethylbenzothiophene II with a halogenating reagent such as NBS, NIS or in a suitable solvent such as DCM, DCE, $CCl_4$, THF, dioxane, DMF and the like or with $Br_2$ in HOAc, at a temperature preferably between 0 and 50° C. can provide the 3-halogenated benzothiophene III wherein X is bromine or iodine. Halogenated benzothiophene III may be reacted with a compound of formula $(R_3)(R_5)$W-M wherein $R_3$, $R_5$ and W are as defined herein, under suitable coupling conditions, to yield the corresponding coupling product of formula IV. A compound of formula $(R_3)(R_5)$W-M is chosen wherein M may be (a) a boronic acid to form a compound of formula $(R_3)(R_5)$W—$B(OH)_2$; (b) a suitably selected boronic ester such as pinacolatoboryl, neopentylglycolatoboryl, and the like; (c) a suitably selected trialkylstannyl such as tri(n-butyl)tin, and the like; (d) a suitably selected trialkylsilyl such as triallylsilyl, and the like; (e) a suitably selected aryldialkylsilyl such as 2-(hydroxymethyl)phenyldimethylsilyl, and the like or (f) suitably selected organo zinc reagents such as $(R_3)(R_5)$W—ZnX wherein X is a halogen such as Cl, Br or I.

For example, a compound of formula $(R_3)(R_5)$W-M where M is preferably —$B(OH)_2$ or a suitably selected W-substituted boronic ester may be reacted with a compound of formula III under Suzuki coupling conditions, more particularly in the presence of a suitably selected palladium catalyst such as palladium (II) acetate, palladium (II) chloride, bis(acetonitrile)-dichloro-palladium(II), allyl-palladium (II) chloride dimer, tris(dibenzylidineacetone) dipalladium (0) $(Pd_2(dba)_3)$, 2-(di-tert-butylphosphino)biphenyl, dichloro-bis(di-tert-butylphenylphosphine)-palladium (II), [1,1'-bis-(diphenylphosphino)-ferrocene]-palladium (II) dichloride dichloromethane adduct $(PdCl_2(dppf)$ 'DCM), tetrakis(triphenylphosphine) palladium(0) (Pd $(PPh_3)_4)$, (1,1'-bis(di-tert-butylphosphino)ferrocene palladium (II) chloride, and the like; optionally in the presence of a suitably selected ligand such as triphenylphosphine, tri-o-tolylphosphine, tributylphosphine, tri(tert-butyl)-phosphine, tricyclohexylphosphine, 1,1'-bis(diphenylphosphino)-ferrocene, 2-(dicyclohexylphosphino)-2',4',6'-tri-i-propyl-1,1'-biphenyl, S-Phos, Ru-Phos, bis[2-(diphenyl-phosphino)phenyl] ether, 2-dicyclohexylphosphino-2',6'-dimethoxybiphenyl, tris(2-furyl)phosphine, 1-butyl-3-methylimidazolium hexafluorophosphate, and the like; in the presence of a suitably selected inorganic base such as cesium carbonate, potassium carbonate, sodium carbonate, cesium fluoride, potassium fluoride, tetrabutylammonium fluoride, potassium tert-butoxide, sodium tert-butoxide, sodium hydroxide, sodium bicarbonate; potassium phosphate or preferably sodium carbonate; in a suitably selected solvent such as ethanol, THF, DMF, toluene, benzene, DME, $H_2O$, 1,4-dioxane, and the like, or a combination thereof; at a temperature ranging from about rt to about 180° C.

Compounds of formula IV may be reacted under Mitsunobu conditions (for a review, see: Mitsunobu, O. *Synthesis* (1981), 1-28) with compounds of formula VI, wherein $R_1$ and $R_6$ are as defined herein, in the presence of triphenylphosphine, tri-n-butylphosphine, tri-tert-butylphosphine, or a resin-bound triphenylphosphine equivalent, such as PS-$PPh_3$ and an azido coupling reagent such as DIAD, ADDP, DBAD or DEAD and the like, in an organic solvent such as THF, MeCN, toluene, N,N-DMA, and the like, at a temperature preferably between 25-100° C., to yield compounds of formula VII.

Alternatively, the alcoholic function of compounds of formula IV may be converted to suitable leaving groups (LG) such as Cl, Br, I, tosylate, mesylate, nosylate and the like, (as described in: March, J. *Advanced Organic Chemistry. Reactions, Mechanisms and Structure*, 2$^{nd}$ ed.; McGraw-Hill Co.: New York, 1977; pp 326) as illustrated by compounds of formula V, which may then react with a compound of formula VI in the presence of a suitable base to provide a compound of formula VII. For example, treatment of a compound of formula IV with a halogenating reactant such as oxalyl chloride, oxalyl bromide, thionyl chloride, thionyl bromide, $Ph_3P.Br_2$, $PBr_3$ and the like, or with sulfonyl halides such as tosyl chloride, mesyl chloride, nosyl chloride and the like; in the presence of a base such as $K_2CO_3$, $Cs_2CO_3$, KOH, NaH, and the like, in a solvent such as NMP, DMF, THF, and the like, at a temperature preferably between 25-150° C. may provide a compound of formula V. Reaction of a compound of formula V may be reacted with a compound of formula VI in the presence of a suitable base such as $K_2CO_3$, $Cs_2CO_3$, KOH, NaH, and the like, in a solvent such as NMP, DMF, THF, and the like, at a temperature preferably between 25-150° C. to provide a compound of formula VII.

Hydrolysis of the ester functionality of a compound of formula VII may be effected under a variety of conditions to provide a compound of formula (I-A) (such as described in T. W. Greene & P. G. M. Wuts, *Protective Groups in Organic Synthesis*, 3$^{rd}$ ed.; John Wiley & Sons, Inc.: New York, 1999). For example, treatment of a compound of formula VII with a base such as NaOH, LiOH, KOH, CsOH and the like, in a solvent such as THF, EtOH, MeOH, dioxane and water and the like, or mixtures thereof, at a temperature between 25° C. and 100° C. may provide a compound of formula (I-A). The preferred method for this transformation includes the treatment of a compound of formula VII with an aqueous base such as NaOH or LiOH, in a mixed solvent such as THF/MeOH, at about room temperature.

It should be understood that in certain compounds of formulas $(R_3)(R_5)W$-M, IV, V, or VII, $R_3$ may contain functionalities that may optionally bear a suitable functional protecting group (P) (such as those described in *Protective Groups in Organic Chemistry*, J. F. W. McOmie, Ed.; Plenum Press: 1973; and T. W. Greene & P. G. M. Wuts, *Protective Groups in Organic Synthesis*, $3^{rd}$ ed.; John Wiley & Sons, Inc.: New York, 1999). In such cases where the $R_3$ is substituted with one or more amino groups, suitable protecting groups such as Boc, Cbz, and the like may be incorporated, which may be deprotected under appropriate conditions known to those skilled in the art to afford a compound of Formula (I-A) of the present invention. For example, Boc-protected amines may be deprotected under acidic conditions using reagents such as HCl, TFA, and the like. Likewise, Cbz-protected amines may be deprotected under acidic conditions or hydrogenolysis. In the case where $R_3$ is substituted with carboxyl groups, suitable protecting groups such as methyl, ethyl and t-butyl esters and the like may be incorporated, which may be deprotected under acidic conditions such as HCl, TFA and the like. In the case where $R_3$ is substituted with hydroxyl groups, suitable protecting groups such as MOM, THP, t-butyl ethers, acetonides (for 1,2-dihydroxylated substituents) and the like may be incorporated, which may be deprotected under acidic conditions such as HCl, TFA and the like. The unmasked functionalities generated by deprotection may be subjected to further chemical transformations according to methods known in the art, to provide additional derivatives of Formula (I-A).

In certain cases, a compound of formula IV of the present invention may be advantageously prepared by an alternative cross-coupling strategy, as illustrated in Scheme B.

Under Suzuki coupling conditions as previously described for Scheme A, a compound of formula III may be reacted with bis(pinacolato)diboron to provide the corresponding borolane of formula VIII. A compound of formula VIII may, in turn, be reacted with an aromatic halide of formula $(R_3)(R_5)W$—X, wherein $(R_3)(R_5)W$ and X are as defined in Scheme A, to provide a compound of formula IV directly. In certain cases, this coupling reaction affords the corresponding aldehydic compound of formula IX, which upon treatment with a suitable reducing agent (as described in: Larock, R. C. *Comprehensive Organic Transformations. A Guide to Functional Group Preparations*, $2^{nd}$ ed.; Wiley-VCH: New York, 1999; pp 61), such as $NaBH_4$, LAH, $B_2H_6$, DIBAL-H, $NaCNBH_3$, $AlH_3$, $LiAlH(O-t-Bu)_3$, $KBH(O-i-Pr)_3$, and the like, preferably $NaBH_4$ or $B_2H_6$, in a solvent such as THF, ether, dioxane, MeOH, EtOH and the like, at a temperature preferably between 0-75° C., may provide an alcohol of formula IV.

Certain compounds of formula IV of the present invention in which $R_3$ is —$OR_{4c}$ can be prepared as illustrated in Scheme C. As defined herein, $R_{4c}$ is $R_4$ wherein the hydroxy-substituted $R_4$ substituents are suitably protected with a conventional hydroxy protecting group.

Scheme B

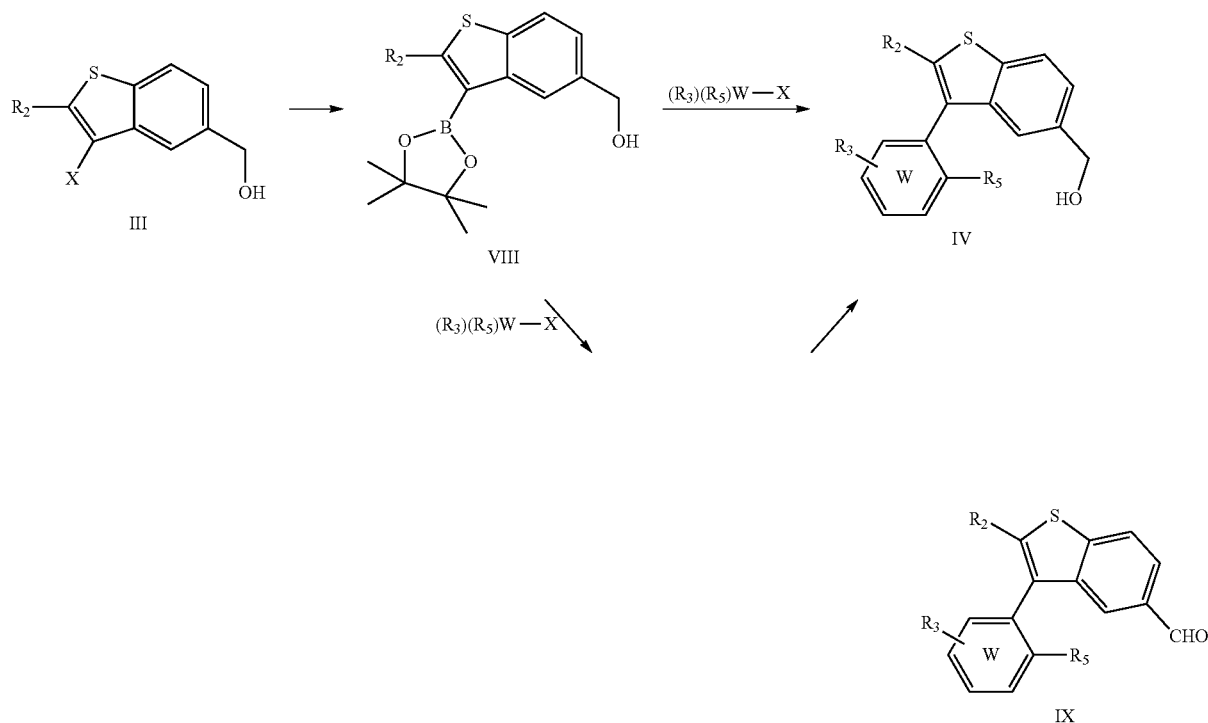

Scheme C

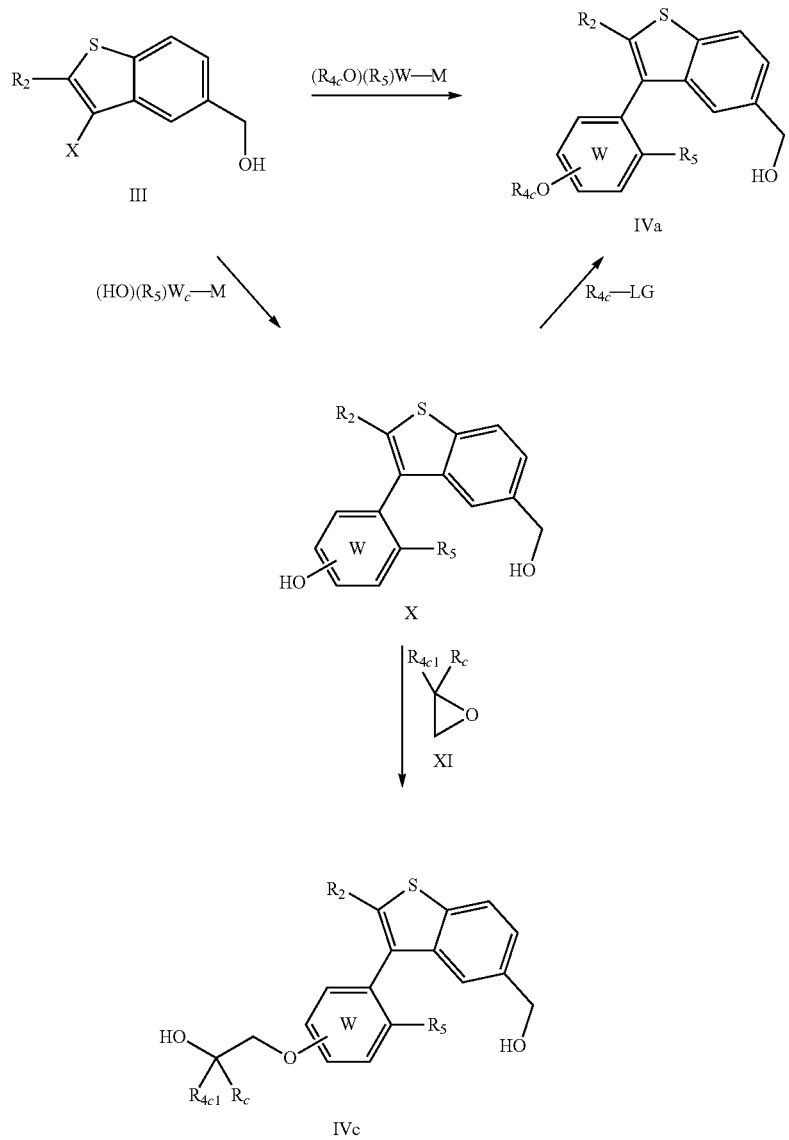

Treatment of a compound of formula III with a compound of formula $(R_{4c}O)(R_5)$W-M, where W, $R_5$, and M are as defined in Scheme A, under coupling conditions previously described may provide a compound of formula IVa directly. Alternatively, a compound of formula III may be reacted with a compound of formula $(HO)(R_5)W_c$-M wherein $W_c$ is phenyl, and M is preferably a boronic acid or boronic ester, under suitable coupling conditions as previously described, to provide the corresponding coupling product of formula X. Alkylation of a compound of formula X with a compound of formula $R_{4c}$-LG, where LG is a suitable leaving group as previously described, in the presence of a base such as $K_2CO_3$, $Cs_2CO_3$, KOH, NaH, and the like, in a solvent such as NMP, DMF, THF, and the like, at a temperature preferably between 25-150° C. may provide a compound of formula IVa. Alternatively, a compound of formula X may be alkylated by reaction with an epoxide of formula XI, wherein $R_c$ is hydrogen and $R_{4c1}$ is defined as $C_{1-6}$alkyl, $C_{3-7}$cycloalkyl, or $C_{1-3}$alkoxy$(C_{1-8})$alkyl, to provide a compound of formula IVc. Similarly, a compound of formula X may be alkylated by reaction with an epoxide of formula XI, wherein $R_c$ and $R_{4c1}$ may be taken together to form a spirofused ring selected from the group consisting of $C_{4-7}$spirocycloalkyl, spirofused 1,1-dioxido-tetrahydro-2H-thiopyran-4-yl, and spirofused tetrahydro-2H-pyran-4-yl, to provide additional compounds of formula IVc. The reaction with an epoxide of formula XI is preferably carried out in the presence of a base such as $K_2CO_3$, $Cs_2CO_3$, KOH, and the like, in a solvent such as NMP, DMF, THF, and the like, at a temperature preferably between about 25 and about 125° C.

Alternatively, certain compounds of formula IV of the present invention in which $R_3$ is —$OR_{4d}$ and $R_5$ is Me or $CF_3$ may be prepared as illustrated in Scheme D. As defined herein, $R_{4d}$ is $R_4$ wherein the hydroxy-substituted $R_4$ substituents are suitably protected with a conventional hydroxy protecting group.

Scheme D

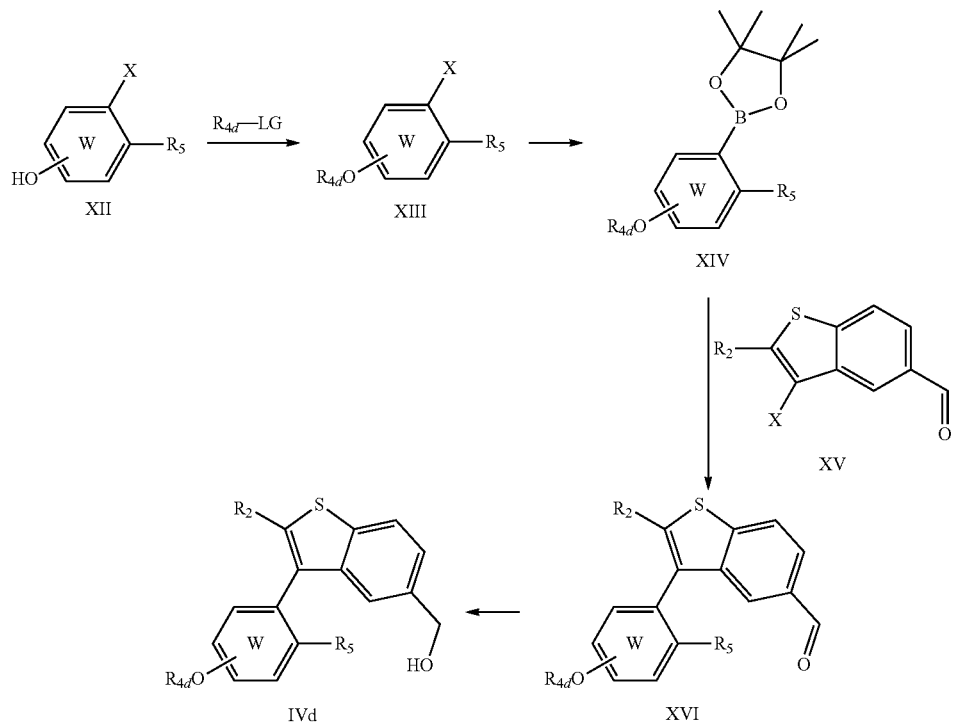

Alkylation of a phenolic compound of formula XII with a compound of formula $R_{4d}$-LG, where LG is a suitable leaving group as previously described, in the presence of a base such as $K_2CO_3$, $Cs_2CO_3$, KOH, NaH, and the like, in a solvent such as NMP, DMF, THF, and the like, at a temperature preferably between about 25° C. to about 150° C. may provide a compound of formula XIII Treatment of a compound of formula XIII with bis(pinacolato)diboron under Suzuki coupling conditions, as defined in Scheme A, may provide the corresponding borolane of formula XIV. A borolane of formula XIV may be reacted with a benzothiophene aldehyde of formula XV under Suzuki coupling conditions, as defined in Scheme A, to provide an arylated benzothiophene aldehyde of formula XVI, which in turn may be reduced upon treatment with a suitably selected reducing agent (as described in Larock, R. C. *Comprehensive Organic Transformations. A Guide to Functional Group Preparations*, 2$^{nd}$ ed.; Wiley-VCH: New York, 1999; pp 61), such as $NaBH_4$, LAH, $B_2H_6$, DIBAL-H, $NaCNBH_3$, $AlH_3$, $LiAlH(O-t-Bu)_3$, $KBH(O-i-Pr)_3$, and the like; preferably $NaBH_4$ or $B_2H_6$, in a solvent such as THF, ether, dioxane, MeOH, EtOH and the like, at a temperature preferably between about 0 to about 75° C., to provide the corresponding benzylic alcohol of formula IVd.

In addition, certain compounds of formula IVe of the present invention in which $R_3$ is 1,1-dioxo-1,4-thiazinane-4-ylcarbonyl can be prepared as illustrated in Scheme E.

Scheme E

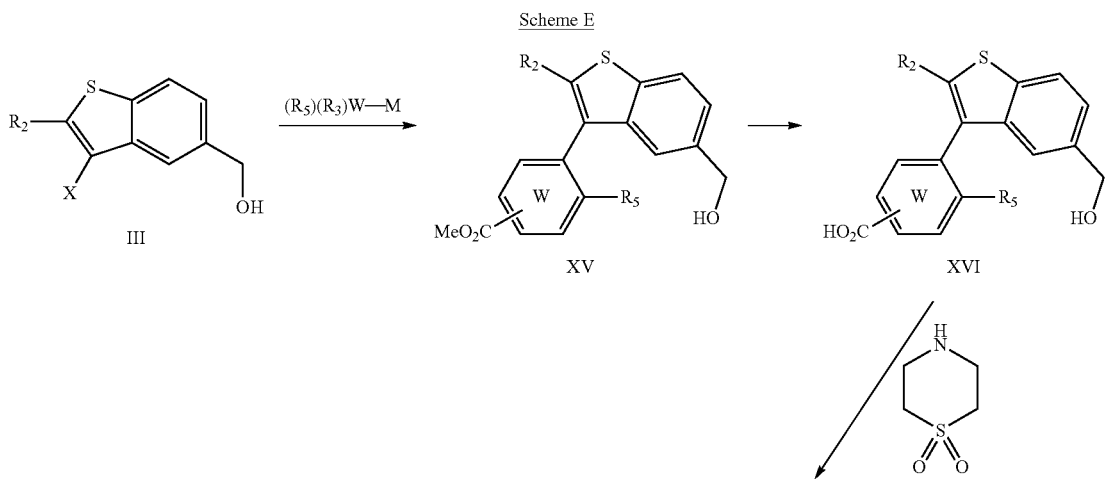

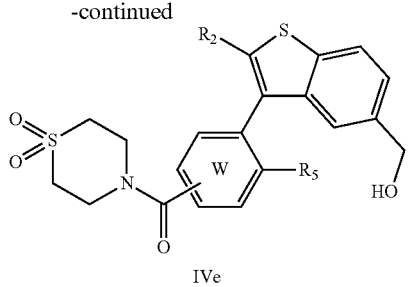

IVe

Compounds of formula III may be reacted with a compound of formula $(R_5)(R_3)$W-M wherein $(R_5)(R_3)$W— is a methoxycarbonyl-substituted phenyl or pyridyl ring, and M is preferably a boronic acid or boronic ester, under suitable coupling conditions as previously described, to provide the corresponding coupling product of formula XV. Hydrolysis of the ester functionality of compounds of formula XV can be effected under a variety of conditions, as previously described. The preferred method for this transformation includes the treatment of compounds of formula XV with an aqueous base such as NaOH or LiOH in a mixed solvent such as THF/MeOH at about room temperature to provide compounds of formula XVI. Reaction of benzoic acid XVI and thiomorpholine 1,1-dioxide with conventional coupling agents (M. Bodansky and A. Bodansky, *The Practice of Peptide Synthesis*, Springer-Verlag: New York, 1984) such as EDCI, CDI, DCC, HATU, HBTU, TBTU, and the like in organic solvents such as DCM, THF, DMF, NMP, N,N-DMA, DMSO, and the like, at ambient temperature may provide the corresponding carboxamide of Formula IVe.

Certain compounds of formula VII of the present invention in which $R_3$ is —$OR_4$ may be prepared as illustrated in Scheme F.

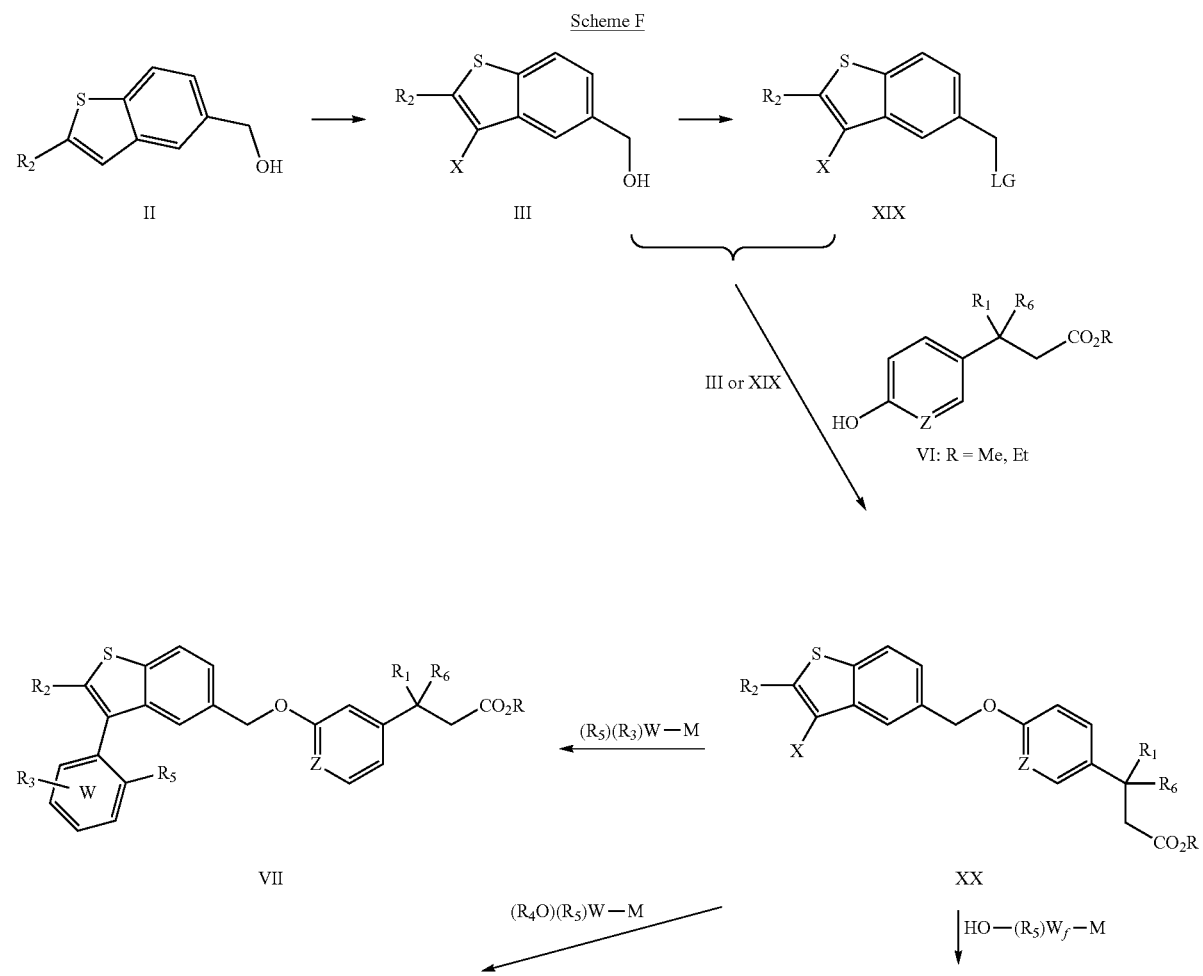

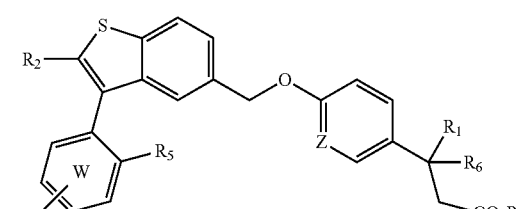

VIIa

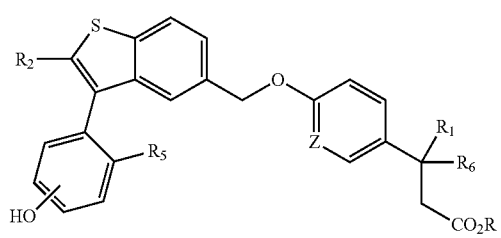

XXI

A compound of formula III may be reacted with a compound of formula VI directly under Mitsunobu conditions, as defined in Scheme A to provide a compound of formula XX. Alternatively, a compound of formula III may be converted to a compound of formula XIX, wherein LG is a suitable leaving group as previously described, and reacted with a phenol of formula VI in the presence of a suitable base as previously described to provide a compound of formula XX. Reaction of a compound of formula XX with a compound of formula $(R_5)(R_3)$W-M, using the methods described in Scheme A, provides a compound of formula VII. In instances wherein $R_3$ is hydroxy and $W_f$ is phenyl, this reaction provides a compound of formula XXI. A compound of formula XXI may be reacted under Mitsunobu conditions as previously described with a compound of formula $R_4$OH, or may be reacted with a compound of formula $R_4$-LG in the presence of a suitable base as previously described, to provide a compound of formula VIIa. Alternatively, a compound of formula XX may be reacted with a compound of formula $(R_4O)(R_5)$W-M to provide a compound of formula VIIa directly.

Certain compounds of Formula (I) of the present invention wherein A is —$OCH_2$— may be prepared as illustrated in Scheme G.

Scheme G

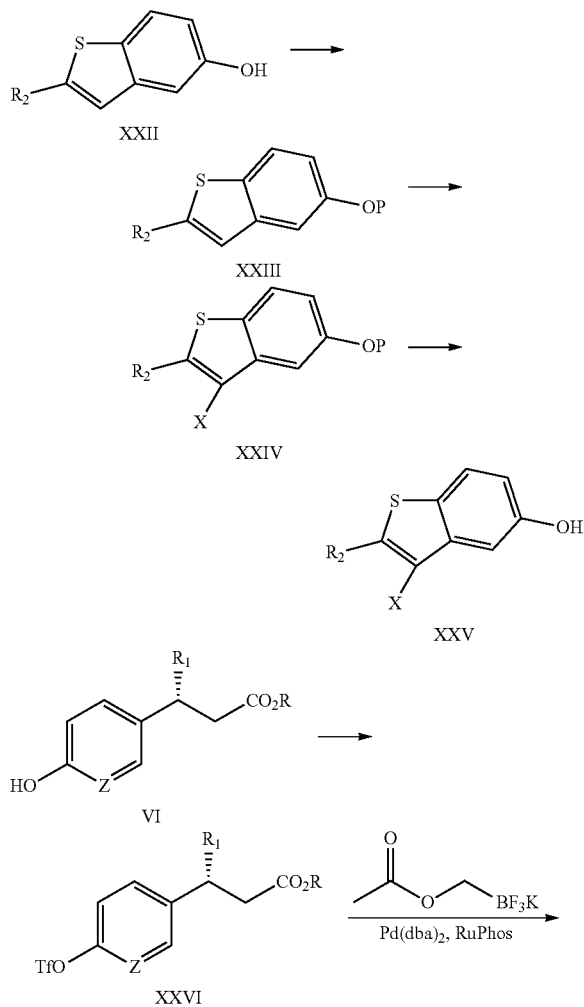

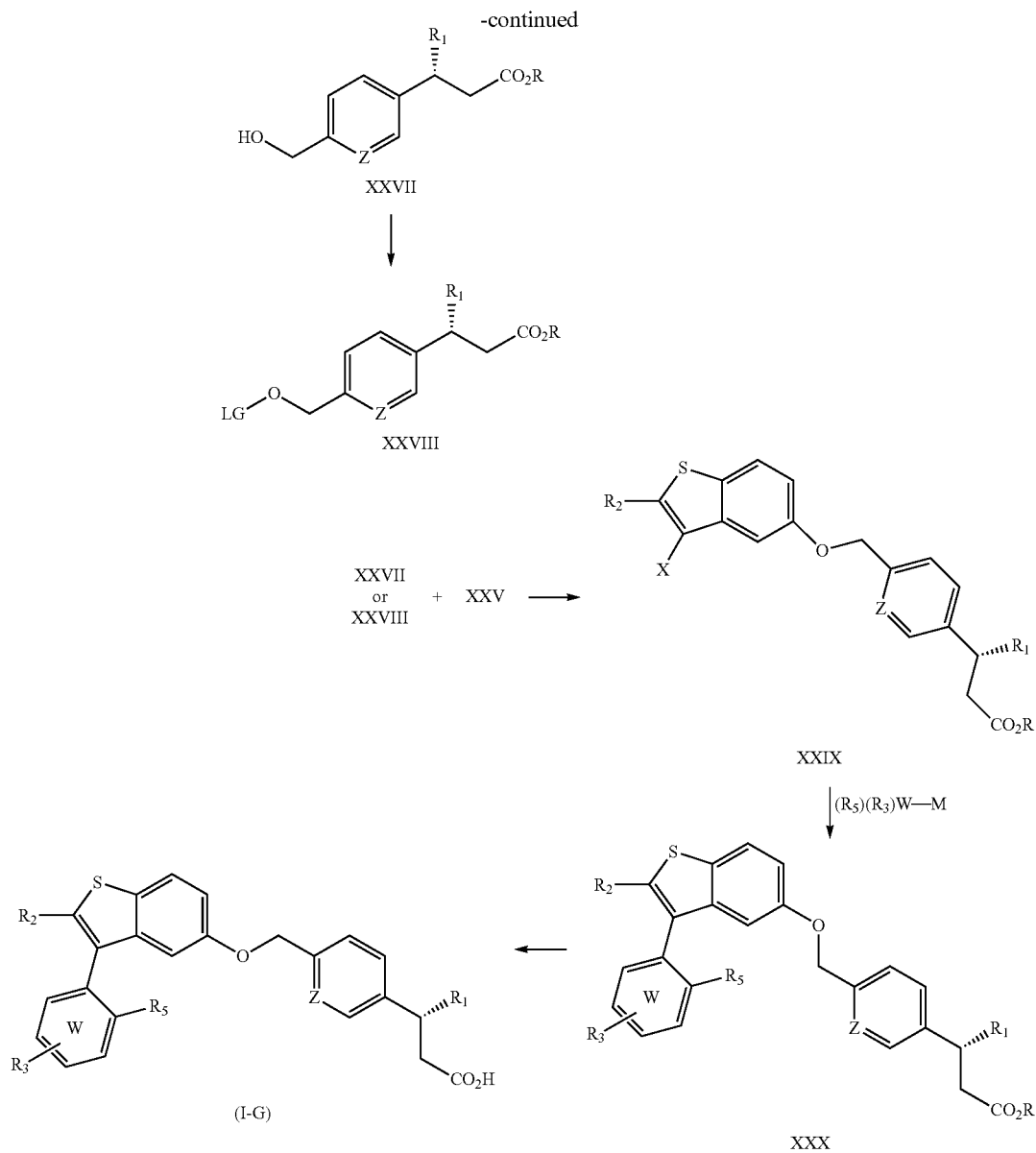

A hydroxybenzothiophene of formula XXII may be transformed to a compound of formula XXIII, wherein the phenolic group bears a suitable functional protecting group (P). Suitable protecting groups including ethers such as THP, MOM, SEM, TBDMS and the like, silyl ethers such as TBDMS and the like, or esters such as acetate, benzoate, pivaloate and the like may be incorporated, which are stable to halogenation conditions.

Halogenation of a compound of formula XXIII provides a compound of formula XXIV, which may be deprotected under appropriate conditions known to those skilled in the art to afford a compound of Formula XXV. A phenol of formula VI may be homologated to the corresponding benzyl alcohol of formula XXVII through the intermediacy of a triflate of formula XXVI. Thus, a triflate of formula XXVI may undergo palladium-catalyzed direct hydroxymethylation with potassium acetoxymethyltrifluoroborate following the conditions described by Murai (Murai, N. et al., *Org. Lett.*, 2012, 14, 1278-1281) to provide a benzylic alcohol of formula XXVII. A compound of formula XXVII may be reacted with a compound of formula XXV directly under Mitsunobu conditions, as defined in Scheme A to provide a compound of formula XXIX. Alternatively, a compound of formula XXVII may be converted to a compound of formula XXVIII, wherein LG is a suitable leaving group as previously described, and reacted with a phenol of formula XXV in the presence of a suitable base as previously described, to provide a compound of formula XXIX. A compound of formula XXIX may be reacted with a compound of formula $(R_5)(R_3)$W-M as defined in Scheme A, wherein M is preferably a boronic acid or boronic ester, under suitable coupling conditions as previously described, to provide the corresponding coupling product of formula XXX. Subsequent ester hydrolysis, as described in Scheme A affords a compound of Formula (I-G).

Compounds of formula VI, wherein $R_1$ taken with $R_6$ is 3-oxocyclobutanyl, may be prepared as illustrated in Scheme H.

Scheme H

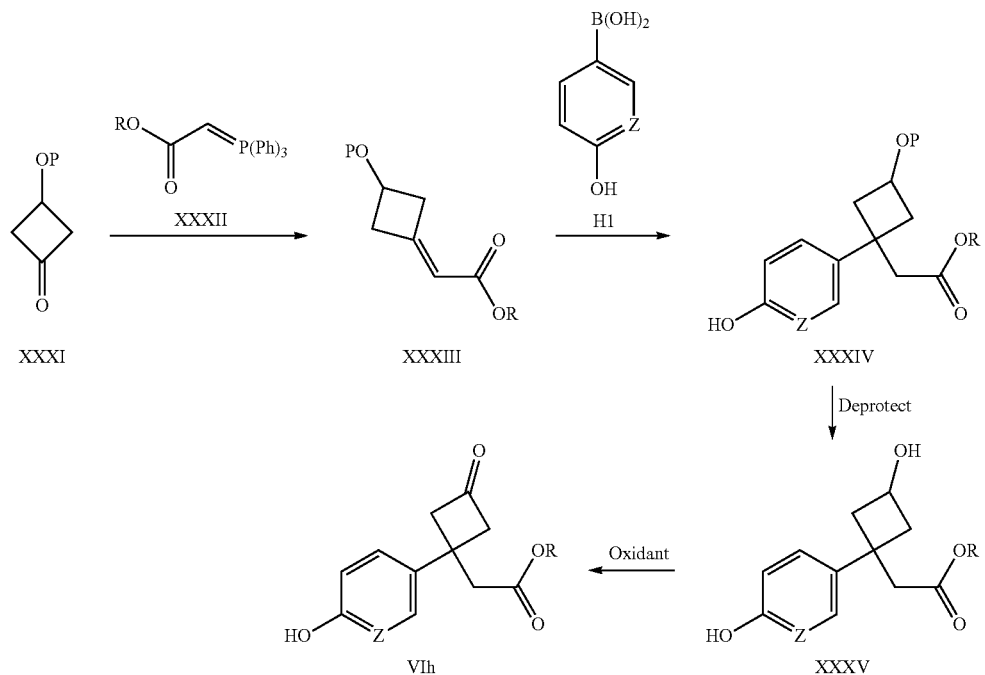

Olefination of a 3-(hydroxy-protected)-cyclobutanone of formula XXXI, wherein P is a suitable protecting group as previously described, with a phosphoranylidene acetate of formula XXXII provides a carboxylidenyl cyclobutane of formula XXXIII, which in turn may undergo a metal-catalyzed conjugate addition reaction with a boronic acid of formula H1 to provide a 3,3-disubstituted cyclobutane of formula XXXIV. Suitable metal catalyst systems include chloro(1,5-cyclooctadiene)rhodium(I) dimer, $(Pd_2(dba)_3)$·$CHCl_3/PPh_3$, $RhCl_3$/BINAP, acetylacetonatobis(ethylene)rhodium(I)/BINAP, $Pd(OAc)_2$/2,2'-bipyridine and the like, in solvents such as THF, dioxane, toluene, water and the like at a temperature between about 25° C. and about 100° C. Subsequent deprotection under appropriate conditions known to those skilled in the art, affords a hydroxycyclobutane of formula XXXV, which may be oxidized to provide a cyclobutanone of formula VIh. Suitable oxidizing agents for carrying out this transformation include, but are not limited to $SO_3$-pyridine complex, PDC, PCC, $MnO_2$, DMSO/NCS, $DMSO/Ac_2O$, DMSO/DCI and the like, in a solvent such as DCM, DCE, DMSO, and the like, at a temperature between about −20° C. and about 80° C.

Certain compounds of Formula (I)-J1), wherein $R_1$ and $R_6$ are taken together to form 3-hydroxycyclobutan-1-yl, may be prepared as illustrated in Scheme J.

Scheme J

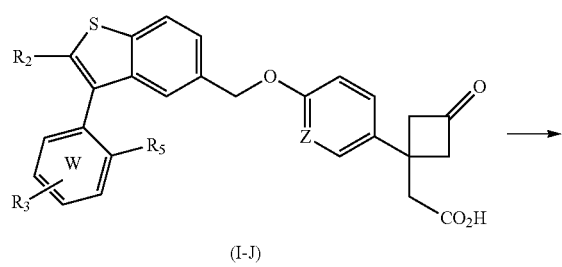

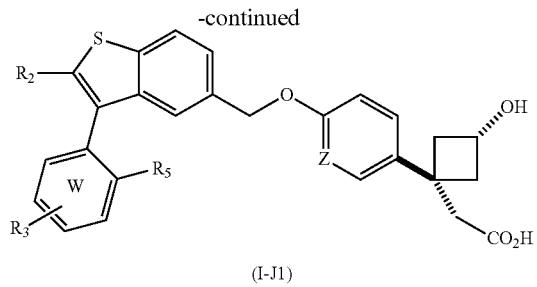

Treatment of a compound of Formula (I-J) with a suitable reducing agent may selectively reduce the ketone while in the presence of the carboxylic acid functionality to provide a compound of formula (I-J1). In particular, a bulky reducing agent is known to effect a stereoselective reduction of a ketone functionality to provide the corresponding alcohol whose relative stereochemical configuration is depicted in a compound of formula (I-J1). Suitable reducing agents preferably include borohydride derivatives such as lithium tri-sec-butylborohydride, potassium tri-sec-butylborohydride, and the like; disiamylborane, 9-BBN, diisopinocampheylborane, and the like; in a solvent such as THF, ether, dioxane, toluene, and the like; at a temperature between about −70° C. and 50° C.

In certain cases, a compound of formula VII of the present invention may be advantageously prepared by an alternative cross-coupling strategy, as illustrated in Scheme K.

Scheme K

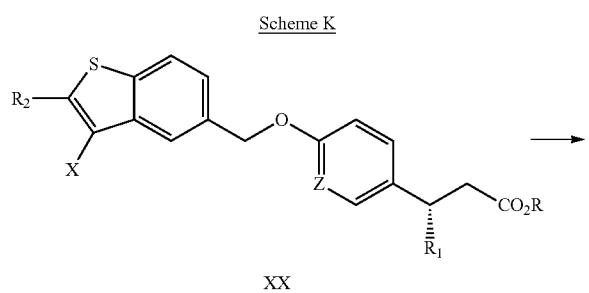

Under Suzuki coupling conditions as previously described for Scheme D, a compound of formula XX may be converted to its corresponding boronate ester of formula XXXVI, which, in turn, may be coupled to an aromatic halide of formula $(R_5)(R_3)W$—X, wherein $(R_5)$ is Me and $CF_3$, and $(R_3)W$—X are defined as in Scheme A, to provide a compound of formula VII directly.

Certain compounds of formula IV of the present invention in which $R_3$ is —$OR_4$, may be prepared as illustrated in Scheme L.

Scheme L

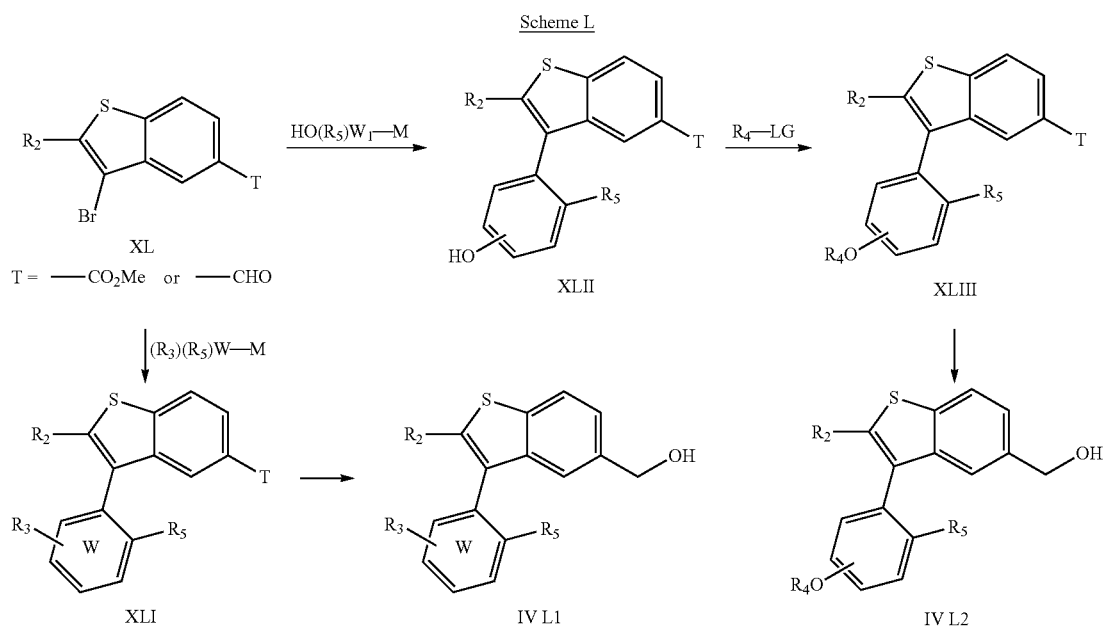

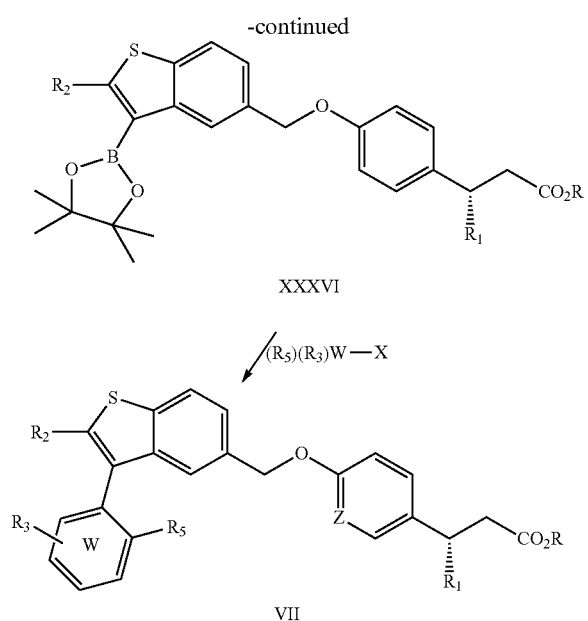

A compound of formula XL may be coupled with a compound of formula $(R_3)(R_5)$W-M as previously defined herein to afford a compound of formula XLI. Reduction of group T (ester or aldehyde) of a compound of formula XLI using conventional methods known to one of skill in the art affords the corresponding methylalcohol of formula IV-L1. Alternatively, a compound of formula XL may be coupled with a compound of formula $HO(R_5)W_1$-M wherein $W_1$ is phenyl to afford a compound of formula XLII. Subsequent reaction with a reagent of formula $R_4$-LG as previously described herein may afford a compound of formula XLIII Reduction of group T (ester or aldehyde) of a compound of formula XLIII using conventional methods known to one of skill in the art affords the corresponding methylalcohol of formula IV-L2.

SPECIFIC EXAMPLES

General Procedure A: A mixture of an arylbromide or aryliodide (1 mmol), an arylboronic acid, aryldioxaborolane or bis(pinacolato)diboron (1.5 mmol), a palladium catalyst (0.1 mmol) and $K_2CO_3$ (2-3 mmol) was placed in a reaction vessel which was then thoroughly purged with argon. Dioxane (3 mL) and water (1.5 mL) were added, and the mixture was stirred at 80-95° C. for 1 to 3 h. After cooling to rt, the mixture was poured into EtOAc/H$_2$O (1:1, 10 mL) and the aqueous layer was extracted with EtOAc (5 mL×2). The combined organic extracts were dried (Na$_2$SO$_4$), filtered and concentrated under reduced pressure. Purification of the resultant residue by silica gel chromatography (EtOAc/heptanes) afforded the desired biaryl product.

General Procedure B: To a mixture of the alcohol (0.2 mmol) and the phenol (0.3 mmol) in dry THF (1 mL) was added a mixture of the phosphine (Ph$_3$P, Bu$_3$P or t-Bu$_3$P; 0.3 mmol) and the azidodicarboxylate (DEAD, DIAD, DBAD or ADDP; 0.3 mmol), and the resultant solution was stirred under argon for 1-16 h. The mixture was then either worked up by an extractive process (ex., quenching with satd. aq. NH$_4$Cl and extraction with EtOAc) or concentrated directly under reduced pressure and the resultant residue was purified by silica gel chromatography (EtOAc/heptanes) or EtOAc/petroleum ether to afford the desired phenolic ether.

General Procedure C: To a solution of the ester (0.16 mmol) in THF (1 mL) and MeOH (0.5 mL) was added the hydroxide base (1N LiOH (aq) or 1N NaOH (aq)) (1 mL) and the resultant mixture was stirred at rt for 1-3 h, or until hydrolysis was complete. The reaction was then acidified to pH 3-4 with either 1-2N HCl or 2M citric acid and poured into a 1:1 mixture of EtOAc/H$_2$O (10 mL). The aqueous layer was extracted with EtOAc (5 mL×2) and the combined organic extract was dried (Na$_2$SO$_4$), filtered and concentrated under reduced pressure. The residue was dissolved in DCM (1 mL) and the product was precipitated with heptanes to afford the pure carboxylic acid.

General Procedure D: To an ice-cooled solution of the benzylic alcohol (0.22 mmol) in DCM (5 mL) was added thionyl chloride (0.45 mmol) in drop-wise fashion. After stirring at 0-5° C. for 2 h, the reaction was quenched by the addition of water (~10 mL) followed by DCM (50 mL). After partitioning the two phases, the organic layer was successively washed with water, satd. NaHCO$_3$ and brine, then dried (Na$_2$SO$_4$), filtered and concentrated to afford the corresponding benzylic chloride which was used without further purification.

General Procedure E: A mixture of the benzylic chloride (0.11 mmol), the phenol (0.14 mmol) and Cs$_2$CO$_3$ (0.17 mmol) in MeCN (2 mL) was stirred at rt for 16 h. EtOAc (50 mL) was then added and the organic layer was successively washed with water and brine, dried (Na$_2$SO$_4$), filtered and concentrated to afford the crude corresponding benzylic phenyl ether, which was purified by silica gel chromatography (EtOAc/heptanes).

General Procedure F: To an ice-cooled solution of the benzothiophenyl aldehyde (1.02 mmol) in THF (4 mL) and MeOH (0.5 mL) was added NaBH$_4$ (2.09 mmol) in a portion-wise fashion. After stirring for 30 min, the reaction was quenched by the addition of satd. NH$_4$Cl (10 mL). The mixture was extracted with EtOAc (3×20 mL) and the combined organic extracts were dried (Na$_2$SO$_4$) and concentrated under reduced pressure. Purification of the resultant residue by silica gel chromatography (0-20% EtOAc/petroleum ether) afforded the corresponding benzylic alcohol.

General Procedure G: To a solution of the 2-(3-oxo-1-arylcyclobutyl)acetic acid (0.57 mmol) in THF (5 mL) was added lithium tri-sec-butylborohydride (1M in THF; 1.14 mL, 1.14 mmol) and the resultant solution was stirred at 50° C. for 20-30 min. 1N HCl was added to adjust the reaction solution pH to 5-6, and the mixture was then extracted with EtOAc (3×10 mL). The combined organic extracts were concentrated under reduced pressure and the residue thus obtained was purified by silica gel chromatography (60% EtOAc in petroleum ether) to provide the anti 2-((1r,3r)-3-hydroxy-1-(aryl)cyclobutyl)acetic acid.

Example 1

3-[4-[[3-(2-Methylphenyl)benzo[b]thiophen-5-yl]methoxy]phenyl]propanoic acid, Cpd 1

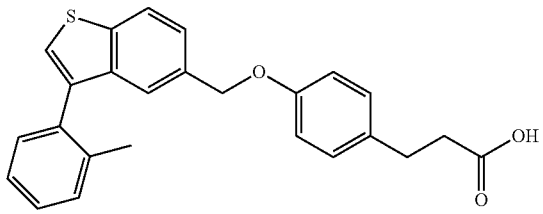 [SMILES: Cc1ccccc1-c1csc2ccc(COc3ccc(CCC(=O)O)cc3)cc12]

(A) To an ice-cooled solution of 5-hydroxymethylbenzothiophene (1.45 g; 8.83 mmol) in THF (15 mL) was added NBS (1.73 g; 9.71 mmol) under an argon atmosphere. The resulting solution was allowed to warm to rt and stirring was continued for 3 h. The reaction was then concentrated under reduced pressure and the residue was purified by silica gel chromatography eluting with 0-20% EtOAc in heptanes to afford 3-bromo-5-hydroxymethylbenzothiophene (968 mg, 45%) as a white solid. $^1$H NMR (CDCl$_3$) δ: 7.78-7.88 (m, 2H), 7.46 (s, 1H), 7.43 (d, J=9.6 Hz, 1H), 4.86 (d, J=5.8 Hz, 2H), 1.84 (t, J=5.8 Hz, 1H).

(B) 5-Hydroxymethyl-3-(2-methylphenyl)benzo[b]thiophene was prepared from 3-bromo-5-hydroxymethylbenzothiophene and 2-methylphenylboronic acid following General Procedure A, using PdCl$_2$(dppf).CH$_2$Cl$_2$ as the palladium catalyst. LC/MS: mass calcd. for C$_{16}$H$_{14}$OS: 254.35, found 277.1 [M+Na]$^+$.

(C) Methyl 3-(4-((3-(2-methylphenyl)benzo[b]thiophen-5-yl)methoxy)phenyl)-propanoate was prepared from 5-hydroxymethyl-3-(2-methylphenyl)benzo[b]-thiophene and methyl 3-(4-hydroxyphenyl)propanoate following General Procedure B using PPh$_3$ and DBAD. LC/MS: mass calcd. for C$_{26}$H$_{24}$O$_3$S: 416.54, found 439.0 [M+Na]$^+$.

(D) 3-[4-[[3-(2-Methylphenyl)benzo[b]thiophen-5-yl]methoxy]phenyl]propanoic acid (Cpd 1) was prepared from methyl 3-(4-((3-(2-methylphenyl)benzo[b]thiophen-5-yl)methoxy)phenyl)-propanoate following General Procedure C using LiOH as base and 2N HCl for reaction acidification. $^1$H NMR (400 MHz, CDCl$_3$) δ 7.93 (d, 1H), 7.42-7.50 (m, 2H), 7.27-7.38 (m, 5H), 7.10 (d, J=8.59 Hz, 2H), 6.87 (d, J=8.59 Hz, 2H), 5.08 (s, 2H), 2.89 (t, J=7.58 Hz, 2H), 2.57-2.69 (t, J=8.08 Hz, 2H), 2.15 (s, 3H). LC/MS: mass calcd. for C$_{25}$H$_{22}$O$_3$S: 402.51, found 425.1 [M+Na]$^+$.

Example 2

(3S)-3-[4-[[3-(2-Methylphenyl)benzo[b]thiophen-5-yl]methoxy]phenyl]hex-4-ynoic acid, Cpd 2

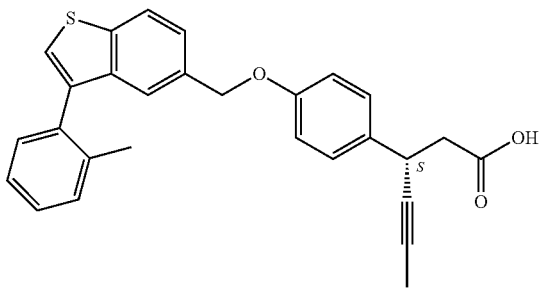

(A) (3S)-Methyl 3-(4-((3-(2-methylphenyl)benzo[b]thiophen-5-yl)methoxy)phenyl)-hex-4-ynoate was prepared from 5-hydroxymethyl-3-(2-methylphenyl)benzo[b]-thiophene (from Example 1) and (3S)-methyl 3-(4-hydroxyphenyl)hex-4-ynoate (prepared as described in WO 2005086661) following General Procedure B using $PPh_3$ and DBAD. LC/MS: mass calcd. for $C_{29}H_{26}O_3S$: 454.59, found 455.1 $[M]^+$, 477.0 $[M+Na]^+$.

(B) (3S)-3-[4-[[3-(2-Methylphenyl)benzo[b]thiophen-5-yl]methoxy]phenyl]hex-4-ynoic acid (Cpd 2) was prepared from (3S)-methyl 3-(4-((3-(2-methylphenyl)benzo[b]thiophen-5-yl)methoxy)phenyl)hex-4-ynoate following General Procedure C using LiOH as base 2N HCl for reaction acidification. $^1$H NMR (400 MHz, $CDCl_3$) δ 7.93 (d, J=9.09 Hz, 1H), 7.41-7.50 (m, 2H), 7.27-7.38 (m, 7H), 6.89 (d, J=8.59 Hz, 2H), 5.08 (s, 2H), 3.97-4.10 (m, 1H), 2.78(dd, J=8.59, 15.66 Hz, 1H), 2.69(dd, J=6.57, 15.66 Hz, 1H), 2.15 (s, 3H), 1.82 (d, J=2.02 Hz, 3H). LC/MS: mass calcd. for $C_{28}H_{24}O_3S$: 440.56, found 463.1 $[M+Na]^+$.

Example 2a

(3S)-3-[4-[[3-(2-Methylphenyl)benzo[b]thiophen-5-yl]methoxy]phenyl]hex-4-ynoic acid, Cpd 2

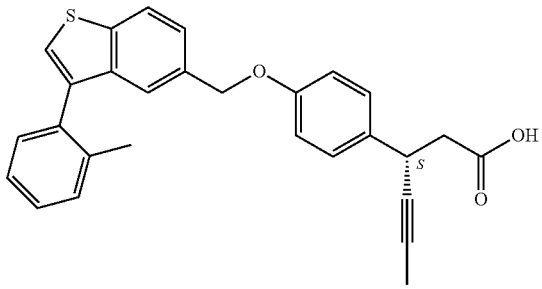

(A) To a cooled (−10° C. to 5° C.) solution of diisopropylamine (422 g, 4.17 mol) in anhydrous THF (4.0 L) was added n-butyllithium (1517 mL of 2.5 M in hexane, 3.79 mol) in drop-wise fashion over a period of 1.5 h under an inert atmosphere of nitrogen. Upon completion of the addition, the reaction solution was stirred at −10° C. to 0° C. for an additional 30 min, and then cooled to −78° C. A solution of 5-bromobenzo[b]thiophene (670 g, 3.16 mol) and TMSCl (512 g, 4.74 mol) in THF (3.4 L) was added in drop-wise fashion and the resulting reaction mixture was stirred at −78° C. After completion of the reaction, as judged by HPLC analysis, aq. $NH_4Cl$ solution (5% w/w, 2 L) was added in drop-wise fashion into the reaction mixture while still under a nitrogen atmosphere and maintaining a temperature between −78° C. and −65° C. The mixture was then allowed to warm to rt and the aqueous phase was removed. Water (2 L) was added to the organic phase and after stirring at room temperature for 15 min, the aqueous phase was removed. The combined aqueous layers were back-extracted with EtOAc (2 L), and the combined organic extracts were washed with sat.d aq. NaCl (2 L), dried ($Na_2SO_4$) and concentrated under reduced pressure to provide (5-bromobenzo[b]thiophen-2-yl)trimethylsilane (867 g, purity: 90.0 LCAP) as a light yellow liquid. $^1$H NMR ($CDCl_3$) δ 7.93 (d, J=1.5 Hz, 1H), 7.72 (d, J=8.4 Hz, 1H), 7.39 (d, J=8.4 Hz, 1H), 7.36 (s, 1H), 0.37 (s, 9H); LC/MS ($APCI^+$) m/z 283.9 $[M]^+$.

(B) To a cooled (−78° C.) solution of (5-bromobenzo[b]thiophen-2-yl)trimethylsilane (884 g, 3.10 mol) in anhydrous THF (4.4 L) under an inert atmosphere of nitrogen was added n-butyllithium (1489 mL of 2.5 M in hexanes, 3.72 mol) in drop-wise fashion over a period of 50 min. After stirring at −78° C. for 20 min, a solution of DMF (271 g, 3.72 mol) in THF (1326 mL) was introduced in drop-wise fashion over a period of 1 h, and the resulting reaction mixture was stirred at −78° C. and monitored by HPLC. After completion of the reaction (20 min), MeOH (150 mL) was added in drop-wise fashion and the mixture was stirred for 15 min at −78° C. Aq. $NH_4Cl$ solution (5% w/w, 2 L) was then added in drop-wise fashion into the reaction mixture, after which the mixture was allowed to warm to rt and the aqueous phase was removed. Water (2 L) was added to the organic phase and after stirring at room temperature for 15 min, the aqueous phase was removed. The combined aqueous layers were back-extracted with EtOAc (2 L), and the combined organic extracts were washed with sat.d aq. NaCl (2 L), dried ($Na_2SO_4$) and concentrated under reduced pressure to provide crude 2-(trimethylsilyl)benzo[b]thiophene-5-carbaldehyde (762 g) as a buff solid. $^1$H NMR ($CDCl_3$) δ 10.10 (s, 1H), 8.28 (s, 1H), 7.99 (d, J=8.4 Hz, 1H), 7.83 (d, J=8.4 Hz, 1H), 7.58 (s, 1H), 0.40-0.38 (m, 9H); LC/MS ($ES^+$) m/z 235.1 $[M+H]^+$.

(C) A mixture of 2-(trimethylsilyl)benzo[b]thiophene-5-carbaldehyde (956 g, 2.9 mol) and TFA (4.5 L) was stirred at 50° C. for 3.5 h. Acetic acid (4.5 L) was then added, and once the temperature again reached 50° C., a solution of $Br_2$ (718.5 g, 4.50 mol) in acetic acid (4.5 L) was added in drop-wise fashion over a period of 2 h. The reaction was stirred at 50° C. for an additional 2 h, and then was allowed to stir overnight at rt. The reaction mixture was then filtered and the filtrate was poured into ice water (65 L, 5-10° C.), stirred for 2 h, and then filtered. The precipitate was washed successively with water, aq. $NaHCO_3$ solution (5% w/w) and water, and then air-dried (4 d) to afford 3-bromobenzo[b]thiophene-5-carbaldehyde (793 g, 83% w/w purity, by $^1$H NMR) as a yellow solid. $^1$H NMR ($CDCl_3$) δ 10.16 (s, 1H), 8.32 (s, 1H), 7.99-7.93 (m, 2H), 7.57 (s, 1H); LC/MS ($ES^+$) m/z 240.9 $[M+H]^+$, 242.9 $[M+H+2]^+$.

(D) A mixture of 3-bromo-1-benzothiophene-5-carbaldehyde (1153 g, 83% w/w purity by $^1$H NMR, 3.988 mol), (2-methylphenyl) boronic acid (purchased from Hebei Meixing Chemical Co., Ltd., 1627 g, 40% w/w purity by $^1$H NMR, 4.786 mol), DME (9.2 L), $H_2O$ (2.3 L), $Na_2CO_3$ (1070 g, 10.09 mol) and $Pd(PPh_3)_3Cl_2$ (140 g, 0.20 mmol), maintained under an inert nitrogen atmosphere, was stirred for 3 h at 80° C., then allowed to cool to rt. After phase separation and removal of the aqueous phase, the organic phase was diluted with MTBE (5.5 L), washed successively with water (2×5.5 L) and satd. aq. NaCl (5.5 L), then concentrated under reduced pressure. The resultant crude solid was dissolved in MeCN (5 L) and quantified by $^1$H NMR (15.0% w/w purity).

The above solution of crude 3-(2-methylphenyl)benzo[b]thiophene-5-carbaldehyde (5334 g, 15.0% w/w by $^1$HNMR assay, 1.0 eq.) was further diluted with acetonitrile (12 L) and the resultant solution was heated to 50° C. with stirring. Satd. aq. NaHSO$_3$ solution (825 g of NaHSO$_3$ in 2007 g of H$_2$O) was added in drop-wise fashion over a period of 1.5 h, maintaining a reaction temperature of 50° C., and the solution was stirred for an additional 2 h then cooled to 5 to 10° C. After 1 h, the cooled mixture was filtered and the precipitate was slurried with MeCN (8 L) and filtered. The precipitate was stirred in water (10.6 L) for 10 min at rt; Na$_2$CO$_3$ (933 g) was added and the mixture was stirred at rt for 1.5 h. DCM (10.6 L) was added and the mixture was stirred for 3.5 h. After phase separation, the aqueous layer was extracted with DCM (1×4 L) and the combined organic extracts were washed with water (2×4 L) and concentrated under reduced pressure to afford 3-(2-methylphenyl)benzo[b]thiophene-5-carbaldehyde as a dark oil (850 g, 91% w/w purity by $^1$H NMR). $^1$H NMR (DMSO-d$_6$) δ 10.06 (s, 1H), 8.29 (d, J=8.4 Hz, 1H), 7.93-7.88 (m, 3H), 7.44-7.31 (m, 4H), 2.15 (s, 3H); LC/MS (ES$^+$) m/z 253.1 [M+H]$^+$.

(E) To a cooled (0-5° C.) solution of 3-(2-methylphenyl)benzo[b]thiophene-5-carbaldehyde (800 g, 91% w/w purity, 2.89 mol), toluene (4 L) and methanol (400 mL), maintained under an inert nitrogen atmosphere, was added NaBH$_4$ (54.6 g, 1.445 mol, 0.50 eq.) in portions. After stirring for 1 h, the reaction was quenched by the drop-wise addition of acetone (110 mL) over 20 min, maintaining a reaction temperature below 20° C. 1N aq. HCl (1.5 L) was then added and after phase separation, the aqueous phase was extracted with toluene (1×4L). The combined organic phase was washed with aq. NaHCO$_3$ (5% w/w, 4 L) and concentrated under reduced pressure. The residue thus obtained was dissolved in EtOH (8 L); Ecosorb C-941 (20% w/w) was added and the resulting suspension was refluxed for 30 min, and then filtered. The filtrate was concentrated under reduced pressure to a volume of ~0.5 L; heptane (4 L) was then added and the resultant solution was stirred at 55-60° C. for 1.5 h. The solution was allowed to gradually cool to rt, then was slowly further cooled to 0-5° C. The resultant suspension was stirred at this temperature for an additional 1 h, and then filtered. The filter cake was collected and dried at 25-30° C. to give 580 g of (3-(2-methylphenyl)benzo[b]thiophen-5-yl)methanol as a white solid (purity: 99.3 LCAP, yield 79%). $^1$H NMR (CDCl$_3$) δ 7.91 (dd, J=8.0, 1.4 Hz, 1H), 7.41-7.28 (m, 7H), 4.74 (s, 2H), 2.17 (s, 3H); LC/MS (ES$^+$) m/z 237.1 [M–OH]$^+$.

(F) To a cooled (0-5° C.) solution of SOCl$_2$ (175.8 g, 1.46 mol, 2.50 eq.) and dichloromethane (1.2 L) under an inert nitrogen atmosphere was added a solution of (3-(2-methylphenyl)benzo[b]thiophen-5-yl)methanol (150 g, 99.3% purity, 0.586 mol) and TEA (23.66 g, 0.234 mol, 0.40 eq.) in dichloromethane (300 mL) in drop-wise fashion over a period of 45 min, and the resultant cooled solution was stirred for an additional 1 h. The reaction was then quenched by the addition of ice water (1.5 L). After phase separation, the organic layer was washed with satd. aq. NaCl (1.5 L) and concentrated under reduced pressure to afford crude 5-(chloromethyl)-3-(2-methylphenyl)benzo[b]thiophene as a red oil (160 g, 97.9% w/w purity by $^1$H NMR). $^1$H NMR (CDCl$_3$) δ 7.89 (dd, J=6.0, 2.7 Hz, 1H), 7.41-7.37 (m, 2H), 7.35-7.27 (m, 5H), 4.63 (s, 2H), 2.16 (s, 3H); LC/MS (ES$^+$) m/z 237.1 [M–Cl]$^+$.

(G) A mixture of 5-(chloromethyl)-3-(2-methylphenyl)benzo[b]thiophene (435 g, 97.9% purity, 1.56 mol), (3S)-ethyl 3-(4-hydroxyphenyl)hex-4-ynoate (available from Synnovator, Inc., Research Triangle Park, N.C.; Cat. #PB05708) (380.4 g, 1.61 mol, 1.05 eq.) and Cs$_2$CO$_3$ (1185 g, 3.56 mol, 2.28 eq.) in MeCN (22 L) was stirred at rt overnight. The mixture was filtered and the filter cake was washed with MeCN (2 L). The combined filtrates were concentrated under reduced pressure and the resultant residue was purified by silica gel chromatography (2-50% EtOAc/n-heptane) to afford (3S)-ethyl 3-(4-((3-(2-methylphenyl)benzo[b]thiophen-5-yl)methoxy)phenyl)hex-4-ynoate (700 g, 94% w/w purity by $^1$H NMR). $^1$H NMR (CDCl$_3$) δ 7.92 (d, J=8.7 Hz, 1H), 7.46-7.34 (m, 2H), 7.37-7.24 (m, 7H), 6.88 (dd, J=11.6, 2.9 Hz, 2H), 5.08 (s, 2H), 4.16-4.01 (m, 3H), 2.76-2.58 (m, 2H), 2.15 (s, 3H), 1.81 (d, J=2.4 Hz, 3H), 1.20 (t, J=7.2 Hz, 3H); LC/MS (ES$^+$) m/z 469.1 [M+H]$^+$.

(H) A mixture of (3S)-ethyl 3-(4-((3-(2-methylphenyl)benzo[b]thiophen-5-yl)methoxy)phenyl)hex-4-ynoate (630 g, 94% purity, 1.25 mol), THF (9.0 L), purified water (1.2 L), MeOH (0.6 L) and anhydrous LiOH (150 g, 6.25 mol) was stirred at rt for 18 h and then concentrated under reduced pressure. The residue thus obtained was taken up in purified water (9.5 L) and acidified to pH 2-3 with 6N HCl (1.1 L). The resulting solution was extracted with EtOAc (2×5 L) and the combined organic extracts were filtered and concentrated under reduced pressure. The residue thus obtained was taken up in HOAc (1 L), and the mixture was concentrated under reduced pressure at 40-45° C. This step was repeated with 400 mL of HOAc. The residue was then taken up in HOAc (2.6 L) and the mixture was heated at 60-65° C. for 3 h, after which time purified water (0.8 L) was added in drop-wise fashion over a period of 3 h. The resulting suspension was stirred at 60-65° C. for 2 h, and then at rt for 14 h. The suspension was filtered and the filter cake was washed successively with a 50% (v/v) solution of AcOH/H$_2$O (2×1.0 L), and purified water (2×0.6 L). The filter cake was dried under vacuum at 50-55° C. for 12 h to provide 550 g of white solid. The solid was dissolved in EtOAc (3.0 L) and after stirring at rt for 1 h, the solution was filtered and concentrated under reduced pressure. The residue was then treated with n-heptane (9.0 L) and the resultant suspension was stirred at rt for 5 h and filtered. The filter cake was dried under vacuum at 50-55° C. to afford (3S)-3-[4-[[3-(2-methylphenyl)benzo[b]thiophen-5-yl]methoxy]phenyl]hex-4-ynoic acid (515 g, purity 99.3% by HPLC, 97.3% ee) as a white solid. $^1$H NMR (DMSO-d$_6$) δ 12.22 (s, 1H), 8.07 (d, J=6.3 Hz, 1H), 7.71 (s, 1H), 7.48 (dd, J=6.2, 1.1 Hz, 1H), 7.40-7.22(m, 7H), 6.90 (d, J=6.6 Hz, 2H), 5.16(s, 2H), 3.92 (td, J=5.7, 1.8 Hz, 1H), 2.59 (dd, J=11.7, 6 Hz, 2H), 2.08 (s, 3H), 1.76 (d, J=1.8 Hz, 3H). $^{13}$C NMR (DMSO-d$_6$) δ 172.3, 157.5, 139.3, 139.0, 137.0, 136.8, 135.2, 134.1, 133.9, 130.8, 130.6, 128.7, 128.5, 126.4, 126.0, 124.8, 123.6, 122.2, 115.3, 81.1, 78.6, 69.7, 43.3, 33.1, 20.3, 3.7; LC/MS (ES$^+$) m/z 441.1 [M+H]$^+$.

Example 3

(3S)-3-[4-[[3-[4-[(4-Hydroxy-1,1-dioxothian-4-yl)methoxy]-2-methylphenyl]-benzo[b]thiophen-5-yl]methoxy]phenyl]hex-4-ynoic acid, Cpd 3

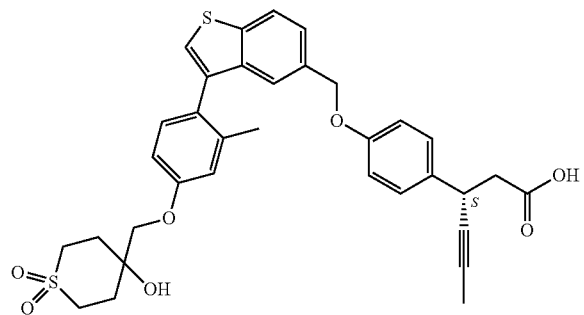

(A) 5-Hydroxymethyl-3-(4-hydroxy-2-methylphenyl)benzo[b]thiophene was prepared from 3-bromo-5-hydroxymethylbenzothiophene (from Example 1, Step A) and 4-hydroxy-2-methylphenylboronic acid following General Procedure A, using $PdCl_2(dppf) \cdot CH_2Cl_2$ as the palladium catalyst. LC/MS: mass calcd. for $C_{16}H_{14}O_2S$: 270.35, found 293.0 $[M+Na]^+$.

(B) A mixture of 5-hydroxymethyl-3-(4-hydroxy-2-methylphenyl)benzo[b]thiophene (162 mg; 0.6 mmol), 1-oxa-6-thiaspiro[2.5]octane 6,6-dioxide (107 mg; 0.66 mmol) and $K_2CO_3$ (138 mg; 1 mmol) in DMF (1.5 mL) was stirred at 90° C. for 6 h. After cooling to rt, the reaction was partitioned between EtOAc and aq $NH_4Cl$ and the aqueous layer was extracted with EtOAc (2×). The combined organic layers were washed with brine, dried ($Na_2SO_4$), filtered and concentrated under reduced pressure. The residue was purified by silica gel chromatography eluting with 5-80% EtOAc in heptanes to afford 4-hydroxy-4-((4-(5-(hydroxymethyl)benzo[b]thiophen-3-yl)-3-methylphenoxy)methyl)tetrahydro-2H-thiopyran 1,1-dioxide (245 mg, 94%). LC/MS: mass calcd. for $C_{22}H_{24}O_5S_2$: 432.56, found 455.0 $[M+Na]^+$.

(C) (3S)-Methyl 3-(4-((3-(4-((4-hydroxy-1,1-dioxidotetrahydro-2H-thiopyran-4-yl)methoxy)-2-methylphenyl)benzo[b]thiophen-5-yl)methoxy)phenyl)hex-4-ynoate was prepared from 4-hydroxy-4-((4-(5-(hydroxymethyl)benzo[b]thiophen-3-yl)-3-methylphenoxy)methyl)tetrahydro-2H-thiopyran 1,1-dioxide and (3S)-methyl 3-(4-hydroxyphenyl)hex-4-ynoate (prepared as described in WO 2005086661) following General Procedure B using $PPh_3$ and DBAD. MS: mass calcd. for $C_{35}H_{36}O_7S_2$: 632.8, found 633.2 $[M]^+$, 655.2 $[M+Na]^+$.

(D) (3S)-3-[4-[[3-[4-[(4-Hydroxy-1,1-dioxothian-4-yl)methoxy]-2-methylphenyl]-benzo[b]thiophen-5-yl]methoxy]phenyl]hex-4-ynoic acid (Cpd 3) was prepared from (3S)-methyl 3-(4-((3-(4-((4-hydroxy-1,1-dioxidotetrahydro-2H-thiopyran-4-yl)methoxy)-2-methylphenyl)benzo[b]thiophen-5-yl)methoxy)phenyl)hex-4-ynoate following General Procedure C using LiOH as base and 2N HCl for reaction acidification. $^1$H NMR (CDCl$_3$) δ 7.92 (d, J=8.1 Hz, 1H), 7.37-7.49 (m, 2H), 7.27-7.32 (m, 3H), 7.22 (d, J=8.1 Hz, 1H), 6.89 (d, J=8.6 Hz, 3H), 6.82 (dd, J=8.1, 2.5 Hz, 1H), 5.09 (s, 2H), 3.98-4.10 (m, 1H), 3.93 (s, 2H), 3.42-3.59 (m, 2H), 2.92-3.02 (m, 2H), 2.80 (dd, J=15.7, 8.1 Hz, 1H), 2.70 (dd, J=15.7, 7.1 Hz, 1H), 2.13 (s, 3H), 1.83 (d, J=2.53 Hz, 3H). LC/MS: mass calcd. for $C_{34}H_{34}O_7S_2$: 618.8, found 619.0 $[M]^+$.

Example 4

(3S)-3-[4-[[3-[2-Methyl-4-(3-methylsulfonylpropoxy)phenyl]benzo[b]thiophen-5-yl]methoxy]phenyl]hex-4-ynoic acid, Cpd 4

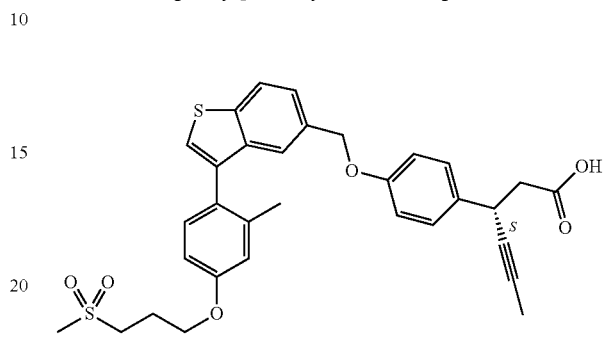

(A) To a solution of 3-methylthiopropanol (1.6 g; 15.07 mmol) and tosyl chloride (3.16 g; 16.57 mmol) in DCM (10 mL) was added pyridine (1.46 mL; 18.08 mmol) in dropwise fashion, and the resultant mixture was stirred at rt for 1 h. The mixture was then concentrated under reduced pressure and the residue thus obtained was purified by silica gel chromatography eluting with 0-50% EtOAc in hexanes to afford 3-(methylthio)propyl 4-methylbenzenesulfonate (3.6 g; 92%) as a colorless oil. LC/MS: mass calcd. for $C_{11}H_{16}O_3S_2$: 260.38, found 283.1 $[M+Na]^+$.

(B) To an ice-cooled solution of 3-(methylthio)propyl 4-methylbenzenesulfonate (3.6 g; 13.8 mmol) in MeOH (70 mL) was added a suspension of monopersulfate compound (17 g; 27.4 mmol) in water (70 mL) in a portion-wise fashion. Upon completion of the addition, the mixture was allowed to warm to rt, and stirring was continued for 20 h. The reaction was partially concentrated to remove the MeOH and the mixture was further diluted with water and extracted with EtOAc (2×). The combined organic extracts were dried ($Na_2SO_4$), filtered and concentrated under reduced pressure. The residue was purified by silica gel chromatography eluting with 0-67% EtOAc in hexanes to afford 3-(methylsulfonyl)propyl 4-methylbenzene-sulfonate (3.72 g, 92%) as a white solid. LC/MS: mass calcd. for $C_{11}H_{16}O_5S_2$: 292.38, found 315.1 $[M+Na]^+$.

(C) A mixture of 5-hydroxymethyl-3-(4-hydroxy-2-methylphenyl)benzo[b]thiophene (from Example 3) (108 mg; 0.4 mmol), 3-(methylsulfonyl)propyl 4-methylbenzenesulfonate (292 mg; 1.0 mmol) and $K_2CO_3$ (82 mg; 0.6 mmol) in DMF (1.0 mL) was stirred at 90° C. for 6 h. After cooling to rt, the reaction was partitioned between EtOAc and aq $NH_4Cl$ and the aqueous layer was extracted with EtOAc (2×). The combined organic layers were washed with brine, dried ($Na_2SO_4$), filtered and concentrated under reduced pressure. The residue was purified by silica gel chromatography eluting with 5-60% EtOAc in heptanes to afford 5-hydroxymethyl-3-(2-methyl-4-(3-(methylsulfonyl)propoxy)phenyl)benzo[b]thiophene (87 mg, 56%). LC/MS: mass calcd. for $C_{20}H_{20}O_4S_2$: 390.52, found 413.1 $[M+Na]^+$.

(D) (3S)-Methyl 3-(4-((3-(2-methyl-4-(3-(methylsulfonyl)propoxy)phenyl)benzo-[b]thiophen-5-yl)methoxy)phenyl)hex-4-ynoate was prepared from 5-hydroxymethyl-3-(2-methyl-4-(3-(methylsulfonyl)propoxy)phenyl)benzo[b]thiophene and (3S)-methyl 3-(4-hydroxyphenyl)hex-4- ynoate (prepared as described in WO 2005086661) following General Procedure B using PPh₃ and DBAD. LC/MS: mass calcd. for $C_{33}H_{34}O_6S_2$: 590.76, found 591.0 [M]⁺, 613.0 [M+Na]⁺.

(E) (35)-3-[4-[[3-[2-Methyl-4-(3-methylsulfonyl-propoxy)phenyl]benzo[b]thiophen-5-yl]methoxy]phenyl]hex-4-ynoic acid (Cpd 4) was prepared from (35)-methyl 3-(4-((3-(2-methyl-4-(3-(methylsulfonyl)propoxy)phenyl)benzo[b]thiophen-5-yl)methoxy)phenyl)hex-4-ynoate following General Procedure C using LiOH as base and 2N HCl for reaction acidification. ¹H NMR (CDCl₃) δ 7.92 (d, J=9.1 Hz, 1H), 7.40-7.48 (m, 2H), 7.27-7.32 (m, 3H), 7.20 (d, J=8.1 Hz, 1H), 6.83-6.95 (m, 3H), 6.80 (dd, J=8.6, 2.5 Hz, 1H), 5.08 (s, 2H), 4.17 (t, J=5.6 Hz, 2H), 3.98-4.09 (m, 1H), 3.25-3.35 (m, 2H), 2.98 (s, 3H), 2.79 (dd, J=15.7, 8.1 Hz, 1H), 2.69 (dd, J=15.7, 7.1 Hz, 1H), 2.12 (s, 3H), 1.82 (d, J=2.5 Hz, 3H). LC/MS: mass calcd. for $C_{32}H_{32}O_6S_2$: 576.73, found 577.0 [M]⁺.

Example 5

(3S)-3-[4-[[3-[4-(1,1-Dioxo-1,4-thiazinane-4-carbonyl)-2-methyl-phenyl]benzo[b]thiophen-5-yl]methoxy]phenyl]hex-4-ynoic acid, Cpd 5

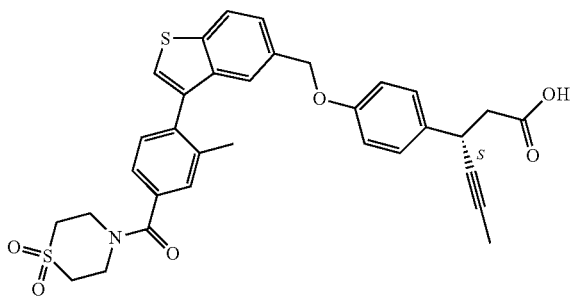

(A) Methyl 4-(5-(hydroxymethyl)benzo[b]thiophen-3-yl)-3-methylbenzoate was prepared from 3-bromo-5-hydroxymethylbenzothiophene (from Example 1A) and methyl 3-methyl-4-(4,4,5,5-tetramethyl-1,3,2-dioxaborolan-2-yl)benzoate following General Procedure A, using PdCl₂(dppf).CH₂Cl₂ as the palladium catalyst. LC/MS: mass calcd. for $C_{18}H_{16}O_3S$: 312.39, found 335.0 [M+Na]⁺.

(B) 4-(5-(Hydroxymethyl)benzo[b]thiophen-3-yl)-3-methylbenzoic acid was prepared from methyl 4-(5-(hydroxymethyl)benzo[b]thiophen-3-yl)-3-methylbenzoate following General Procedure C. LC/MS: mass calcd. for $C_{17}H_{14}O_3S$: 298.36, found 321.0 [M+Na]⁺.

(C) To a solution of 4-(5-(hydroxymethyl)benzo[b]thiophen-3-yl)-3-methylbenzoic acid (179 mg; 0.6 mmol), thiomorpholine 1,1-dioxide (162 mg; 1.2 mmol) and HATU (456 mg; 1.2 mmol) in DMF (2 mL) was added DIEA (0.41 mL; 2.4 mmol) and the resultant solution was stirred at rt for 4 h. The mixture was diluted with EtOAc and washed sequentially with aq. NH₄Cl and water. The organic layer was dried (Na₂SO₄), filtered and concentrated under reduced pressure. The resultant residue was partially purified by silica gel chromatography eluting with 30-70% EtOAc in heptanes to afford (1,1-dioxidothiomorpholino)(4-(5-(hydroxymethyl)benzo[b]thiophen-3-yl)-3-methylphenyl)methanone (245 mg, 69%; 75% purity), which was used directly in the next step. LC/MS: mass calcd. for $C_{21}H_{21}NO_4S_2$: 415.53, found 416.1 [M+Na]⁺.

(D) (3S)-Methyl 3-(4-((3-(4-(1,1-dioxidothiomorpholine-4-carbonyl)-2-methylphenyl)benzo[b]thiophen-5-yl)methoxy)phenyl)hex-4-ynoate was prepared from (1,1-dioxidothiomorpholino)(4-(5-(hydroxymethyl)benzo[b]thiophen-3-yl)-3-methylphenyl)methanone and (3S)-methyl 3-(4-hydroxyphenyl)hex-4-ynoate (prepared as described in WO 2005086661) following General Procedure B using PPh₃ and DBAD. LC/MS: mass calcd. for $C_{34}H_{33}NO_6S_2$: 615.77, found 616.2 [M]⁺, 638.2 [M+Na]⁺.

(E) (3S)-3-[4-[[3-[4-(1,1-Dioxo-1,4-thiazinane-4-carbonyl)-2-methylphenyl]benzo[b]thiophen-5-yl]methoxy]phenyl]hex-4-ynoic acid (Cpd 5) was prepared from (3S)-methyl 3-(4-((3-(4-(1,1-dioxidothiomorpholine-4-carbonyl)-2-methylphenyl)benzo[b]thiophen-5-yl)methoxy)phenyl)hex-4-ynoate following General Procedure C using LiOH as base and 2N HCl for reaction acidification. ¹H NMR (CDCl₃) δ 7.94 (d, J=8.6 Hz, 1H), 7.37-7.48 (m, 3H), 7.31-7.37 (m, 2H), 7.27-7.31 (m, 3H), 6.87 (d, J=9.1 Hz, 2H), 5.15 (s, 2H), 3.92-4.40 (m, 5H), 3.13 (br. s., 4H), 2.83 (dd, J=15.7, 7.1 Hz, 1H), 2.70 (dd, J=15.7, 8.1 Hz, 1H), 1.82 (d, 3H). LC/MS: mass calcd. for $C_{33}H_{31}NO_6S_2$: 601.74, found 602.1 [M]⁺, 625.0 [M+Na]⁺.

Example 6

(3S)-3-[4-[[3-[4-(1,1-Dioxo-3,6-dihydro-2H-thiopyran-4-yl)-2-methyl-phenyl]benzo[b]thiophen-5-yl]methoxy]phenyl]hex-4-ynoic acid, Cpd 6

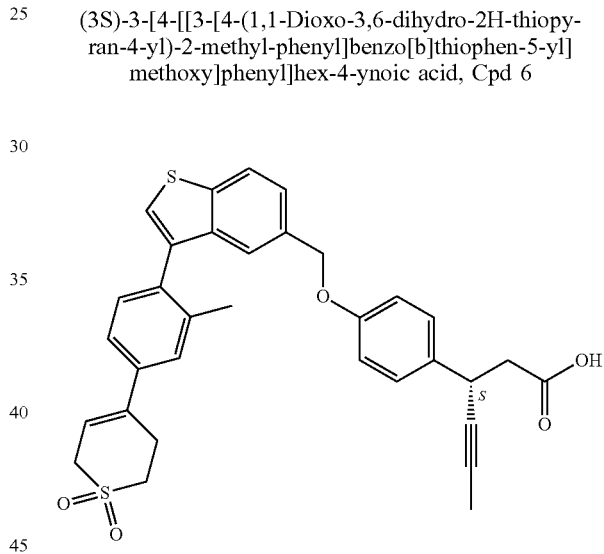

(A) 4-(4-Bromo-3-methylphenyl)-3,6-dihydro-2H-thiopyran was prepared from 2-bromo-5-iodotoluene and 2-(3,6-dihydro-2H-thiopyran-4-yl)-4,4,5,5-tetramethyl-1,3,2-dioxaborolane following General Procedure A, using PdCl₂(dppf).CH₂Cl₂ as the palladium catalyst. LC/MS: mass calcd. for $C_{12}H_{13}BrS$: 269.21, found 269.0 [M]⁺.

(B) To an ice-cooled solution of 4-(4-bromo-3-methylphenyl)-3,6-dihydro-2H-thiopyran (1.12 g; 4.16 mmol) in DCM (15 mL) was added a solution of mCPBA (1.865 g; 8.32 mmol) in DCM (15 mL) in drop-wise fashion. After stirring at 0° C. for 0.5 h, the reaction mixture was poured into a mixture of DCM (30 mL) and satd. aq. Na₂CO₃ (60 mL). The aqueous layer was extracted with DCM and the combined organic extracts were washed with satd. aq. Na₂CO₃, dried (Na₂SO₄), filtered and concentrated under reduced pressure. The resultant residue was purified by silica gel chromatography eluting with 5-40% EtOAc in DCM to afford 4-(4-bromo-3-methylphenyl)-3,6-dihydro-2H-thiopyran 1,1-dioxide (815 mg, 65%). MS: mass calcd. for $C_{12}H_{13}BrO_2S$: 301.20, found 323.0 [M+Na]⁺, 325.0 [M+2+Na]⁺.

(C) 4-(3-Methyl-4-(4,4,5,5-tetramethyl-1,3,2-dioxaborolan-2-yl)phenyl)-3,6-dihydro-2H-thiopyran 1,1-dioxide was prepared from 4-(4-bromo-3-methylphenyl)-3,6-dihydro-2H-thiopyran 1,1-dioxide and bis(pinacolato)diboron following General Procedure A, using PdCl$_2$(dppf).CH$_2$Cl$_2$ as the palladium catalyst and KOAc in place of K$_2$CO$_3$. LC/MS: mass calcd. for C$_{18}$H$_{25}$BO$_4$S: 348.27, found 349.2 [M+H]$^+$.

(D) 4-(4-(5-(Hydroxymethyl)benzo[b]thiophen-3-yl)-3-methylphenyl)-3,6-dihydro-2H-thiopyran 1,1-dioxide was prepared from 4-(3-methyl-4-(4,4,5,5-tetramethyl-1,3,2-dioxaborolan-2-yl)phenyl)-3,6-dihydro-2H-thiopyran 1,1-dioxide and 3-bromo-5-hydroxymethylbenzothiophene (from Example 1A) following General Procedure A, using PdCl$_2$(dppf).CH$_2$Cl$_2$ as the palladium catalyst. LC/MS: mass calcd. for C$_{21}$H$_{20}$O$_3$S$_2$: 384.52, found 407.0 [M+Na]$^{30}$.

(E) (3S)-Methyl 3-(4-((3-(4-(1,1-dioxido-3,6-dihydro-2H-thiopyran-4-yl)-2-methylphenyl)benzo[b]thiophen-5-yl)methoxy)phenyl)hex-4-ynoate was prepared from 4-(4-(5-(hydroxymethyl)benzo[b]thiophen-3-yl)-3-methylphenyl)-3,6-dihydro-2H-thiopyran 1,1-dioxide and (3S)-methyl 3-(4-hydroxyphenyl)hex-4-ynoate (prepared as described in WO 2005086661) following General Procedure B using PPh$_3$ and DBAD. The product was taken directly onto the following step.

(F) (3S)-3-[4-[[3-[4-(1,1-Dioxo-3,6-dihydro-2H-thiopyran-4-yl)-2-methyl-phenyl]benzo[b]thiophen-5-yl]methoxy]phenyl]hex-4-ynoic acid (Cpd 6) was prepared from (3S)-methyl 3-(4-((3-(4-(1,1-dioxido-3,6-dihydro-2H-thiopyran-4-yl)-2-methylphenyl)benzo[b]thiophen-5-yl)methoxy)phenyl)hex-4-ynoate following General Procedure C using LiOH as base and 2N HCl for reaction acidification. Purification of the product thus obtained was carried out by silica gel chromatography eluting first with 40-100% EtOAc in heptanes, then with 2-4% MeOH in EtOAc. $^1$H NMR (CDCl$_3$) δ 7.93 (d, J=8.1 Hz, 1H), 7.41-7.50 (m, 6H), 7.21-7.36 (m, 6H [overlapping with CHCl$_3$ signal]), 6.89 (d, J=8.6 Hz, 2H), 5.96 (t, J=4.3 Hz, 1H), 5.09 (s, 2H), 3.97-4.12 (m, 1H), 3.84 (d, J=2.0 Hz, 2H), 3.15-3.37 (m, 4H), 2.80 (dd, J=15.7, 8.1 Hz, 1H), 2.69 (dd, J=15.7, 7.1 Hz, 1H), 2.16 (s, 3H), 1.82 (d, J=2.5 Hz, 3H). LC/MS: mass calcd. for C$_{33}$H$_{30}$O$_5$S$_2$: 570.73, found 571.0 [M]$^+$, 593.1 [M+Na]$^+$, 610.0 [M+K]$^+$.

Example 7

(3S)-3-[4-[[3-(4-Hydroxy-2-methylphenyl)benzo[b]thiophen-5-yl]methoxy]phenyl]hex-4-ynoic acid, Cpd 7

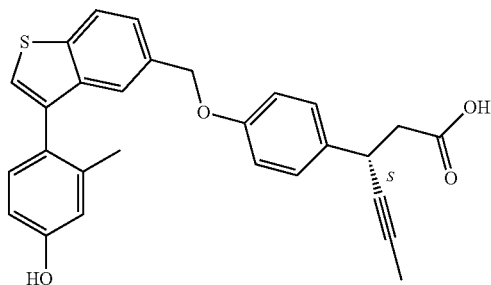

(A) To an ice-cooled solution of 4-bromo-3-methylphenol (43 g; 229.9 mmol) in THF (300 mL) was added NaH (13.8 g; 575 mmol) portion-wise. After stirring for 0.5 h, methoxymethyl chloride (22.8 mL; 298.9 mmol) was added in drop-wise fashion to the cooled reaction mixture and after warming to rt, the resultant solution was stirred for an additional 2 h. Ether (300 mL) was then added and the mixture was washed with 3M NaOH (2×100 mL), dried (Na$_2$SO$_4$), filtered and concentrated under reduced pressure to afford 1-bromo-4-(methoxymethoxy)-2-methylbenzene. $^1$H NMR (DMSO-d$_6$) δ 7.47-7.45 (m, 1H), 7.03 (d, J=2.8 Hz, 1H), 6.83-6.80 (m, 1H), 5.18 (s, 2H), 3.34 (s, 3H), 2.38 (s, 3H).

(B) 2-(4-(Methoxymethoxy)-2-methylphenyl)-4,4,5,5-tetramethyl-1,3,2-dioxaborolane was prepared from 1-bromo-4-(methoxymethoxy)-2-methylbenzene and bis(pinacolato)diboron following General Procedure A, using PdCl$_2$(dppf).CH$_2$Cl$_2$ as the palladium catalyst, KOAc in place of K$_2$CO$_3$, and DMSO as solvent in place of dioxane/water. The isolated product was used directly in the subsequent step without further characterization.

(C) (3-(4-(Methoxymethoxy)-2-methylphenyl)benzo[b]thiophen-5-yl)methanol was prepared from 2-(4-(methoxymethoxy)-2-methylphenyl)-4,4,5,5-tetramethyl-1,3,2-dioxaborolane and 3-bromo-5-hydroxymethylbenzothiophene (from Example 1A) following General Procedure A, using PdCl$_2$(dppf).CH$_2$Cl$_2$ as the palladium catalyst. $^1$H NMR (DMSO-d$_6$) δ 7.97-7.95 (m, 1H), 7.57 (s, 1H), 7.34-7.32 (m, 2H), 7.18 (d, J=8.4 Hz, 1H), 7.04-7.03 (m, 1H), 6.98-6.95 (m, 1H), 5.241 (s, 2H), 4.57-4.55 (m, 2H), 3.43 (s, 3H), 2.09 (s, 3H).

(D) (3S)-Methyl 3-(4-((3-(4-hydroxy-2-methylphenyl)benzo[b]thiophen-5-yl)methoxy)phenyl)hex-4-ynoate was prepared from (3-(4-(methoxymethoxy)-2-methylphenyl)benzo[b]thiophen-5-yl)methanol and (3S)-methyl 3-(4-hydroxyphenyl)hex-4-ynoate (prepared as described in WO 2005086661) following General Procedure B using PPh$_3$ and DBAD. $^1$H NMR (DMSO-d$_6$) δ 8.06 (d, J=8.4 Hz, 1H), 7.66 (s, 1H), 7.49-7.43 (m, 2H), 7.25-7.17 (m, 3H), 7.04-7.03 (m, 1H), 6.98-6.91 (m, 3H), 5.25 (s, 4H), 3.98-3.94 (m, 1H), 3.57 (s, 3H), 3.42 (s, 3H), 2.69-2.67 (m, 2H), 2.06 (s, 3H), 1.77-1.76 (s, 3H).

(E) To a solution of (3S)-methyl 3-(4-((3-(4-hydroxy-2-methylphenyl)benzo[b]thiophen-5-yl)methoxy)phenyl)hex-4-ynoate (1.9 g; 3.69 mmol) in MeOH (50 mL) was added conc. HCl (0.05 mL) and the resultant solution was stirred at 62° C. for 1 h. The reaction was then concentrated under reduced pressure and the residue was purified by silica gel chromatography eluting with EtOAc/petroleum ether (1:5) to provide methyl (3S)-3-(4-[[3-(4-hydroxy-2-methylphenyl)-1-benzothiophen-5-yl]methoxy]phenyl)hex-4-ynoate as a light yellow solid (1.4 g; 80%). $^1$H NMR (CDCl$_3$) δ 9.48 (s, 1H), 8.03-8.02 (m, 1H), 7.60 (s, 1H), 7.48-7.47 (m, 2H), 7.44-7.42 (m, 2H), 6.93-6.90 (m, 2H), 6.76-6.68 (m, 2H), 5.17 (s, 2H), 3.56 (s, 3H), 2.70-2.67 (m, 2H), 2.00-1.99 (m, 3H), 1.77-1.76 (m, 3H). LC/MS: mass calcd. for C$_{29}$H$_{26}$O$_4$S: 470.58, found 469.1 [M−H]$^-$.

(F) (3S)-3-[4-[[3-(4-Hydroxy-2-methylphenyl)benzo[b]thiophen-5-yl]methoxy]phenyl]hex-4-ynoic acid (Cpd 7) was prepared from (3S)-methyl 3-(4-((3-(4-hydroxy-2-methylphenyl)benzo[b]thiophen-5-yl)methoxy)phenyl)hex-4-ynoate following General Procedure C using NaOH as base, THF/water as solvent 2N HCl for reaction acidification. Following extraction of the crude product, the residue was purified by silica gel chromatography eluting with 3% MeOH in DCM. $^1$H NMR (CDCl$_3$) δ 7.90 (d, J=9.1 Hz, 1H), 7.39-7.49 (m, 2H), 7.27 (m, 3H), 7.13 (d, J=8.1 Hz, 1H), 6.88 (d, J=8.1 Hz, 2H), 6.79 (s, 1H), 6.73 (d, J=8.1 Hz, 1H), 5.08 (s, 2H), 4.04 (m, 1H), 2.61-2.87 (m, 2H), 2.07 (s, 3H), 1.81 (s, 3H). LC/MS: mass calcd. for $C_{28}H_{24}O_4S$: 456.56, found 457.2 $[M]^+$, 479.2 $[M+Na]^+$.

Example 8

(3S)-3-[4-[[3-[4-(1,1-Dioxothian-4-yl)-2-methyl-phenyl]benzo[b]thiophen-5-yl]methoxy]phenyl]hex-4-ynoic acid, Cpd 8

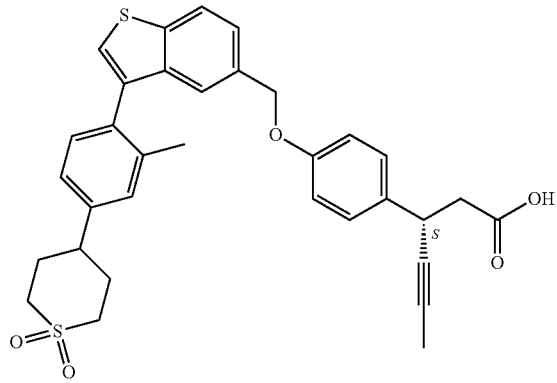

(A) A mixture of 4-(4-(5-(hydroxymethyl)benzo[b]thiophen-3-yl)-3-methylphenyl)-3,6-dihydro-2H-thiopyran 1,1-dioxide (from Example 6) (192 mg; 0.5 mmol) and 10% Pd/C (80 mg) in EtOH (6 mL) was prepared under an inert $N_2$ atmosphere and warmed to 45-50° C. A solution of ammonium formate (472 mg, 7.5 mmol) in water (1 mL) was added and the mixture was stirred for 5 h. After cooling to rt, the mixture was diluted with EtOAc (10 mL), filtered and concentrated under reduced pressure. The residue was treated with a mixture of EtOAc/water (2/20 mL), followed by heptanes (30 mL), and the resulting solid product was filtered and washed successively with water and heptanes to afford pure 4-(4-(5-(hydroxymethyl)benzo[b]thiophen-3-yl)-3-methylphenyl)tetrahydro-2H-thiopyran 1,1-dioxide (136 mg, 70%). LC/MS: mass calcd. for $C_{21}H_{22}O_3S_2$: 386.54, found 409.0 $[M+Na]^+$.

(B) (3S)-Methyl 3-(4-((3-(4-(1,1-dioxidotetrahydro-2H-thiopyran-4-yl)-2-methylphenyl)benzo[b]thiophen-5-yl)methoxy)phenyl)hex-4-ynoate was prepared from 4-(4-(5-(hydroxymethyl)benzo[b]thiophen-3-yl)-3-methylphenyl)tetrahydro-2H-thiopyran 1,1-dioxide and (3S)-methyl 3-(4-hydroxyphenyl)hex-4-ynoate (prepared as described in WO 2005086661) following General Procedure B using $PPh_3$ and DBAD. LC/MS: mass calcd. for $C_{34}H_{34}O_5S_2$: 486.77, found 587.3 $[M]^+$; 609.2 $[M+Na]^+$.

(C) (3S)-3-[4-[[3-[4-(1,1-Dioxothian-4-yl)-2-methylphenyl]benzo[b]thiophen-5-yl]methoxy]phenyl]hex-4-ynoic acid (Cpd 8) was prepared from (3S)-methyl 3-(4-((3-(4-(1,1-dioxidotetrahydro-2H-thiopyran-4-yl)-2-methylphenyl)benzo[b]thiophen-5-yl)methoxy)phenyl)hex-4-ynoate following General Procedure C, using NaOH as base and 2M citric acid for reaction acidification. $^1H$ NMR (CDCl$_3$) δ 7.92 (d, J=8.6 Hz, 1H), 7.42-7.48 (m, 2H), 7.22-7.32 (m, 4H), 7.19 (s, 1H), 7.13 (d, J=7.6 Hz, 1H), 6.89 (d, J=9.1 Hz, 2H), 5.08 (s, 2H), 4.00-4.08 (m, 1H), 3.14-3.23 (m, 4H), 2.74-2.87 (m, 2H), 2.64-2.73 (m, 1H), 2.40-2.57 (m, 2H), 2.29 (d, J=14.7 Hz, 2H), 2.14 (s, 3H), 1.82 (d, J=2.5 Hz, 3H). LC/MS: mass calcd. for $C_{33}H_{32}O_5S_2$: 572.75, found 595.3 $[M+Na]^+$.

Example 9

(3S)-3-[4-[[3-[4-(1,1-Dioxothian-4-yl)oxy-2-methyl-phenyl]-2-methyl-benzo[b]thiophen-5-yl]methoxy]phenyl]hex-4-ynoic acid, Cpd 9

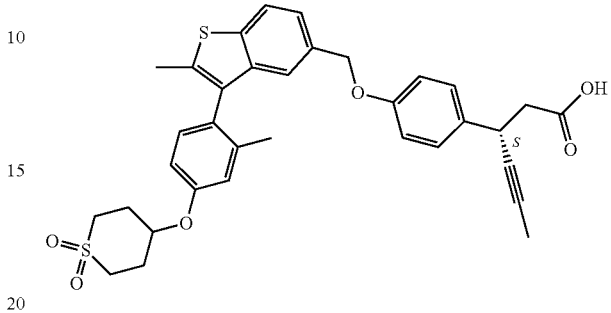

(A) Methyl 3-(4-hydroxy-2-methylphenyl)-2-methyl-benzo[b]thiophene-5-carboxylate was prepared from methyl 3-bromo-2-methylbenzo[b]thiophene-5-carboxylate and (4-hydroxy-2-methylphenyl)boronic acid following General Procedure A, using $PdCl_2(dppf).CH_2Cl_2$ as the palladium catalyst. MS: mass calcd. for $C_{18}H_{16}O_3S$: 312.39, found 313.2 $[M+H]^+$, 335.1 $[M+Na]^+$.

(B) Methyl 3-(4-((1,1-dioxidotetrahydro-2H-thiopyran-4-yl)oxy)-2-methylphenyl)-2-methylbenzo[b]thiophene-5-carboxylate was prepared from methyl 3-(4-hydroxy-2-methylphenyl)-2-methylbenzo[b]thiophene-5-carboxylate and 4-hydroxytetrahydro-2H-thiopyran 1,1-dioxide following General Procedure B using $PPh_3$ and DBAD. MS: mass calcd. for $C_{23}H_{24}O_5S_2$: 444.57, found 445.0 $[M]^+$, 467.1 $[M+Na]^+$.

(C) To an ice-cooled solution of methyl 3-(4-((1,1-dioxidotetrahydro-2H-thiopyran-4-yl)oxy)-2-methylphenyl)-2-methylbenzo[b]thiophene-5-carboxylate (290 mg; 0.65 mmol) in dry DCM (3 mL) under argon was added DIBAL-H (1M in DCM, 2 mL; 2 mmol). After stirring for 0.5 h, the mixture was poured into a vigorously stirring mixture of sodium potassium tartrate (1M in water, 8 mL) and DCM (5 mL) and stirring was continued for 1 h. The two phases were separated, and the aqueous phase was extracted with DCM (10 mL×2). The combined organic extracts were dried ($Na_2SO_4$), filtered and concentrated under reduced pressure to afford 4-(4-(5-(hydroxymethyl)-2-methylbenzo[b]thiophen-3-yl)-3-methylphenoxy)tetrahydro-2H-thiopyran 1,1-dioxide (265 mg, 98%). LC/MS: mass calcd. for $C_{22}H_{24}O_4S_2$: 416.56, found 399.1 $[M-OH]^+$, 439.0 $[M+Na]^+$.

(D) 4-(4-(5-(Chloromethyl)-2-methylbenzo[b]thiophen-3-yl)-3-methylphenoxy)-tetrahydro-2H-thiopyran 1,1-dioxide was prepared from 4-(4-(5-(hydroxymethyl)-2-methylbenzo[b]thiophen-3-yl)-3-methylphenoxy)tetrahydro-2H-thiopyran 1,1-dioxide following General Procedure D. $^1H$ NMR (CDCl$_3$) δ 7.78 (d, J=8.6 Hz, 1H), 7.29-7.34 (m, 1H), 7.14 (s, 1H), 7.11 (d, J=8.1 Hz, 1H), 6.93 (d, J=2.5 Hz, 1H), 6.85 (dd, J=8.1, 2.5 Hz, 1H), 4.72 (br. s., 1H), 4.61 (s, 2H), 3.42-3.55 (m, 2H), 2.99 (d, J=13.1 Hz, 2H), 2.50-2.60 (m, 2H), 2.36-2.48 (m, 2H), 2.34 (s, 3H), 2.04 (s, 3H).

(E) (3S)-Methyl 3-(4-((3-(4-((1,1-dioxidotetrahydro-2H-thiopyran-4-yl)oxy)-2-methylphenyl)-2-methylbenzo[b]thiophen-5-yl)methoxy)phenyl)hex-4-ynoate was prepared from 4-(4-(5-(chloromethyl)-2-methylbenzo[b]thiophen-3-yl)-3-methylphenoxy)-tetrahydro-2H-thiopyran 1,1-dioxide and (3S)-methyl 3-(4-hydroxyphenyl)hex-4-ynoate (prepared as described in WO 2005086661) following General Procedure E. $^1$H NMR (CDCl$_3$) δ 7.80 (d, J=8.6 Hz, 1H), 7.36 (d, J=8.6 Hz, 1H), 7.22-7.28 (m, 2H), 7.17 (s, 1H), 7.11 (d, J=8.6 Hz, 1H), 6.80-6.93 (m, 4H), 5.02 (s, 2H), 4.71 (br. s., 1H), 3.99-4.08 (m, 1H), 3.65 (s, 3H), 3.43-3.54 (m, 2H), 2.93-3.03 (m, 2H), 2.70-2.79 (m, 1H), 2.59-2.68 (m, 1H), 2.49-2.59 (m, 2H), 2.36-2.47 (m, 2H), 2.34 (s, 3H), 2.02 (s, 3H), 1.82 (d, J=2.5 Hz, 3H).

(F) (3S)-3-[4-[[3-[4-(1,1-Dioxothian-4-yl)oxy-2-methylphenyl]-2-methyl-benzo[b]thiophen-5-yl]methoxy]phenyl]hex-4-ynoic acid (Cpd 9) was prepared from (3S)-methyl 3-(4-((3-(4-((1,1-dioxidotetrahydro-2H-thiopyran-4-yl)oxy)-2-methylphenyl)-2-methylbenzo[b]thiophen-5-yl)methoxy)phenyl)hex-4-ynoate following General Procedure C, using NaOH as base and 2M citric acid for reaction acidification. $^1$H NMR (CDCl$_3$) δ 7.79 (d, J=8.1 Hz, 1H), 7.35 (d, J=8.1 Hz, 1H), 7.28 (s, 1H), 7.17 (s, 1H), 7.11 (d, J=8.1 Hz, 1H), 6.80-6.93 (m, 5H), 5.02 (s, 2H), 4.71 (br. s., 1H), 3.99-4.08 (m, 1H), 3.42-3.55 (m, 2H), 2.93-3.04 (m, 2H), 2.73-2.83 (m, 1H), 2.63-2.73 (m, 1H), 2.48-2.59 (m, 2H), 2.35-2.46 (m, 2H), 2.34 (s, 3H), 2.02 (s, 3H), 1.82 (d, J=2.53 Hz, 3H). LC/MS: mass calcd. for C$_{34}$H$_{34}$O$_6$S$_2$: 602.77, found 603.1 [M]$^+$, 625.2 [M+Na]$^+$.

Example 10

(3S)-3-[4-[[3-(2,6-Dimethylphenyl)benzo[b]thiophen-5-yl]methoxy]phenyl]hex-4-ynoic acid, Cpd 10

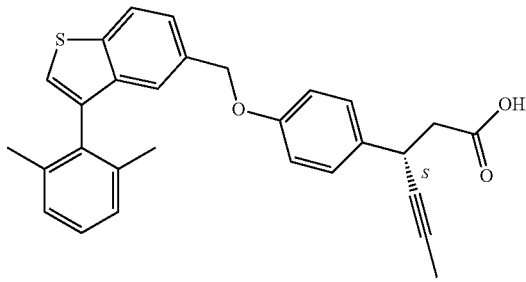

(A) 5-Hydroxymethyl-3-(2,6-dimethylphenyl)benzo[b]thiophene was prepared from 3-bromo-5-hydroxymethyl-benzothiophene (from Example 1A) and 2,6-dimethylphenylboronic acid following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{17}$H$_{16}$OS: 268.37, found 251.0 [M-17]$^+$.

(B) 5-Chloromethyl-3-(2,6-dimethylphenyl)benzo[b]thiophene was prepared from 5-hydroxymethyl-3-(2,6-dimethylphenyl)benzo[b]thiophene following General Procedure D.

(C) (3S)-Methyl 3-(4-((3-(2,6-dimethylphenyl)benzo[b]thiophen-5-yl)methoxy)phenyl)hex-4-ynoate was prepared from 5-chloromethyl-3-(2,6dimethylphenyl)benzo[b]-thiophene and (3S)-methyl 3-(4-hydroxyphenyl)hex-4-ynoate (prepared as described in WO 2005086661) following General Procedure E using DMF as solvent and stirring overnight at 40° C. LC/MS: mass calcd. for C$_{30}$H$_{28}$O$_3$S: 468.61, found 469.0 [M]$^+$.

(D) (3S)-3-(4-((3-(2,6-Dimethylphenyl)benzo[b]thiophen-5-yl)methoxy)phenyl)hex-4-ynoic acid (Cpd 10) was prepared from (3S)-methyl 3-(4-((3-(2,6-dimethylphenyl)benzo[b]thiophen-5-yl)methoxy)phenyl)hex-4-ynoate following General Procedure C, using LiOH as base and 1N HCl for reaction acidification. $^1$H NMR (DMSO-d$_6$) δ 8.08 (d, J=8.3 Hz, 1H), 7.63 (s, 1H), 7.48 (d, J=8.1 Hz, 1H), 7.12-7.36 (m, 6H), 6.87 (d, J=8.5 Hz, 2H), 5.14 (s, 2H), 3.85-4.03 (m, 1H), 2.31-2.44 (m, 2H), 1.93 (s, 6H), 1.76 (d, J=2.3 Hz, 3H) LC/MS: mass calcd. for C$_{29}$H$_{26}$O$_3$S: 454.58, found 453.1 [M–H]$^-$.

Example 11

(3S)-3-(4-((3-(4-(2-(1-Hydroxycyclopropyl)ethoxy)-2-methylphenyl)benzo[b]thiophen-5-yl)methoxy)phenyl)hex-4-ynoic acid, Cpd 11

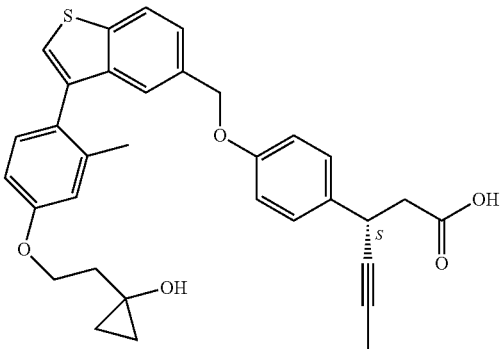

(A) To a solution of benzyl 3-hydroxypropanoate (3.35 g, 18.59 mmol), and dihydropyran (3.12 g, 37.09 mmol) in DCM (100 mL) was added PPTS (5.6 g, 22.28 mmol) portion-wise and the resulting solution was stirred overnight at rt. Water (50 mL) was added and after mixing, the phases were separated and the aqueous layer was further extracted with DCM (2×50 mL). The combined organic layers were concentrated under reduced pressure and the residue obtained was purified by silica gel chromatography (0-5% EtOAc/petroleum ether) to provide benzyl 3-(tetrahydro-2H-pyran-2-yloxy)propanoate as colorless oil (4.1 g, 83.0% yield). LC/MS: mass calcd. for C$_{15}$H$_{20}$O$_4$: 264.32, found: 265.1 [M+H]$^+$.

(B) To a solution of benzyl 3-(oxan-2-yloxy)propanoate (4.1 g, 15.51 mmol) and THF (60 mL) was added Ti(O-iPr)$_4$ (2.4 mL, 8.0 mmol) and the resultant mixture was stirred for 30 min. EtMgBr (13.3 mL, 3M, 4 mmol) was then added in drop-wise fashion and the resulting solution was stirred at rt for 3 h. The reaction was then quenched by the addition of satd. aq. NH$_4$Cl (100 mL) and the mixture was extracted with ethyl acetate (3×50 mL). The combined organic layers were concentrated under reduced pressure and the residue thus obtained was purified by silica gel chromatography (0-10% EtOAc/petroleum ether) to obtain 1-[2-(tetrahydro-2H-pyran-2-yloxy)ethyl]-cyclopropanol as a colorless oil (2.1 g, 65.0% yield). LC/MS: mass calcd. for C$_{10}$H$_{18}$O$_3$: 186.25, found: 187.1 [M+H]$^+$.

(C) A solution of 1-[2-(oxan-2-yloxy)ethyl]cyclopropan-1-ol (800 mg, 4.30 mmol) and PPTS (110 mg, 0.44 mmol) in methanol (40 mL) was stirred overnight at 40° C. The resulting mixture was then concentrated under reduced pressure and the resultant residue was purified by silica gel chromatography (10-50% EtOAc/petroleum ether) to afford 1-(2-hydroxyethyl)cyclopropanol as colorless oil (374 mg, 85.3% yield). LC/MS: mass calcd. for C$_5$H$_{10}$O$_2$: 102.13, found: 102.2 [M+H]$^+$.

(D) 3-Bromo-5-(chloromethyl)benzo[b]-thiophene was prepared from 3-bromo-5-hydroxymethylbenzothiophene (from Example 1A) following General Procedure D.

(E) A mixture of 3-bromo-5-(chloromethyl)-1-benzothiophene (200 mg, 0.76 mmol), (3S)-ethyl 3-(4-hydroxyphenyl)hex-4-ynoate (180 mg, 0.77 mmol) (available from Synnovator, Inc., Research Triangle Park, N.C.; Cat. #PB05708) and $K_2CO_3$ (420 mg, 1.29 mmol) in MeCN (20 mL) was stirred overnight at 50° C. The reaction was then quenched by the addition of satd. aq. $NH_4Cl$ (40 mL) and the resulting solution was extracted with ethyl acetate (3×40 mL) and the combined organic extracts were concentrated under reduced pressure. The resultant residue was purified by silica gel chromatography (0-20% EtOAC/petroleum ether) to provide (3S)-ethyl 3-(4-((3-bromobenzo[b]thiophen-5-yl)methoxy)phenyl)hex-4-ynoate as a colorless oil (300 mg, 86% yield). LC/MS: mass calcd. for $C_{23}H_{21}BrO_3S$: 457.38, found: 459.0 [M+H]$^+$.

(F) (3S)-Ethyl 3-(4-((3-(4-hydroxy-2-methylphenyl)benzo[b]thiophen-5-yl)methoxy)phenyl)hex-4-ynoate was prepared from (3S)-ethyl 3-4-((3-bromobenzo[b]thiophen-5-yl)methoxy)phenyl)hex-4-ynoate and 4-hydroxy-2-methylphenylboronic acid following General Procedure A using $PdCl_2(dppf).CH_2Cl_2$ as the palladium catalyst and $Cs_2CO_3$ in place of $K_2CO_3$. LC/MS: mass calcd. for $C_{30}H_{28}O_4S$: 484.61, found: 485.2 [M+H]$^+$.

(G) (3S)-Ethyl 3-(4-((3-(4-(2-(1-hydroxycyclopropyl)ethoxy)-2-methylphenyl)benzo[b]thiophen-5-yl)methoxy)phenyl)hex-4-ynoate was prepared from (3S)-ethyl 3-(4-((3-(4-hydroxy-2-methylphenyl)benzo[b]thiophen-5-yl)methoxy)-phenyl)hex-4-ynoate and 1-(2-hydroxyethyl)cyclopropan-1-ol following General Procedure B using PPh$_3$ and ADDP. LC/MS: mass calcd. for $C_{35}H_{36}O_5S$: 568.72 found: 569.2 [M$^+$].

(H) (3S)-3-(4-((3-(4-(2-(1-Hydroxycyclopropyl)ethoxy)-2-methylphenyl)benzo[b]thiophen-5-yl)methoxy)phenyl) hex-4-ynoic acid (Cpd 11) was prepared from (3S)-ethyl 3-(4-((3-(4-(2-(1-hydroxycyclopropyl)ethoxy)-2-methylphenyl)benzo[b]thiophen-5-yl)methoxy)phenyl)-hex-4-ynoate following General Procedure C using LiOH as base, EtOH in place of MeOH and 1N HCl for reaction acidification. Product purification was accomplished by preparative HPLC on a preparative C18, 5µ column (19×100 mm) using an acetonitrile/water (0.5% TFA) gradient (50-75%). $^1$H NMR (DMSO-d$_6$) δ 8.06 (d, J=8.4 Hz, 1H), 7.63 (s, 1H), 7.47 (d, J=8.4 Hz, 1H), 7.41 (s, 1H), 7.24 (d, J=8.4 Hz, 2H), 7.16 (d, J=8.1 Hz, 1H), 6.86-6.93 (m, 4H), 5.17 (s, 2H), 4.21 (t, J=6.9 Hz, 2H), 3.91-3.93 (m, 1H), 2.57-2.58 (m, 2H), 2.06 (s, 3H), 1.95 (t, J=6.9 Hz, 2H), 1.76 (s, 3H), 0.58-0.62 (m, 2H), 0.46-0.50 (m, 2H). LC/MS: mass calcd. for $C_{33}H_{32}O_5S$: 540.67, found: 539.2 [M–H]$^-$.

Example 12

(3S)-3-(4-((3-(4-(3-Hydroxy-3-methylbutoxy)-2-methylphenyl)benzo[b]thiophen-5-yl)methoxy)phenyl)hex-4-ynoic acid, Cpd 12

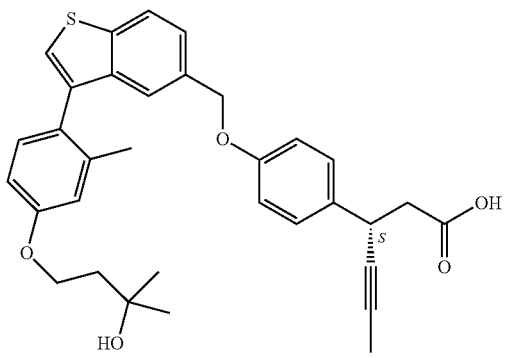

(A) (3S)-Ethyl 3-(4-((3-(4-(3-hydroxy-3-methylbutoxy)-2-methylphenyl)benzo[b]thiophen-5-yl)methoxy)phenyl) hex-4-ynoate was prepared from 3-(4-((3-(4-hydroxy-2-methylphenyl)benzo[b]thiophen-5-yl)methoxy)phenyl)hex-4-ynoate (from Example 11F) and 3-methylbutane-1,3-diol following General Procedure B using PPh$_3$ and ADDP. LC/MS: mass calcd. for $C_{35}H_{38}O_5S$: 570.74, found: 571.2 [M+H]$^+$.

(B) (3S)-3-(4-((3-(4-(3-Hydroxy-3-methylbutoxy)-2-methylphenyl)benzo[b]thiophen-5-yl)methoxy)phenyl)hex-4-ynoic acid (Cpd 12) was prepared from (3S)-ethyl 3-(4-((3-(4-(3-hydroxy-3-methylbutoxy)-2-methylphenyl)benzo[b]thiophen-5-yl)methoxy)phenyl)hex-4-ynoate following General Procedure C using LiOH as base, EtOH in place of MeOH and 1N HCl for reaction acidification. $^1$H NMR (CD$_3$OD) δ 7.96 (m, 1H), 7.48 (m, 1H), 7.38 (s, 2H), 7.22-7.28 (m, 2H), 7.13-7.16 (m, 1H), 6.81-6.95 (m, 4H), 5.16 (s, 2H), 4.19-4.22 (m, 2H), 3.39-4.01 (m, 1H), 2.62-2.67 (m, 2H), 2.01-2.08 (m, 5H), 1.82 (s, 3H), 1.38 (s, 6H). LC/MS: mass calcd. for $C_{33}H_{34}O_5S$: 542.69, found: 543.2 [M+H]$^+$.

Example 13

(3S)-3-(4-((3-(4-(2,3-Dihydroxypropoxy)-2-methylphenyl)benzo[b]thiophen-5-yl)methoxy)phenyl)hex-4-ynoic acid, Cpd 13

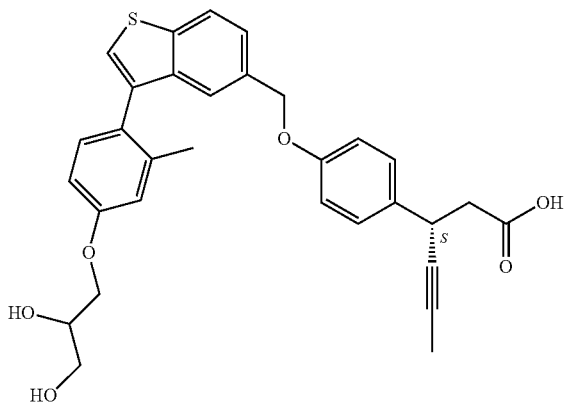

(A) 4-((4-Bromo-3-methylphenoxy)methyl)-2,2-dimethyl-1,3-dioxolane was prepared from 4-bromo-3-methylphenol and (2,2-dimethyl-1,3-dioxolan-4-yl)methanol following General Procedure B using PPh$_3$ and ADDP in toluene (in place of THF) at 60° C. $^1$H NMR (CDCl$_3$) δ 7.38 (d, J=8.8 Hz, 1H), 6.80 (d, J=2.8 Hz, 1H), 6.62 (dd, J=3.2, 8.8 Hz, 1H), 4.42-4.48 (m, 1H), 4.13-4.17 (m, 1H), 3.99-4.02 (m, 1H), 3.86-3.91 (m, 2H), 2.35 (s, 3H), 1.48 (s, 3H), 1.40 (s, 3H).

(B) 2-(4-((2,2-Dimethyl-1,3-dioxolan-4-yl)methoxy)-2-methylphenyl)-4,4,5,5-tetramethyl-1,3,2-dioxaborolane was prepared from 4-((4-bromo-3-methylphenoxy)methyl)-2,2-dimethyl-1,3-dioxolane and bis(pinacolato)diboron following General Procedure A, using $PdCl_2(dppf).CH_2Cl_2$ as the palladium catalyst and $Cs_2CO_3$ in place of $K_2CO_3$ and a reaction temperature of 85° C. overnight. $^1$H NMR (CDCl$_3$) δ 7.70 (d, J=8.0 Hz, 1H), 6.69-6.72 (m, 2H), 4.45-4.48 (m, 1H), 4.14-4.18 (m, 1H), 4.05-4.08 (m, 1H), 3.87-3.96 (m, 2H), 2.51 (s, 3H), 1.46 (s, 3H), 1.40 (s, 3H), 1.32 (s, 12H).

(C) To a solution of 5-bromo-1-benzothiophene (12 g, 56.31 mmol) in dry THF (300 mL) under an inert atmosphere was added isopropyl magnesium chloride-lithium chloride complex (1.3 M in THF; 150 mL, 195 mmol) in drop-wise fashion, and the resultant solution was stirred at rt, overnight. DMF (30 mL) was then added in drop-wise fashion and the resultant solution was stirred at rt for 30 min. Water (500 mL) was added and the resulting solution was extracted with ethyl acetate (3×500 mL). The combined organic extracts were concentrated under reduced pressure and the resultant residue was purified by silica gel chromatography (0-2% EtOAC/petroleum ether) to provide benzo[b]thiophene-5-carbaldehyde (6.9 g, 68%) as a yellow solid. $^1$H NMR (DMSO-d$_6$) δ 10.12 (s, 1H), 8.32 (s, 1H), 8.01 (d, J=8.4 Hz, 1H), 7.86-7.89 (m, 1H), 7.57-7.61 (m, 1H), 7.47-7.50 (m, 1H).

(D) To a cooled (15° C.) solution of benzo[b]thiophene-5-carbaldehyde (6.9 g, 52.54 mmol) in HOAc (80 mL) was added a solution of bromine (10.5 g, 65.7 mmol) in HOAc (20 mL) in drop-wise fashion. After stirring at 15° C. for 2 h, water (500 mL) was added, whereupon the solid product precipitated from the mixture. The precipitate was collected by filtration and dried under vacuum to provide 3-bromobenzo[b]thiophene-5-carbaldehyde (7.8 g, 38% yield) as a yellow solid. $^1$H NMR (CDCl$_3$) δ 10.17 (s, 1H), 8.32 (s, 1H), 7.93-7.98 (m, 2H), 7.78 (s, 1H).

(E) 3-(4-((2,2-Dimethyl-1,3-dioxolan-4-yl)methoxy)-2-methylphenyl)benzo[b]thiophene-5-carbaldehyde was prepared from 2-(4-((2,2-dimethyl-1,3-dioxolan-4-yl)methoxy)-2-methylphenyl)-4,4,5,5-tetramethyl-1,3,2-dioxaborolane and 3-bromobenzo[b]thiophene-5-carbaldehyde following General Procedure A, using PdCl$_2$(dppf).CH$_2$Cl$_2$ as the palladium catalyst and Cs$_2$CO$_3$ in place of K$_2$CO$_3$. $^1$H NMR: (CDCl$_3$) δ 10.02 (s, 1H), 8.02-8.04 (m, 1H), 7.89-7.90 (m, 2H), 7.37 (s, 1H), 7.20-7.26 (m, 1H), 6.82-7.00 (m, 2H), 4.50-4.53 (m, 1H), 4.14-4.24 (m, 2H), 3.93-4.08 (m, 2H), 2.15 (s, 3H), 1.48-1.50 (m, 3H), 1.42-1.43 (m, 3H).

(F) (3-(4-((2,2-Dimethyl-1,3-dioxolan-4-yl)methoxy)-2-methylphenyl)benzo[b]thiophen-5-yl)methanol was prepared from 3-(4-((2,2-dimethyl-1,3-dioxolan-4-yl)methoxy)-2-methylphenyl)benzo[b]thiophene-5-carbaldehyde following General Procedure F. LC/MS: mass calcd. for C$_{22}$H$_{24}$O$_4$S: 384.49, found: 367.1 [M−OH]$^+$.

(G) 4-((4-(5-(Chloromethyl)benzo[b]thiophen-3-yl)-3-methylphenoxy)methyl)-2,2-dimethyl-1,3-dioxolane was prepared from (3-(4-((2,2-dimethyl-1,3-dioxolan-4-yl)methoxy)-2-methylphenyl)benzo[b]thiophen-5-yl)methanol following General Procedure D.

(H) (3S)-Ethyl 3-(4-((3-(4-((2,2-dimethyl-1,3-dioxolan-4-yl)methoxy)-2-methylphenyl)benzo[b]thiophen-5-yl)methoxy)phenyl)hex-4-ynoate was prepared from 4-((4-(5-(chloromethyl)benzo[b]thiophen-3-yl)-3-methylphenoxy)methyl)-2,2-dimethyl-1,3-dioxolane and (3S)-ethyl 3-(4-hydroxyphenyl)hex-4-ynoate (available from Synnovator, Inc., Research Triangle Park, N.C.; Cat. #PB05708) following General Procedure E. LC/MS: mass calcd. for C$_{36}$H$_{38}$O$_6$S: 598.75, found: 599.2 [M+H]$^+$.

(I) A solution of (3S)-ethyl 3-(4-((3-(4-((2,2-dimethyl-1,3-dioxolan-4-yl)methoxy)-2-methylphenyl)benzo[b]thiophen-5-yl)methoxy)phenyl)hex-4-ynoate (200 mg, 0.33 mmol) in THF (4 mL) was treated with 2N HCl (4 mL) and the resulting solution was stirred at 60° C. for 30 min. Water (10 mL) was then added and the mixture was extracted with EtOAc (3×10 mL). The combined organic extracts were dried (Na$_2$SO$_4$) and concentrated under reduced pressure. Purification of the resultant residue by silica gel chromatography (0-50% EtOAc/petroleum ether) afforded (3S)-ethyl 3-(4-((3-(4-(2,3-dihydroxypropoxy)-2-methylphenyl)benzo[b]thiophen-5-yl)methoxy)phenyl)hex-4-ynoate (140 mg, 75% yield) as a colorless oil. LC/MS: mass calcd. for C$_{33}$H$_{34}$O$_6$S: 558.68, found: 559.2 [M+H]$^+$.

(J) (3S)-3-(4-((3-(4-(2,3-Dihydroxypropoxy)-2-methylphenyl)benzo[b]thiophen-5-yl)methoxy)phenyl)hex-4-ynoic acid (Cpd 13) was prepared from (3S)-ethyl 3-(4-((3-(4-(2,3-dihydroxypropoxy)-2-methylphenyl)benzo[b]thiophen-5-yl)methoxy)phenyl)hex-4-ynoate following General Procedure C using LiOH as base, EtOH in place of MeOH and 1N HCl for reaction acidification. $^1$H NMR (DMSO-d6) δ 8.06 (d, J=8.4 Hz, 1H), 7.65 (s, 1H), 7.47 (d, J=8.4 Hz, 1H), 7.42 (s, 1H), 7.23-7.25 (m, 2H), 7.16 (d, J=8.4 Hz, 1H), 6.86-6.95 (m, 4H), 5.17 (s, 2H), 4.98-5.02 (m, 1H), 4.06-4.07 (m, 1H), 4.03-4.07 (m, 1H), 3.82-3.93 (m, 3H), 3.46-3.47 (m, 2H), 2.63-2.67 (m, 2H), 2.06 (s, 3H), 1.76 (s, 3H). LC/MS: mass calcd. for C$_{31}$H$_{30}$O$_6$S: 530.63, found: 529.2[M−H]$^−$.

Example 14

(3S)-3-(4-((3-(2-Methyl-4-((3-methyloxetan-3-yl)methoxy)phenyl)benzo[b]thiophen-5-yl)methoxy)phenyl)hex-4-ynoic acid, Cpd 14

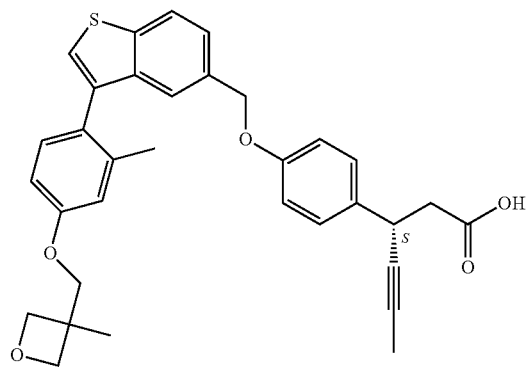

(A) 3-((4-Bromo-3-methylphenoxy)methyl)-3-methyloxetane was prepared from 4-bromo-3-methylphenol and (3-methyloxetan-3-yl)methanol following General Procedure B using PPh$_3$ and DBAD at a reaction temperature of 50° C. overnight. LC/MS: mass calcd. for C$_{12}$H$_{15}$BrO$_2$: 271.15, found: 271.0 [M]$^+$.

(B) 4,4,5,5-Tetramethyl-2-(2-methyl-4-((3-methyloxetan-3-yl)methoxy)phenyl)-1,3,2-dioxaborolane was prepared from 3-(4-bromo-3-methylphenoxymethyl)-3-methyloxetane and bis(pinacolato)diboron following General Procedure A, using PdCl$_2$(dppf).CH$_2$Cl$_2$ as the palladium catalyst, KOAc in place of K$_2$CO$_3$ and DMSO as solvent in place of dioxane/water. LC/MS: mass calcd. for C$_{18}$H$_{27}$BO$_4$: 318.22, found: 319.2 [M+H]$^+$.

(C) (3S)-Ethyl 3-(4-((3-(2-methyl-4-((3-methyloxetan-3-yl)methoxy)phenyl)benzo[b]-thiophen-5-yl)methoxy)phenyl)hex-4-ynoate was prepared from 4,4,5,5-tetramethyl-2-(2-methyl-4-((3-methyloxetan-3-yl)methoxy)phenyl)-1,3,2-dioxaborolane and (3S)-ethyl 3-(4-((3-bromobenzo[b]thiophen-5-yl)methoxy)phenyl)hex-4-ynoate (from Example 11E) following General Procedure A using PdCl$_2$(dppf).CH$_2$Cl$_2$ as the palladium catalyst and Cs$_2$CO$_3$ in place of K$_2$CO$_3$. LC/MS: mass calcd. for C$_{35}$H$_{36}$O$_5$S: 568.72, found: 569.2 [M]$^+$.

(D) (3S)-3-(4-((3-(2-Methyl-4-((3-methyloxetan-3-yl)methoxy)phenyl)benzo[b]thiophen-5-yl)methoxy)phenyl)hex-4-ynoic acid (Cpd 14) was prepared from (3S)-ethyl 3-(4-((3-(2-methyl-4-((3-methyloxetan-3-yl)methoxy)phenyl)benzo[b]-thiophen-5-yl)methoxy)phenyl)hex-4-ynoate following General Procedure C using LiOH as base, EtOH in place of MeOH and 1N HCl for reaction acidification. Product purification was accomplished by preparative HPLC on a preparative C18, 5µ column (19×100 mm) using anacetonitrile/water (0.5% TFA) gradient (65-95%). $^1$H NMR (CD$_3$OD) δ 7.96 (d, J=8.0 Hz, 1H), 7.47 (d, J=6.8 Hz, 1H), 7.40-7.42 (m, 2H), 7.28 (d, J=8.4 Hz, 2H), 7.19 (d, J=8.4 Hz, 1H), 6.99 (s, 1H), 6.90-6.94 (m, 3H), 5.16 (s, 2H), 4.73 (d, J=5.6 Hz, 2H), 4.50 (d, J=6.0 Hz, 2H), 4.12 (s, 2H), 3.95-4.05 (m, 1H), 2.57-2.61 (m, 2H), 2.01 (s, 3H), 1.81 (s, 3H), 1.49 (s, 3H). LC/MS: mass calcd. for C$_{33}$H$_{32}$O$_5$S: 540.67, found: 539.2 [M−H]$^-$.

Example 15

(3S)-3-(4-((3-(2-Methyl-4-(tetrahydro-2H-pyran-4-yloxy)phenyl)benzo[b]thiophen-5-yl)methoxy)phenyl)hex-4-ynoic acid, Cpd 15

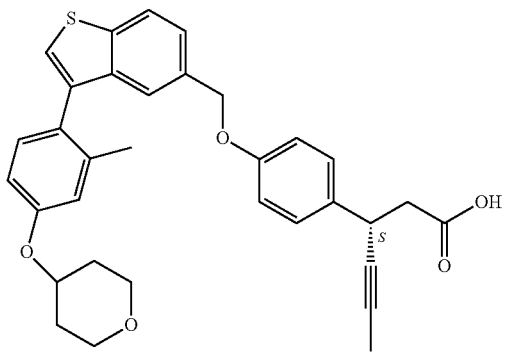

(A) 4-(4-Bromo-3-methylphenoxy)-tetrahydro-2H-pyran was prepared from 4-bromo-3-methylphenol and oxan-4-ol following General Procedure B using PPh$_3$ and DBAD at a reaction temperature of 50° C. overnight. $^1$H NMR (CDCl$_3$) δ 7.41 (d, J=8.6 Hz, 1H), 6.81 (d, J=3.0 Hz, 1H), 6.62 (dd, J=8.7, 3.0 Hz, 1H), 4.39-4.47 (m, 1H), 3.93-4.00 (m, 2H), 3.53-3.60 (m, 2H), 2.35 (s, 3H), 1.95-2.03 (m, 2H), 1.70-1.82 (m, 2H); LC/MS: Calcd. for C$_{12}$H$_{15}$BrO$_2$: 271.2, found: 271.0 [M]$^+$, 273.0 [M+2]$^+$.

(B) 4,4,5,5-Tetramethyl-2-(2-methyl-4-(tetrahydro-2H-pyran-4-yloxy)phenyl)-1,3,2-dioxaborolane was prepared from 4-(4-bromo-3-methylphenoxy)-tetrahydro-2H-pyran and bis(pinacolato)diboron following General Procedure A, using PdCl$_2$(dppf)CH$_2$Cl$_2$ as the palladium catalyst, KOAc in place of K$_2$CO$_3$ and a reaction temperature of 70° C. overnight. LC/MS: mass calcd. for C$_{18}$H$_{27}$BO$_4$: 318.2, found: 319.2 [M]$^+$.

(C) 3-(2-Methyl-4-(tetrahydro-2H-pyran-4-yloxy)phenyl)benzo[b]thiophene-5-carbaldehyde was prepared from 3-bromobenzo[b]thiophene-5-carbaldehyde (from Example 13D) and 4,4,5,5-tetramethyl-2-[2-methyl-4-(oxan-4-yloxy)phenyl]-1,3,2-dioxaborolane following General Procedure A using PdCl$_2$(dppf).CH$_2$Cl$_2$ as the palladium catalyst and Cs$_2$CO$_3$ in place of K$_2$CO$_3$. LC/MS: mass calcd. for C$_{21}$H$_{20}$O$_3$S: 352.45, found: 353.1 [M+H]$^+$.

(D) (3-(2-Methyl-4-(tetrahydro-2H-pyran-4-yloxy)phenyl)benzo[b]thiophen-5-yl)methanol was prepared from 3-(2-methyl-4-(tetrahydro-2H-pyran-4-yloxy)phenyl)benzo[b]thiophene-5-carbaldehyde following General Procedure F. LC/MS: mass calcd. for C$_{21}$H$_{22}$O$_3$S: 354.46, found: 355.1 [M+H]$^+$.

(E) 4-(4-(5-(Chloromethyl)benzo[b]thiophen-3-yl)-3-methylphenoxy)-tetrahydro-2H-pyran was prepared from (3-(2-methyl-4-(tetrahydro-2H-pyran-4-yloxy)phenyl)benzo[b]thiophen-5-yl)methanol following General Procedure D.

(F) (3S)-Ethyl 3-(4-((3-(2-methyl-4-(tetrahydro-2H-pyran-4-yloxy)phenyl)benzo[b]thiophen-5-yl)methoxy)phenyl)hex-4-ynoate was prepared from 4-(4-(5-(chloromethyl)benzo[b]thiophen-3-yl)-3-methylphenoxy)-tetrahydro-2H-pyran and (3S)-ethyl 3-(4-hydroxyphenyl)hex-4-ynoate (available from Synnovator, Inc., Research Triangle Park, N.C.; Cat. #PB05708) following General Procedure E using DMF as solvent at a reaction temperature of 60° C. for 1 h. LC/MS: mass calcd. for C$_{35}$H$_{36}$O$_5$S: 568.72, found: 569.2 [M]$^+$.

(G) (3S)-3-(4-((3-(2-Methyl-4-(tetrahydro-2H-pyran-4-yloxy)phenyl)benzo[b]thiophen-5-yl)methoxy)phenyl)hex-4-ynoic acid (Cpd 15) was prepared from (3S)ethyl 3-(4-((3-(2-methyl-4-(tetrahydro-2H-pyran-4-yloxy)phenyl)benzo[b]thiophen-5-yl)methoxy)phenyl)hex-4-ynoate following General Procedure C using LiOH as base and 1N HCl for reaction acidification. $^1$H NMR (DMSO-d$_6$) δ 12.35 (br. s, 1H), 8.00-8.04 (m, 1H), 7.65 (s, 1H), 7.42-7.49 (m, 2H), 7.23-7.26 (m, 2H), 7.14-7.17 (m, 1H), 6.98-6.99 (m, 1H), 6.90-6.93 (m, 3H), 5.17 (s, 2H), 4.60-4.66 (m, 1H), 3.84-3.95 (m, 3H), 3.47-3.55 (m, 2H), 2.56-2.59 (m, 2H), 1.99-2.05 (m, 5H), 1.76 (s, 3H), 1.56-1.68 (m, 2H). LC/MS: mass calcd. for C$_{33}$H$_{32}$O$_5$S: 540.67, found: 541.2 [M+H]$^+$.

Example 16

(3S)-3-(4-((3-(4-(2-Methoxyethoxy)-2-methylphenyl)benzo[b]thiophen-5-yl)methoxy)phenyl)hex-4-ynoic acid, Cpd 16

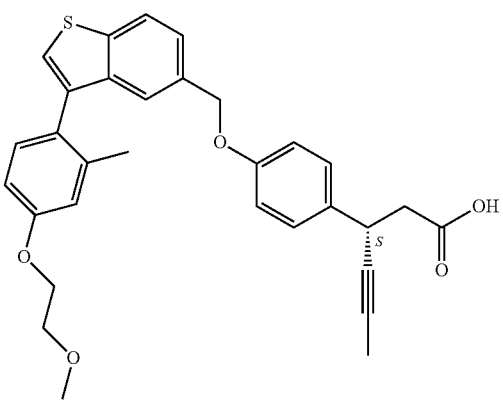

(A) A mixture of 4-bromo-3-methylphenol (5 g, 26.7 mmol), 1-bromo-2-methoxyethane (4.4 g, 31.7 mmol) and K$_2$CO$_3$ (15 g, 108.5 mmol) in MeCN (100 mL) was stirred overnight at 80° C. After cooling to rt, the reaction was filtered and the filtrate was concentrated under reduced pressure to afford 1-bromo-4-(2-methoxyethoxy)-2-methylbenzene as a yellow oil. $^1$H NMR (CDCl$_3$) δ 7.38 (d, J=8.8 Hz, 1H), 6.81 (d, J=2.8 Hz, 1H), 6.63 (dd, J=8.4, 2.8 Hz, 1H), 4.06 (t, J=4.8 Hz, 2H), 3.72 (t, J=4.8 Hz, 2H), 3.43 (s, 3H), 2.34 (s, 3H).

(B) 2-(4-(2-Methoxyethoxy)-2-methylphenyl)-4,4,5,5-tetramethyl-1,3,2-dioxaborolane was prepared from 1-bromo-4-(2-methoxyethoxy)-2-methylbenzene and bis(pinacolato)diboron following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{16}$H$_{25}$BO$_4$: 292.18, found: 293.2 [M±H]$^+$.

(C) 3-(4-(2-Methoxyethoxy)-2-methylphenyl)benzo[b]thiophene-5-carbaldehyde was prepared from 2-(4-(2-methoxyethoxy)-2-methylphenyl)-4,4,5,5-tetramethyl-1,3,2-dioxaborolane and 3-bromobenzo[b]thiophene-5-carbaldehyde (from Example 13D) following General Procedure A, using PdCl$_2$(dppf).CH$_2$Cl$_2$ as the palladium catalyst and Cs$_2$CO$_3$ in place of K$_2$CO$_3$. $^1$H NMR (CDCl$_3$) δ 10.02 (s, 1H), 8.02-8.04 (m, 1H), 7.88-7.90 (m, 2H), 7.37 (s, 1H), 7.20-7.26 (m, 1H), 6.83-6.94 (m, 2H), 4.19-4.21 (m, 2H), 3.37-3.82 (m, 2H), 3.49 (s, 3H), 2.14 (s, 3H).

(D) (3-(4-(2-Methoxyethoxy)-2-methylphenyl)benzo[b]thiophen-5-yl)methanol was prepared 3-(4-(2-methoxyethoxy)-2-methylphenyl)benzo[b]thiophene-5-carbaldehyde following General Procedure F. LC/MS: mass calcd. for C$_{19}$H$_{20}$O$_3$S: 328.43, found: 311.0 [M−OH]$^+$.

(E) 5-(Chloromethyl)-3-(4-(2-methoxyethoxy)-2-methylphenyl)benzo[b]thiophene was prepared from (3-(4-(2-methoxyethoxy)-2-methylphenyl)benzo[b]thiophen-5-yl)methanol following General Procedure D. LC/MS: mass calcd. for C$_{19}$H$_{19}$ClO$_2$S: 346.87, found: 347.1 [M]$^+$.

(F) (3S)-Ethyl 3-(4-((3-(4-(2-methoxyethoxy)-2-methylphenyl)benzo[b]thiophen-5-yl)methoxy)phenyl)hex-4-ynoate was prepared from 5-(chloromethyl)-3-(4-(2-methoxyethoxy)-2-methylphenyl)benzo[b]thiophene and (3S)-ethyl 3-(4-hydroxyphenyl)hex-4-ynoate (available from Synnovator, Inc., Research Triangle Park, N.C.; Cat. #PB05708) following General Procedure E. LC/MS: mass calcd. for C$_{33}$H$_{34}$O$_5$S: 542.69, found: 543.2 [M+H]$^+$.

(G) (3S)-3-(4-((3-(4-(2-Methoxyethoxy)-2-methylphenyl)benzo[b]thiophen-5-yl)methoxy)phenyl)hex-4-ynoic acid (Cpd 16) was prepared from (3S)-ethyl 3-(4-((3-(4-(2-methoxyethoxy)-2-methylphenyl)benzo[b]thiophen-5-yl)methoxy)phenyl)hex-4-ynoate following General Procedure C using LiOH as base, EtOH in place of MeOH and 1N HCl for reaction acidification. $^1$H NMR (DMSO-d$_6$) δ 8.06 (d, J=8.4 Hz, 1H), 7.65 (s, 1H), 7.47 (d, J=8.4 Hz, 1H), 7.41 (s, 1H), 7.23-7.25 (m, 2H), 7.16 (d, J=8.0 Hz, 1H), 6.86-6.96 (m, 4H), 5.17 (s, 2H), 4.13-4.16 (m, 2H), 3.90-3.95 (m, 1H), 3.68-3.70 (m, 2H), 3.33 (s, 3H), 2.54-2.58 (m, 2H), 2.05 (s, 3H), 1.76 (s, 3H). LC/MS: mass calcd. for C$_{31}$H$_{30}$O$_5$S: 514.63, found: 515.2 [M+H]$^+$.

Example 17

(3S)-3-{4-[(3-[(1,1-Dioxo-tetrahydro-2H-thiopyran-4-yl)methyl]-2-methylphenyl}-1-benzothiophen-5-yl)methoxy]phenyl hex-4-ynoic acid, Cpd 17

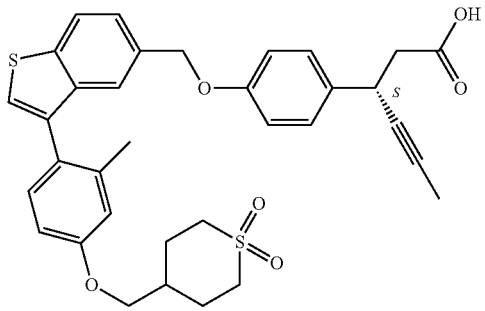

(A) To a solution of 4-(hydroxymethyl)tetrahydro-2H-thiane-1,1-dione (2.84 g, 17.29 mmol), 4-dimethylaminopyridine (633 mg, 5.18 mmol) and pyridine (4.10 g, 51.83 mmol) in CHCl$_3$ (20 mL) was added 4-methylbenzene-1-sulfonyl chloride (6.61 g, 34.67 mmol) in portions and the resulting mixture was stirred at rt for 2 d. Water (30 mL) was then added and the mixture was then extracted with CHCl$_3$ (3×30 mL). The combined organic extracts were washed with water (2×50 mL) and then concentrated under reduced pressure. Purification of the resultant residue by silica gel chromatography (0-10% EtOAc/petroleum ether) afforded (1,1-dioxotetrahydro-2H-thian-4-yl)methyl 4-methylbenzene-1-sulfonate (5.3 g, 96%) as a white solid. LC/MS: mass calcd. for C$_{13}$H$_{18}$O$_5$S$_2$: 318.41, found: 319.1 [M+H]$^+$.

(B) A mixture of ethyl (3S)-3-(4-[[3-(4-hydroxy-2-methylphenyl)-1-benzothiophen-5-yl]methoxy]phenyl)hex-4-ynoate (70 mg, 0.14 mmol) (from Example 11F), (1,1-dioxotetrahydro-2H-thiopyran-4-yl)methyl 4-methylbenzene-1-sulfonate (55 mg, 0.17 mmol) and Cs$_2$CO$_3$ (94 mg, 0.29 mmol) in MeCN (5 mL) was stirred overnight at 50° C. Water (20 mL) was then added, the mixture was extracted with EtOAc (3×15 mL) and the combined organic extracts were dried (Na$_2$SO$_4$) and concentrated under reduced pressure. Purification of the resultant residue by silica gel chromatography (0-25% EtOAc/petroleum ether) afforded ethyl (3S)-3-{4-[(3-{4-[(1,1-dioxotetrahydro-2H-thiopyran-4-yl)methoxy]-2-methylphenyl}-1-benzothiophen-5-yl)methoxy]phenyl}hex-4-ynoate (63 mg, 69.1% yield) as a colorless oil. LC/MS: mass calcd. for C$_{36}$H$_{38}$O$_6$S$_2$: 630.81, found: 631.2 [M]$^+$.

(C) (3S)-3-{4-[(3-{4-[(1,1-Dioxo-tetrahydro-2H-thiopyran-4-yl)methoxy]-2-methylphenyl}-1-benzothiophen-5-yl)methoxy]phenyl}hex-4-ynoic acid (Cpd 17) was prepared from ethyl (3S)-3-{4-[(3-{4-[(1,1-dioxo-tetrahydro-2H-thiopyran-4-yl)methoxy]-2-methylphenyl}-1-benzothiophen-5-yl)methoxy]phenyl}hex-4-ynoate following General Procedure C using LiOH as base, EtOH in place of MeOH and 2N HCl for reaction acidification. $^1$H NMR (DMSO-d$_6$) δ 8.06 (d, J=8.4 Hz, 1H), 7.63 (s, 1H), 7.48 (d, J=8.8 Hz, 1H), 7.41 (s, 1H), 7.24 (d, J=8.4 Hz, 2H), 7.17 (d, J=8.4 Hz, 1H), 6.88-7.00 (m, 4H), 5.16 (s, 2H), 3.93-3.95 (m, 3H), 3.18-3.24 (m, 2H), 3.08-3.11 (m, 2H), 2.57-2.59 (m, 2H), 2.12-2.19 (m, 3H), 2.05 (s, 3H), 1.76-1.84 (m, 5H). LC/MS: mass calcd. for C$_{34}$H$_{34}$O$_6$S$_2$: 602.76, found: 603.2 [M]$^+$.

Example 18

(3S)-3-{4-[(3-{2-Methyl-4-[(3-methyl-1,1-dioxo-thietane-3-yl)methoxy]phenyl}-1-benzothiophen-5-yl)methoxy]phenyl}hex-4-ynoic acid, Cpd 18

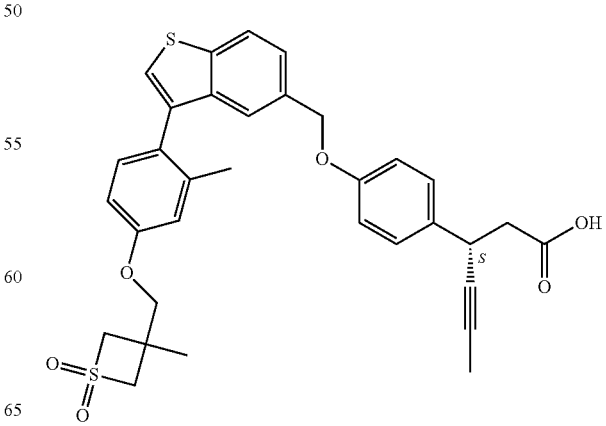

(A) To an ice-cooled solution of 4-bromo-3-methylphenol (300 mg, 1.60 mmol), (3-methylthietan-3-yl)methanol (300 mg, 2.54 mmol) and (n-Bu)$_3$P (810 mg, 4.02 mmol) in toluene (10 mL) was added ADDP (1020 mg, 4.07 mmol). Upon completion of addition, the reaction mixture was warmed to 60° C. and stirred for 2 h. The reaction was treated with satd. aq. NH$_4$Cl (50 mL), extracted with EtOAc (2×50 mL) and the combined organic extracts were concentrated under reduced pressure. Purification of the resultant residue by silica gel chromatography (0-2% EtOAc/petroleum ether) afforded 3-((4-bromo-3-methylphenoxy)methyl)-3-methylthietane (0.67 g, crude) as a white solid. $^1$H NMR (CDCl$_3$) δ 7.36-7.42 (m, 1H), 6.84-6.85 (m, 1H), 6.63-6.67 (m, 1H), 3.90 (s, 2H), 3.18 (d, J=6.3 Hz, 2H), 2.95 (d, J=6.3 Hz, 2H), 2.37 (s, 3H), 1.46 (s, 3H).

(B) To a solution of 3-((4-bromo-3-methylphenoxy)methyl)-3-methylthietane (570 mg, 1.37 mmol) and Na$_2$WO$_4$2H$_2$O (110 mg, 0.35 mmol) in MeOH (50 mL) was added 30% H$_2$O$_2$ (1.92 g, 16.94 mmol) in drop-wise fashion, and the resulting mixture was stirred at rt for 2 h. The mixture was then concentrated under reduced pressure and purified directly by silica gel chromatography (0-10% EtOAc/petroleum ether) to afford 3-(4-bromo-3-methylphenoxymethyl)-3-methylthietane-1,1-dioxide (412 mg, 94% yield) as a colorless oil. $^1$H NMR (CDCl$_3$) δ 7.41-7.44 (m, 1H), 6.82-6.83 (m, 1H), 6.61-6.65 (m, 1H), 4.20-4.25 (m, 2H), 3.97 (s, 2H), 3.83-3.88 (m, 2H), 2.37 (s, 3H), 1.60 (s, 3H).

(C) 3-Methyl-3-[3-methyl-4-(tetramethyl-1,3,2-dioxaborolan-2-yl)phenoxymethyl]-thietane-1,1-dioxide was prepared from 3-(4-bromo-3-methylphenoxymethyl)-3-methylthietane-1,1-dioxide and bis(pinacolato)diboron following General Procedure A, using PdCl$_2$(dppf).CH$_2$Cl$_2$ as the palladium catalyst, dioxane as solvent and Cs$_2$CO$_3$ in place of K$_2$CO$_3$ at a reaction temperature of 80° C. overnight. $^1$H NMR (CDCl$_3$) δ 7.44-7.46 (m, 1H), 6.85-6.86 (m, 1H), 6.64-6.67 (m, 1H), 4.23-4.29 (m, 2H), 3.99 (s, 2H), 3.85-3.90 (m, 2H), 2.37 (s, 3H), 1.63 (s, 3H), 1.35 (s, 12H).

(D) 3-{2-Methyl-4-[(3-methyl-1,1-dioxo-thietan-3-yl)methoxy]phenyl}-1-benzothiophene-5-carbaldehyde was prepared from 3-methyl-3-[3-methyl-4-(tetramethyl-1,3,2-dioxaborolan-2-yl)phenoxymethyl]-thietane-1,1-dioxide and 3-bromobenzo[b]thiophene-5-carbaldehyde (from Example 13D) following General Procedure A, using PdCl$_2$(dppf).CH$_2$Cl$_2$ as the palladium catalyst and Cs$_2$CO$_3$ in place of K$_2$CO$_3$ at a reaction temperature of 80° C. overnight. $^1$H NMR (CDCl$_3$) δ 7.44-7.46 (m, 1H), 6.85-6.86 (m, 1H), 6.64-6.67 (m, 1H), 4.23-4.29 (m, 2H), 3.99 (s, 2H), 3.85-3.90 (m, 2H), 2.37 (s, 3H), 1.63 (s, 3H), 1.35 (s, 12H).

(E) 3-{4-[5-(Hydroxymethyl)-1-benzothiophen-3-yl]-3-methylphenoxymethyl}-3-methyl-thietane-1,1-dione was prepared from 3-{2-methyl-4-[(3-methyl-1,1-dioxo-thietan-3-yl)methoxy]phenyl}-1-benzothiophene-5-carbaldehyde following General Procedure F. LC/MS: mass calcd. for C$_{21}$H$_{22}$O$_4$S$_2$: 402.53, found: 403.1 [M+H]$^+$.

(F) 3-{4-[5-(Chloromethyl)-1-benzothiophen-3-yl]-3-methylphenoxymethyl}-3-methyl-thietane-1,1-dione was prepared from 3-{4-[5-(hydroxymethyl)-1-benzothiophen-3-yl]-3-methylphenoxymethyl}-3-methyl-thietane-1,1-dione following General Procedure D. LC/MS: mass calcd. for C$_{21}$H$_{21}$ClO$_3$S$_2$: 420.97; found: 421.1 [M]$^+$.

(G) Ethyl (3S)-3-{4-[(3-{2-methyl-4-[(3-methyl-1,1-dioxo-thietan-3-yl)methoxy]phenyl}-1-benzothiophen-5-yl)methoxy]phenyl}hex-4-ynoate was prepared from 3-{4-[5-(chloromethyl)-1-benzothiophen-3-yl]-3-methylphenoxymethyl}-3-methyl-thietane-1,1-dione and (3S)-ethyl 3-(4-hydroxyphenyl)hex-4-ynoate (available from Synnovator, Inc., Research Triangle Park, N.C.; Cat. #PB05708) following General Procedure E at a reaction temperature of 60° C. for 4 h. LC/MS: mass calcd. for C$_{35}$H$_{36}$O$_6$S$_2$: 616.79, found: 617.2 [M]$^+$.

(H) (3S)-3-{4-[(3-{2-Methyl-4-[(3-methyl-1,1-dioxo-thietane-3-yl)methoxy]phenyl}-1-benzothiophen-5-yl)methoxy]phenyl}hex-4-ynoic acid (Cpd 18) was prepared from ethyl (3S)-3-{4-[(3-{2-methyl-4-[(3-methyl-1,1-dioxo-thietan-3-yl)methoxy]phenyl}-1-benzothiophen-5-yl)methoxy]phenyl}hex-4-ynoate following General Procedure C using LiOH as base, EtOH in place of MeOH and 1N HCl for reaction acidification. Product purification was accomplished by preparative HPLC on a preparative C18, 5μ column (19×100 mm) using an acetonitrile/water (0.5% TFA) gradient (65-73%). $^1$H NMR (DMSO-d$_6$+D$_2$O) δ 8.06 (d, J=8.4 Hz, 1H), 7.63 (s, 1H), 7.47 (d, J=8.4 Hz, 1H), 7.40 (s, 1H), 7.18-7.26 (m, 3H), 7.00-7.01 (m, 1H), 6.91-6.95 (m, 3H), 5.17 (s, 2H), 4.21-4.26 (m, 2H), 4.11 (s, 2H), 3.90-4.02 (m, 3H), 2.57-2.60 (m, 2H), 2.06 (s, 3H), 1.76 (s, 3H), 1.52 (s, 3H). LC/MS: mass calcd. for C$_{33}$H$_{32}$O$_6$S$_2$: 588.73, found: 589.2 [M]$^+$.

Example 19

(3S)-3-(4-((3-(2-Chlorophenyl)benzo[b]thiophen-5-yl)methoxy)phenyl)hex-4-ynoic acid, Cpd 19

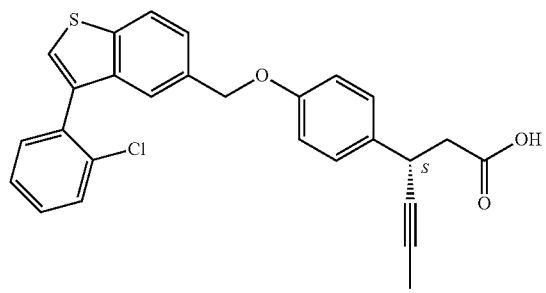

(A) (3S)-Ethyl 3-(4-((3-(2-chlorophenyl)benzo[b]thiophen-5-yl)methoxy)phenyl)hex-4-ynoate was prepared from (3S)-ethyl 3-(4-((3-bromobenzo[b]thiophen-5-yl)methoxy)phenyl)hex-4-ynoate (from Example 11E) and 2-chlorophenylboronic acid following General Procedure A, using PdCl$_2$(dppf).CH$_2$Cl$_2$ as the palladium catalyst and Cs$_2$CO$_3$ in place of K$_2$CO$_3$ at a reaction temperature of 90° C. overnight. LC/MS: mass calcd. for C$_{29}$H$_{25}$ClO$_3$S: 489.02, found: 489.1 [M]$^+$.

(B) (3S)-3-(4-((3-(2-Chlorophenyl)benzo[b]thiophen-5-yl)methoxy)phenyl)hex-4-ynoic acid (Cpd 19) was prepared from (3S)-ethyl 3-(4-((3-(2-chlorophenyl)benzo[b]thiophen-5-yl)methoxy)phenyl)hex-4-ynoate following General Procedure C using LiOH as base, EtOH in place of MeOH and 1N HCl for reaction acidification. Product purification was accomplished by preparative HPLC on a preparative C18, 5μ column (19×100 mm) using an acetonitrile/water (0.5% TFA) gradient (40-95%). $^1$H NMR (DMSO-d$_6$) δ 8.09 (d, J=8.0 Hz, 1H), 7.86 (s, 1H), 7.64-7.66 (m, 1H), 7.47-7.53 (m, 5H), 7.24 (d, J=8.4 Hz, 2H), 6.92 (d, J=8.8 Hz, 2H), 5.17 (s, 2H), 3.90-3.93 (m, 1H), 2.57 (d, J=7.6 Hz, 2H), 1.76 (s, 3H). LC/MS: mass calcd. for C$_{27}$H$_{21}$ClO$_3$S: 460.97, found: 459.1 [M−H]$^-$, 461.1 [M−H+2]$^-$.

Example 20

(3S)-3-(4-((3-(2-Bromophenyl)benzo[b]thiophen-5-yl)methoxy)phenyl)hex-4-ynoic acid, Cpd 20

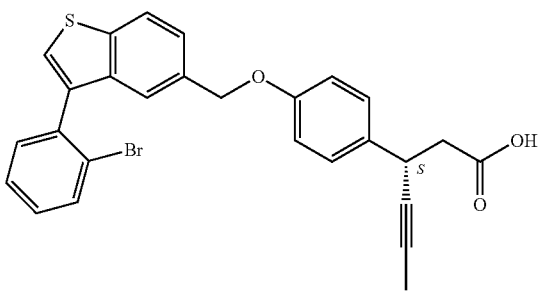

(A) 3-(2-Bromophenyl)benzo[b]thiophene-5-carbaldehyde was prepared from 3-bromobenzo[b]thiophene-5-carbaldehyde (from Example 13D) and 2-bromophenylboronic acid following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{15}$H$_9$BrOS: 317.20, found: 317.0 [M]$^+$, 319.0 [M+2]$^+$.

(B) (3-(2-Bromophenyl)benzo[b]thiophen-5-yl)methanol was prepared from 3-(2-bromophenyl)benzo[b]thiophene-5-carbaldehyde following General Procedure F. LC/MS: mass calcd. for C$_{15}$H$_{11}$BrOS: 319.22, found: 319.0 [M]$^+$, 321.0 [M+2]$^+$.

(C) 3-(2-Bromophenyl)-5-(chloromethyl)benzo[b]thiophene was prepared from (3-(2-bromophenyl)benzo[b]thiophen-5-yl)methanol following General Procedure D.

(D) (3S)-Ethyl 3-(4-((3-(2-bromophenyl)benzo[b]thiophen-5-yl)methoxy)phenyl)hex-4-ynoate was prepared from 3-(2-bromophenyl)-5-(chloromethyl)benzo[b]thiophene and (3S)-ethyl 3-(4-hydroxyphenyl)hex-4-ynoate (available from Synnovator, Inc., Research Triangle Park, N.C.; Cat. #PB05708) following General Procedure E at a reaction temperature of 50° C. for 2 h. LC/MS: mass calcd. for C$_{29}$H$_{25}$BrO$_3$S: 533.48, found: 533.1 [M]$^+$, 535.1 [M+H]$^+$.

(E) (3S)-3-(4-((3-(2-Bromophenyl)benzo[b]thiophen-5-yl)methoxy)phenyl)hex-4-ynoic acid (Cpd 20) was prepared from (3S)-ethyl 3-(4-((3-(2-bromophenyl)benzo[b]thiophen-5-yl)methoxy)phenyl)hex-4-ynoate following General Procedure C using LiOH as base, EtOH in place of MeOH and 2N HCl for reaction acidification. $^1$H NMR (DMSO-d$_6$) δ 8.08 (d, J=8.1 Hz, 1H), 7.80-7.85 (m, 2H), 7.40-7.56 (m, 5H), 7.24 (d, J=8.7 Hz, 2H), 6.92 (d, J=8.4 Hz, 2H), 5.16 (s, 2H), 3.89-3.94 (m, 1H), 2.58 (d, J=7.5 Hz, 2H), 1.77 (s, 3H). LC/MS: mass calcd. for C$_{27}$H$_{21}$BrO$_3$S: 505.42, found: 505.0 [M]$^-$, 507.0, [M+2]$^-$.

Example 21

(3S)-3-(4-((3-(2-(Trifluoromethyl)phenyl)benzo[b]thiophen-5-yl)methoxy)phenyl)hex-4-ynoic acid, Cpd 21

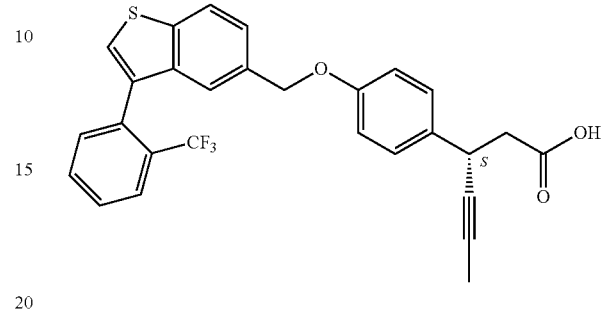

(A) (3S)-Ethyl 3-(4-((3-(2-(trifluoromethyl)phenyl)benzo[b]thiophen-5-yl)methoxy)phenyl)hex-4-ynoate was prepared from 2-(trifluoromethyl)phenylboronic acid and (3S)-ethyl 3-(4-((3-bromobenzo[b]thiophen-5-yl)methoxy)phenyl)hex-4-ynoate (from Example 11E) following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{30}$H$_{25}$F$_3$O$_3$S: 522.58, found: 523.1 [M+H]$^+$.

(B) (3S)-3-(4-((3-(2-(Trifluoromethyl)phenyl)benzo[b]thiophen-5-yl)methoxy)phenyl)hex-4-ynoic acid (Cpd 21) was prepared from (3S)-ethyl 3-(4-((3-(2-(trifluoromethyl)phenyl)benzo[b]thiophen-5-yl)methoxy)phenyl)hex-4-ynoate following General Procedure C using LiOH as base, EtOH in place of MeOH, 2N HCl for reaction acidification and a reaction temperature of 30° C. overnight. $^1$H NMR (DMSO-d$_6$) δ 8.08 (d, J=8.4 Hz, 1H), 7.93 (d, J=7.6 Hz, 1H), 7.69-7.82 (m, 3H), 7.48-7.51 (m, 2H), 7.43 (s, 1H), 7.24 (d, J=8.8 Hz, 2H), 6.89 (d, J=8.4 Hz, 2H), 5.13 (s, 2H), 3.91-3.93 (m, 1H), 2.58-2.67 (m, 2H), 1.77 (s, 3H). LC/MS: mass calcd. for C$_{28}$H$_{21}$F$_3$O$_3$S: 494.52, found: 493.1 [M+H]$^+$.

Example 22

(3S)-3-(4-((3-(2-Methylpyridin-3-yl)benzo[b]thiophen-5-yl)methoxy)phenyl)hex-4-ynoic acid, Cpd 22

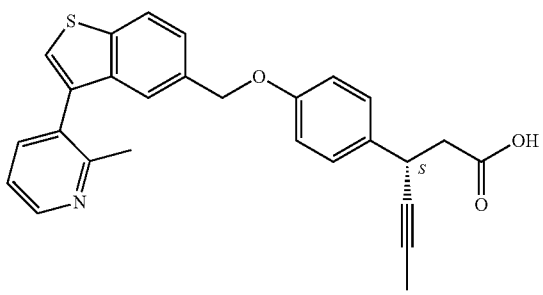

(A) (3S)-Ethyl 3-(4-((3-(2-methylpyridin-3-yl)benzo[b]thiophen-5-yl)methoxy)phenyl)hex-4-ynoate was prepared from (3S)-ethyl 3-(4-((3-bromobenzo[b]thiophen-5-yl)

methoxy)phenyl)hex-4-ynoate (from Example 11E) and (2-methylpyridin-3-yl)boronic acid following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{29}$H$_{27}$NO$_3$S: 469.59, found: 470.2 [M+H]$^+$.

(B) (3S)-3-(4-((3-(2-Methylpyridin-3-yl)benzo[b]thiophen-5-yl)methoxy)phenyl)hex-4-ynoic acid (Cpd 22) was prepared from (3S)-ethyl 3-(4-((3-(2-methylpyridin-3-yl)benzo[b]thiophen-5-yl)methoxy)phenyl)hex-4-ynoate following General Procedure C using LiOH as base, EtOH in place of MeOH and 2N HCl for reaction acidification. $^1$H NMR (DMSO-d$_6$) δ 12.24 (s, 1H), 8.56 (dd, J=1.6, 4.8 Hz, 1H), 8.11 (d, J=8.4 Hz, 1H), 7.85 (s, 1H), 7.68 (dd, J=1.6, 7.6 Hz, 1H), 7.51 (d, J=8.4 Hz, 1H), 7.44 (s, 1H), 7.34-7.38 (m, 1H), 7.24 (d, J=8.4 Hz, 2H), 6.91 (d, J=8.8 Hz, 2H), 5.18 (s, 2H), 3.90-3.92 (m, 1H), 2.56 (d, J=7.6 Hz, 2H), 2.29 (s, 3H), 1.77 (s, 3H). LC/MS: mass calcd. for C$_{27}$H$_{23}$NO$_3$S: 441.54, found: 442.1 [M+H]$^+$.

Example 23

(3S)-3-(4-(((3-(2-Methylphenyl)benzo[b]thiophen-5-yl)oxy)methyl)phenyl) hex-4-ynoic acid, Cpd 23

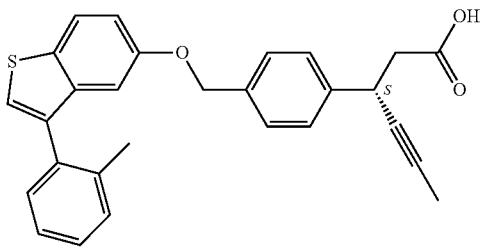

(A) To an ice-cold solution of 1-benzothiophen-5-ol (4.2 g, 27.96 mmol) in pyridine (50 mL) was added acetyl chloride (2.4 g, 30.57 mmol) in drop-wise fashion. The resulting solution was allowed to stir at rt for 2 h. The reaction was then quenched by the addition of water (50 mL) and the resulting solution was extracted with ethyl acetate (3×50 mL) and the organic layers combined and concentrated under reduced pressure. The residue thus obtained was purified by silica gel chromatography (0-10% EtOAc/petroleum ether) to obtain benzo[b]thiophen-5-yl acetate as a white solid (4.8 g, 89% yield). LC/MS: Calcd. for C$_{10}$H$_8$O$_2$S: 192.23, found: 193.0 [M+H]$^+$.

(B) To a solution of benzo[b]thiophen-5-yl acetate (5.8 g, 30.17 mmol) in AcOH (30 mL) was added a solution of Br$_2$ (5.3 g, 33.16 mmol) in AcOH (70 mL) in dropwise fashion and the resulting solution was stirred at rt for 1 h. Water (100 mL) was then added and the resulting solution was extracted with ethyl acetate (3×100 mL). The combined organic extracts were concentrated under reduced pressure and the residue thus obtained was purified by silica gel chromatography (0-10% EtOAc/petroleum ether) to provide 3-bromobenzo[b]thiophen-5-yl acetate as a white solid (3 g, 37% yield). LC/MS: Calcd. for C$_{10}$H$_7$BrO$_2$S: 271.13, found: 270.9 [M$^+$], 272.9 [M+2]$^+$.

(C) A mixture of 3-bromo-1-benzo[b]thiophen-5-yl acetate (203 mg, 0.75 mmol) and K$_2$CO$_3$ (516 mg, 3.73 mmol) in methanol (20 mL) and water (2 mL) was stirred at rt for 2 h. The reaction was then quenched by the addition of satd. aq. NH$_4$Cl (30 mL) and the resulting solution was extracted with ethyl acetate (3×10 mL). The combined organic extracts were dried (Na$_2$SO$_4$) and concentrated under reduced pressure to afford 3-bromo-1-benzo[b]thiophen-5-ol as a white solid (172 mg, crude) that was used directly without further purification. $^1$H NMR (CDCl$_3$) δ 7.69-7.71 (m, 1H), 7.45 (s, 1H), 7.24 (s, 1H), 7.98-7.00 (m, 1H).

(D) To an ice-cooled solution of (3S)-ethyl 3-(4-hydroxyphenyl)hex-4-ynoate (5.2 g, 22.39 mmol) (available from Synnovator, Inc., Research Triangle Park, N.C.; Cat. #PB05708) and triethylamine (6.8 g, 67.20 mmol) in DCM (200 mL) was added trifluoromethanesulfonic anhydride (7.55 g, 26.76 mmol) in drop-wise fashion. After stirring for 2 h at rt, the reaction was then quenched by the addition of 400 mL of satd. aq. NaHCO$_3$. The resulting solution was extracted with DCM (2×200 mL) and the combined organic extracts were dried (Na$_2$SO$_4$) and concentrated under reduced pressure to afford (3S)-ethyl 3-(4-(trifluoromethylsulfonyloxy)phenyl)hex-4-ynoate as dark red oil (8.1 g, crude), which was used directly without further purification.

(E) To a mixture of (3S)-ethyl 3-(4-(trifluoromethylsulfonyloxy)phenyl)hex-4-ynoate (8.1 g, 22.23 mmol), Pd$_2$(dba)$_3$(2 g, 2.18 mmol), RuPhos (2.6 g, 5.5 mmol) and (Na$_2$CO$_3$) (4.7 g, 44.34 mmol) in dioxane (200 mL) and water (20 mL) was added potassium acetoxymethyltrifluoroborate (8 g, 41.24 mmol). The resulting solution was stirred for 30 min at 50° C. and then for 3 h at 100° C. After cooling to rt, water (1 L) was added and the resulting solution was extracted with EtOAc (2×1 L) of ethyl acetate and the combined organic extracts were concentrated under reduced pressure. The residue thus obtained was purified by silica gel chromatography (0-10% ethyl acetate/petroleum ether) to afford (3S)-ethyl 3-(4-(hydroxymethyl)phenyl)hex-4-ynoate (2.6 g, 46%) as a pale yellow oil. $^1$H NMR (DMSO-d$_6$) δ 7.24-7.33 (m, 4H), 5.14 (t, J=5.7 Hz, 1H), 4.46 (d, J=5.7 Hz, 2H), 3.99-4.09 (m, 3H), 2.70 (d, J=7.5 Hz, 2H), 1.77 (s, 3H), 1.15 (t, J=3.0 Hz, 3H).

(F) (3S)-Ethyl 3-(4-((3-bromobenzo[b]thiophen-5-yl)oxy)methyl)phenyl)hex-4-ynoate was prepared from 3-bromo-1-benzo[b]thiophen-5-ol and (3S)-ethyl 3-(4-(hydroxymethyl)phenyl)hex-4-ynoate following General Procedure B using (Bu)$_3$P and ADDP at a reaction temperature of 50° C. for 3 h. LC/MS: Calcd. for C$_{23}$H$_{21}$BrO$_3$S: 457.38, found: 457.1 [M]$^+$, 459.0 [M+2]$^+$.

(G) (3S)-Ethyl 3-(4-((3-(2-methylphenyl)benzo[b]thiophen-5-yl)oxy)methyl)phenyl)hex-4-ynoate was prepared from (3S)-ethyl 3-(4-(((3-bromobenzo[b]thiophen-5-yl)oxy)methyl)-phenyl)hex-4-ynoate and (2-methylphenyl)boronic acid following General Procedure A, using PdCl$_2$(dppf) .CH$_2$Cl$_2$ as the palladium catalyst, Cs$_2$CO$_3$ in place of K$_2$CO$_3$ and a reaction temperature of 80° C. for 2 h. LC/MS: Calcd. for C$_{30}$H$_{28}$O$_3$S: 468.61, found: 469.2 [M+H]$^+$.

(H) (3S)-3-(4-((3-(2-Methylphenyl)benzo[b]thiophen-5-yl)oxy)methyl)phenyl)hex-4-ynoic acid (Cpd 23) was prepared from (3S)-ethyl 3-(4-(((3-(2-methylphenyl)benzo[b]thiophen-5-yl)oxy)methyl)phenyl)hex-4-ynoate following General Procedure C, using LiOH as base, EtOH in place of MeOH, a reaction temperature of 30° C. overnight and 2N HCl for reaction acidification. $^1$H NMR (DMSO-d$_6$) δ 7.94 (d, J=8.8 Hz, 1H), 7.66 (s, 1H), 7.28-7.41 (m, 7H), 7.20 (d, J=7.6 Hz, 1H), 7.13 (d, J=2.4 Hz, 1H), 6.80 (s, 1H), 5.02 (s, 2H), 3.98-4.03 (m, 1H), 2.60-2.67 (m, 2H), 2.02 (s, 3H), 1.79 (s, 3H); LC/MS: Calcd. for C$_{28}$H$_{24}$O$_3$S: 440.55, found: 439.0 [M−H]$^+$.

Example 24

(3S)-3-(4-(((3-(2-Methyl-4-(3-(methylsulfonyl)propoxy)phenyl)benzo[b]thiophen-5-yl)oxy)methyl)phenyl)hex-4-ynoic acid, Cpd 24

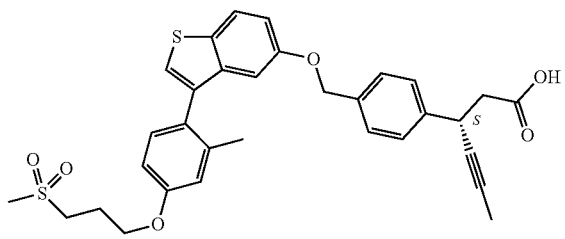

(A) To a mixture of 4-bromo-3-methylphenol (1 g, 5.35 mmol) and $K_2CO_3$ (1.1 g, 7.96 mmol) in DMF (10 mL) was added 3-(methylsulfonyl)propyl 4-methylbenzenesulfonate (1.72 g, 5.88 mmol) and the resultant mixture was stirred at 80° C. for 2 h. After cooling to rt, satd. aq. $NH_4Cl$ (10 mL) was added and the resultant solution was extracted with EtOAc (3×20 mL). The combined organic extracts were concentrated under reduced pressure and the residue thus obtained was purified by silica gel chromatography (0-30% ethyl acetate/petroleum ether) to afford 1-bromo-4-(3-methanesulfonylpropoxy)-2-methylbenzene (1.5 g, 91%) as a white solid. $^1$H NMR (CDCl$_3$) δ 7.40 (d, J=8.7 Hz, 1H), 6.78 (d, J=2.7 Hz, 1H), 6.59 (dd, J=3.0, 8.7 Hz, 1H), 4.06-4.16 (m, 2H), 3.24(t, J=7.8 Hz, 2H), 2.95 (s, 3H), 2.29-2.38(m, 5H).

(B) 2-[4-(3-Methanesulfonylpropoxy)-2-methylphenyl]-4,4,5,5-tetramethyl-1,3,2-dioxaborolane was prepared from 1-bromo-4-(3-methanesulfonylpropoxy)-2-methylbenzene and bis(pinacolato)diboron following General Procedure A, using PdCl$_2$(dppf).CH$_2$Cl$_2$ as the palladium catalyst and KOAc in place of $K_2CO_3$ at a reaction temperature of 90° C. overnight. LC/MS: mass calcd. for $C_{17}H_{27}BO_5S$: 354.3, found: 355.3 [M+H]$^+$.

(C) (3S)-Ethyl 3-(4-(((3-(2-methyl-4-(3-(methylsulfonyl)propoxy)phenyl)benzo[b]thiophen-5-yl)oxy)methyl)phenyl)hex-4-ynoate was prepared from (3S)-ethyl 3-(4-(((3-bromobenzo[b]thiophen-5-yl)oxy)methyl)phenyl)hex-4-ynoate (from Example 23F) and 2-[4-(3-methanesulfonylpropoxy)-2-methylphenyl]-4,4,5,5-tetramethyl-1,3,2-dioxaborolane following General Procedure A, using PdCl$_2$(dppf).CH$_2$Cl$_2$ as the palladium catalyst, Cs$_2$CO$_3$ in place of $K_2CO_3$ and a reaction temperature of 80° C. for 2 h. LC/MS: Calcd. for $C_{34}H_{36}O_6S_2$: 604.78, found: 605.2 [M]$^+$.

(D) (3S)-3-(4-(((3-(2-Methyl-4-(3-(methylsulfonyl)propoxy)phenyl)benzo[b]thiophen-5-yl)oxy)methyl)phenyl)hex-4-ynoic acid (Cpd 24) was prepared from (3S)-ethyl 3-(4-(((3-(2-methyl-4-(3-(methylsulfonyl)propoxy)phenyl)benzo[b]thiophen-5-yl)oxy)methyl)phenyl)hex-4-ynoate following General Procedure C, using LiOH as base, EtOH in place of MeOH, a reaction temperature of 30° C. overnight and 2N HCl for reaction acidification. $^1$H NMR (DMSO-d$_6$) δ 7.92 (d, J=7.6 Hz, 1H), 7.59 (s, 1H), 7.33-7.38 (m, 4H), 7.10-7.14 (m, 1H), 6.81-6.95 (m, 3H), 5.03 (s, 2H), 4.15 (t, J=6.0 Hz, 2H), 3.98-4.03 (m, 1H), 3.31 (t, J=7.6 Hz, 2H), 3.04 (s, 3H), 2.66 (d, J=8.0 Hz, 2H), 2.15-2.22 (m, 2H), 2.00 (s, 3H), 1.88 (s, 3H). LC/MS: Calcd. for $C_{32}H_{32}O_6S_2$: 576.72, found: 575.0 [M−H]$^−$.

Example 25

(3S)-3-(4-(((3-(4-(1,1-Dioxido-3,6-dihydro-2H-thiopyran-4-yl)-2-methylphenyl)-benzo[b]thiophen-5-yl)oxy)methyl)phenyl)hex-4-ynoic acid, Cpd 25

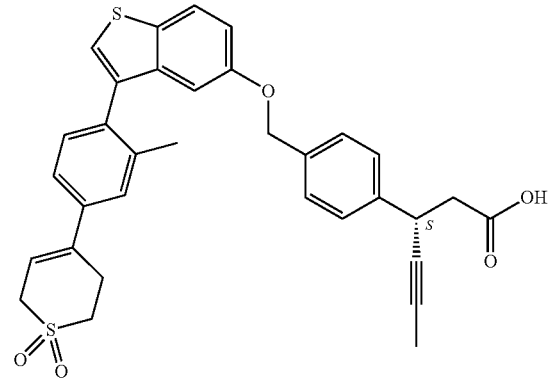

(A) (3S)-3-{4-[({3-[4-(1,1-dioxo-3,6-dihydro-2H-thiopyran-4-yl)-2-methylphenyl]-1-benzothiophen-5-yl}oxy)methyl]phenyl}hex-4-ynoate was prepared from (3S)-ethyl 3-(4-(((3-bromobenzo[b]thiophen-5-yl)oxy)methyl)phenyl)hex-4-ynoate (from Example 23F) and 4-(3-methyl-4-(4,4,5,5-tetramethyl-1,3,2-dioxaborolan-2-yl)phenyl)-3,6-dihydro-2H-thiopyran 1,1-dioxide (from Example 6C) following General Procedure A, using PdCl$_2$(dppf).CH$_2$Cl$_2$ as the palladium catalyst and Cs$_2$CO$_3$ in place of $K_2CO_3$. LC/MS: mass calcd. for $C_{35}H_{34}O_5S_2$: 598.77, found 599.1 [M]$^+$.

(B) (3S)-3-(4-(((3-(4-(1,1-dioxido-3,6-dihydro-2H-thiopyran-4-yl)-2-methylphenyl)-benzo[b]thiophen-5-yl)oxy)methyl)phenyl)hex-4-ynoic acid (Cpd 25) was prepared from (3S)-3-{4-[({3-[4-(1,1-dioxo-3,6-dihydro-2H-thiopyran-4-yl)-2-methylphenyl]-1-benzothiophen-5-yl}oxy)methyl]phenyl}hex-4-ynoate following General Procedure C, using LiOH as base, EtOH in place of MeOH, a reaction temperature of 30° C. overnight and 2N HCl for reaction acidification. $^1$14NMR (DMSO-d$_6$) δ 12.27 (br. s, 1H), 7.94 (d, J=8.8 Hz, 1H), 7.69 (s, 1H), 7.46 (s, 1H), 7.32-7.39 (m, 5H), 7.21 (d, J=8.0 Hz, 1H), 7.13 (dd, J=2.4, 8.8 Hz, 1H), 6.83 (d, J=2.4 Hz, 1H), 6.09 (d, J=4.4 Hz, 1H), 5.03 (s, 2H), 3.94-4.03 (m, 3H), 3.37-3.40 (m, 2H), 3.11-3.12 (m, 2H), 2.64 (d, J=7.6 Hz, 2H), 2.05 (s, 3H), 1.78 (s, 3H). LC/MS: Calcd. for $C_{33}H_{30}O_5S_2$: 570.72, found: 569.0 [M−H]$^−$.

Example 26

(3S)-3-(4-(((3-(4-(1,1-Dioxidotetrahydro-2H-thiopyran-4-yl)-2-methylphenyl)benzo[b]thiophen-5-yl)oxy)methyl)phenyl)hex-4-ynoic acid, Cpd 26

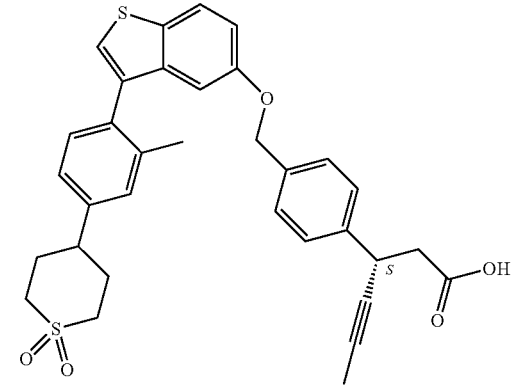

(A) A mixture of 4-(4-bromo-3-methylphenyl)-3,6-dihydro-2H-thiopyran-1,1-dioxide (301 mg, 1.00 mmol) (from Example 6B) and PtO$_2$ (23 mg, 0.1 mmol) in ethyl acetate (10 mL) was hydrogenated at rt at a pressure of about 50 psi overnight. The mixture was then filtered and the filtrate was concentrated under reduced pressure to afford 4-(4-bromo-3-methylphenyl)tetrahydro-2H-thiopyran 1,1-dioxide as a white solid (290 mg, 96%). $^1$H NMR (CDCl$_3$) δ 7.48 (d, J=8.1 Hz, 1H), 7.08-7.10 (m, 1H), 6.91 (d, J=8.1 Hz, 1H), 3.12-3.15 (m, 4H), 2.68-2.76 (m, 1H), 2.31-2.45 (m, 5H), 2.16-2.21 (m, 2H).

(B) 4-(3-Methyl-4-(4,4,5,5-tetramethyl-1,3,2-dioxaborolan-2-yl)phenyl)tetrahydro-2H-thiopyran 1,1-dioxide was prepared from 4-(4-bromo-3-methylphenyl)tetrahydro-2H-thiopyran 1,1-dioxide and bis(pinacolato)diboron following General Procedure A, using PdCl$_2$(dppf).CH$_2$Cl$_2$ as the palladium catalyst, KOAc in place of K$_2$CO$_3$ and dioxane as solvent. LC/MS: mass calcd. for C$_{18}$H$_{27}$BO$_4$S: 350.28, found 351.2 [M+H]$^+$.

(C) (3S)-Ethyl 3-(4-(((3-(4-(1,1-dioxidotetrahydro-2H-thiopyran-4-yl)-2-methylphenyl)benzo[b]thiophen-5-yl)oxy)methyl)phenyl)hex-4-ynoate was prepared from 4-(3-methyl-4-(4,4,5,5-tetramethyl-1,3,2-dioxaborolan-2-yl)phenyl)tetrahydro-2H-thiopyran 1,1-dioxide and (3S)-ethyl 3-(4-(((3-bromobenzo[b]thiophen-5-yl)oxy)methyl)phenyl)hex-4-ynoate (from Example 23F) following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{35}$H$_{36}$O$_5$S$_2$: 600.79, found 601.2 [M]$^{3O}$.

(D) (3S)-3-(4-(((3-(4-(1,1-Dioxidotetrahydro-2H-thiopyran-4-yl)-2-methylphenyl)benzo-[b]thiophen-5-yl)oxy) methyl)phenyl)hex-4-ynoic acid (Cpd 26) was prepared from (3S)-ethyl 3-(4-(((3-(4-(1,1-dioxidotetrahydro-2H-thiopyran-4-yl)-2-methylphenyl)benzo[b]thiophen-5-yl) oxy)methyl)phenyl)hex-4-ynoate following General Procedure C, using LiOH as base, EtOH in place of MeOH, a reaction temperature of 30° C. overnight and 2N HCl for reaction acidification. $^1$H NMR (DMSO-d$_6$) δ 7.93 (d, J=8.8 Hz, 1H), 7.63 (s, 1H), 7.32-7.37 (m, 4H), 7.25 (s, 1H), 7.11-7.18 (m, 3H), 6.81 (d, J=2.4 Hz, 1H), 5.03 (s, 2H), 4.00-4.01 (m, 1H), 3.35-3.40 (m, 2H), 3.13-3.16 (m, 2H), 2.95-3.05 (m, 1H), 2.64 (d, J=7.6 Hz, 2H), 2.16-2.20 (m, 4H), 2.03 (s, 3H), 1.78 (s, 3H). LC/MS: Calcd. for C$_{33}$H$_{32}$O$_5$S$_2$: 572.73, found: 571.0 [M−H]$^−$.

Example 27

(3S)-3-(4-(((3-(2,6-Dimethylphenyl)benzo[b]thiophen-5-yl)oxy)methyl)phenyl)hex-4-ynoic acid, Cpd 27

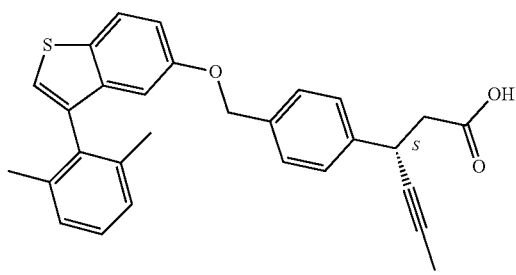

(A) A mixture of (3S)-ethyl 3-(4-(((3-bromobenzo[b]thiophen-5-yl)oxy)methyl)phenyl)hex-4-ynoate (150 mg, 0.33 mmol) (from Example 23F), (2,6-dimethylphenyl)boronic acid (150 mg, 1.00 mmol), Pd$_2$(dba)$_3$ (12 mg, 0.01 mmol), SPhos (22 mg, 0.05 mmol) and K$_3$PO$_4$ (212 mg, 1.00 mmol) in toluene (2 mL) was stirred at 100° C. in a sealed tube for 2 h. After cooling to rt, water (15 mL) was added and the mixture was extracted with EtOAc (3×10 mL). The combined organic extracts were dried (Na$_2$SO$_4$), filtered, and concentrated under reduced pressure. The residue thus obtained was purified by silica gel chromatography (0-5% EtOAc/petroleum ether) to provide (3S)-ethyl 3-(4-(((3-(2,6-dimethylphenyl)benzo[b]thiophen-5-yl)oxy)methyl)phenyl)hex-4-ynoate as yellow oil (80 mg, 51% yield). LC/MS: Calcd. for C$_{31}$H$_{30}$O$_3$S: 482.63, found: 483.2 [M+H]$^+$.

(B) (3S)-3-(4-(((3-(2,6-Dimethylphenyl)benzo[b]thiophen-5-yl)oxy)methyl)phenyl)hex-4-ynoic acid (Cpd 27) was prepared from (3S)-ethyl 3-(4-(((3-(2,6-dimethylphenyl)benzo[b]-thiophen-5-yl)oxy)methyl)phenyl)hex-4-ynoate following General Procedure C, using LiOH as base, EtOH in place of MeOH, and 2N HCl for reaction acidification. $^1$H NMR (DMSO-d$_6$) δ 7.94 (d, J=9.0 Hz, 1H), 7.56 (s, 1H), 7.23-7.35 (m, 5H), 7.09-7.18 (m, 3H), 6.57 (d, J=2.4 Hz, 1H), 4.98 (s, 2H), 3.96-4.02 (m, 1H), 2.63 (d, J=7.5 Hz, 1H), 1.89 (s, 3H), 1.88 (s, 3H), 1.78 (s, 3H). LC/MS: Calcd. for C$_{29}$H$_{26}$O$_3$S: 454.58, found: 453.1 [M−H]$^−$.

Example 28

2-(1-(4-((3-(4-(1,1-Dioxido-3,6-dihydro-2H-thiopyran-4-yl)-2-methylphenyl)benzo[b]thiophen-5-yl) methoxy)phenyl)-3-oxocyclobutyl)acetic acid, Cpd 28

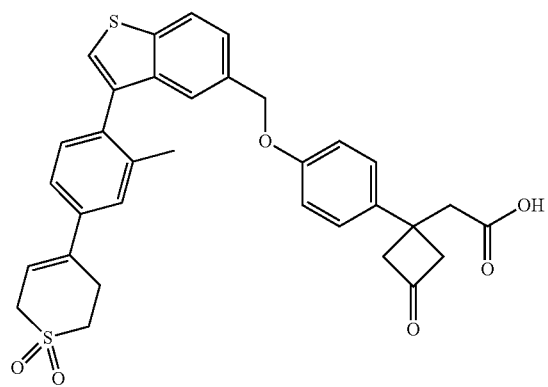 [SMILES: Cc1cc(C2=CCS(=O)(=O)CC2)ccc1-c1csc2ccc(COc3ccc(C4(CC(=O)O)CC(=O)C4)cc3)cc12]

(A) To an ice-cold solution of 3-acetoxycyclobutanone (2.563 g, 20 mmol) in anhydrous DCM (100 mL) was added ethyl triphenylphosphoranylidene acetate (9.06 g, 26 mmol) and the resulting mixture was stirred at rt for 18 h. The reaction was then concentrated under reduced and the resultant residue was purified by silica gel chromatography (0-20% EtOAc/heptanes) to provide ethyl 2-(3-acetoxycyclobutylidene)acetate (2.15 g, 54%) as a slightly yellowish oil. LC/MS: Calcd. for C$_{10}$H$_{14}$O$_4$: 198.22, found: 199.1 [M+H]$^+$.

(B) To a solution of chloro(1,5-cyclooctadiene)rhodium (I) dimer (197 mg, 0.4 mmol) in dioxane (20 mL) under a nitrogen atmosphere at was added IN NaOH (14 mL, 14 mmol) was added 4-hydroxyphenylboronic acid (2.206 g, 16 mmol), followed by a solution of ethyl 2-(3-acetoxycyclobutylidene)acetate (1.586 g, 8 mmol) in dioxane (6 mL), and the mixture was heated at 50° C. for 1 h. After cooling to rt, the reaction was poured into a mixture of EtOAc (60 mL) and water (60 mL) and 2N HCl was then added to acidify the aqueous phase to a pH of 4. After phase separation, the aqueous phase was extracted with EtOAc (2×10 mL) and the combined extracts were dried ($Na_2SO_4$), filtered, and concentrated under reduced pressure. Purification of the resultant residue by silica gel chromatography (20-60% EtOAc/heptanes) to provide ethyl 2-[3-acetoxy-1-(4-hydroxyphenyl)cyclobutyl]acetate as mixture of syn- and anti-isomers, that was used as such. LC/MS: Calcd. for $C_{16}H_{20}O_5$: 292.33, found: 315.0 $[M+Na]^+$.

(C) A mixture of ethyl 2-[3-acetoxy-1-(4-hydroxyphenyl) cyclobutyl]acetate (1.0 g, 3.42 mmol) and $K_2CO_3$ (1.89 g, 13.68 mmol) in EtOH (20 mL) was stirred at 40° C. overnight, then concentrated under reduced pressure. The residue thus obtained was partitioned between EtOAc (30 mL) and water (30 mL), and treated with 2N HCl to acidify the aqueous phase to pH 5-6. After phase separation, the aqueous phase was extracted with EtOAc (30 mL) and the combined extracts were dried ($Na_2SO_4$), filtered, and concentrated under reduced pressure. Purification of the resultant residue by silica gel chromatography (20-60% EtOAc/heptanes) to provide ethyl 2-[3-hydroxy-1-(4-hydroxyphenyl)cyclobutyl]acetate as mixture of syn- and anti-isomers, that was used as such. LC/MS: Calcd. for $C_{14}H_{18}O_4$: 250.29, found: 251.1 $[M+H]^+$, 273.0 $[M+Na]^+$.

(D) To a solution of ethyl 2-[3-hydroxy-1-(4-hydroxyphenyl)cyclobutyl]acetate (745 mg, 2.98 mmol) in DCM (15 mL) and DMSO (5 mL) was added DIEA (3.08 mL, 17.86 mmol) followed by sulfur trioxide-pyridine complex (1.895 g, 11.91 mmol) and the resultant mixture was stirred at rt for 2 h. The mixture was then partitioned between EtOAc (60 mL) and water (60 mL), and treated with 2N HCl to acidify the aqueous phase to pH 3-4. After phase separation, the aqueous phase was extracted with EtOAc (50 mL) and the combined extracts were washed with water (80 mL), dried ($Na_2SO_4$), filtered, and concentrated under reduced pressure. Purification of the resultant residue by silica gel chromatography (5-20% EtOAc/DCM) to provide ethyl 2-(1-(4-hydroxyphenyl)-3-oxocyclobutyl)acetate (537 mg, 73%) as a colorless oil. LC/MS: Calcd. for $C_{14}H_{16}O_4$: 248.28, found: 249.1 $[M\pm H]^+$.

(E) Ethyl 2-(1-(4-((3-(4-(1,1-dioxido-3,6-dihydro-2H-thiopyran-4-yl)-2-methylphenyl)benzo[b]thiophen-5-yl) methoxy)phenyl)-3-oxocyclobutyl)acetate was prepared from ethyl 2-(1-(4-hydroxyphenyl)-3-oxocyclobutyl)acetate and 4-(4-(5-(hydroxymethyl)benzo[b]thiophen-3-yl)-3-methylphenyl)-3,6-dihydro-2H-thiopyran 1,1-dioxide (from Example 6D) following General Procedure B, using $Ph_3P$ and DBAD. LC/MS: Calcd. for $C_{35}H_{34}O_6S_2$: 614.78, found: 615.1 $[M]^+$, 637.2 $[M+Na]^+$.

(F) 2-(1-(4-((3-(4-(1,1-Dioxido-3,6-dihydro-2H-thiopyran-4-yl)-2-methylphenyl)benzo[b]thiophen-5-yl)methoxy) phenyl)-3-oxocyclobutyl)acetic acid (Cpd 28) was prepared from ethyl 2-(1-(4-((3-(4-(1,1-dioxido-3,6-dihydro-2H-thiopyran-4-yl)-2-methylphenyl)benzo[b]thiophen-5-yl) methoxy)phenyl)-3-oxocyclobutyl)acetate following General Procedure C, using LiOH as base and 2N HCl for reaction acidification. $^1H$ NMR ($CDCl_3$) δ 7.94 (d, 1H), 7.40-7.50 (m, 2H), 7.28-7.36 (m, 3H), 7.23 (d, J=8.6 Hz, 3H), 6.92 (d, J=8.6 Hz, 2H), 5.95 (t, J=4.3 Hz, 1H), 5.10 (s, 2H), 3.81-3.88 (m, 2H), 3.37-3.57 (m, 4H), 3.16-3.33 (m, 4H), 2.91 (s, 2H), 2.16 (s, 3H). LC/MS: Calcd. for $C_{33}H_{30}O_6S_2$: 586.73, found: 587.3 $[M+H]^+$.

Example 29

2-(1-(4-((3-(4-(1,1-Dioxidotetrahydro-2H-thiopyran-4-yl)-2-methylphenyl)benzo[b]thiophen-5-yl) methoxy)phenyl)-3-oxocyclobutyl)acetic acid, Cpd 29

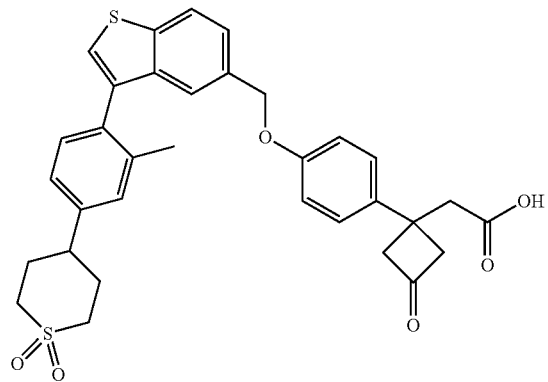 [SMILES: Cc1cc(C2CCS(=O)(=O)CC2)ccc1-c1csc2ccc(COc3ccc(C4(CC(=O)O)CC(=O)C4)cc3)cc12]

(A) To a mixture of 4-(4-(5-(hydroxymethyl)benzo[b] thiophen-3-yl)-3-methylphenyl)-3,6-dihydro-2H-thiopyran 1,1-dioxide (from Example 6D) and Pd/C (10% wt, 80 mg, 0.075 mmol) in EtOH (6 mL) under nitrogen was added a solution of ammonium formate (472 mg, 7.5 mmol) in water (1 mL), and the resultant mixture was stirred at 50° C. for 5 h. After cooling to rt, the mixture was diluted with EtOAc (10 mL) and filtered. The filtered solids were washed with EtOAc (30 mL) and the combined filtrate and washings were concentrated. EtOAc (2 mL) and water (20 mL) were added, followed by heptanes (30 mL). The resultant solid thus obtained was filtered, washed successively with water (3×5 mL) and heptanes (5 mL) and dried to provide 4-(4-(5-(hydroxymethyl)benzo[b]-thiophen-3-yl)-3-methylphenyl) tetrahydro-2H-thiopyran 1,1-dioxide (136 mg, 70%) which was used directly without further purification.

(B) Ethyl 2-(1-(4-((3-(4-(1,1-dioxidotetrahydro-2H-thiopyran-4-yl)-2-methylphenyl)benzo[b]thiophen-5-yl) methoxy)phenyl)-3-oxocyclobutyl)acetate was prepared from 4-(4-(5-(hydroxymethyl)benzo[b]-thiophen-3-yl)-3-methylphenyl)tetrahydro-2H-thiopyran 1,1-dioxide and ethyl 2-(1-(4-hydroxyphenyl)-3-oxocyclobutyl)acetate (from Example 28D) following General Procedure B, using $Ph_3P$ and DBAD. $^1H$ NMR ($CDCl_3$) δ 7.94 (d, J=9.1 Hz, 1H), 7.41-7.50 (m, 2H), 7.27-7.35 (m, 2H), 7.20 (d, J=8.6 Hz, 3H), 7.14 (d, J=8.1 Hz, 1H), 6.92 (d, J=8.6 Hz, 2H), 5.10 (s, 2H), 3.99 (q, J=7.4 Hz, 2H), 3.46 (s, 4H), 3.10-3.25 (m, 4H), 2.83 (s, 3H), 2.38-2.60 (m, 2H), 2.23-2.38 (m, 2H), 2.15 (s, 3H), 1.11 (t, J=7.1 Hz, 3H).

(C) 2-(1-(4-((3-(4-(1,1-Dioxidotetrahydro-2H-thiopyran-4-yl)-2-methylphenyl)benzo[b]thiophen-5-yl)methoxy)phenyl)-3-oxocyclobutyl)acetic acid (Cpd 29) was prepared from ethyl 2-(1-(4-((3-(4-(1,1-dioxidotetrahydro-2H-thiopyran-4-yl)-2-methylphenyl)benzo[b]thiophen-5-yl) methoxy)phenyl)-3-oxocyclobutyl)acetate following General Procedure C, using LiOH as base, MeCN in place of THF, a reaction temperature of 50° C. for 3 h, and 2N HCl for reaction acidification. $^1H$-1NMR ($CDCl_3$) δ 7.93 (d, 1H), 7.38-7.47 (m, 2H), 7.30 (s, 1H), 7.23 (dd, J=8.1, 2.5 Hz, 3H), 7.18 (s, 1H), 7.12 (dd, J=7.6, 1.5 Hz, 1H), 6.91 (d, J=9.1 Hz, 2H), 5.12 (s, 2H), 3.39-3.55 (m, 4H), 3.11-3.24 (m, 4H), 2.92 (s, 2H), 2.76-2.88 (m, 1H), 2.38-2.56 (m, 2H), 2.23-2.35 (m, 2H), 2.12 (s, 3H). LC/MS: Calcd. for $C_{33}H_{32}O_6S_2$: 588.75, found: 589.0 $[M]^+$.

Example 30

2-(3-Oxo-1-(4-((3-(2-methylphenyl)benzo[b]thiophen-5-yl)methoxy)phenyl)cyclobutyl)acetic acid, Cpd 30

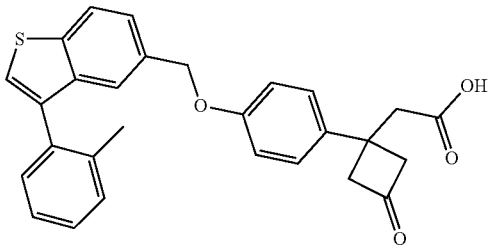 [SMILES: Cc1ccccc1-c1csc2ccc(COc3ccc(C4(CC(=O)O)CC(=O)C4)cc3)cc12]

(A) Ethyl 2-(3-acetoxy-1-(4-((3-(2-methylphenyl)benzo[b]thiophen-5-yl)methoxy)phenyl)cyclobutyl)acetate was prepared from 5-hydroxymethyl-3-(2-methylphenyl)benzo[b]-thiophene (from Example 1B) ethyl 2-(1-(4-hydroxyphenyl)-3-oxocyclobutyl)acetate (from Example 28D) following General Procedure B using PBu$_3$ and ADDP in toluene as solvent (in place of THF) at 60° C. for 2h. $^1$H NMR (CDCl$_3$) δ 7.92-7.94 (m, 1H), 7.45-7.47 (m, 2H), 7.17-7.37 (m, 7H), 6.89-6.94 (m, 2H), 5.09 (s, 2H), 3.99 (dd, J=7.2, 14.4 Hz, 2H), 3.46 (s, 4H), 2.82 (s, 2H), 2.16 (s, 3H), 1.10 (t, J=7.2 Hz, 3H).

(B) 2-(3-Oxo-1-(4-((3-(2-methylphenyl)benzo[b]thiophen-5-yl)methoxy)phenyl)-cyclobutyl)acetic acid (Cpd 30) was prepared from ethyl 2-(3-acetoxy-1-(4-((3-(2-methylphenyl)benzo[b]thiophen-5-yl)methoxy)phenyl)cyclobutyl)acetate following General Procedure C, using LiOH as base, EtOH in place of MeOH and 1N HCl for reaction acidification. $^1$H NMR (CD$_3$OD) δ 7.97 (d, J=8.1 Hz, 1H), 7.26-7.50 (m, 9H), 6.93-6.97 (m, 2H), 5.17 (s, 2H), 3.41-3.56 (m, 4H), 2.82 (s, 2H), 2.10 (s, 3H). LC/MS: mass calcd. for $C_{28}H_{24}O_4S$: 456.56, found 455.2 $[M-H]^-$.

Example 31

2-((1r,3O-3-Hydroxy-1-(4-((3-(2-methylphenyl)benzo[b]thiophen-5-yl)methoxy)phenyl)cyclobutyl)acetic acid, Cpd 31

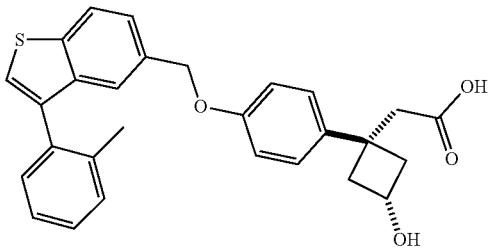

2-((1r,3r)-3-Hydroxy-1-(4-((3-(2-methylphenyl)benzo[b]thiophen-5-yl)methoxy)phenyl)cyclobutyl)acetic acid (Cpd 31) was prepared from 2-(3-oxo-1-(4-((3-(2-methylphenyl)benzo[b]thiophen-5-yl)methoxy)phenyl)-cyclobutyl)acetic acid (from Example 30) following General Procedure G. $^1$H NMR (CD$_3$OD) δ 7.93 (d, J=8.1 Hz, 1H), 7.22-7.46 (m, 9H), 6.85-6.88 (m, 2H), 5.12 (s, 2H), 3.88-3.93 (m, 1H), 2.76-2.83 (m, 2H), 2.57 (s, 2H), 2.24-2.31 (m, 2H), 2.07 (s, 3H). LC/MS: mass calcd. for $C_{28}H_{26}O_4S$: 456.56, found 457.1 $[M]^-$.

Example 32

2-(1-(4-((3-(4-(2-Ethoxyethoxy)-2-methylphenyl)benzo[b]thiophen-5-yl)methoxy)phenyl)-3-oxocyclobutyl)acetic acid, Cpd 32

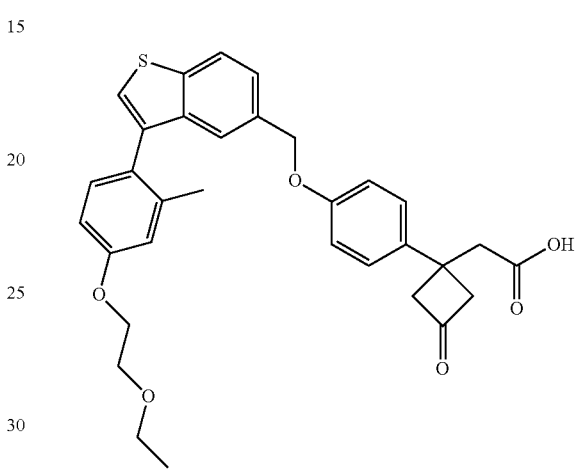

(A) A mixture of 4-bromo-3-methylphenol (10 g, 53.47 mmol), 1-bromo-2-ethoxyethane (10.62 g, 69.40 mmol) and K$_2$CO$_3$ (11.13 g, 79.95 mmol) in DMF (100 mL) was stirred overnight at 75° C. After cooling to rt, brine (250 mL) was added and the mixture was extracted with EtOAc (4×100 mL). The combined organic extracts were washed with brine (4×100 mL), dried (Na$_2$SO$_4$), filtered, and concentrated under reduced pressure. Purification of the resultant residue by silica gel chromatography (5% EtOAc/petroleum ether afforded 1-bromo-4-(2-ethoxyethoxy)-2-methylbenzene (12.25 g, 88%) as light yellow oil which was used directly.

(B) 2-[4-(2-Ethoxyethoxy)-2-methylphenyl]-4,4,5,5-tetramethyl-1,3,2-dioxaborolane was prepared from 1-bromo-4-(2-ethoxyethoxy)-2-methylbenzene and bis(pinacolato)diboron following General Procedure A, using PdCl$_2$(dppf).CH$_2$Cl$_2$ as the palladium catalyst and KOAc in place of K$_2$CO$_3$ at a reaction temperature of 100° C. overnight. LC/MS: mass calcd. for $C_{18}H_{27}BO_4$: 306.20, found: 307.1 $[M+H]^+$.

(C) Ethyl 2-(1-(4-((3-bromobenzo[b]thiophen-5-yl)methoxy)phenyl)-3-oxocyclobutyl)acetate was prepared from 3-bromo-5-hydroxymethylbenzothiophene (from Example 1A) and ethyl 2-(1-(4-hydroxyphenyl)-3-oxocyclobutyl)acetate (from Example 28D) following General Procedure B using PBu$_3$ and ADDP in toluene as solvent (in place of THF). LC/MS: mass calcd. for $C_{23}H_{21}BrO_4S$: 473.38, found 473.1 $[M]^+$, 475.0 $[M+2]^+$.

(D) Ethyl 2-(1-(4-((3-(4-(2-ethoxyethoxy)-2-methylphenyl)benzo[b]thiophen-5-yl)methoxy)phenyl)-3-oxocyclobutyl)acetate was prepared from ethyl 2-(1-(4-((3-bromobenzo[b]thiophen-5-yl)methoxy)phenyl)-3-oxocyclobutyl)acetate and 2-(4-(2-ethoxyethoxy)-2-methylphenyl)-4,4,5,5-tetramethyl-1,3,2-dioxaborolane following General Procedure A, using PdCl$_2$(dppf).CH$_2$Cl$_2$ as the palladium catalyst, DMF as solvent at a reaction temperature of 60° C. overnight. LC/MS: mass calcd. for $C_{34}H_{36}O_6S$: 572.71, found 573.4 [M+H]$^+$, 595.4 [M+Na]$^+$.

(E) 2-(1-(4-((3-(4-(2-Ethoxyethoxy)-2-methylphenyl)benzo[b]thiophen-5-yl)methoxy)phenyl)-3-oxocyclobutyl) acetic acid (Cpd 32) was prepared from ethyl 2-(1-(4-((3-(4-(2-ethoxyethoxy)-2-methylphenyl)benzo[b]thiophen-5-yl)methoxy)phenyl)-3-oxocyclobutyl)acetate following General Procedure C, using NaOH (10 eq.) as base, MeCN/H$_2$O (4:1 v/v) as solvent and 1N HCl for reaction acidification. Product purification was accomplished by silica gel chromatography (0-80% EtOAc in petroleum ether). $^1$H NMR (DMSO-d$_6$) δ 8.06 (d, J=8.4 Hz, 1H), 7.64 (s, 1H), 7.44-7.52 (m, 1H), 7.42 (s, 1H), 7.15-7.26 (m, 3H), 6.86-6.96 (m, 4H), 5.17 (s, 2H), 4.13-4.15 (m, 2H), 3.71-3.74 (m, 2H), 3.53 (dd, J=7.2, 14.0 Hz, 2H), 3.27-3.41 (m, 4H), 2.80 (s, 2H), 2.05 (s, 3H), 1.15 (t, J=7.2 Hz, 3H). LC/MS: mass calcd. for $C_{32}H_{32}O_6S$: 543.66, found 543.1 [M]$^-$.

Example 33

2-(1-(4-((3-(4-((1,1-Dioxidotetrahydro-2H-thiopyran-4-yl)oxy)-2-methylphenyl)benzo[b]thiophen-5-yl)methoxy)phenyl)-3-oxocyclobutyl)acetic acid, Cpd 33

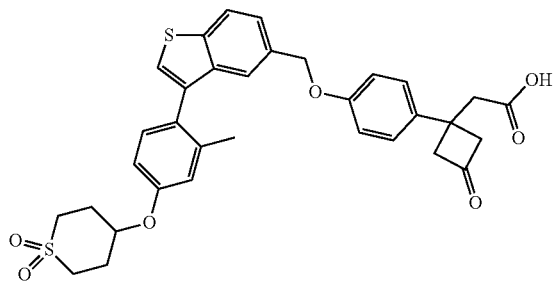 [SMILES: Cc1cc(OC2CCS(=O)(=O)CC2)ccc1-c1csc2ccc(COc3ccc(C4(CC(=O)O)CC(=O)C4)cc3)cc12]

(A) 4-(4-Bromo-3-methylphenoxy)tetrahydro-2H-thiopyran 1,1-dioxide was prepared from 4-bromo-3-methylphenol and 4-hydroxytetrahydro-2H-thiopyran 1,1-dioxide following General Procedure B, using DBAD and Ph$_3$P at a reaction temperature of 50° C. overnight. $^1$H NMR (CDCl$_3$) δ 7.43 (d, J=8.7 Hz, 1H), 6.84 (d, J=3.0 Hz, 1H), 6.64 (dd, J=2.7, 8.7 Hz, 1H), 4.59-4.61 (m, 1H), 3.33-3.43 (m, 2H), 2.90-2.96 (m, 2H), 2.30-2.48 (m, 7H).

(B) 4-(3-Methyl-4-(4,4,5,5-tetramethyl-1,3,2-dioxaborolan-2-yl)phenoxy)tetrahydro-2H-thiopyran 1,1-dioxide was prepared from 4-(4-bromo-3-methylphenoxy)tetrahydro-2H-thiopyran 1,1-dioxide and bis(pinacolato)diboron following General Procedure A, using PdCl$_2$(dppf).CH$_2$Cl$_2$ as the palladium catalyst, and KOAc in place of K$_2$CO$_3$ using dioxane as solvent at a reaction temperature of 100° C. overnight. $^1$H NMR (CDCl$_3$) δ 7.73 (d, J=7.6 Hz, 1H), 6.70-6.73 (m, 2H), 4.65-4.75 (m, 1H), 3.36-3.44 (m, 2H), 2.89-2.93 (m, 2H), 2.52 (s, 3H), 2.44-2.49 (m, 2H), 2.32-2.38 (m, 2H), 1.27 (s, 12H).

(C) Ethyl 2-(1-(4-((3-(4-((1,1-dioxidotetrahydro-2H-thiopyran-4-yl)oxy)-2-methylphenyl)benzo[b]thiophen-5-yl)methoxy)phenyl)-3-oxocyclobutyl)acetate was prepared from ethyl 2-(1-(4-((3-bromobenzo[b]thiophen-5-yl)methoxy)phenyl)-3-oxocyclobutyl)acetate (from Example 32C) and 4-(3-methyl-4-(4,4,5,5-tetramethyl-1,3,2-dioxaborolan-2-yl)phenoxy)tetrahydro-2H-thiopyran 1,1-dioxide following General Procedure A, using PdCl$_2$(dppf).CH$_2$Cl$_2$ as the palladium catalyst, DMF as solvent at a reaction temperature of 80° C. overnight. LC/MS: mass calcd. for $C_{35}H_{36}O_7S_2$: 632.79, found 655.4 [M+Na]$^+$.

(D) 2-(1-(4-((3-(4-((1,1-Dioxidotetrahydro-2H-thiopyran-4-yl)oxy)-2-methylphenyl)benzo[b]thiophen-5-yl)methoxy)phenyl)-3-oxocyclobutyl)acetic acid was prepared from ethyl 2-(1-(4-((3-(4-((1,1-dioxidotetrahydro-2H-thiopyran-4-yl)oxy)-2-methylphenyl)benzo[b]thiophen-5-yl)methoxy)phenyl)-3-oxocyclobutyl)acetate following General Procedure C, using NaOH as base, MeCN in place of THF and 1N HCl for reaction acidification. Product purification was accomplished by silica gel chromatography (50% EtOAc in petroleum ether). $^1$H NMR (CD$_3$OD) δ 7.94 (d, J=8.1 Hz, 1H), 7.46-7.38 (m, 3H), 7.28-7.25 (m, 2H), 7.20-7.17 (m, 1H), 6.96-6.95 (m, 1H), 6.93-6.87 (m, 3H), 5.147(s, 2H), 4.79-4.78 (m, 1H), 3.54-3.32 (m, 6H), 3.10-3.05 (m, 2H), 2.81 (s, 2H), 2.49-2.32 (m, 4H), 2.06 (s, 3H). LC/MS: mass calcd. for $C_{33}H_{32}O_7S_2$: 604.73, found 622.1 [M+NH$_3$]$^+$.

Example 34

2-(1-(4-((3-(2-Methyl-4-((tetrahydro-2H-pyran-4-yl)oxy)phenyl)benzo[b]thiophen-5-yl)methoxy)phenyl)-3-oxocyclobutyl)acetic acid, Cpd 34

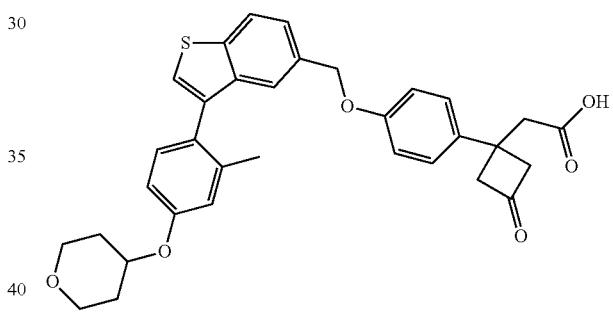

(A) Ethyl 2-[1-[4-([3-[2-methyl-4-(oxan-4-yloxy)phenyl]-1-benzothiophen-5-yl]methoxy)phenyl]-3-oxocyclobutyl]acetate was prepared from 4,4,5,5-tetramethyl-2-(2-methyl-4-(tetrahydro-2H-pyran-4-yloxy)phenyl)-1,3,2-dioxaborolane (from Example 15B) and ethyl 2-(1-(4-((3-bromobenzo[b]thiophen-5-yl)methoxy)phenyl)-3-oxocyclobutyl)acetate (from Example 32C) following General Procedure A, using PdCl$_2$(dppf).CH$_2$Cl$_2$ as the palladium catalyst, DMF as solvent at a reaction temperature of 80° C. overnight. LC/MS: mass calcd. for $C_{35}H_{36}O_6S$: 584.72, found 607.4 [M+Na]$^+$.

(B) 2-(1-(4-((3-(2-Methyl-4-((tetrahydro-2H-pyran-4-yl)oxy)phenyl)benzo[b]thiophen-5-yl)methoxy)phenyl)-3-oxocyclobutyl)acetic acid (Cpd 34) was prepared from ethyl 2-[1-[4-([3-[2-methyl-4-(oxan-4-yloxy)phenyl]-1-benzothiophen-5-yl]methoxy)phenyl]-3-oxocyclobutyl]acetate following General Procedure C, using NaOH as base, MeCN in place of THF and 1N HCl for reaction acidification. Product purification was accomplished by silica gel chromatography (50% EtOAc in petroleum ether). $^1$H NMR (CD$_3$OD) δ 7.93 (d, J=8.1 Hz, 1H), 7.46-7.37 (m, 3H), 7.28-7.25 (m, 2H), 7.17-7.14 (m, 1H), 6.93-6.86 (m, 4H), 5.14 (s, 2H), 4.70-4.60 (m, 1H), 4.02-3.95 (m, 2H), 3.67-3.59 (m, 2H), 3.52-3.35 (m, 4H), 2.81 (s, 2H), 2.10-2.05 (m, 5H), 1.82-1.80 (m, 2H). LC/MS: mass calcd. for $C_{33}H_{32}O_6S$: 556.67, found 557.1 [M+H]$^+$, 574.2 [M+NH$_3$]$^+$.

Example 35

2-((1r,3r)-3-Hydroxy-1-(4-((3-(4-(2-ethoxyethoxy)-2-methylphenyl)benzo[b]thiophen-5-yl)methoxy)phenyl)cyclobutyl)acetic acid, Cpd 35

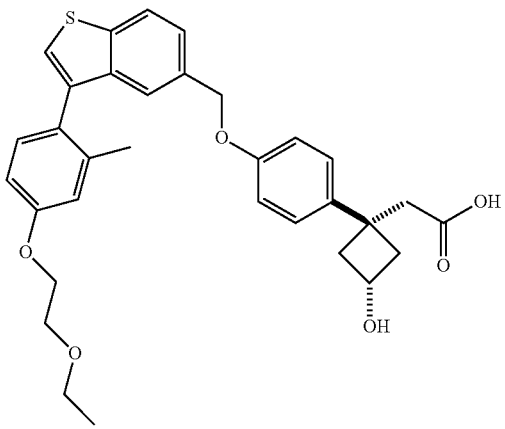

2-((1r,3r)-3-Hydroxy-1-(4-((3-(4-(2-ethoxyethoxy)-2-methylphenyl)benzo[b]thiophen-5-yl)methoxy)phenyl)cyclobutyl)acetic acid (Cpd 35) was prepared from 2-(1-(4-((3-(4-(2-ethoxyethoxy)-2-methylphenyl)benzo[b]thiophen-5-yl)methoxy)phenyl)-3-oxocyclobutyl)acetic acid (from Example 32) following General Procedure G. $^1$H NMR (CD$_3$OD) δ 7.95 (d, J=8.1 Hz, 1H), 7.48-7.39 (m, 3H), 7.30-7.27 (m, 2H), 7.19-7.16 (m, 1H), 6.95-6.86 (m, 4H), 5.14 (s, 2H), 4.20-4.17 (m, 2H), 3.96-3.93 (m, 1H), 3.86-3.82 (m, 2H), 3.65 (dd, J=7.2, 14.1 Hz, 2H), 2.85-2.79 (m, 2H), 2.61 (s, 2H), 2.35-2.28 (m, 2H), 2.08 (s, 3H), 1.26 (t, J=7.2 Hz, 3H). LC/MS: mass calcd. for $C_{32}H_{34}O_6S$: 546.67, found 547.4 [M+H]$^+$.

Example 36

2-((1r,3r)-1-(4-((3-(4-((1,1-Dioxidotetrahydro-2H-thiopyran-4-yl)oxy)-2-methylphenyl)benzo[b]thiophen-5-yl)methoxy)phenyl)-3-hydroxycyclobutyl)acetic acid, Cpd 36

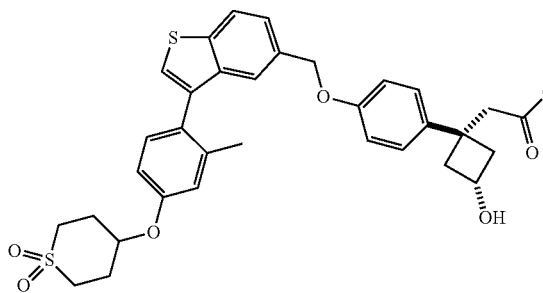

2-((1r,3r)-1-(4-((3-(4-((1,1-Dioxidotetrahydro-2H-thiopyran-4-yl)oxy)-2-methylphenyl)benzo[b]thiophen-5-yl)methoxy)phenyl)-3-hydroxycyclobutyl)acetic acid (Cpd 36) was prepared from 2-(1-(4-((3-(4-((1,1-dioxidotetrahydro-2H-thiopyran-4-yl)oxy)-2-methylphenyl)benzo[b]thiophen-5-yl)methoxy)phenyl)-3-oxocyclobutyl)acetic acid (from Example 33D) following General Procedure G. $^1$H NMR (CD$_3$OD) δ 7.94 (d, J=8.4 Hz, 1H), 7.47-7.39 (m, 3H), 7.28-7.18 (m, 3H), 7.01-6.87 (m, 4H), 5.14 (s, 2H), 4.81-4.79 (m, 1H), 3.97-3.92 (m, 1H), 3.39-32 (m, 2H), 3.32-3.06 (m, 2H), 2.83-2.79 (m, 2H), 2.62 (s, 2H), 2.45-2.29 (m, 6H), 2.07 (s, 3H). LC/MS: mass calcd. for $C_{33}H_{34}O_7S_2$: 606.75, found 605.0 [M–H]$^-$.

Example 37

2-((1r,3r)-3-Hydroxy-1-(4-((3-(2-methyl-4-((tetrahydro-2H-pyran-4-yl)oxy)phenyl)benzo[b]thiophen-5-yl)methoxy)phenyl)cyclobutyl)acetic acid, Cpd 37

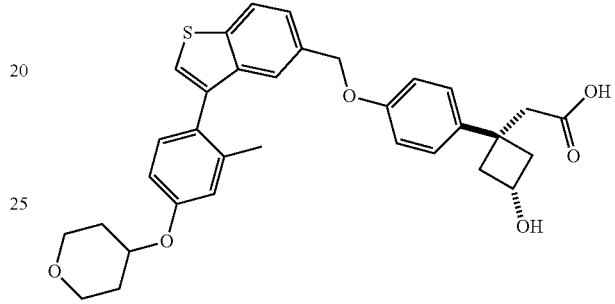

2-((1r,3r)-3-Hydroxy-1-(4-((3-(2-methyl-4-((tetrahydro-2H-pyran-4-yl)oxy)phenyl)benzo[b]thiophen-5-yl)methoxy)phenyl)cyclobutyl)acetic acid (Cpd 37) was prepared from 2-(1-(4-((3-(2-methyl-4-((tetrahydro-2H-pyran-4-yl)oxy)phenyl)benzo[b]thiophen-5-yl)methoxy)phenyl)-3-oxocyclobutyl)acetic acid (from Example 34B) following General Procedure G. $^1$H NMR (CD$_3$OD) δ 7.94 (d, J=8.4 Hz, 1H), 7.48-7.42 (m, 3H), 7.38-7.28 (m, 2H), 7.19-7.16 (m, 1H), 6.95-6.87 (m, 4H), 5.14 (s, 2H), 4.68-4.63 (m, 1H), 4.04-3.98 (m, 2H), 3.97-3.90 (m, 1H), 3.68-3.60 (m, 2H), 2.80-2.76 (m, 2H), 2.51 (s, 2H), 2.40-2.33 (m, 2H), 2.12-2.07 (m, 5H), 1.81-1.75 (m, 2H). LC/MS: mass calcd. for $C_{33}H_{34}O_6S$: 558.68, found 557.0 [M–H]$^-$.

Example 38

2-(1-(4-((3-(2-Methylpyridin-3-yl)benzo[b]thiophen-5-yl)methoxy)phenyl)-3-oxocyclobutyl)acetic acid, Cpd 38

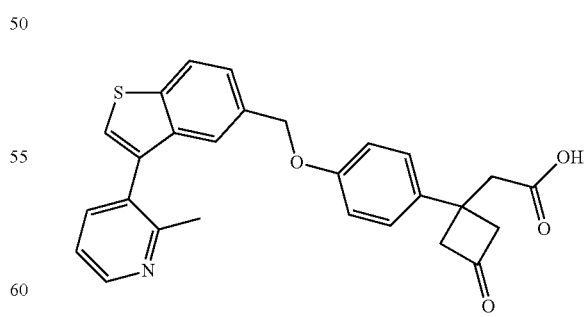

(A) Ethyl 2-(1-(4-((3-(2-methylpyridin-3-yl)benzo[b]thiophen-5-yl)methoxy)phenyl)-3-oxocyclobutyl)acetate was prepared from ethyl 2-(1-(4-((3-bromobenzo[b]thiophen-5-yl)methoxy)phenyl)-3-oxocyclobutyl)acetate (from Example 32C) and (2-methylpyridin-3-yl)boronic acid following General Procedure A, using PdCl$_2$(dppf).CH$_2$Cl$_2$ as the palladium catalyst and DMF as solvent at a reaction temperature of 60° C. overnight. LC/MS: mass calcd. for C$_{29}$H$_{27}$NO$_4$S: 485.59, found: 486.3 [M+H]$^+$.

(B) 2-(1-(4-((3-(2-Methylpyridin-3-yl)benzo[b]thiophen-5-yl)methoxy)phenyl)-3-oxocyclobutyl)acetic acid (Cpd 38) was prepared from ethyl 2-(1-(4-((3-(2-methylpyridin-3-yl)benzo[b]thiophen-5-yl)methoxy)phenyl)-3-oxocyclobutyl)acetate following General Procedure C, using NaOH as base, MeCN in place of THF and 1N HCl for reaction acidification. Product purification was accomplished by silica gel chromatography (0-10% MeOH in DCM). $^1$H NMR (CD$_3$OD) δ 8.53-8.51 (m, 1H), 8.03-8.00 (m, 1H), 7.77-7.74 (m, 1H), 7.62 (s, 1H), 7.54-7.51 (m, 1H), 7.43-7.39 (m, 2H), 7.30-7.26 (m, 2H), 6.97-6.93 (m, 2H), 5.20 (s, 2H), 3.50-3.41 (m, 4H), 2.86 (s, 2H), 2.33 (s, 3H). LC/MS: mass calcd. for C$_{27}$H$_{23}$NO$_4$S: 457.54, found: 458.2 [M+H]$^+$.

Example 39

2-((1r,3r)-3-Hydroxy-1-(4-((3-(2-methylpyridin-3-yl)benzo[b]thiophen-5-yl)methoxy)phenyl)cyclobutyl)acetic acid, Cpd 39

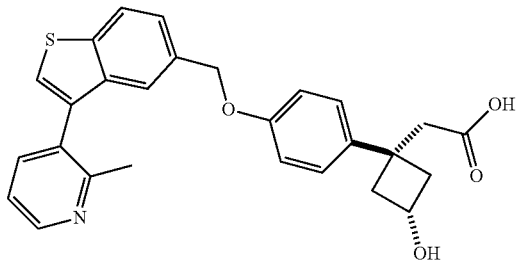

2-((1r,3r-3-Hydroxy-1-(4-((3-(2-methylpyridin-3-yl)benzo[b]thiophen-5-yl)methoxy)phenyl)cyclobutyl)acetic acid (Cpd 39) was prepared from 2-(1-(4-((3-(2-methylpyridin-3-yl)benzo[b]thiophen-5-yl)methoxy)phenyl)-3-oxocyclobutyl)acetic acid (from Example 38) following General Procedure G. $^1$H NMR (DMSO-d$_6$) δ 8.56-8.54 (m, 1H), 8.11-8.09 (m, 1H), 7.84 (s, 1H), 7.68-7.66 (m, 1H), 7.52-7.50 (m, 1H), 7.43 (s, 1H), 7.37-7.33 (m, 1H), 7.22-7.20 (m, 2H), 6.88-6.85 (m, 2H), 5.15 (s, 2H), 3.79-3.77 (m, 1H), 2.64-2.62 (m, 2H), 2.51-2.50 (m, 2H), 2.28 (s, 3H), 2.17-2.15 (m, 2H). LC/MS: mass calcd. for C$_{27}$H$_{25}$NO$_4$S: 459.56, found: 458.0 [M−H]$^-$.

Example 40

2-(1-(4-((3-(4-(1,1-Dioxido-1-thia-6-azaspiro[3.3]heptan-6-yl)-2-methylphenyl)benzo[b]thiophen-5-yl)methoxy)phenyl)-3-oxocyclobutyl)acetic acid, Cpd 40

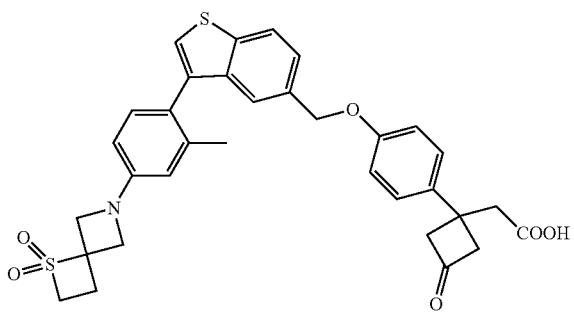 [SMILES: Cc1cc(N2CC3(CCS3(=O)=O)C2)ccc1-c1csc2ccc(COc3ccc(C4(CC(=O)O)CC(=O)C4)cc3)cc12]

(A) To a solution of tert-butyl 3-oxoazetidine-1-carboxylate (40.0 g, 233.65 mmol) in DCM (1 L) was added (triphenylphosphoranylidene)acetaldehyde (80 g, 262.88 mmol, 1.13 equiv) in several batches. After stirring at 40° C. overnight, the mixture was concentrated under reduced pressure. The residue thus obtained was purified by silica gel chromatography (5-10% EtOAc/petroleum ether) to provide tert-butyl 3-(2-oxoethylidene)azetidine-1-carboxylate (45.8 g, 99%) as a colorless oil. $^1$H NMR (CDCl$_3$) δ 9.61 (d, J=6.3 Hz, 1H), 4.92 (d, J=2.4 Hz, 2H), 4.71 (d, J=2.4 Hz, 2H), 1.47 (s, 9H).

(B) A solution of tert-butyl 3-(2-oxoethylidene)azetidine-1-carboxylate (45.8 g, 232.2 mmol), piperidine (1.38 g, 16.2 mmol), and thioacetic acid (26.5 g, 348.7 mmol) in THF (1 L) was stirred overnight at rt. The mixture was then concentrated under reduced pressure and the residue thus obtained was purified by silica gel chromatography (10-25% EtOAc/petroleum ether) to provide tert-butyl 3-(acetylsulfanyl)-3-(2-oxoethyl)azetidine-1-carboxylate (43 g, 68%) as a yellow oil. $^1$H NMR (CDCl$_3$) δ 9.69 (s, 1H), 4.04-4.09 (m, 4H), 3.30 (s, 2H), 2.30 (s, 3H), 1.47 (s, 9H).

(C) To an ice-cooled solution of tert-butyl 3-(acetylsulfanyl)-3-(2-oxoethyl)azetidine-1-carboxylate (43 g, 157.3 mmol) in ether (1 L) was added LAH (12 g, 316.2 mmol)) in several portions, and the resultant mixture was stirred at rt overnight. The reaction was quenched by the addition of satd. aq. NaHCO$_3$ (1.25 L) and the mixture was extracted with EtOAc (3×500 mL). The combined extracts were dried (Na$_2$SO$_4$), filtered, and concentrated under reduced pressure to afford tert-butyl 3-(2-hydroxyethyl)-3-sulfanylazetidine-1-carboxylate (23 g, 63%) as a red oil. $^1$H NMR (CDCl$_3$) δ 4.07-4.10 (m, 2H), 3.86-3.95 (m, 4H), 2.21 (s, 1H), 2.11 (t, J=6.3 Hz, 2H), 1.44 (s, 9H).

(D) To a cooled (−30° C.) solution of triphenylphosphine (80 g, 305.0 mmol) in THF (1 L) under nitrogen was added DIAD (61.7 g, 305.1 mmol) in dropwise fashion. After stirring at rt for 1 h, EtOH (28g, 607.8 mmol) was added and stirring was continued at rt for 1 h. The mixture was then concentrated under reduced pressure and the mixture was diluted with hexane (1 L). The resulting precipitate was filtered, and the filtrate was concentrated under reduced pressure to provide diethyl triphenylphosphonite (76 g, 71%) as a colorless oil. $^{31}$P NMR (C$_6$D$_6$) δ−41.6.

(E) To a cooled (−30° C.) solution of diethyl triphenylphosphonite (52 g, 147.56 mmol) in toluene (250 mL) under a nitrogen atmosphere was added a solution of tert-butyl 3-(2-hydroxyethyl)-3-sulfanylazetidine-1-carboxylate (23 g, 98.57 mmol) in toluene (250 mL) in drop-wise fashion, and the resultant solution was stirred overnight at rt. EtOAc (500 mL) was then added and the solution was washed with brine (3×300 mL). The organic phase was then dried (Na$_2$SO$_4$), filtered, and concentrated under reduced pressure to afford tert-butyl 1-thia-6-azaspiro[3.3]heptane-6-carboxylate (8 g, 38%) as a colorless oil. $^1$H NMR (CDCl$_3$) δ 4.07-4.16 (m, 4H), 3.05-3.15 (m, 4H), 1.42-1.51 (m, 9H).

(F) To an ice-cooled solution of tert-butyl 1-thia-6-azaspiro[3.3]heptane-6-carboxylate (8 g, 37.16 mmol) in DCM (250 mL) was added mCPBA (12.8g, 74.17 mmol) and the resultant solution was stirred overnight at rt. DCM (200 mL) was then added and the solution was successively extracted with 1N NaOH (3×150 mL) then with satd. aq. NaHCO$_3$ (3×150 mL). The organic phase was dried (Na$_2$SO$_4$), filtered, concentrated under reduced pressure and the resultant residue was purified by silica gel chromatography (9-33% EtOAc/petroleum ether) to afford tert-butyl 1-thia-6-azaspiro[3.3]heptane-6-carboxylate 1,1-dioxide (4 g, 41%) as a white solid. $^1$H NMR (CDCl$_3$) δ 4.57 (d, J=11.2 Hz, 2H), 4.00-4.06 (m, 4H), 2.37 (t, J=8.4 Hz, 2H), 1.14 (s, 9H).

(G) A solution of tert-butyl 1-thia-6-azaspiro[3.3]heptane-6-carboxylate 1,1-dioxide (3.4 g, 13.75 mmol), DCM (8 mL) and TFA (4 mL) was stirred for 2 h at rt, then concentrated under reduced pressure. The residue was taken up in water (20 mL) and dried by lyophilization to afford the TFA salt of 1-thia-6-azaspiro[3.3]heptane 1,1-dioxide (3.2 g, 86%) as a white solid. $^1$H NMR (DMSO-d$_6$) δ 4.30-4.40 (m, 4H), 4.06-4.12 (m, 2H), 2.41-2.47 (m, 2H).

(H) Under an inert atmosphere of nitrogen, a mixture of 1-thia-6-azaspiro[3.3]heptane 1,1-dioxide TFA (244 mg, 1 mmol), 1-bromo-4-iodo-2-methylbenzene (385 mg, 1.30 mmol), Pd$_2$(dba)$_3$ (46 mg, 0.05 mmol), CyJohnPhos (35 mg, 0.10 mmol) and t-BuONa (240 mg, 2.50 mmol) in toluene (3 mL) was stirred at 50° C. overnight. Water (10 mL) was then added and the mixture was extracted with EtOAc (3×15 mL). The combined organic extracts were washed with brine (1×15 mL), dried (Na$_2$SO$_4$), filtered, and concentrated under reduced pressure. Purification of the resultant residue by silica gel chromatography (40% EtOAc/petroleum ether) afforded 6-(4-bromo-3-methylphenyl)-1-thia-6-azaspiro[3.3]heptane 1,1-dioxide (278 mg, 88%) as a yellow solid. LC/MS: mass calcd. for C$_{12}$H$_{14}$BrNO$_2$S: 316.21, found: 316.1, 318.1 [M]$^+$.

(I) Ethyl 2-(3-oxo-1-(4-((3-(4,4,5,5-tetramethyl-1,3,2-dioxaborolan-2-yl)benzo[b]thiophen-5-yl)methoxy)phenyl)cyclobutyl)acetate was prepared from and ethyl 2-(1-(4-((3-bromobenzo[b]thiophen-5-yl)methoxy)phenyl)-3-oxocyclobutyl)acetate (from Example 32C) and bis(pinacolato)diboron following General Procedure A, using PdCl$_2$(dppf).CH$_2$Cl$_2$ as the palladium catalyst, KOAc in place of K$_2$CO$_3$ and DMSO as solvent at a reaction temperature of 100° C. overnight. LC/MS: mass calcd. for C$_{29}$H$_{33}$BO$_6$S: 520.44, found 543.4 [M+Na]$^+$.

(J) Ethyl 2-(1-(4-((3-(4-(1,1-dioxido-1-thia-6-azaspiro[3.3]heptan-6-yl)-2-methylphenyl)benzo[b]thiophen-5-yl)methoxy)phenyl)-3-oxocyclobutyl)acetate was prepared from ethyl 2-(3-oxo-1-(4-((3-(4,4,5,5-tetramethyl-1,3,2-dioxaborolan-2-yl)benzo[b]thiophen-5-yl)methoxy)phenyl)cyclobutyl)acetate and 6-(4-bromo-3-methylphenyl)-1-thia-6-azaspiro[3.3]heptane 1,1-dioxide following General Procedure A, using PdCl$_2$(dppf).CH$_2$Cl$_2$ as the palladium catalyst and DMF as solvent at a reaction temperature of 80° C. overnight. LC/MS: mass calcd. for C$_{35}$H$_{35}$NO$_6$S$_2$: 629.79, found: 630.4 [M+H]$^+$.

(K) 2-(1-(4-((3-(4-(1,1-Dioxido-1-thia-6-azaspiro[3.3]heptan-6-yl)-2-methylphenyl)benzo[b]thiophen-5-yl)methoxy)phenyl)-3-oxocyclobutyl)acetic acid (Cpd 40) was prepared from ethyl 2-(1-(4-((3-(4-(1,1-dioxido-1-thia-6-azaspiro[3.3]heptan-6-yl)-2-methylphenyl)benzo[b]thiophen-5-yl)methoxy)phenyl)-3-oxocyclobutyl)acetate following General Procedure C, using NaOH as base, MeCN in place of THF and 1N HCl for reaction acidification. Product purification was accomplished by silica gel chromatography (70% EtOAc/petroleum ether). $^1$H NMR (CD$_3$OD) δ 7.93-7.93 (m, 1H), 7.46-7.42 (m, 2H), 7.35 (s, 1H), 7.29-7.27 (m, 2H), 7.18-7.11 (m, 1H), 6.98-6.93 (m, 2H), 6.54-6.49 (m, 2H), 5.16 (s, 2H), 4.53 (d, J=9.6 Hz, 2H), 4.13-4.08 (m, 2H), 4.03 (d, J=9.6 Hz, 2H), 3.52-3.39 (m, 4H), 2.84 (s, 2H), 2.50-2.42 (m, 2H), 2.06 (s, 3H). LC/MS: mass calcd. for C$_{33}$H$_{31}$NO$_6$S$_2$: 601.73, found: 602.0 [M]$^+$.

Example 41

(3S)-3-(4-((3-(2-Methyl-5-(methylsulfonyl)phenyl)benzo[b]thiophen-5-yl)methoxy)phenyl)hex-4-ynoic acid, Cpd 41

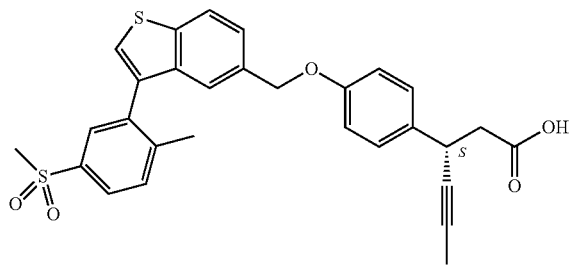

(A) (3-(4,4,5,5-Tetramethyl-1,3,2-dioxaborolan-2-yl)benzo[b]thiophen-5-yl)methanol was prepared from 3-bromo-5-hydroxymethylbenzothiophene (from Example 1A) and bis(pinacolato)diboron following General Procedure A, using PdCl$_2$(dppf).CH$_2$Cl$_2$ as the palladium catalyst and KOAc in place of K$_2$CO$_3$. LC/MS: mass calcd. for C$_{15}$H$_{19}$BO$_3$S: 290.19, found: 273.1[M−OH]$^+$.

(B) 3-(2-Methyl-5-(methylsulfonyl)phenyl)benzo[b]thiophene-5-carbaldehyde was prepared from (3-(4,4,5,5-tetramethyl-1,3,2-dioxaborolan-2-yl)benzo[b]thiophen-5-yl)methanol and 2-bromo-4-methanesulfonyl-1-methylbenzene following General Procedure A, using PdCl$_2$(dppf).CH$_2$Cl$_2$ as the palladium catalyst, Cs$_2$CO$_3$ in place of K$_2$CO$_3$. LC/MS: mass calcd. for C$_{17}$H$_{14}$O$_3$S$_2$: 330.42, found: 331.0 [M+H]$^+$.

(C) To an ice-cooled solution of 3-(2-methyl-5-(methylsulfonyl)phenyl)benzo[b]thiophene-5-carbaldehyde (120 mg, 0.36 mmol) in MeOH (2 mL) was added NaBH$_4$ (21 mg, 0.56 mmol). After stirring for 30 min at 0° C., the reaction was quenched by the addition of satd. aq. NH$_4$Cl (5 mL) and the mixture was extracted with EtOAc (3×10 mL). The combined organic extracts were dried (Na$_2$SO$_4$) and concentrated under reduced pressure. The residue thus obtained was purified by silica gel chromatography (0-40% EtOAc/petroleum ether) to afford (3-(2-methyl-5-(methylsulfonyl)phenyl)benzo[b]-thiophen-5-yl)methanol as a light yellow oil (40 mg, 33%). LC/MS: mass calcd. for C$_{17}$H$_{16}$O$_3$S$_2$: 332.44, found: 315.0 [M−OH]$^+$.

(D) (3S)-Ethyl 3-(4-((3-(2-methyl-5-(methylsulfonyl)phenyl)benzo[b]thiophen-5-yl)methoxy)phenyl)hex-4-ynoate was prepared from (3-(2-methyl-5-(methylsulfonyl)phenyl)benzo[b]-thiophen-5-yl)methanol and (3S)-ethyl 3-(4-hydroxyphenyl)hex-4-ynoate (available from Synnovator, Inc., Research Triangle Park, N.C.; Cat. #PB05708) following General Procedure B, using Bu$_3$P and ADDP at a reaction temperature of 60° C. for 1 h. LC/MS: mass calcd. for C$_{31}$H$_{30}$O$_5$S$_2$: 546.70, found: 547.1 [M]$^+$.

(E) (3S)-3-(4-((3-(2-Methyl-5-(methylsulfonyl)phenyl)benzo[b]thiophen-5-yl)methoxy)phenyl)hex-4-ynoic acid (Cpd 41) was prepared from (3S)-ethyl 3-(4-((3-(2-methyl-5-(methylsulfonyl)phenyl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-d$_6$) δ 8.12 (d, J=8.0 Hz, 1H), 7.92 (dd, J=1.0, 8.0 Hz, 1H), 7.88 (s, 1H), 7.79-7.80 (m, 1H), 7.67 (d, J=8.0 Hz, 1H), 7.52 (dd, J=1.2, 8.4 Hz, 1H), 7.43 (s, 1H), 7.24 (d, J=8.8 Hz, 2H), 6.91 (d, J=8.8

Hz, 2H), 5.18 (s, 2H), 3.90-3.94 (m, 1H), 3.26 (s, 3H), 2.54-2.58 (m, 2H), 2.17 (s, 3H), 1.76 (s, 3H). LC/MS: mass calcd. for $C_{29}H_{26}O_5S_2$: 518.64, found: 518.9 $[M]^+$.

Example 42

(3S)-3-(4-((3-(2-Methyl-4-(methylsulfonyl)phenyl)benzo[b]thiophen-5-yl)methoxy)phenyl)hex-4-ynoic acid, Cpd 42

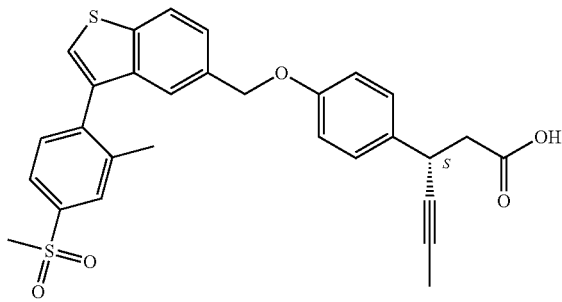

(A) 3-(2-Methyl-4-(methylsulfonyl)phenyl)benzo[b]thiophene-5-carbaldehyde was prepared from (3-(4,4,5,5-tetramethyl-1,3,2-dioxaborolan-2-yl)benzo[b]thiophen-5-yl)methanol (from Example 41A) and 1-bromo-4-methanesulfonyl-2-methylbenzene following General Procedure A, using $PdCl_2(dppf).CH_2Cl_2$ as the palladium catalyst, $Cs_2CO_3$ in place of $K_2CO_3$. LC/MS: mass calcd. for $C_{17}H_{14}O_3S_2$: 330.42, found: 331.1 $[M+H]^+$.

(B) (3-(2-Methyl-4-(methylsulfonyl)phenyl)benzo[b]thiophen-5-yl)methanol was prepared from 3-(2-methyl-4-(methylsulfonyl)phenyl)benzo[b]thiophene-5-carbaldehyde and $NaBH_4$, following the procedure described in Example 41C. LC/MS: mass calcd. for $C_{17}H_{16}O_3S_2$: 332.44, found: 314.9 $[M–OH]^+$.

(C) (3S)-Ethyl 3-(4-((3-(2-methyl-4-(methylsulfonyl)phenyl)benzo[b]thiophen-5-yl)methoxy)phenyl)hex-4-ynoate was prepared from (3-(2-methyl-5-(methylsulfonyl)phenyl)benzo[b]-thiophen-5-yl)methanol and (3S)-ethyl 3-(4-hydroxyphenyl)hex-4-ynoate (available from Synnovator, Inc., Research Triangle Park, N.C.; Cat. #PB05708) following General Procedure B, using $Bu_3P$ and ADDP at a reaction temperature of 60° C. overnight. LC/MS: mass calcd. for $C_{31}H_{30}O_5S_2$: 546.70, found: 547.2 $[M]^+$.

(D) (3S)-3-(4-((3-(2-Methyl-4-(methyl sulfonyl)phenyl)benzo[b]thiophen-5-yl)methoxy)phenyl)hex-4-ynoic acid (Cpd 42) was prepared from (3S)-ethyl 3-(4-((3-(2-methyl-4-(methylsulfonyl)phenyl)benzo[b]thiophen-5-yl)methoxy)phenyl)hex-4-ynoate following General Procedure C, using LiOH as base, EtOH in place of MeOH and 1N HCl for reaction acidification. $^1H$ NMR (DMSO-$d_6$) δ 12.23 (br. s, 1H), 8.11 (d, J=8.4 Hz, 1H), 7.96 (s, 1H), 7.85-7.87 (m, 2H), 7.51-7.57 (m, 2H), 7.45 (s, 1H), 7.24 (d, J=8.4 Hz, 2H), 6.92 (d, J=8.4 Hz, 2H), 5.17 (s, 2H), 3.90-3.95 (m, 1H), 3.29 (s, 3H), 2.54-2.59 (m, 2H), 2.21 (s, 3H), 1.76 (s, 3H). LC/MS: mass calcd. for $C_{29}H_{26}O_5S_2$: 518.64, found: 519.0 $[M]^+$.

Example 43

(3S)-3-(4-((3-(2-Methyl-5-(methylsulfonamido)phenyl)benzo[b]thiophen-5-yl)methoxy)phenyl)hex-4-ynoic acid, Cpd 43

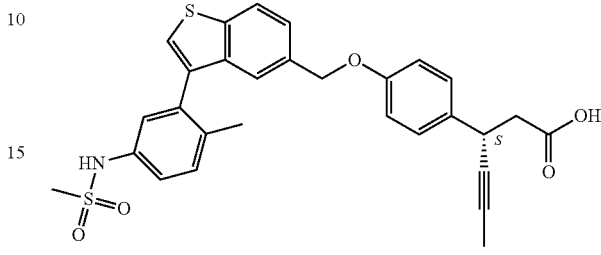

(A) (3-(5-Amino-2-methylphenyl)benzo[b]thiophen-5-yl)methanol was prepared from 3-bromo-4-methylaniline and (3-(4,4,5,5-tetramethyl-1,3,2-dioxaborolan-2-yl)benzo[b]thiophen-5-yl)methanol (from Example 41A) following General Procedure A, using $PdCl_2(dppf).CH_2Cl_2$ as the palladium catalyst and $Cs_2CO_3$ in place of $K_2CO_3$. LC/MS: mass calcd. for $C_{16}H_{15}NOS$: 269.36, found: 270.1 $[M+H]^+$.

(B) (3S)-Ethyl 3-(4-((3-(5-amino-2-methylphenyl)benzo[b]thiophen-5-yl)methoxy)phenyl)hex-4-ynoate was prepared from (3-(5-amino-2-methylphenyl)benzo[b]thiophen-5-yl)methanol and (3S)-ethyl 3-(4-hydroxyphenyl)hex-4-ynoate (available from Synnovator, Inc., Research Triangle Park, N.C.; Cat. #PB05708) following General Procedure B, using $Bu_3P$ and ADDP at a reaction temperature of 60° C. for 1 h. LC/MS: mass calcd. for $C_{30}H_{29}NO_3S$: 483.62, found: 484.0 $[M]^+$.

(C) To an ice-cooled solution of (3S)-ethyl 3-(4-((3-(5-amino-2-methylphenyl)benzo[b]thiophen-5-yl)methoxy)phenyl)hex-4-ynoate (200 mg, 0.41 mmol) and pyridine (0.07 mL, 0.83 mmol) in DCM (2 mL) was added MSCl (0.05 mL, 0.62 mmol) and the resultant solution was stirred overnight at rt. Water (5 mL) was added and the mixture was extracted with DCM (5 mL). The organic extracts were washed with 1N HCl (3×5 mL), dried ($Na_2SO_4$) and concentrated under reduced pressure. The residue thus obtained was purified by silica gel chromatography (0-20% EtOAc/petroleum ether) to afford (3S)-ethyl 3-(4-((3-(2-methyl-5-(methylsulfonamido)phenyl)benzo[b]thiophen-5-yl)methoxy)phenyl)hex-4-ynoate as a light yellow oil (200 mg, 78% yield). LC/MS: mass calcd. for $C_{31}H_{31}NO_5S_2$: 561.71, found: 562.1 $[M]^+$.

(D) (3S)-3-(4-((3-(2-Methyl-5-(methylsulfonamido)phenyl)benzo[b]thiophen-5-yl)methoxy)phenyl)hex-4-ynoic acid was prepared from (3S)-ethyl 3-(4-((3-(2-methyl-5-(methylsulfonamido)phenyl)benzo[b]thiophen-5-yl)methoxy)phenyl)hex-4-ynoate following General Procedure C, using LiOH as base, EtOH in place of MeOH and 1N HCl for reaction acidification. $^1H$ NMR (DMSO-$d_6$) δ 8.06 (d, J=8.4 Hz, 1H), 7.79 (s, 1H), 7.56 (s, 1H), 7.44-7.49 (m, 1H), 7.41 (d, J=8.4 Hz, 1H), 7.23-7.30 (m, 3H), 7.17 (d, J=1.6 Hz, 1H), 6.92 (d, J=8.8 Hz, 2H), 5.16 (s, 2H), 3.90-3.94 (m, 1H), 2.67 (s, 3H), 2.56-2.61 (m, 2H), 2.34 (s, 3H), 1.79 (s, 3H). LC/MS: mass calcd. for $C_{29}H_{27}NO_5S_2$: 533.66, found: 550.9 $[M+NH_3]^+$.

Example 44

(3S)-3-(4-((3-(2-Methyl-6-(methylsulfonamido)phenyl)benzo[b]thiophen-5-yl)methoxy)phenyl)hex-4-ynoic acid, Cpd 44

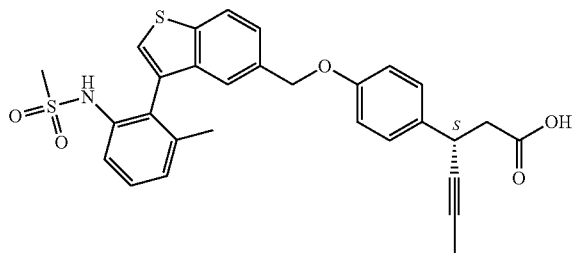

(A) (3-(2-Amino-6-methylphenyl)benzo[b]thiophen-5-yl)methanol was prepared from 2-bromo-3-methylaniline and (3-(4,4,5,5-tetramethyl-1,3,2-dioxaborolan-2-yl)benzo[b]thiophen-5-yl)methanol (from Example 41A) following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{16}$H$_{15}$NOS: 269.36, found: 270.1 [M+H]$^+$.

(B) (3S)-Ethyl 3-(4-((3-(2-amino-6-methylphenyl)benzo[b]thiophen-5-yl)methoxy)phenyl)hex-4-ynoate was prepared from (3-(2-amino-6-methylphenyl)benzo[b]thiophen-5-yl)methanol and (3S)-ethyl 3-(4-hydroxyphenyl)hex-4-ynoate (available from Synnovator, Inc., Research Triangle Park, N.C.; Cat. #PB05708) following General Procedure B, using Bu$_3$P and ADDP at a reaction temperature of 60° C. for 1 h. LC/MS: mass calcd. for C$_{30}$H$_{29}$NO$_3$S: 483.62, found: 484.0 [M]$^+$.

(C) (3S)-Ethyl 3-(4-((3-(2-methyl-6-(methylsulfonamido)phenyl)benzo[b]thiophen-5-yl)methoxy)phenyl)hex-4-ynoate was prepared from (3S)-ethyl 3-(4-((3-(2-amino-6-methylphenyl)benzo[b]thiophen-5-yl)methoxy)phenyl)hex-4-ynoate and MsCl, following the procedure described in Example 43C. LC/MS: mass calcd. for C$_{31}$H$_{31}$NO$_5$S$_2$: 561.71, found: 562.1 [M]$^+$.

(D) (3S)-3-(4-((3-(2-Methyl-6-(methylsulfonamido)phenyl)benzo[b]thiophen-5-yl)methoxy)phenyl)hex-4-ynoic acid (Cpd 44) was prepared from (3S)-ethyl 3-(4-((3(2-methyl-6-(methylsulfonamido)phenyl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-d$_6$) δ 12.24 (br. s, 1H), 8.46 (br. s, 1H), 8.07 (d, J=8.0 Hz, 1H), 7.70 (s, 1H), 7.47 (d, J=8.0 Hz, 1H),.7.37-7.39 (m, 2H), 7.21-7.23 (m, 4H), 6.89 (d, J=8.0 Hz, 2H), 5.14 (s, 2H), 3.91-3.92 (m, 1H), 2.68 (s, 3H), 2.54-2.58 (m, 2H), 1.88 (s, 3H), 1.79 (s, 3H). LC/MS: mass calcd. for C$_{29}$H$_{27}$NO$_5$S$_2$: 533.66, found: 551.0 [M+NH$_3$]$^+$.

Example 45

3-(6-((3-(2-Methylphenyl)benzo[b]thiophen-5-yl)methoxy)pyridin-3-yl)hex-4-ynoic acid, Cpd 45

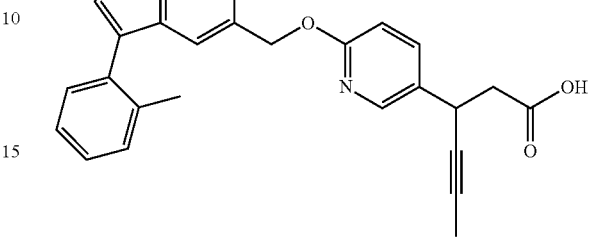

(A) A solution of 6-methoxypyridine-3-carbaldehyde (10 g, 73.00 mmol) and 2,2-dimethyl-1,3-dioxane-4,6-dione (11 g, 76.70 mmol) in water (150 mL) was stirred for 2 h at 75° C., and then cooled in a water/ice bath. The resulting solids were collected by filtration and dried in an oven under reduced pressure to provide 5-((6-methoxypyridin-3-yl)methylene)-2,2-dimethyl-1,3-dioxane-4,6-dione as a yellow powder (18 g, 99%). LC/MS: mass calcd. for C$_{13}$H$_{13}$NO$_5$: 263.25, found: 264.0 [M+H]$^+$.

(B) To a solution of bromo(prop-1-yn-1-yl)magnesium (114 mL, 57.03 mmol, 0.5 N in THF) in THF (300 mL) was added a solution of 5-((6-methoxypyridin-3-yl)methylene)-2,2-dimethyl-1,3-dioxane-4,6-dione (10 g, 38.02 mmol) in THF (100 mL) in drop-wise fashion and the resulting solution was stirred at rt overnight. The reaction was then quenched by the addition of of satd. aq. NH$_4$Cl (100 mL). The resulting mixture was extracted with 300 mL of hexane (which was discarded) and the aqueous layer was collected. The pH of the aqueous layer was adjusted to 2 with 1N HCl and the resulting solution was extracted with EtOAc (3×200 mL). The combined EtOAc extracts were dried (Na$_2$SO$_4$) and concentrated under reduced pressure to provide 5-(1-(6-methoxypyridin-3-yl)but-2-ynyl)-2,2-dimethyl-1,3-dioxane-4,6-dione (10 g, 87%) as a yellow solid. LC/MS: mass calcd. for C$_{16}$H$_{17}$NO$_5$: 303.31, found: 304.0 [M+H]$^+$.

(C) A solution of 5-(1-(6-methoxypyridin-3-yl)but-2-ynyl)-2,2-dimethyl-1,3-dioxane-4,6-dione (5 g, 16.48 mmol), DMF (100 mL) and water (10 mL) was stirred overnight at 100° C. The reaction was then quenched by the addition of satd. aq. NH$_4$Cl (200 mL) and the resulting mixture was extracted with EtOAc (3×200 mL). The combined organic extracts were dried (Na$_2$SO$_4$) and concentrated under reduced pressure to provide 3-(6-methoxypyridin-3-yl)hex-4-ynoic acid (3.5 g, 97%) as a red oil, which was used directly without further purification. LC/MS: mass calcd. for C$_{12}$H$_{13}$NO$_3$: 219.24, found: 220.1 [M+H]$^+$.

(D) A solution of 3-(6-methoxypyridin-3-yl)hex-4-ynoic acid (8.8 g, 40.18 mmol), dioxane (20 mL), water (20 mL) and conc. HCl (5 mL) was stirred overnight at 100° C. After cooling to rt, the solution was neutralized to pH 5 by the addition of satd. aq. NaHCO$_3$ and the resulting mixture was extracted with EtOAc (3×100 mL). The combined organic extracts were dried (Na$_2$SO$_4$) and concentrated under reduced pressure to provide 3-(6-hydroxypyridin-3-yl)hex-4-ynoic acid (7.6 g, 92%) as a brown oil, which was used directly without further purification. LC/MS: mass calcd. for C$_{11}$H$_{11}$NO$_3$: 205.21, found: 206.0 [M+H]$^+$.

(E) A solution of 3-(6-hydroxypyridin-3-yl)hex-4-ynoic acid (8 g, 39.00 mmol) in EtOH (45 mL) was treated with conc. $H_2SO_4$ (2 mL) and the resultant solution was stirred for 2 h at 80° C. After cooling to rt, the solution was neutralized to pH 5 by the addition of satd. aq. $NaHCO_3$ and the resulting mixture was extracted with EtOAc (3×100 mL). The combined organic extracts were dried ($Na_2SO_4$) and concentrated under reduced pressure. The residue thus obtained was purified by silica gel chromatography (0-20% MeOH/DCM) to afford ethyl 3-(6-hydroxypyridin-3-yl)hex-4-ynoate (2.2 g, 24.2%). $^1$H NMR ($CDCl_3$) δ 7.46-7.53 (m, 2H), 6.57 (d, J=9.3 Hz, 1H), 4.17 (q, J=7.2 Hz, 2H), 3.88-3.94 (m, 1H), 2.55-2.71 (m, 2H), 1.82 (d, J=2.4 Hz, 3H), 1.24 (t, J=7.2 Hz, 3H).

(F) To an ice-cooled solution of 5-hydroxymethyl-3-(2-methylphenyl)benzo[b]-thiophene (from Example 1) (200 mg, 0.79 mmol) in DCM (10 mL) was added $PBr_3$ (640 mg, 2.36 mmol) in drop-wise fashion, followed by DMF (0.05 mL, cat.). After stirring at rt for 1 h, water (10 mL) was added and the mixture was extracted with DCM (3×10 mL). The combined organic extracts were dried ($Na_2SO_4$) and concentrated under reduced pressure to afford 5-(bromomethyl)-3-(2-methylphenyl)benzo[b]thiophene (150 mg, 60%) as a yellow oil, which was used directly in the following reaction.

(G) A mixture of 5-(bromomethyl)-3-(2-methylphenyl)benzo[b]thiophene (150 mg, 0.47 mmol), ethyl 3-(6-hydroxypyridin-3-yl)hex-4-ynoate (220 mg, 0.95 mmol) and $Ag_2CO_3$ (130 mg, 0.47 mmol) in toluene (5 mL) was stirred for 2 h at 50° C. Water (20 mL) was then added and the mixture was extracted with EtOAc (3×10 mL). The combined organic extracts were dried ($Na_2SO_4$), concentrated under reduced pressure and the residue thus obtained was purified by silica gel chromatography (0-5% EtOAc/petroleum ether) to provide ethyl 3-(6-((3-(2-methylphenyl)benzo[b]thiophen-5-yl)methoxy)pyridin-3-yl)hex-4-ynoate (90 mg, 41%) as a colorless oil. LC/MS: mass calcd. for $C_{29}H_{27}NO_3S$: 469.59, found: 470.0 $[M]^+$.

(H) 3-(6-((3-(2-Methylphenyl)benzo[b]thiophen-5-yl)methoxy)pyridin-3-yl)hex-4-ynoic acid (Cpd 45) was prepared from ethyl 3-(6-((3-(2-methylphenyl)benzo[b]thiophen-5-yl)methoxy)pyridin-3-yl)hex-4-ynoate following General Procedure C, using LiOH as base, EtOH in place of MeOH and 2N HCl for reaction acidification. $^1$H NMR (DMSO-$d_6$) δ 8.04-8.09 (m, 2H), 6.69-7.71 (m, 2H), 7.48 (dd, J=1.2, 8.4 Hz,1H), 7.22-7.42 (m, 5H), 6.78 (d, J=8.8 Hz, 1H), 5.40 (s, 2H), 3.97-4.01 (m, 1H), 2.58-2.66 (m, 2H), 2.07 (s, 3H), 1.77 (s, 3H). LC/MS: mass calcd. for $C_{27}H_{23}NO_3S$: 441.54, found: 439.9 $[M-H]^-$.

Example 46

3-(6-((3-(2-Methyl-4-((tetrahydro-2H-pyran-4-yl)oxy)phenyl)benzo[b]thiophen-5-yl)methoxy)pyridin-3-yl)hex-4-ynoic acid, Cpd 46

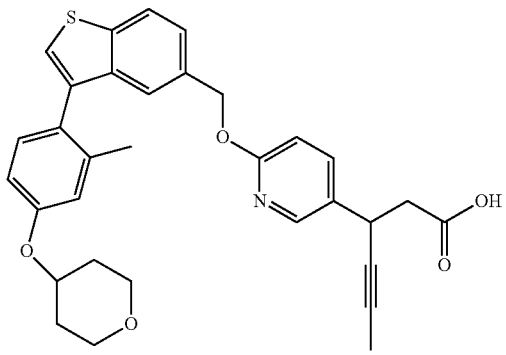 [SMILES: CC#CC(CC(=O)O)c1ccc(OCc2ccc3scc(-c4ccc(OC5CCOCC5)cc4C)c3c2)nc1]

(A) To a solution of (3-(2-methyl-4-(tetrahydro-2H-pyran-4-yloxy)phenyl)benzo[b]thiophen-5-yl)methanol (240 mg, 0.68 mmol; from Example 15D) in DCM (20 mL) was added $PBr_3$ (0.16 mL, 1.69 mmol) in drop-wise fashion. After stirring at rt for 1 h, satd. aq. $NH_4Cl$ (30 mL) was added and the mixture was extracted with DCM (2×30 mL). The combined organic extracts were dried ($Na_2SO_4$) and concentrated under reduced pressure. The residue thus obtained was purified by flash chromatography (0-15% EtOAc/petroleum ether) to afford 4-(4-(5-(bromomethyl)benzo[b]thiophen-3-yl)-3-methylphenoxy)tetrahydro-2H-pyran (240 mg, 85%) as a colorless oil, which was used directly in the following reaction.

(B) Ethyl 3-(6-((3-(2-methyl-4-(tetrahydro-2H-pyran-4-yloxy)phenyl)benzo[b]thiophen-5-yl)methoxy)pyridin-3-yl)hex-4-ynoate was prepared from 4-(4-(5-(bromomethyl)benzo[b]thiophen-3-yl)-3-methylphenoxy)tetrahydro-2H-pyran and ethyl 3-(6-hydroxypyridin-3-yl)hex-4-ynoate (from Example 45E) following the procedure described in Example 45G at a reaction temperature of 60° C. overnight. LC/MS: mass calcd. for $C_{34}H_{35}NO_5S$: 569.71, found: 570.4 $[M+H]^+$.

(C) 3-(6-((3-(2-Methyl-4-((tetrahydro-2H-pyran-4-yl)oxy)phenyl)benzo[b]thiophen-5-yl)methoxy)pyridin-3-yl)hex-4-ynoic acid (Cpd 46) was prepared from ethyl 3-(6-((3-(2-methyl-4-(tetrahydro-2H-pyran-4-yloxy)phenyl)benzo[b]thiophen-5-yl)methoxy)pyridin-3-yl)hex-4-ynoate following General Procedure C, using LiOH as base, EtOH in place of MeOH and 1N HCl for reaction acidification. $^1$H NMR (DMSO-$d_6$) δ 8.09 (s, 1H), 8.04 (d, J=8.4 Hz, 1H), 7.70 (dd, J=2.4, 8.4 Hz, 1H), 7.64 (s, 1H), 7.43-7.48 (m, 2H), 7.15 (d, J=8.4 Hz, 1H), 6.98 (d, J=2.4 Hz, 1H), 6.91 (dd, J=2.4, 8.4 Hz, 1H), 6.79 (d, J=8.4 Hz, 1H), 5.40 (s, 2H), 4.55-4.69 (m, 1H), 3.96-4.04 (m, 1H), 3.85-3.89 (m, 2H), 3.54 (t, J=6.8 Hz, 2H), 2.54-2.63 (m, 2H), 2.00-2.05 (m, 5H), 1.78 (d, J=2.4 Hz, 3H), 1.60-1.65 (m, 2H). LC/MS: mass calcd. for $C_{32}H_{31}NO_5S$: 541.66, found: 542.2 $[M]^+$.

Example 47

3-(6-((3-(4-(2-Methoxyethoxy)-2-methylphenyl)benzo[b]thiophen-5-yl)methoxy)pyridin-3-yl)hex-4-ynoic acid, Cpd 47

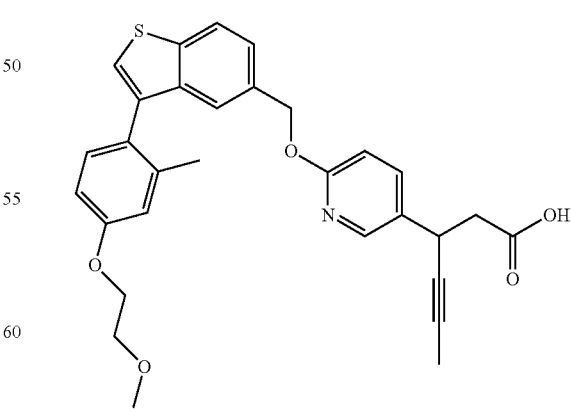

(A) 5-(Bromomethyl)-3-(4-(2-methoxyethoxy)-2-methylphenyl)benzo[b]thiophene was prepared from [3-[4-(2-methoxyethoxy)-2-methylphenyl]-1-benzothiophen-5-yl]

methanol (from Example 16D) and PBr3, following the procedure described in Example 46A, and used directly in the next step.

(B) Ethyl 3-(6-((3-(4-(2-methoxyethoxy)-2-methylphenyl)benzo[b]thiophen-5-yl)methoxy)pyridin-3-yl)hex-4-ynoate was prepared from 5-(bromomethyl)-3-(4-(2-methoxyethoxy)-2-methylphenyl)benzo[b]thiophene and ethyl 3-(6-hydroxypyridin-3-yl)hex-4-ynoate (from Example 45E) following the procedure described in Example 45G at a reaction temperature of 60° C. overnight. LC/MS: mass calcd. for $C_{32}H_{33}NO_5S$: 543.67, found: 544.4 [M+H]$^+$.

(C) 3-(6-((3-(4-(2-Methoxyethoxy)-2-methylphenyl)benzo[b]thiophen-5-yl)methoxy)pyridin-3-yl)hex-4-ynoic acid (Cpd 47) was prepared from ethyl 3--(6-((3-(4-(2-methoxyethoxy)-2-methylphenyl)benzo[b]thiophen-5-yl)methoxy)pyridin-3-yl)hex-4-ynoate following General Procedure C, using LiOH as base, EtOH in place of MeOH and 1N HCl for reaction acidification. $^1$H NMR (DMSO-d$_6$) δ 12.31 (br. s, 1H), 8.10 (d, J=2.4 Hz, 1H), 8.04 (d, J=8.4 Hz, 1H), 7.71 (dd, J=2.4, 8.4 Hz, 1H), 7.64 (s, 1H), 7.42-7.48 (m, 2H), 7.16 (d, J=8.4 Hz, 1H), 6.96 (d, J=2.4 Hz, 1H), 6.88 (dd, J=2.7, 8.4 Hz, 1H), 6.80 (d, J=8.4 Hz, 1H), 5.40 (s, 2H), 4.14-4.17(m, 2H), 3.96-4.02 (m, 1H), 3.68-3.71 (m, 2H), 3.33 (s, 3H), 2.63-2.66 (m, 2H), 2.01(s, 3H), 1.78 (s, 3H). LC/MS: mass calcd. for $C_{30}H_{29}NO_5S$: 515.62, found: 516.3 [M+H]$^+$.

Example 48

(3S)-3-(4-((3-(5-(2-Methoxyethoxy)-3-methylpyridin-2-yl)benzo[b]thiophen-5-yl)methoxy)phenyl)hex-4-ynoic acid, Cpd 48

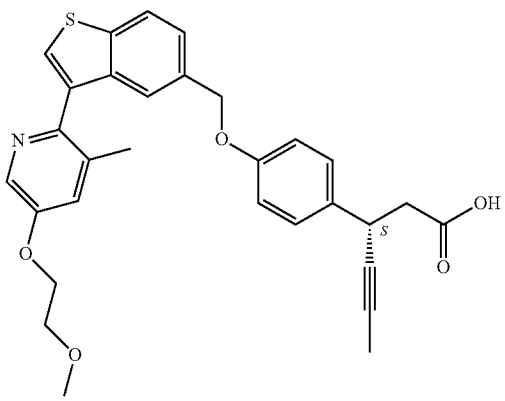

(A) A mixture of 6-bromo-5-methylpyridin-3-ol (1 g, 5.32 mmol), 1-bromo-2-methoxyethane (730 mg, 5.25 mmol) and K$_2$CO$_3$ (1.5 g, 10.87 mmol) in MeCN (20 mL) was stirred at rt overnight, after which the reaction was quenched by the addition of water (100 mL). The resulting solution was extracted with EtOAc (2×100 mL) and the combined organic phase was dried (Na$_2$SO$_4$) and concentrated under reduced pressure. The resultant residue was purified by silica gel chromatography (0-15% EtOAc/petroleum ether) to afford 2-bromo-5-(2-methoxyethoxy)-3-methylpyridine (500 mg, 38%) as colorless oil. LC/MS: mass calcd. for $C_9H_{12}BrNO_2$: 246.10, found: 246.0 [M]$^+$, 248.0 [M+2]$^+$.

(B) (3-(5-(2-Methoxyethoxy)-3-methylpyridin-2-yl)benzo[b]thiophen-5-yl)methanol was prepared from 2-bromo-5-(2-methoxyethoxy)-3-methylpyridine and (3-(4,4,5,5-tetramethyl-1,3,2-dioxaborolan-2-yl)benzo[b]thiophen-5-yl)methanol (from Example 41A) following General Procedure A, using PdCl$_2$(dppf).CH$_2$Cl$_2$ as the palladium catalyst, Cs$_2$CO$_3$ in place of K$_2$CO$_3$. LC/MS: mass calcd. for $C_{18}H_{19}NO_3S$: 329.41, found: 330.0[M+H]$^+$.

(C) (3S)-Ethyl 3-(4-((3-(5-(2-methoxyethoxy)-3-methylpyridin-2-yl)benzo[b]thiophen-5-yl)methoxy)phenyl)hex-4-ynoate was prepared from (3-(5-(2-methoxyethoxy)-3-methylpyridin-2-yl)benzo[b]thiophen-5-yl)methanol and (3S)-ethyl 3-(4-hydroxyphenyl)hex-4-ynoate (available from Synnovator, Inc., Research Triangle Park, N.C.; Cat. #PB05708) following General Procedure B, using Bu$_3$P and ADDP at a reaction temperature of 50° C. in toluene for 2 h. LC/MS: mass calcd. for $C_{32}H_{33}NO_5S$: 543.67, found: 544.3 [M+H]$^+$.

(D) (3S)-3-(4-((3-(5-(2-Methoxyethoxy)-3-methylpyridin-2-yl)benzo[b]thiophen-5-yl)methoxy)phenyl)hex-4-ynoic acid (Cpd 48) was prepared from (3S)-ethyl 3-(4-((3-(5-(2-methoxyethoxy)-3-methylpyridin-2-yl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-d$_6$) δ 12.23 (br. s, 1H), 8.27 (s, 1H), 8.06 (d, J=8.4 Hz, 1H), 7.86 (s, 1H), 7.69 (s, 1H), 7.43-7.52 (m, 2H), 7.25 (d, J=8.7 Hz, 2H), 6.93 (d, J=8.7 Hz, 2H), 5.15 (s, 2H), 4.23-4.28 (m, 2H), 3.91-3.96 (m, 1H), 3.72 (d, J=4.5 Hz, 2H), 3.33 (s, 3H), 2.58 (d, J=7.5 Hz, 2H), 2.24 (s, 3H), 1.77 (d, J=2.4 Hz, 3H). LC/MS: mass calcd. for $C_{30}H_{29}NO_5S$: 515.62, found: 516.2 [M+H]$^+$.

Example 49

(3S)-3-(4-((3-(5-(2-Methoxyethoxy)-2-methylpyridin-3-yl)benzo[b]thiophen-5-yl)methoxy)phenyl)hex-4-ynoic acid, Cpd 49

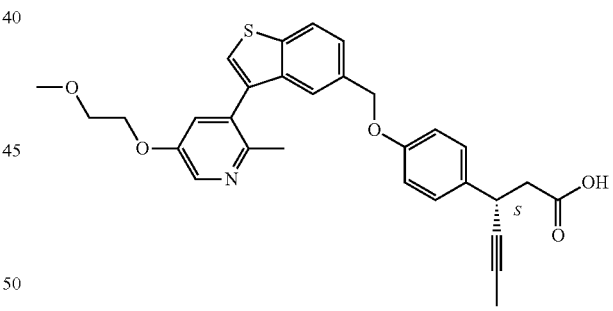

(A) 3-Bromo-5-(2-methoxyethoxy)-2-methylpyridine was prepared from 5-bromo-6-methylpyridin-3-ol and 1-bromo-2-methoxyethane following the procedure described in Example 48A. LC/MS: mass calcd. for $C_9H_{12}BrNO_2$: 246.10, found: 246.0[M]$^+$, 248.0 [M+2]$^+$.

(B) 5-(2-Methoxyethoxy)-2-methyl-3-(4,4,5,5-tetramethyl-1,3,2-dioxaborolan-2-yl)pyridine was prepared from 3-bromo-5-(2-methoxyethoxy)-2-methylpyridine and bis(pinacolato)diboron following General Procedure A, using PdCl$_2$(dppf).CH$_2$Cl$_2$ as the palladium catalyst, KOAc in place of K$_2$CO$_3$ and DMSO as reaction solvent at a reaction temperature of 85° C. overnight. LC/MS: mass calcd. for $C_{15}H_{24}BNO_4$: 293.17, found: 294.1 [M+H]$^+$.

(C) (3S)-Ethyl 3-(4-((3-(5-(2-methoxyethoxy)-2-methyl-pyridin-3-yl)benzo[b]thiophen-5-yl)methoxy)phenyl)hex-4- ynoate was prepared from 5-(2-methoxyethoxy)-2-methyl-3-(4,4,5,5-tetramethyl-1,3,2-dioxaborolan-2-yl)pyridine and (3S)-ethyl-3-(4-((3-bromobenzo[b]thiophen-5-yl)methoxy)phenyl)hex-4-ynoate (from Example 11E) following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{32}$H$_{33}$NO$_5$S: 543.67, found: 544.2 [M+H]$^+$.

(D) (3S)-3-(4-((3-(5-(2-Methoxyethoxy)-2-methylpyridin-3-yl)benzo[b]thiophen-5-yl)methoxy)phenyl)hex-4-ynoic acid (Cpd 49) was prepared from (3S)-ethyl 3-(4-((3-(5-(2-methoxyethoxy)-2-methylpyridin-3-yl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-d$_6$) δ 8.28 (d, J=3.0 Hz, 1H), 8.10 (d, J=8.4 Hz, 1H), 7.84 (s, 1H), 7.48-7.52 (m, 2H), 7.30 (d, J=2.7 Hz, 1H), 7.24 (d, J=8.7 Hz, 2H), 6.92 (d, J=8.7 Hz, 2H), 5.18 (s, 2H), 4.17-4.20 (m, 2H), 3.90-3.94 (m, 1H), 3.65-3.68 (m, 2H), 3.32 (s, 3H), 2.54-2.57 (m, 2H), 2.20 (s, 3H), 1.76 (d, J=2.4 Hz, 3H). LC/MS: mass calcd. for C$_{30}$H$_{29}$NO$_5$S: 515.62, found: 516.2 [M+H]$^+$.

Example 50

(3S)-3-(4-((3-(6-(2-Methoxyethoxy)-2-methylpyridin-3-yl)benzo[b]thiophen-5-yl)methoxy)phenyl)hex-4-ynoic acid, Cpd 50

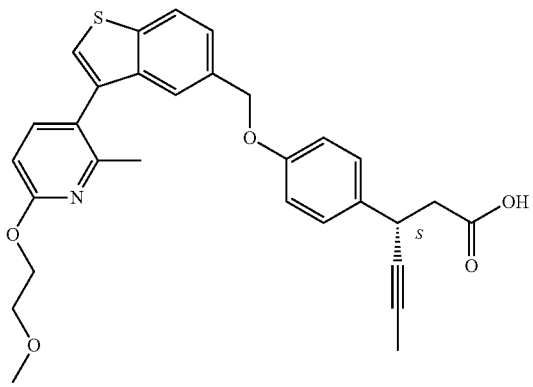

(A) To a solution of 2-methoxyethan-1-ol (5.53 g, 72.8 mmol) in anhydrous THF (80 mL) was added NaH (60% wt in mineral oil; 2.91 g, 72.8 mmol) in portions. After stirring at rt for 30 min, a solution of 3-bromo-6-chloro-2-methylpyridine (5 g, 24.3 mmol) in THF (20 mL) was added in drop-wise fashion. Following the addition, the mixture was stirred at 85° C. overnight. The reaction was then quenched by the addition of satd. aq. NH$_4$Cl (100 mL) and the mixture was extracted with EtOAc (2×100 mL). The combined organic extracts were dried (Na$_2$SO$_4$) and concentrated under reduced pressure. The residue obtained was purified by silica gel chromatography (0-10% EtOAc/petroleum ether) to afford 3-bromo-6-(2-methoxyethoxy)-2-methylpyridine (5.6 g, 94% yield) as a colorless oil. LC/MS: mass calcd. for C$_9$H$_{12}$BrNO$_2$: 246.10, found: 246.0 [M]$^+$, 247.9 [M+2]$^+$.

(B) 6-(2-Methoxyethoxy)-2-methyl-3-(4,4,5,5-tetramethyl-1,3,2-dioxaborolan-2-yl)pyridine was prepared from 3-bromo-6-(2-methoxyethoxy)-2-methylpyridine and bis(pinacolato)diboron following General Procedure A, using PdCl$_2$(dppf).CH$_2$Cl$_2$ as the palladium catalyst, KOAc in place of K$_2$CO$_3$ and DMSO as reaction solvent at a reaction temperature of 85° C. overnight. LC/MS: mass calcd. for C$_{15}$H$_{24}$BNO$_4$: 293.17, found: 294.3 [M+H]$^+$.

(C) (3S)-Ethyl 3-(4-((3-(6-(2-methoxyethoxy)-2-methylpyridin-3-yl)benzo[b]thiophen-5-yl)methoxy)phenyl)hex-4-ynoate was prepared from 6-(2-methoxyethoxy)-2-methyl-3-(4,4,5,5-tetramethyl-1,3,2-dioxaborolan-2-yl)pyridine and (3)-ethyl 3-(4-((3-bromobenzo[b]thiophen-5-yl)methoxy)phenyl)hex-4-ynoate (from Example 11E) following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{32}$H$_{33}$NO$_5$S: 543.67, found: 544.2 [M+H]$^+$.

(D) (3S)-3-(4-((3-(6-(2-Methoxyethoxy)-2-methylpyridin-3-yl)benzo[b]thiophen-5-yl)methoxy)phenyl)hex-4-ynoic acid (Cpd 50) was prepared from (3S)-ethyl 3-(4-((3-(6-(2-methoxyethoxy)-2-methylpyridin-3-yl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-d$_6$) δ 8.07 (d, J=8.1 Hz, 1H), 7.68 (d, J=2.7 Hz, 1H), 7.57 (d, J=8.4 Hz, 1H), 7.51 (d, J=8.7 Hz, 1H), 7.41 (s, 1H), 7.25 (d, J=8.7 Hz, 2H), 6.92 (d, J=8.7 Hz, 2H), 6.80 (d, J=8.1 Hz, 1H), 5.19 (s, 2H), 4.42-4.44 (m, 2H), 3.86-3.94 (m, 1H), 3.71-3.74 (m, 2H), 3.34 (s, 3H), 2.18 (s, 3H), 1.76 (d, J=2.1 Hz, 3H). LC/MS: mass calcd. for C$_{30}$H$_{29}$NO$_5$S: 515.62, found: 516.2 [M+H]$^+$.

Example 51

(3S)-3-(4-((3-(6-(2-Methoxyethoxy)-4-methylpyridin-3-yl)benzo[b]thiophen-5-yl)methoxy)phenyl)hex-4-ynoic acid, Cpd 51

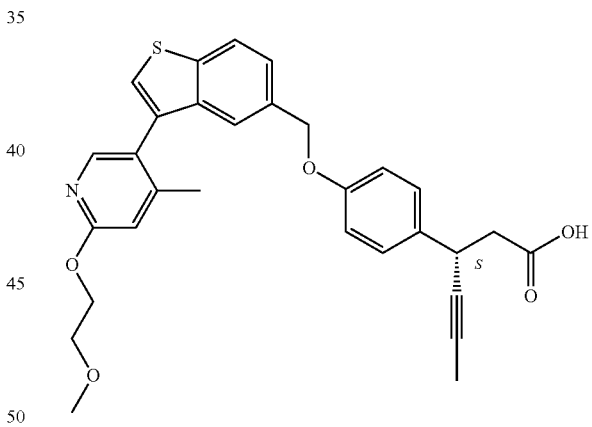

(A) To a solution of 2-methoxyethan-1-ol (1.82 g, 24 mmol) in anhydrous THF (20 mL) was added NaH (60% wt in mineral oil; 960 mg, 24 mmol) in portions. After stirring at rt for 30 min, the mixture was cooled to 0° C. and a solution of 2,5-dibromo-4-methylpyridine (2 g, 8 mmol) in THF (10 mL) was added in drop-wise fashion. The resultant mixture was then heated at 80° C. overnight. The reaction was then quenched by the addition of satd. aq. NH$_4$Cl (100 mL) and the mixture was extracted with EtOAc (2×100 mL). The combined organic extracts were dried (Na$_2$SO$_4$) and concentrated under reduced pressure. The residue obtained was purified by silica gel chromatography (0-10% EtOAc/petroleum ether) to afford 5-bromo-2-(2-methoxyethoxy)-4-methylpyridine (1.2 g, 61% yield) as a light yellow oil. LC/MS: mass calcd. for C$_9$H$_{12}$BrNO$_2$: 246.10, found: 246.0 [M]$^+$, 248.0 [M+2]$^+$.

(B) 2-(2-Methoxyethoxy)-4-methyl-5-(4,4,5,5-tetramethyl-1,3,2-dioxaborolan-2-yl)pyridine was prepared from 5-bromo-2-(2-methoxyethoxy)-4-methylpyridine and bis(pinacolato)diboron following General Procedure A, using PdCl$_2$(dppf).CH$_2$Cl$_2$ as the palladium catalyst, KOAc in place of K$_2$CO$_3$ and DMSO as reaction solvent at a reaction temperature of 85° C. overnight. LC/MS: mass calcd. for C$_{15}$H$_{24}$BNO$_4$: 293.17, found: 294.1 [M+H]$^+$.

(C) (3S)-Ethyl 3-(4-((3-(6-(2-methoxyethoxy)-4-methylpyridin-3-yl)benzo[b]thiophen-5-yl)methoxy)phenyl)hex-4-ynoate was prepared from 2-(2-methoxyethoxy)-4-methyl-5-(4,4,5,5-tetramethyl-1,3,2-dioxaborolan-2-yl)pyridine and (3S)-ethyl 3-(4-((3-bromobenzo[b]thiophen-5-yl)methoxy)phenyl)hex-4-ynoate (from Example 11E) following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{32}$H$_{33}$NO$_5$S: 543.67, found: 544.2 [M+H]$^+$.

(D) (3S)-3-(4-((3-(6-(2-Methoxyethoxy)-4-methylpyridin-3-yl)benzo[b]thiophen-5-yl)methoxy)phenyl)hex-4-ynoic acid was prepared from (3S)-ethyl 3-(4-((3-(6-(2-methoxyethoxy)-4-methylpyridin-3-yl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-d$_6$) δ 12.23 (br. s, 1H), 8.08 (d, J=8.1 Hz, 1H), 8.02 (s, 1H), 7.77 (s, 1H), 7.50 (d, J=1.2 Hz, 1H), 7.48 (s, 1H), 7.24 (d, J=8.7 Hz, 2H), 6.92 (d, J=8.4 Hz, 2H), 6.87 (s, 1H), 5.18 (s, 2H), 4.41-4.44 (m, 2H), 3.89-3.94 (m, 1H), 3.66 (t, J=4.8 Hz, 2H), 3.33 (s, 3H), 2.58 (d, J=7.5 Hz, 2H), 2.04 (s, 3H), 1.76 (d, J=2.4Hz, 3H). LC/MS: mass calcd. for C$_{30}$H$_{29}$NO$_5$S: 515.62, found: 516.2 [M+H]$^+$.

Example 52

(3S)-3-(4-((3-(2-Chloro-5-methylpyridin-4-yl)benzo[b]thiophen-5-yl)methoxy)phenyl)hex-4-ynoic acid, Cpd 52

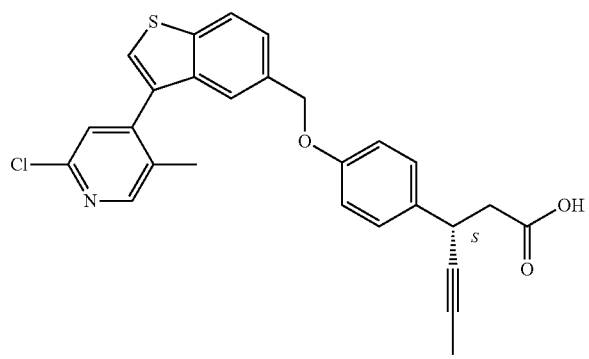

(A) (3-(2-Chloro-5-methylpyridin-4-yl)benzo[b]thiophen-5-yl)methanol was prepared from 4-bromo-2-chloro-5-methylpyridine and (3-(4,4,5,5-tetramethyl-1,3,2-dioxaborolan-2-yl)benzo[b]thiophen-5-yl)methanol (from Example 41A) following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{15}$H$_{12}$ClNOS: 289.78, found: 290.0 [M]$^+$, 292.0 [M+2]$^+$.

(B) (3S)-Ethyl 3-(4-((3-(2-chloro-5-methylpyridin-4-yl)benzo[b]thiophen-5-yl)methoxy)phenyl)hex-4-ynoate was prepared from (3-(2-chloro-5-methylpyridin-4-yl)benzo[b]thiophen-5-yl)methanol and (3S)-ethyl 3-(4-hydroxyphenyl)hex-4-ynoate (available from Synnovator, Inc., Research Triangle Park, N.C.; Cat. #PB05708) following General Procedure B, using Bu$_3$P and ADDP at a reaction temperature of 60° C. in toluene overnight. LC/MS: mass calcd. for C$_{29}$H$_{26}$ClNO$_3$S: 504.04, found: 504.1 [M]$^+$, 506.1 [M+2]$^+$.

(C) (3S)-3-(4-((3-(2-Chloro-5-methylpyridin-4-yl)benzo[b]thiophen-5-yl)methoxy)phenyl)hex-4-ynoic acid (Cpd 52) was prepared (3S)-ethyl 3-(4-((3-(2-chloro-5-methylpyridin-4-yl)benzo[b]thiophen-5-yl)methoxy)phenyl)hex-4-ynoate following General Procedure C, using NaOH as base, MeOH as solvent and a reaction temperature of 60° C. for 2 h. For workup, the reaction mixture was filtered and concentrated, then purified directly by preparative HPLC on a Waters SunFire™ Prep C18, 5µ column (19×100 mm) using an acetonitrile/water (0.5% NH$_4$HCO$_3$) gradient (65-75%). $^1$H NMR (CD$_3$OD) δ 8.31 (s, 1H), 7.97 (d, J=8.4 Hz, 1H), 7.66 (s, 1H), 7.49 (d, J=8.7 Hz, 1H), 7.41 (s, 1H), 7.36 (s, 1H), 7.24 (d, J=8.4 Hz, 2H), 6.86 (d, J=8.4 Hz, 2H), 5.16 (s, 2H), 3.90-3.98 (m, 1H), 2.48-2.63 (m, 2H), 2.05 (s, 3H), 1.76 (s, 3H). LC/MS: mass calcd. for C$_{27}$H$_{22}$ClNO$_3$S: 475.99, found: 476.1 [M]$^+$, 478.1 [M+2]$^+$.

Example 53

3-(4-((3-(2-Methylphenyl)benzo[b]thiophen-5-yl)oxy)methyl)phenyl)propanoic acid, Cpd 53

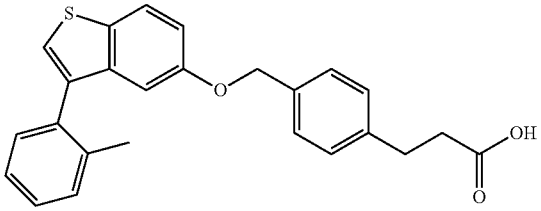

(A) A mixture of 4-bromobenzaldehyde (2 g, 10.81 mmol), ethyl prop-2-enoate (1.62 g, 16.18 mmol), P(o-tol)$_3$ (327 mg, 1.08 mmol), Pd(OAc)$_2$ (120 mg, 0.53 mmol) and triethylamine (3.26 g, 32.22 mmol) in DMF (10 mL) was stirred overnight at 100° C. under an inert atmosphere of nitrogen in a sealed tube. After cooling to rt, satd. aq. NH$_4$Cl (100 mL) was added and the mixture was extracted with EtOAc (3×100 mL). The combined organic extracts were washed with water (2×50 mL), concentrated under reduced pressure, and the resultant residue was purified by silica gel chromatography (0-10% EtOAc/petroleum ether) to afford (E)-ethyl 3-(4-formylphenyl)acrylate (2 g, 91%) as a yellow liquid. LC/MS: mass calcd. for C$_{12}$H$_{12}$O$_3$: 204.22, found: 205.1 [M+H]$^+$.

(B) A mixture of (E)-ethyl 3-(4-formylphenyl)acrylate (2 g, 9.79 mmol), Pd/C (1 g, 10% wt) and ethanol (50 mL) was hydrogenated at 3.5 atm for 2 h, then filtered. The filtrate was concentrated under reduced pressure and the resultant residue was purified by silica gel chromatography (0-15% EtOAc/petroleum ether) to provide ethyl 3-(4-(hydroxymethyl)phenyl)propanoate (1.54 g, 76%) as a colorless liquid. LC/MS: mass calcd. for C$_{12}$H$_{16}$O$_3$: 208.25, found: 191.0 [M−OH]$^+$.

(C) Ethyl 3-(4-((3-bromobenzo[b]thiophen-5-yloxy)methyl)phenyl)propanoate was prepared from ethyl 3-(4-(hydroxymethyl)phenyl)propanoate and 3-bromo-1-benzothiophen-5-ol (from Example 23C) following General Procedure B using PBu$_3$ and ADDP in toluene as solvent (in place of THF) at a temperature of 60° C. overnight. $^1$H NMR (DMSO-$d_6$) δ 7.95-8.00 (m, 2H), 7.41 (d, J=8.1 Hz, 2H), 7.16-7.28 (m, 4H), 5.18 (s, 2H), 4.03 (dd, J=6.9, 14.1 Hz, 2H), 2.86 (t, J=7.5 Hz, 2H), 2.61 (t, J=7.5 Hz, 2H), 1.14 (t, J=7.5 Hz, 3H).

(D) Ethyl 3-(4-((3-(2-methylphenyl)benzo[b]thiophen-5-yloxy)methyl)phenyl)propanoate was prepared from ethyl 3-(4-((3-bromobenzo[b]thiophen-5-yloxy)methyl)phenyl) and 2-methylphenylboronic acid following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{27}$H$_{26}$O$_3$S: 430.56, found: 431.3 [M+H]$^+$.

(E) 3-(4-(((3-(2-Methylphenyl)benzo[b]thiophen-5-yl)oxy)methyl)phenyl)propanoic acid (Cpd 53) was prepared from ethyl 3-(4-((3-(2-methylphenyl)benzo[b]thiophen-5-yloxy)methyl)phenyl)propanoate following General Procedure C, using LiOH as base, EtOH in place of MeOH, a rt reaction temperature overnight and 1N HCl for reaction acidification. $^1$H NMR (DMSO-$d_6$) δ 7.94 (d, J=8.7 Hz, 1H), 7.65 (s, 1H), 7.13-7.36 (m, 8H), 7.10 (d, J=2.4 Hz, 1H), 6.81 (d, J=2.4 Hz, 1H), 5.00 (s, 2H), 2.79 (t, J=7.8 Hz, 2H), 2.42 (t, J=7.8 Hz, 2H), 2.05 (s, 3H). LC/MS: mass calcd. for C$_{25}$H$_{22}$O$_3$S: 402.51, found: 401.1 [M–H]$^-$.

Example 54

(3S)-3-[4-[((3-[4-(3-Hydroxy-3-methylbutoxy)-2-methylphenyl]-1-benzothiophen-5-yl]oxy)methyl]phenyl]hex-4-ynoic acid, Cpd 54

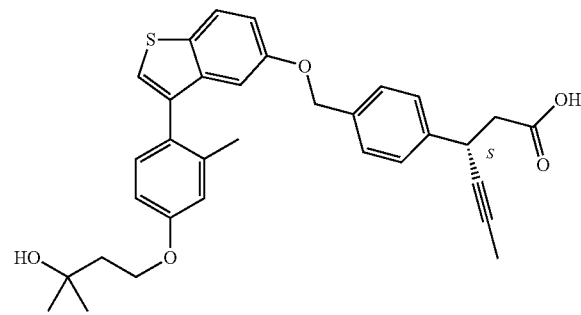

(A) Ethyl (3S)-3-[4-([[3-(4-hydroxy-2-methylphenyl)-1-benzothiophen-5-yl]oxy]methyl)phenyl]hex-4-ynoate was prepared from ethyl (3S)-3-(4-[[(3-bromo-1-benzothiophen-5-yl)oxy]methyl]phenyl]hex-4-ynoate (from Example 23F) and (4-hydroxy-2-methylphenyl)boronic acid following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{30}$H$_{28}$O$_4$S: 484.61, found: 485.3 [M+H]$^+$.

(B) Ethyl (3S)-3-[4-[([3-[4-(3-hydroxy-3-methylbutoxy)-2-methylphenyl]-1-benzothiophen-5-yl]oxy)methyl]phenyl] hex-4-ynoate was prepared from ethyl (3S)-3-[4-([[3-(4-hydroxy-2-methylphenyl)-1-benzothiophen-5-yl]oxy] methyl)phenyl]hex-4-ynoate and 3-methylbutane-1,3-diol following General Procedure B, using PBu$_3$ (10% in hexane) and ADDP in toluene as solvent (in place of THF) at a temperature of 60° C. overnight. LC/MS: mass calcd. for C$_{35}$H$_{38}$O$_5$S: 570.74, found: 571.5 [M+H]$^+$.

(C) (3S)-3-[4-[([3-[4-(3-Hydroxy-3-methylbutoxy)-2-methylphenyl]-1-benzothiophen-5-yl]oxy)methyl]phenyl] hex-4-ynoic acid (Cpd 54) was prepared from ethyl (3S)-3-[4-[([3-[4-(3-hydroxy-3-methylbutoxy)-2-methylphenyl]-1-benzothiophen-5-yl]oxy)methyl]phenyl]hex-4-ynoate following General Procedure C, using LiOH as base, EtOH in place of MeOH, a rt reaction temperature overnight and 2N HCl for reaction acidification. $^1$H NMR (CD$_3$OD) δ 7.76-7.78 (m, 1H), 7.36-7.45 (m, 2H), 7.27-7.36 (m, 3H), 7.04-7.15 (m, 2H), 6.79-6.94 (m, 3H), 5.03 (s, 2H), 4.21 (t, J=6.8 Hz, 2H), 4.02-4.13 (m, 1H), 2.59-2.76 (m, 2H), 2.04 (t, J=6.8 Hz, 2H), 1.97 (s, 3H), 1.84 (d, J=2.4 Hz, 3H), 1.28 (s, 6H). LC/MS: mass calcd. for C$_{33}$H$_{34}$O$_5$S: 542.69, found: 541.2 [M–H]$^-$.

Example 55

(3S)-3-[4-[([3-[4-(2,3-Dihydroxypropoxy)-2-methylphenyl]-1-benzothiophen-5-yl]oxy)methyl]phenyl] hex-4-ynoic acid, Cpd 55

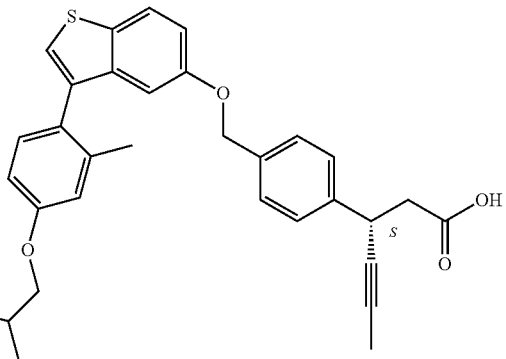

(A) Ethyl (3S)-3-(4-[[(3-[4-[(2,2-dimethyl-1,3-dioxolan-4-yl)methoxy]-2-methylphenyl]-1-benzothiophen-5-yl)oxy] methyl]phenyl)hex-4-ynoate was prepared from 2-(4-((2,2-dimethyl-1,3-dioxolan-4-yl)methoxy)-2-methylphenyl)-4,4,5,5-tetramethyl-1,3,2-dioxaborolane (from Example 13B) and (3S)-ethyl 3-(4-(((3-bromobenzo[b]thiophen-5-yl)oxy)methyl)phenyl)hex-4-ynoate (from Example 23F) following General Procedure A, using PdCl$_2$(dppf).CH$_2$Cl$_2$ as the palladium catalyst and Cs$_2$CO$_3$ in place of K$_2$CO$_3$. LC/MS: mass calcd for C$_{36}$H$_{38}$O$_6$S: 598.75, found 599.3 [M+H]$^+$.

(B) A solution of ethyl (3S)-3-(4-[[(3-[4-[(2,2-dimethyl-1,3-dioxolan-4-yl)methoxy]-2-methylphenyl]-1-benzothiophen-5-yl)oxy]methyl]phenyl)hex-4-ynoate (200 mg, 0.33 mmol), THF (2 mL) and 2N HCl (2 mL, 2 mmol) was stirred at rt overnight. Water (20 mL) was then added and the mixture was extracted with EtOAc (3×20 mL). The combined organic extracts were dried (Na$_2$SO$_4$), concentrated under reduced pressure and purified by silica gel chromatography [ethyl acetate/petroleum ether (0-50%)] to afford ethyl (3S)-3-[4-[([3-[4-(2,3-dihydroxypropoxy)-2-methylphenyl]-1-benzothiophen-5-yl]oxy)methyl]phenyl]hex-4-ynoate (60 mg, 19%) as light yellow oil. LC/MS: mass calcd for C$_{33}$H$_{34}$O$_6$S: 558.68, found 559.2 [M+H]$^+$.

(C) (3S)-3-[4-[([3-[4-(2,3-Dihydroxypropoxy)-2-methylphenyl]-1-benzothiophen-5-yl]oxy)methyl]phenyl]hex-4-ynoic acid (Cpd 55) was prepared from ethyl (3S)-3-[4-[([3-[4-(2,3-dihydroxypropoxy)-2-methylphenyl]-1-benzothiophen-5-yl]oxy)methyl]phenyl]hex-4-ynoate following General Procedure C, using LiOH as base, EtOH in place of MeOH, a rt reaction temperature overnight and 1N HCl for reaction acidification. $^1$H NMR (DMSO-$d_6$) δ 7.91 (d, J=8.8 Hz, 1H), 7.58 (s, 1H), 7.32-7.37 (m, 4H), 7.09-7.11 (m, 2H), 6.92-6.93 (m, 1H), 6.81-6.87 (m, 2H), 5.03 (s, 2H), 4.97-5.02 (m, 1H), 4.64-4.69 (m, 1H), 3.93-4.07 (m, 2H), 3.89-3.92 (m, 1H), 3.81-3.85 (m, 1H), 3.47-3.48 (d, J=5.6 Hz, 2H), 2.63 (d, J=5.6 Hz, 2H), 2.01 (s, 3H), 1.77 (s, 3H). LC/MS: mass calcd for C$_{31}$H$_{30}$O$_6$S: 530.63, found 529.1 [M–H]$^-$.

Example 56

(3S)-3-(4-[[3-[2-Methyl-4-[(3-methyloxetan-3-yl)methoxy]phenyl]-1-benzothiophen-5-yl]oxy]methyl]phenyl)hex-4-ynoic acid, Cpd 56

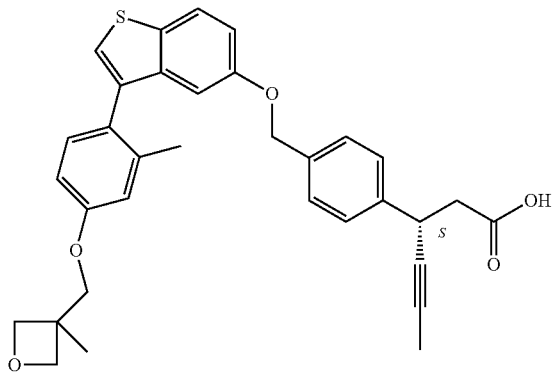

(A) Ethyl (3S)-3-(4-[[3-[2-methyl-4-[(3-methyloxetan-3-yl)methoxy]phenyl]-1-benzothiophen-5-yl]oxy]methyl]phenyl)hex-4-ynoate was prepared from 4,4,5,5-tetramethyl-2-(2-methyl-4-((3-methyloxetan-3-yl)methoxy)phenyl)-1,3,2-dioxaborolane (from Example 14B) and ethyl (3S)-3-(4-[[(3-bromo-1-benzothiophen-5-yl)oxy]methyl]phenyl)hex-4-ynoate (from Example 23F) following General Procedure A, using PdCl$_2$(dppf).CH$_2$Cl$_2$ as the palladium catalyst and Cs$_2$CO$_3$ in place of K$_2$CO$_3$. LC/MS: mass calcd for C$_{35}$H$_{36}$O$_5$S: 568.72, found 569.2 [M]$^+$.

(B) (3S)-3-(4-[[(3-[2-Methyl-4-[(3-methyloxetan-3-yl)methoxy]phenyl]-1-benzothiophen-5-yl)oxy]methyl]phenyl)hex-4-ynoic acid (Cpd 56) was prepared from ethyl (3S)-3-(4-[[(3-[2-methyl-4-[(3-methyloxetan-3-yl)methoxy]phenyl]-1-benzothiophen-5-yl)oxy]methyl]phenyl)hex-4-ynoate following General Procedure C, using LiOH as base, EtOH in place of MeOH, a rt reaction temperature overnight and 1N HCl for reaction acidification. $^1$H NMR (DMSO-d$_6$) δ 7.92 (d, J=8.7 Hz, 1H), 7.58 (s, 1H), 7.32-7.38 (m, 4H), 7.06-7.18 (m, 2H), 6.99 (d, J=2.1 Hz, 2H), 6.88-6.92 (m, 1H), 6.83 (d, J=2.4 Hz, 2H), 5.03 (s, 2H), 4.53 (d, J=5.7 Hz, 2H), 4.34 (d, J=5.7 Hz, 2H), 4.11 (s, 2H), 3.95-4.05 (m, 1H), 2.60 (d, J=7.5 Hz, 2H), 2.02 (s, 3H), 1.77 (d, J=2.4 Hz, 3H), 1.40 (s, 3H). LC/MS: mass calcd for C$_{33}$H$_{32}$O$_5$S: 540.67, found 541.2 [M+H]$^+$, 558.2 [M+NH$_3$]$^+$.

Example 57

(3S)-3-[4-[([3-[2-Methyl-4-(oxan-4-yloxy)phenyl]-1-benzothiophen-5-yl]oxy)methyl]phenyl]hex-4-ynoic acid, Cpd 57

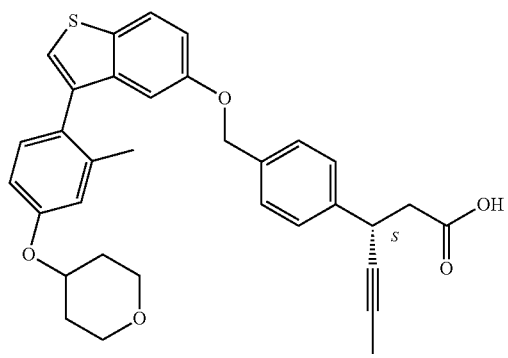

(A) Ethyl (3S)-3-[4-[([3-[2-methyl-4-(oxan-4-yloxy)phenyl]-1-benzothiophen-5-yl]oxy)methyl]phenyl]hex-4-ynoate was prepared from 4,4,5,5-tetramethyl-2-[2-methyl-4-(oxan-4-yloxy)phenyl]-1,3,2-dioxaborolane (from Example 15B) and ethyl (3S)-3-(4-[[(3-bromo-1-benzothiophen-5-yl)oxy]methyl]phenyl)hex-4-ynoate (from Example 23F) following General Procedure A, using PdCl$_2$(dppf).CH$_2$Cl$_2$ as the palladium catalyst and Cs$_2$CO$_3$ in place of K$_2$CO$_3$. LC/MS: mass calcd for C$_{35}$H$_{36}$O$_5$S: 568.72, found 569.4 [M+H]$^+$.

(B) (3S)-3-[4-[([3-[2-methyl-4-(oxan-4-yloxy)phenyl]-1-benzothiophen-5-yl]oxy)methyl]phenyl]hex-4-ynoic acid (Cpd 57) was prepared from ethyl (3S)-3-[4-[([3-[2-methyl-4-(oxan-4-yloxy)phenyl]-1-benzothiophen-5-yl]oxy)methyl]phenyl]hex-4-ynoate following General Procedure C, using LiOH as base, EtOH in place of MeOH, a rt reaction temperature overnight and 1N HCl for reaction acidification. The residue thus obtained was partially purified by silica gel chromatography [EtOAc/petroleum ether (50-75%). Further purification was carried out by preparative HPLC on a Waters SunFire™ Prep C18, 5µ column (19×100 mm) using an isocratic acetonitrile/water (0.05% TFA) eluent (71%). $^1$H NMR (DMSO-d$_6$) δ 7.92 (d, J=8.7 Hz, 1H), 7.59 (s, 1H), 7.35 (s, 4H), 7.17-7.04 (m, 2H), 7.00-6.86 (m, 2H), 6.82 (d, J=2.4 Hz, 1H), 5.04 (s, 2H), 4.70-4.55 (m, 1H), 4.00-4.09 (m, 1H), 3.89-3.92 (m, 2H), 3.52-3.59 (m, 2H), 2.64 (d, J=7.5 Hz, 2H), 1.96-2.04 (m, 5H), 1.78 (s, 3H), 1.63-1.70 (m, 2H). LC/MS: mass calcd for C$_{33}$H$_{32}$O$_5$S: 540.67, found 539.1 [M–H]$^-$.

Example 58

(3S)-3-[4-[([3-[4-(2-Methoxyethoxy)-2-methylphenyl]-1-benzothiophen-5-yl]oxy)methyl]phenyl]hex-4-ynoic acid, Cpd 58

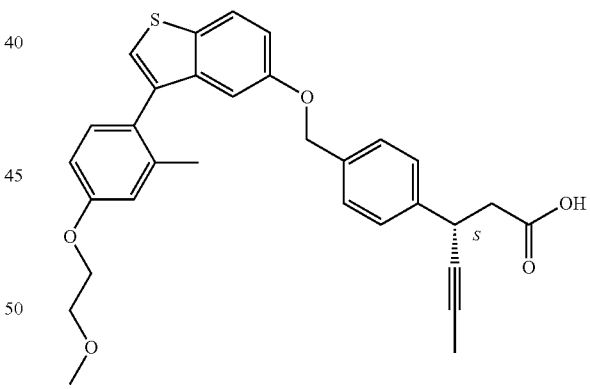

(A) Ethyl (3S)-3-[4-[([3-[4-(2-methoxyethoxy)-2-methylphenyl]-1-benzothiophen-5-yl]oxy)methyl]phenyl]hex-4-ynoate was prepared from 2-(4-(2-methoxyethoxy)-2-methylphenyl)-4,4,5,5-tetramethyl-1,3,2-dioxaborolane (from Example 16B) and ethyl (3S)-3-(4-[[(3-bromo-1-benzothiophen-5-yl)oxy]methyl]phenyl)hex-4-ynoate (from Example 23F) following General Procedure A, using PdCl$_2$(dppf).CH$_2$Cl$_2$ as the palladium catalyst and Cs$_2$CO$_3$ in place of K$_2$CO$_3$. LC/MS: mass calcd for C$_{33}$H$_{34}$O$_5$S: 542.69, found 543.2 [M+H]$^+$.

(B) (3S)-3-[4-[([3-[4-(2-Methoxyethoxy)-2-methylphenyl]-1-benzothiophen-5-yl]oxy)methyl]phenyl]hex-4-ynoic acid (Cpd 58) was prepared from ethyl (3S)-3-[4-[([3-[4-(2- methoxyethoxy)-2-methylphenyl]-1-benzothiophen-5-yl]oxy)methyl]phenyl]hex-4-ynoate following General Procedure C, using LiOH as base, EtOH in place of MeOH, a rt reaction temperature overnight and 1N HCl for reaction acidification. $^1$H NMR (DMSO-d$_6$) δ 12.27 (s, 1H), 7.92 (d, J=8.7 Hz, 1H), 7.59 (s, 1H), 7.32-7.42 (m, 4H), 7.09-7.13 (m, 2H), 6.81-6.94 (m, 3H), 5.03 (s, 2H), 4.14-4.17 (m, 2H), 3.92-4.01 (m, 1H), 3.68-3.71 (m, 2H), 3.34 (s, 3H), 2.64 (d, J=7.5 Hz, 2H), 2.00 (s, 3H), 1.77 (s, 3H). LC/MS:

mass calcd for C$_{31}$H$_{30}$O$_5$S: 514.63, found 513.0 [M−H]$^−$.

Example 59

(3S)-3-{4-[((3-{4-[(1,1-Dioxo-tetrahydro-2H-thiopyran-4-yl)methoxy]-2-methylphenyl}-1-benzothiophen-5-yl)oxy)methyl]phenyl}hex-4-ynoic acid, Cpd 59

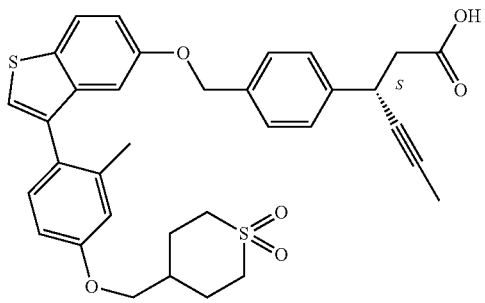

(A) (3S)-Ethyl 3-(4-(((3-(4-((1,1-dioxidotetrahydro-2H-thiopyran-4-yl)methoxy)-2-methylphenyl)benzo[b]thiophen-5-yl)oxy)methyl)phenyl)hex-4-ynoate was prepared from ethyl (3S)-3-[4-([[3-(4-hydroxy-2-methylphenyl)-1-benzothiophen-5-yl]oxy]methyl]phenyl]hex-4-ynoate (from Example 54A) and (1,1-dioxotetrahydro-2H-thian-4-yl) methyl 4-methylbenzene-1-sulfonate (from Example 17A) following the procedure described in Example 17B at a reaction temperature of 60° C. LC/MS: mass calcd for C$_{36}$H$_{38}$O$_6$S$_2$: 630.81, found 631.5 [M+H]$^+$.

(B) (3S)-3-{4-[((3-{4-[(1,1-Dioxo-tetrahydro-2H-thiopyran-4-yl)methoxy]-2-methylphenyl}-1-benzothiophen-5-yl)oxy)methyl]phenyl}hex-4-ynoic acid (Cpd 59) was prepared from (3S)-ethyl 3-(4-(((3-(4-((1,1-dioxidotetrahydro-2H-thiopyran-4-yl)methoxy)-2-methylphenyl)benzo[b]thiophen-5-yl)oxy)methyl)phenyl)hex-4-ynoate following General Procedure C, using LiOH as base, EtOH in place of MeOH, a rt reaction temperature overnight and 2N HCl for reaction acidification. $^1$H NMR (CD$_3$OD) δ 7.74 (d, J=8.8 Hz, 1H), 7.21-7.37 (m, 5H), 7.00-7.10 (m, 2H), 6.72-6.89 (m, 3H), 4.95 (s, 2H), 3.99-4.04 (m, 1H), 3.92 (d, J=6.0 Hz, 2H), 2.99-3.23 (m, 4H), 2.62-2.65 (m, 2H), 2.25-2.29 (m, 2H), 2.08-2.12 (m, 1H), 1.84-2.04 (m, 5H), 1.78 (d, J=2.4 Hz, 3H). LC/MS: mass calcd. for C$_{34}$H$_{34}$O$_6$S$_2$: 602.76, found: 601.1 [M]$^−$.

Example 60

(3S)-3-(4-(((3-(2-Methyl-4-((3-methyl-1,1-dioxidothietan-3-yl)methoxy)phenyl)benzo[b]thiophen-5-yl)oxy)methyl)phenyl)hex-4-ynoic acid, Cpd 60

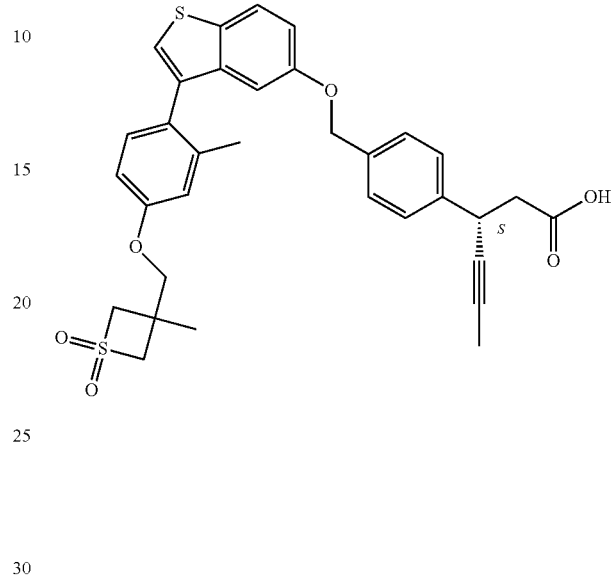

(A) (3S)-Ethyl 3-(4-(((3-(2-methyl-4-((3-methyl-1,1-dioxidothietan-3-yl)methoxy)phenyl)benzo[b]thiophen-5-yl)oxy)methyl)phenyl)hex-4-ynoate was prepared from 3-methyl-3-[3-methyl-4-(tetramethyl-1,3,2-dioxaborolan-2-yl)phenoxymethyl]-thietane-1,1-dioxide (from Example 18C) and ethyl (3S)-3-(4-[[(3-bromo-1-benzothiophen-5-yl)oxy]methyl]phenyl]hex-4-ynoate (from Example 23F) following General Procedure A, using PdCl$_2$(dppf).CH$_2$Cl$_2$ as the palladium catalyst and Cs$_2$CO$_3$ in place of K$_2$CO$_3$. LC/MS: mass calcd for C$_{35}$H$_{36}$O$_6$S$_2$: 616.79, found 617.4 [M+H]$^+$. (B) (3S)-3-(4-(((3-(2-Methyl-4-((3-methyl-1,1-dioxidothietan-3-yl)methoxy)phenyl)benzo[b]thiophen-5-yl)oxy)methyl)phenyl)hex-4-ynoic acid (Cpd 60) was prepared from (3S)-ethyl 3-(4-(((3-(2-methyl-4-((3-methyl-1,1-dioxidothietan-3-yl)methoxy)phenyl)benzo[b]thiophen-5-yl)oxy)methyl)phenyl)hex-4-ynoate following General Procedure C, using LiOH as base, EtOH in place of MeOH, a rt reaction temperature overnight and 1N HCl for reaction acidification. Product purification was carried out by preparative HPLC on a Waters SunFire™ Prep C18, 5µ column (19×100 mm) using an acetonitrile/water (0.05% NH$_4$HCO$_3$) gradient (30-95%). $^1$H NMR (DMSO-d$_6$) δ 7.94 (d, J=8.8 Hz, 1H), 7.60 (s, 1H), 7.30-7.36 (m, 4H), 7.10-7.21 (m, 2H), 6.99 (d, J=2.1 Hz, 1H), 6.92 (d, J=2.4 Hz, 1H), 6.82 (d, J=2.4 Hz, 1H), 5.04 (s, 2H), 4.21-4.26 (m, 2H), 4.14 (s, 2H), 3.97-4.09 (m, 3H), 2.61 (d, J=7.2 Hz, 2H), 2.03 (s, 3H), 1.78 (s, 3H), 1.53 (s, 3H). LC/MS: mass calcd for C$_{33}$H$_{32}$O$_6$S$_2$: 588.73, found 587.1 [M−H]$^−$.

Example 61

3-[6-([3-[4-(3-Hydroxy-3-methylbutoxy)-2-methylphenyl]-1-benzothiophen-5-yl]methoxy)pyridin-3-yl]hex-4-ynoic acid, Cpd 61

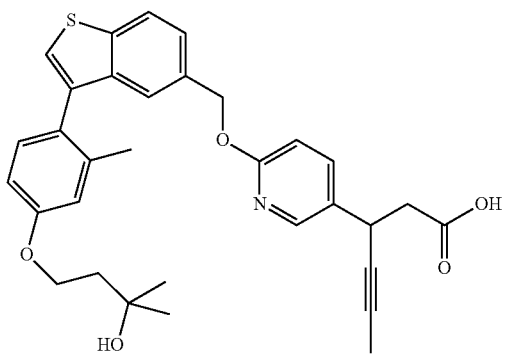 [SMILES: CC#CC(CC(=O)O)c1ccc(OCc2ccc3scc(-c4ccc(OCCC(C)(C)O)cc4C)c3c2)nc1]

(A) To a solution of (3-bromo-1-benzothiophen-5-yl)methanol (1.0 g, 4.11 mmol) (from Example 1A) in DCM (20 mL) and DMF (1 mL) was added phosphorous tribromide (1 mL, 10.6 mmol) in drop-wise fashion, and the resultant solution was stirred at rt for 1 h. Water (40 mL) was then added and the mixture was extracted with DCM (3×40 mL). The combined organic extracts were dried ($Na_2SO_4$) and concentrated under reduced pressure to afford 3-bromo-5-(bromomethyl)-1-benzothiophene (1.1 g, 87%) as colorless oil, which was used directly without further purification.

(B) A mixture of 3-bromo-5-(bromomethyl)-1-benzothiophene (1.1 g, 3.59 mmol), ethyl 3-(6-hydroxypyridin-3-yl)hex-4-ynoate (880 mg, 3.77 mmol) (from Example 45E) and $Ag_2CO_3$ (0.79g, 2.86 mmol) in toluene (30 mL) was stirred at 60° C. overnight. The mixture was then concentrated under reduced pressure and the resultant residue was purified directly by silica gel chromatography [EtOAc/petroleum ether (0-11%) to provide ethyl 3-[6-[(3-bromo-1-benzothiophen-5-yl)methoxy]pyridin-3-yl]hex-4-ynoate (950 mg, 58%) as light yellow oil. LC/MS: mass calcd for $C_{22}H_{20}BrNO_3S$: 458.37, found 458.2 $[M]^+$, 460.2 $[M+2]^+$.

(C) Ethyl 3-(6-[[3-(4-hydroxy-2-methylphenyl)-1-benzothiophen-5-yl]methoxy]pyridin-3-yl)hex-4-ynoate was prepared from ethyl 3-[6-[(3-bromo-1-benzothiophen-5-yl)methoxy]pyridin-3-yl]hex-4-ynoate and (4-hydroxy-2-methylphenyl)boronic acid following General Procedure A, using $PdCl_2(dppf).CH_2Cl_2$ as the palladium catalyst and $Cs_2CO_3$ in place of $K_2CO_3$. LC/MS: mass calcd for $C_{29}H_{27}NO_4S$: 485.59, found 486.2 $[M+H]^+$.

(D) Ethyl 3-[6-([3-[4-(3-hydroxy-3-methylbutoxy)-2-methylphenyl]-1-benzothiophen-5-yl]methoxy)pyridin-3-yl]hex-4-ynoate was prepared from ethyl 3-(6-[[3-(4-hydroxy-2-methylphenyl)-1-benzothiophen-5-yl]methoxy]pyridin-3-yl)hex-4-ynoate and 3-methylbutane-1,3-diol following General Procedure B using $PBu_3$ and ADDP with toluene as solvent and a reaction temperature of 60° C. overnight. LC/MS: mass calcd. for $C_{34}H_{37}NO_5S$: 571.73, found: 572.2 $[M+H]^+$.

(E) 3-[6-([3-[4-(3-Hydroxy-3-methylbutoxy)-2-methylphenyl]-1-benzothiophen-5-yl]methoxy)pyridin-3-yl]hex-4-ynoic acid (Cpd 61) was prepared from ethyl 3-[6-([3-[4-(3-hydroxy-3-methylbutoxy)-2-methylphenyl]-1-benzothiophen-5-yl]methoxy)pyridin-3-yl]hex-4-ynoate following General Procedure C, using LiOH as base, EtOH in place of MeOH, a rt reaction temperature overnight and 1N HCl for reaction acidification. Product purification was carried out by preparative HPLC on a Waters SunFire™ Prep C18, 5µ column (19×100 mm) using an acetonitrile/water (0.05% $NH_4HCO_3$) gradient (35-75%). $^1H$ NMR (DMSO-$d_6$) δ 8.10 (d, J=2.4 Hz, 1H), 8.03 (d, J=8.1 Hz, 1H), 7.70 (dd, J=8.4 Hz, 2.4 Hz, 1H), 7.63 (s, 1H), 7.43-7.48 (m, 2H), 7.15 (d, J=8.4 Hz, 1H), 6.93 (d, J=2.7 Hz, 1H), 6.84-6.88 (m, 1H), 6.79 (d, J=8.7 Hz, 1H), 5.40 (s, 2H), 4.14 (t, J=6.9 Hz, 2H), 3.95-4.00 (m, 1H), 2.61-2.63 (m, 2H), 2.05 (s, 3H), 1.88 (t, J=7.2 Hz, 2H), 1.77 (d, J=2.4 Hz, 3H), 1.19 (s, 6H). LC/MS: mass calcd for $C_{32}H_{33}NO_5S$: 543.67, found 544.3 $[M+H]^+$.

Example 62

3-(6-((3-(4-(2,3-Dihydroxypropoxy)-2-methylphenyl)benzo[b]thiophen-5-yl)methoxy)pyridin-3-yl)hex-4-ynoic acid, Cpd 62

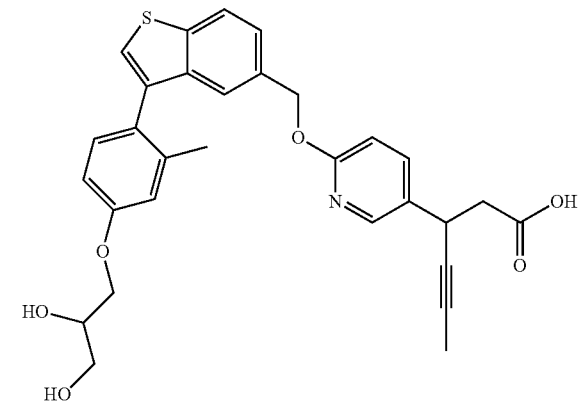 [SMILES: CC#CC(CC(=O)O)c1ccc(OCc2ccc3scc(-c4ccc(OCC(O)CO)cc4C)c3c2)nc1]

(A) A mixture of ethyl 3-(6-[[3-(4-hydroxy-2-methylphenyl)-1-benzothiophen-5-yl]methoxy]pyridin-3-yl)hex-4-ynoate (200 mg, 0.41 mmol) (from Example 61C), (2,2-dimethyl-1,3-dioxolan-4-yl)methyl 4-methylbenzene-1-sulfonate (235 mg, 0.82 mmol) and $Cs_2CO_3$ (269 mg, 0.83 mmol) in DMF (5 mL) was stirred at 80° C. overnight. Water (20 mL) was then added and the mixture was extracted with EtOAc (3×20 mL). The combined organic extracts were dried ($Na_2SO_4$), concentrated under reduced pressure and purified by silica gel chromatography [ethyl acetate/petroleum ether (0-20%)] to afford ethyl 3-[6-[(3-[4-[(2,2-dimethyl-1,3-dioxolan-4-yl)methoxy]-2-methylphenyl]-1-benzothiophen-5-yl)methoxy]pyridin-3-yl]hex-4-ynoate (100 mg, 41%) as light yellow oil. LC/MS: mass calcd for $C_{35}H_{37}NO_6S$: 599.74, found 600.4 $[M+H]^+$.

(B) A mixture of ethyl 3-[6-[(3-[4-[(2,2-dimethyl-1,3-dioxolan-4-yl)methoxy]-2-methylphenyl]-1-benzothiophen-5-yl)methoxy]pyridin-3-yl]hex-4-ynoate (100 mg, 0.17 mmol), THF (2 mL) and 2N aq. HCl (2 mL, 2 mmol) was stirred at rt overnight. Water (10 mL) was then added and the mixture was extracted with EtOAc (3×10 mL). The combined organic extracts were dried ($Na_2SO_4$), concentrated under reduced pressure and purified by silica gel chromatography [ethyl acetate/petroleum ether (0-20%)] to afford ethyl 3-[6-([3-[4-(2,3-dihydroxypropoxy)-2-methylphenyl]-1-benzothiophen-5-yl]methoxy)pyridin-3-yl]hex-4-ynoate (70 mg, 75%) as light yellow oil. LC/MS: mass calcd for $C_{32}H_{33}NO_6S$: 559.67, found 560.3 $[M+H]^+$.

(C) 3-(6-((3-(4-(2,3-Dihydroxypropoxy)-2-methylphenyl)benzo[b]thiophen-5-yl)methoxy)pyridin-3-yl)hex-4-ynoic acid (Cpd 62) was prepared from ethyl 3-[6-([3-[4-(2,3-dihydroxypropoxy)-2-methylphenyl]-1-benzothiophen-5-yl]methoxy)pyridin-3-yl]hex-4-ynoate following General Procedure C, using LiOH as base, EtOH in place of MeOH, a rt reaction temperature overnight and 1N HCl for reaction acidification. $^1$H NMR (DMSO-d$_6$) δ 8.08 (s, 1H), 8.02 (d, J=8.4 Hz, 1H), 7.69 (dd, J=2.8, 8.8 Hz, 1H), 7.62 (s, 1H), 7.46 (d, J=8.8 Hz, 1H), 7.41 (s, 1H), 7.13 (d, J=8.8 Hz, 1H), 6.94 (d, J=2.4 Hz, 1H), 6.86 (dd, J=8.8, 2.8 Hz, 1H), 6.77 (d, J=8.8 Hz, 1H), 5.40 (s, 2H), 4.05-4.08 (m, 1H), 3.94-4.04 (m, 1H), 3.85-3.93 (m, 1H), 3.83-3.74 (m, 1H), 3.47 (d, J=5.6 Hz, 2H), 2.53-2.58 (m, 2H), 2.03 (s, 3H), 1.76 (s, 3H). LC/MS: mass calcd for $C_{30}H_{29}NO_6S$: 531.62, found 532.1 [M+H]$^+$.

Example 63

3-(6-((3-(4-((1,1-Dioxidotetrahydro-2H-thiopyran-4-yl)methoxy)-2-methylphenyl)benzo[b]thiophen-5-yl)methoxy)pyridin-3-yl)hex-4-ynoic acid, Cpd 63

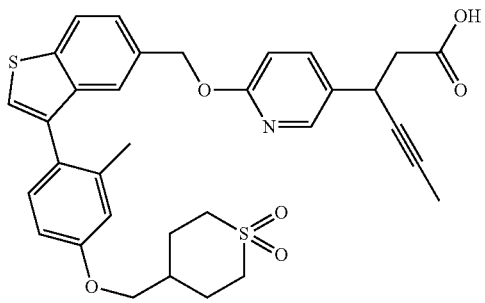 [SMILES: CC#CC(CC(=O)O)c1ccc(OCc2ccc3scc(-c4ccc(OCC5CCS(=O)(=O)CC5)cc4C)c3c2)nc1]

(A) Ethyl 3-(6-((3-(4-((1,1-dioxidotetrahydro-2H-thiopyran-4-yl)methoxy)-2-methylphenyl)benzo[b]thiophen-5-yl)methoxy)pyridin-3-yl)hex-4-ynoate was prepared from ethyl 3-(6-[[3-(4-hydroxy -2-methylphenyl)-1-benzothiophen-5-yl]methoxy]pyridin-3-yl)hex-4-ynoate (from Example 61C) and (1,1-dioxotetrahydro-2H-thian-4-yl)methyl 4-methylbenzene-1-sulfonate (from Example 17A) following the procedure described for Example 17B, at a reaction temperature of 60° C. LC/MS: mass calcd for $C_{35}H_{37}NO_6S_2$: 631.80, found 632.3 [M+H]$^+$.

(B) 3-(6-((3-(4-((1,1-Dioxidotetrahydro-2H-thiopyran-4-yl)methoxy)-2-methylphenyl)benzo[b]thiophen-5-yl)methoxy)pyridin-3-yl)hex-4-ynoic acid (Cpd 63) was prepared from ethyl 3-(6-((3-(4-((1,1-dioxidotetrahydro-2H-thiopyran-4-yl)methoxy)-2-methylphenyl)benzo[b]thiophen-5-yl)methoxy)pyridin-3-yl)hex-4-ynoate following General Procedure C, using LiOH as base, EtOH in place of MeOH, a rt reaction temperature overnight and 1N HCl for reaction acidification. $^1$H NMR (DMSO-d$_6$) δ 12.25-12.40 (m, 1H), 8.10 (s, 1H), 8.04 (d, J=8.4 Hz, 1H), 7.71 (dd, J=2.4, 8.4 Hz,1H), 7.64(s, 1H), 7.43-7.51 (m, 3H), 7.17 (d, J=8.4 Hz, 1H), 6.96 (d, J=2.4 Hz, 1H), 6.89 (dd, J=2.4, 8.4 Hz, 1H), 6.80 (d, J=8.8 Hz, 1H), 5.40 (s, 2H), 3.95-4.00 (m, 3H), 3.19-3.33 (m, 2H), 3.08-3.12 (m, 2H), 2.59-2.69 (m, 2H), 2.16-2.20 (m, 3H), 2.06 (s, 3H), 1.78-1.85 (m, 5H). LC/MS: mass calcd for $C_{33}H_{33}NO_6S_2$: 603.75, found 604.4 [M+H]$^+$.

Example 64

3-(6-((3-(2-Methyl-4-((3-methyl-1,1-dioxidothietan-3-yl)methoxy)phenyl)benzo[b]thiophen-5-yl)methoxy)pyridin-3-yl)hex-4-ynoic acid, Cpd 64

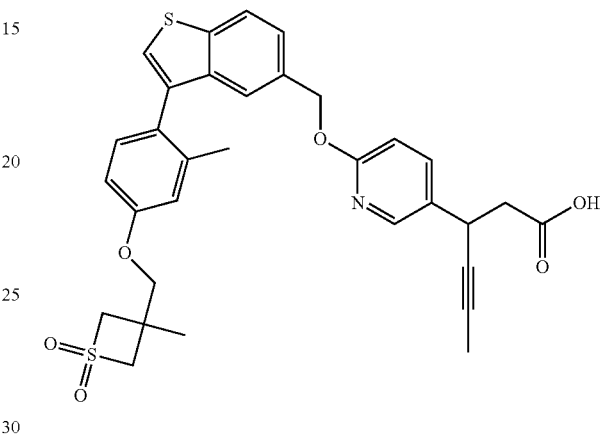

(A) Ethyl 3-(6-((3-(2-methyl-4-((3-methyl-1,1-dioxidothietan-3-yl)methoxy)phenyl)benzo[b]thiophen-5-yl)methoxy)pyridin-3-yl)hex-4-ynoate was prepared from ethyl 3-[6-[(3-bromo-1-benzothiophen-5-yl)methoxy]pyridin-3-yl]hex-4-ynoate (from Example 61B) and 3-methyl-3-[3-methyl-4-(tetramethyl-1,3,2-dioxaborolan-2-yl)phenoxymethyl]-thietane-1,1-dioxide (from Example 18C) following General Procedure A, using PdCl$_2$(dppf).CH$_2$Cl$_2$ as the palladium catalyst and Cs$_2$CO$_3$ in place of K$_2$CO$_3$. LC/MS: mass calcd for $C_{34}H_{35}NO_6S_2$: 617.77, found 618.2 [M+H]$^+$.

(B) 3-(6-((3-(2-Methyl-4-((3-methyl-1,1-dioxidothietan-3-yl)methoxy)phenyl)benzo[b]thiophen-5-yl)methoxy)pyridin-3-yl)hex-4-ynoic acid, (Cpd 64) was prepared from ethyl 3-(6-((3-(2-methyl-4-((3-methyl-1,1-dioxidothietan-3-yl)methoxy)phenyl)benzo[b]thiophen-5-yl)methoxy)pyridin-3-yl)hex-4-ynoate following General Procedure C, using LiOH as base, EtOH in place of MeOH, a rt reaction temperature overnight and 1N HCl for reaction acidification. Product purification was carried out by preparative HPLC on a Waters SunFire™ Prep C18, 5µ column (19×100 mm) using an acetonitrile/water (0.05% NH$_4$HCO$_3$) gradient (35-65%). $^1$H NMR (DMSO-d$_6$) δ 8.10 (d, J=2.4 Hz, 1H), 8.04 (d, J=8.1 Hz, 1H), 7.71 (dd, J=8.7, 2.4 Hz, 1H), 7.64 (s, 1H), 7.47 (dd, J=8.4, 1.5 Hz, 1H), 7.42 (s, 1H), 7.19 (d, J=8.4 Hz, 1H), 7.00 (d, J=2.4 Hz, 1H), 6.91 (dd, J=8.4, 2.4 Hz, 1H), 6.79 (d, J=8.4 Hz, 1H), 5.39 (s, 2H), 4.17-4.26 (m, 2H), 4.12 (s, 2H), 3.93-4.06 (m, 3H), 2.51-2.73 (m, 2H), 2.06 (s, 3H), 1.77 (s, 3H), 1.52 (s, 3H). LC/MS: mass calcd for $C_{32}H_{31}NO_6S_2$: 589.72, found 588.1 [M−H]$^-$.

Example 65

(3S)-3-[4-([3-[5-(2-Methoxyethoxy)-2-methylphenyl]-1-benzothiophen-5-yl]methoxy)phenyl]hex-4-ynoic acid, Cpd 65

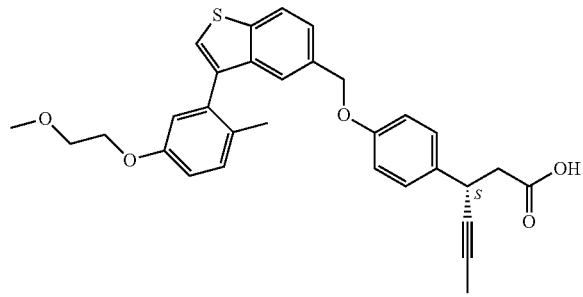

(A) 2-Bromo-4-(2-methoxyethoxy)-1-methylbenzene was prepared from 3-bromo-4-methylphenol and 1-bromo-2-methoxyethane following the procedure described in Example 16A. GC/MS: mass calcd. for $C_{10}H_{13}BrO_2$: 244.01, found: 244.1 $[M]^+$, 246.1 $[M+2]^+$.

(B) 2-[5-(2-Methoxyethoxy)-2-methylphenyl]-4,4,5,5-tetramethyl-1,3,2-dioxaborolane was prepared from 2-bromo-4-(2-methoxyethoxy)-1-methylbenzene and bis(pinacolato)diboron following General Procedure A, using $PdCl_2(dppf)$·$CH_2Cl_2$ as the palladium catalyst, KOAc in place of $K_2CO_3$ and DMSO as solvent. $^1H$ NMR ($CDCl_3$) δ 7.31-7.32 (m, 1H), 7.05-7.10 (m, 1H), 6.88-6.93 (m, 1H), 4.11-4.14 (m, 2H), 3.72-3.75 (m, 2H), 3.44 (s, 3H), 2.46 (s, 3H), 1.33 (s, 12H).

(C) Ethyl (3S)-3-[4-([3-[5-(2-methoxyethoxy)-2-methylphenyl]-1-benzothiophen-5-yl]methoxy)phenyl]hex-4-ynoate was prepared from ethyl (3S)-3-[4-[(3-bromo-1-benzothiophen-5-yl)methoxy]phenyl]hex-4-ynoate (from Example 11E) and 2-[5-(2-methoxyethoxy)-2-methylphenyl]-4,4,5,5-tetramethyl-1,3,2-dioxaborolane following General Procedure A, using $PdCl_2(dppf)$·$CH_2Cl_2$ as the palladium catalyst and $Cs_2CO_3$ in place of $K_2CO_3$. $^1H$ NMR ($CDCl_3$) δ 7.80-7.90 (m, 1H), 7.45-7.58 (m, 2H), 7.30-7.35 (m, 2H), 7.13-7.20 (m, 2H), 6.86-6.90 (m, 4H), 5.08 (s, 2H), 4.05-4.13 (m, 4H), 3.73-3.76 (m, 2H), 3.44 (s, 3H), 2.63-2.71 (m, 2H), 2.06 (s, 3H), 1.81 (s, 3H), 1.15-1.25 (m, 3H).

(D) (3S)-3-[4-([3-[5-(2-Methoxyethoxy)-2-methylphenyl]-1-benzothiophen-5-yl]methoxy)phenyl]hex-4-ynoic acid (Cpd 65) was prepared from ethyl (3S)-3-[4-([3-[5-(2-methoxyethoxy)-2-methylphenyl]-1-benzothiophen-5-yl]methoxy)phenyl]hex-4-ynoate following General Procedure C, using LiOH as base, EtOH in place of MeOH, a reaction temperature of 30° C. overnight and 1N HCl for reaction acidification. Additional product purification was carried out by silica gel chromatography [EtOAc/petroleum ether (1:1)]. $^1H$ NMR (DMSO-$d_6$) δ 8.07 (d, J=8.4 Hz, 1H), 7.71 (s, 1H), 7.45-7.49 (m, 2H), 7.23-7.28 (m, 3H), 6.90-6.96 (m, 3H), 6.82 (d, J=2.8 Hz, 1H), 5.18 (s, 2H), 4.07-4.09 (m, 2H), 3.90-3.94 (m, 1H), 3.64 (t, J=4.4 Hz, 2H), 3.29 (s, 3H), 2.56 (d, J=8.4 Hz, 2H), 1.99 (s, 3H), 1.76 (s,3H). LC/MS: mass calcd for $C_{31}H_{30}O_5S$: 514.63, found 515.2 $[M+H]^+$, 537.2 $[M+Na]^+$.

Example 66

(3S)-3-[4-([3-[2-(2-Methoxyethoxy)-6-methylphenyl]-1-benzothiophen-5-yl]methoxy)phenyl]hex-4-ynoic acid, Cpd 66

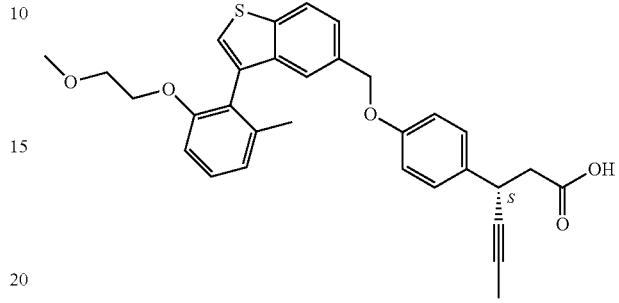

(A) 2-Bromo-3-(2-methoxyethoxy)-1-methylbenzene was prepared from 2-bromo-3-methylphenol and 1-bromo-2-methoxyethane following the procedure described in Example 16A. GC/MS: mass calcd. for $C_{10}H_{13}BrO_2$: 244.01, found: 244.1 $[M]^+$, 246.1 $[M+2]^+$.

(B) [3-[2-(2-Methoxyethoxy)-6-methylphenyl]-1-benzothiophen-5-yl]methanol was prepared from 2-bromo-3-(2-methoxyethoxy)-1-methylbenzene and [3-(tetramethyl-1,3,2-dioxaborolan-2-yl)-1-benzothiophen-5-yl]methanol (from Example 41A) following General Procedure A, using $Pd(OAc)_2$ as the palladium catalyst, $P(o-Tol)_3$ as an additional ligand (0.1 eq) and DME as solvent at 100° C. overnight. $^1H$ NMR (DMSO-$d_6$) δ 7.93 (d, J=8.0 Hz, 1H), 7.53 (s, 1H), 7.28-7.32 (m, 2H), 7.17 (s, 1H), 6.98 (t, J=7.6 Hz, 2H), 5.15-5.17 (m, 1H), 4.54 (d, J=4.4 Hz, 2H), 3.95-4.05 (m, 2H), 3.28-3.39 (m, 2H), 2.96 (s, 3H), 1.99 (s, 3H).

(C) Ethyl (3S)-3-[4-([3-[2-(2-methoxyethoxy)-6-methylphenyl]-1-benzothiophen-5-yl]methoxy)phenyl]hex-4-ynoate was prepared from [3-[2-(2-methoxyethoxy)-6-methylphenyl]-1-benzothiophen-5-yl]methanol and (3S)-ethyl 3-(4-hydroxyphenyl)hex-4-ynoate (available from Synnovator, Inc., Research Triangle Park, N.C.; Cat. #PB05708) following General Procedure B, using $Bu_3P$ and ADDP at a reaction temperature of 60° C. overnight. LC/MS: mass calcd. for $C_{33}H_{34}O_5S$: 542.69, found: 543.2 $[M+H]^+$.

(D) (3S)-3-[4-([3-[2-(2-Methoxyethoxy)-6-methylphenyl]-1-benzothiophen-5-yl]methoxy)phenyl]hex-4-ynoic acid (Cpd 66) was prepared from ethyl (3S)-3-[4-([3-[2-(2-methoxyethoxy)-6-methylphenyl]-1-benzothiophen-5-yl]methoxy)phenyl]hex-4-ynoate following General Procedure C, using LiOH as base, EtOH in place of MeOH, a reaction temperature of 30° C. overnight and satd. aq. $NH_4Cl$ for reaction acidification. Following an extractive workup (EtOAc), product purification was carried out by silica gel chromatography [DCM/MeOH (11:1)]. $^1H$ NMR (DMSO-$d_6$) δ 8.01 (d, J=8.0 Hz, 1H), 7.59 (s, 1H), 7.45 (dd, J=1.2, 8.4 Hz, 1H), 7.22-7.32 (m, 4H), 6.89-6.99 (m, 4H), 5.13 (s, 2H), 3.89-4.01 (m, 3H), 3.22-3.28 (m, 2H), 3.22 (s, 3H), 2.57 (d, J=8.0 Hz, 2H), 1.98 (s, 3H), 1.76 (s, 3H). LC/MS: mass calcd. for $C_{31}H_{30}O_5S$: 514.63, found: 515.2 $[M+H]^+$, 537.2 $[M+Na]^+$.

Example 67

(3S)-3-[4-([3-[3-(2-Methoxyethoxy)-2-methylphenyl]-1-benzothiophen-5-yl]methoxy)phenyl]hex-4-ynoic acid, Cpd 67

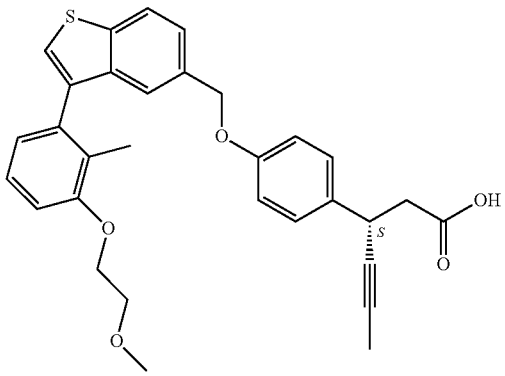

(A) 1-Bromo-3-(2-methoxyethoxy)-2-methylbenzene was prepared from 3-bromo-2-methylphenol and 1-bromo-2-methoxyethane following the procedure described in Example 16A. GC/MS: mass calcd. for $C_{10}H_{13}BrO_2$: 244.01, found: 244.0 [M]$^+$, 246.0 [M+2]$^+$.

(B) 2-[3-(2-Methoxyethoxy)-2-methylphenyl]-4,4,5,5-tetramethyl-1,3,2-dioxaborolane was prepared from 1-bromo-3-(2-methoxyethoxy)-2-methylbenzene and bis(pinacolato)diboron following General Procedure A, using PdCl$_2$(dppf).CH$_2$Cl$_2$ as the palladium catalyst, KOAc in place of K$_2$CO$_3$ and DMSO as solvent at a reaction temperature of 90° C. overnight. $^1$H NMR (CDCl$_3$) δ 7.35 (dd, J=7.5, 1.2 Hz, 1H), 7.13 (t, J=7.5 Hz, 1H), 6.91-6.93 (m, 1H), 4.09-4.12 (m, 2H), 3.75-3.78 (m, 2H), 3.46 (s, 3H), 2.44 (s, 3H), 1.34 (s, 12H).

(C) Ethyl (3S)-3-[4-([3[3-(methoxymethoxy)-2-methylphenyl]-1-benzothiophen-5-yl]methoxy)phenyl]hex-4-ynoate was prepared from 2-[3-(2-methoxyethoxy)-2-methylphenyl]-4,4,5,5-tetramethyl-1,3,2-dioxaborolane and ethyl (3S)-3-[4-[(3-bromo-1-benzothiophen-5-yl)methoxy]phenyl]hex-4-ynoate (from Example 11E) following General Procedure A, using PdCl$_2$(dppf).CH$_2$Cl$_2$ as the palladium catalyst and Cs$_2$CO$_3$ in place of K$_2$CO$_3$. LC/MS: mass calcd. for $C_{33}H_{34}O_5S$: 542.69, found: 543.2 [M+H]$^+$.

(D) (3S)-3-[4-([3-[3-(2-Methoxyethoxy)-2-methylphenyl]-1-benzothiophen-5-yl]methoxy)phenyl]hex-4-ynoic acid (Cpd 67) was prepared from ethyl (3S)-3-[4-([3-[3-(methoxymethoxy)-2-methylphenyl]-1-benzothiophen-5-yl]methoxy)phenyl]hex-4-ynoate following General Procedure C, using LiOH as base, EtOH in place of MeOH and 1N HCl for reaction acidification. $^1$H NMR (300 MHz, DMSO-d$_6$) δ 8.06 (d, J=8.1 Hz, 1H), 7.67 (s, 1H), 7.47 (d, J=8.4 Hz, 1H), 7.39-7.40 (m, 1H), 7.21-7.28 (m, 3H), 7.04-7.07 (m, 1H), 6.85-6.90 (m, 3H), 5.15 (s, 2H), 4.15-4.18 (m, 2H), 3.89-3.95 (m, 1H), 3.71-3.74 (m, 2H), 3.35 (s, 3H), 2.36-2.44 (m, 2H), 1.92 (s, 3H), 1.75 (s, 3H). LC/MS: mass calcd. for $C_{31}H_{30}O_5S$: 514.63, found: 515.2 [M+H]$^+$, 537.2 [M+Na]$^-$.

Example 68

(3S)-3-[4-([3-[2-(2-Methoxyethoxy)phenyl]-1-benzothiophen-5-yl]methoxy)phenyl]hex-4-ynoic acid, Cpd 68

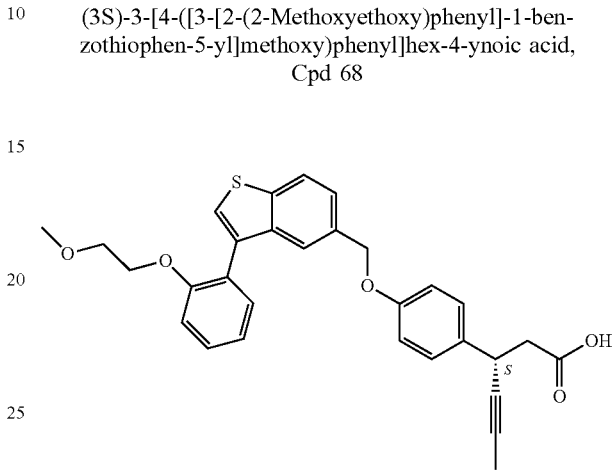

(A) Ethyl (3S)-3-[4-([[3-(2-hydroxyphenyl)-1-benzothiophen-5-yl]oxy]methyl)phenyl]hex-4-ynoate was prepared from ethyl (3S)-3-[4-[(3-bromo-1-benzothiophen-5-yl)methoxy]phenyl]hex-4-ynoate (from Example 11E) and (2-hydroxyphenyl)boronic acid following General Procedure A, using PdCl$_2$(dppf).CH$_2$Cl$_2$ as the palladium catalyst, Cs$_2$CO$_3$ in place of K$_2$CO$_3$ and a reaction temperature of 80° C. overnight. $^1$H NMR (CDCl$_3$) δ 7.93 (d, J=3.3 Hz, 1H), 7.65 (s, 1H), 7.48-7.52 (m, 2H), 7.29-7.37 (m, 4H), 7.01-7.07 (m, 2H), 6.90 (dd, J=1.8, 6.6 Hz, 2H), 5.12 (s, 2H), 4.04-4.13 (m, 3H), 2.64-2.72 (m, 2H), 1.83 (s, 3H), 1.19-1.28 (m, 3H).

(B) Ethyl (3S)-3-[4-[([3-[2-(2-methoxyethoxy)phenyl]-1-benzothiophen-5-yl]oxy)methyl]phenyl]hex-4-ynoate was prepared from ethyl (3S)-3-[4-([[3-(2-hydroxyphenyl)-1-benzothiophen-5-yl]oxy]methyl)phenyl]hex-4-ynoate and 1-bromo-2-methoxyethane following the procedure described in Example 16A. LC/MS: mass calcd. for $C_{32}H_{32}O_5S$: 528.66, found: 546.2 [M+NH$_3$]$^+$.

(C) (3S)-3-[4-([3-[2-(2-Methoxyethoxy)phenyl]-1-benzothiophen-5-yl]methoxy)phenyl]hex-4-ynoic acid (Cpd 68) was prepared from ethyl (3S)-3-[4-[([3-[2-(2-methoxyethoxy)phenyl]-1-benzothiophen-5-yl]oxy)methyl]phenyl]hex-4-ynoate following General Procedure C, using LiOH as base, EtOH in place of MeOH, a reaction temperature of 30° C. overnight and 1N HCl for reaction acidification. $^1$H NMR (DMSO-d$_6$) δ 8.02 (d, J=8.4 Hz, 1H), 7.72 (s, 1H), 7.62 (s, 1H), 7.34-7.47 (m, 3H), 7.18-7.26 (m, 3H), 7.05-7.09 (m, 1H), 6.92 (d, J=8.8 Hz, 2H), 5.16 (s, 2H), 4.09 (t, J=4.8 Hz, 2H), 3.91-3.93 (m, 1H), 3.44 (t, J=8.4 Hz, 2H), 3.04 (s, 3H), 2.49-2.51 (m, 2H), 1.76 (s, 3H). LC/MS: mass calcd. for $C_{30}H_{28}O_5S$: 500.61, found: 501.2 [M+H]$^+$.

Example 69

(3S)-3-(4-[[3-(2-Methanesulfonylphenyl)-1-benzothiophen-6-yl]methoxy]phenyl)hex-4-ynoic acid, Cpd 69

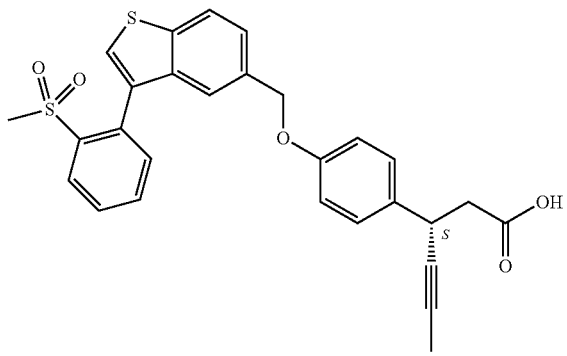

(A) [3-(2-Methanesulfonylphenyl)-1-benzothiophen-5-yl]methanol was prepared from (3-(4,4,5,5-tetramethyl-1,3,2-dioxaborolan-2-yl)benzo[b]thiophen-5-yl)methanol (from Example 41A) and 1-bromo-2-methanesulfonylbenzene following General Procedure A, using Pd(OAc)$_2$ as the palladium catalyst, P(o-Tol)$_3$ as an additional ligand (0.1 eq) and DME as solvent at 100° C. for 2 h. LC/MS: mass calcd. for $C_{16}H_{14}O_3S_2$: 318.41, found: 301.0 [M–OH]$^+$.

(B) Ethyl (3S)-3-(4-[[3-(2-methanesulfonylphenyl)-1-benzothiophen-5-yl]methoxy]phenyl)hex-4-ynoate was prepared from [3-(2-methanesulfonylphenyl)-1-benzothiophen-5-yl]methanol and (3S)-ethyl 3-(4-hydroxyphenyl)hex-4-ynoate (available from Synnovator, Inc., Research Triangle Park, N.C.; Cat. #PB05708) following General Procedure B, using Bu$_3$P, ADDP and toluene as solvent (in place of THF) at a reaction temperature of 50° C. for 2 h. LC/MS: mass calcd. for $C_{30}H_{28}O_5S_2$: 532.67, found: 533.2 [M+H]$^+$, 555.2 [M+Na]$^+$.

(C) (3S)-3-(4-[[3-(2-Methanesulfonylphenyl)-1-benzothiophen-6-yl]methoxy]phenyl)hex-4-ynoic acid (Cpd 69) was prepared from ethyl (3S)-3-(4-[[3-(2-methanesulfonylphenyl)-1-benzothiophen-5-yl]methoxy]phenyl)hex-4-ynoate following General Procedure C, using LiOH as base, EtOH in place of MeOH, a rt reaction temperature overnight and 1N HCl for reaction acidification. $^1$H NMR (CD$_3$OD) δ 8.24 (d, J=1.2 Hz, 1H), 8.00 (d, J=8.1 Hz, 1H), 7.70-7.84 (m, 3H), 7.46-7.52 (m, 2H), 7.38 (s, 1H), 7.24 (d, J=8.7 Hz, 2H), 6.86 (d, J=8.7 Hz, 2H), 5.15 (s, 2H), 3.96-3.98 (m, 1H), 2.57-2.68 (m, 5H), 1.80 (d, J=2.4 Hz, 3H). LC/MS: mass calcd. for $C_{28}H_{24}O_5S_2$: 504.62, found: 505.1 [M+H]$^+$.

Examples 70 and 71

(3S)-3-(6-((3-(4-(3-Hydroxy-3-methylbutoxy)-2-methylphenyl)benzo[b]thiophen-5-yl)methoxy)pyridin-3-yl)hex-4-ynoic acid (Cpd 70) and (3R)-3-(6-((3-(4-(3-Hydroxy-3-methylbutoxy)-2-methylphenyl)benzo[b]thiophen-5-yl)methoxy)pyridin-3-yl)hex-4-ynoic acid (Cpd 71)

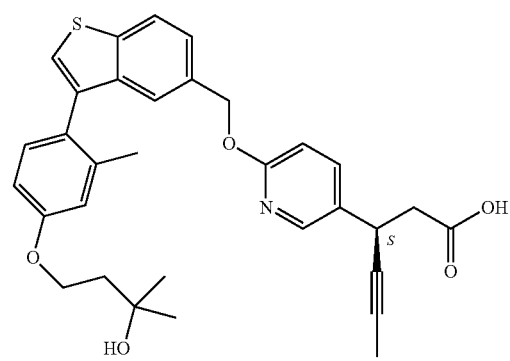

Cpd 70

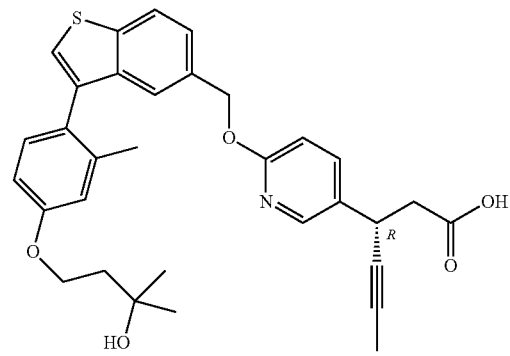

Cpd 71

(A) Enantiomeric resolution of (3RS)-3-(6-((3-(4-(3-hydroxy-3-methylbutoxy)-2-methylphenyl)benzo[b]thiophen-5-yl)methoxy)pyridin-3-yl)hex-4-ynoic acid (Cpd 61) was carried out by chiral chromatography on a ChiralPak AS-H 5µ column (2×25 cm) using an isocratic mobile phase [hexane (0.1% HOAc)/EtOH (85:15); 20 mL/min] to afford (3S)-3-(6-((3-(4-(3-hydroxy-3-methylbutoxy)-2-methylphenyl)benzo[b]thiophen-5-yl)methoxy)pyridin-3-yl)hex-4-ynoic acid (Cpd 70) (RT=9.0 min) and (3R)-3-(6-((3-(4-(3-hydroxy-3-methylbutoxy)-2-methylphenyl)benzo[b]thiophen-5-yl)methoxy)pyridin-3-yl)hex-4-ynoic acid (Cpd 71) (RT=12.5 min).

(Cpd 70): $^1$H NMR (DMSO-d$_6$) δ 8.10 (d, J=2.4 Hz, 1H), 8.03 (d, J=8.1 Hz, 1H), 7.70 (dd, J=8.4, 2.4 Hz, 1H), 7.63 (s, 1H), 7.43-7.48 (m, 2H), 7.15 (d, J=8.4 Hz, 1H), 6.94 (d, J=2.7 Hz, 1H), 6.85-6.88 (m, 1H), 6.79 (d, J=8.7 Hz, 1H), 5.40 (s, 2H), 4.14 (t, J=6.9 Hz, 2H), 3.95-4.05 (m, 1H), 2.61-2.73 (m, 2H), 2.05 (s, 3H), 1.88 (t, J=7.2 Hz, 2H), 1.77 (d, J=2.4 Hz, 3H), 1.19 (s, 6H). LC/MS: mass calcd. for $C_{34}H_{37}NO_5S$: 571.73, found: 572.2 [M+H]$^+$. LC/MS: mass calcd. for $C_{32}H_{33}NO_5S$: 543.67, found: 541.9 [M–H]$^-$.

(Cpd 71): $^1$H NMR (DMSO-d$_6$) δ 8.10 (d, J=2.4 Hz, 1H), 8.03 (d, J=8.1 Hz, 1H), 7.70 (dd, J=8.4, 2.4 Hz, 1H), 7.63 (s, 1H), 7.43-7.48 (m, 2H), 7.15 (d, J=8.4 Hz, 1H), 6.94 (d,

J=2.7 Hz, 1H), 6.85-6.88 (m, 1H), 6.79 (d, J=8.7 Hz, 1H), 5.40 (s, 2H), 4.14 (t, J=6.9 Hz, 2H), 3.95-4.05 (m, 1H), 2.61-2.73 (m, 2H), 2.05 (s, 3H), 1.88 (t, J=7.2 Hz, 2H), 1.77 (d, J=2.4 Hz, 3H), 1.19 (s, 6H). LC/MS: mass calcd. for $C_{34}H_{37}NO_5S$: 571.73, found: 572.2 [M+H]$^+$. LC/MS: mass calcd. for $C_{32}H_{33}NO_5S$: 543.67, found: 542.1 [M−H]$^−$.

Examples 72 and 73

(3S)-3-(6-((3-(2-Methyl-4-((tetrahydro-2H-pyran-4-yl)methoxy)phenyl)benzo[b]thiophen-5-yl)methoxy)pyridin-3-yl)hex-4-ynoic acid (Cpd 72) and (3R)-3-(6-((3-(2-Methyl-4-((tetrahydro-2H-pyran-4-yl)methoxy)phenyl)benzo[b]thiophen-5-yl)methoxy)pyridin-3-yl)hex-4-ynoic acid (Cpd 73)

Cpd 72

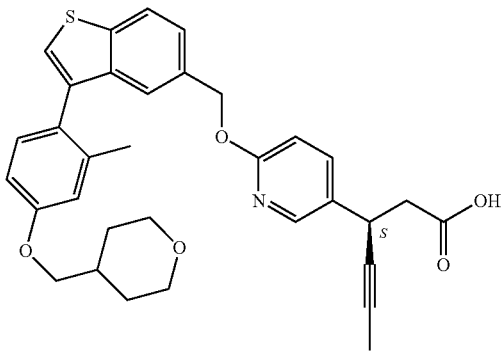

Cpd 73

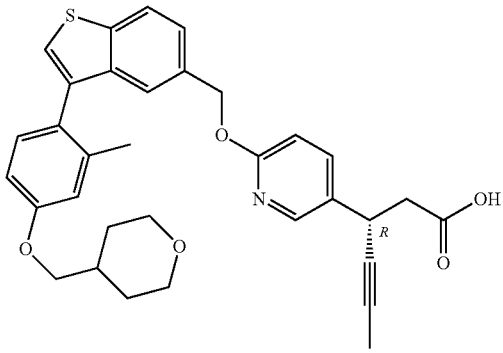

(A) [3-[2-Methyl-4-(oxan-4-yloxy)phenyl]-1-benzothiophen-5-yl]methanol was prepared from (3-bromo-1-benzothiophen-5-yl)methanol (from Example 1A) and 4,4,5,5-tetramethyl-2-[2-methyl-4-(oxan-4-yloxy)phenyl]-1,3,2-dioxaborolane (from Example 15B) following General Procedure A, using PdCl$_2$(dppf).CH$_2$Cl$_2$ as the palladium catalyst and Cs$_2$CO$_3$ in place of K$_2$CO$_3$. LC/MS: mass calcd for $C_{21}H_{22}O_3S$: 354.46, found 337.2 [M−OH]$^+$.

(B) To a solution of [3-[2-methyl-4-(oxan-4-yloxy)phenyl]-1-benzothiophen-5-yl]methanol (240 mg, 0.68 mmol) in DCM (20 mL) was added PBr$_3$ (0.16 mL, 1.7 mmol) in dropwise fashion. After stirring at rt for 1 h, the reaction was quenched by the addition of NH$_4$Cl (30 mL) and the mixture was extracted with EtOAc (2×30 mL), dried (Na$_2$SO$_4$) and concentrated under reduced pressure. The resultant residue was purified by silica gel chromatography (11% EtOAc/hexane) to afford 4-[4-[5-(bromomethyl)-1-benzothiophen-3-yl]-3-methylphenoxy]oxane (140 mg, 50%) as colorless oil, which was used directly without characterization.

(C) A mixture of 4-[4-[5-(bromomethyl)-1-benzothiophen-3-yl]-3-methylphenoxy]oxane (240 mg, 0.58 mmol), ethyl 3-(6-hydroxypyridin-3-yl)hex-4-ynoate (237 mg, 1.02 mmol) (from Example 45E) and Ag$_2$CO$_3$ (150 mg, 0.54 mmol) in toluene (8 mL) was stirred at 60° C. overnight. The the reaction was quenched by the addition of NH$_4$Cl (10 mL) and the mixture was extracted with EtOAc (3×10 mL), dried (Na$_2$SO$_4$) and concentrated under reduced pressure. Purification of the resultant residue by silica gel chromatography [EtOAc/petroleum ether (14%) afforded ethyl 3-[6-([3-[2-methyl-4-(oxan-4-yloxy)phenyl]-1-benzothiophen-5-yl]methoxy)pyridin-3-yl]hex-4-ynoate (80 mg, 24%) as colorless oil. LC/MS: mass calcd for $C_{34}H_{35}NO_5S$: 569.71, found 570.4 [M+H]$^+$.

(D) 3-[6-([3-[2-Methyl-4-(oxan-4-yloxy)phenyl]-1-benzothiophen-5-yl]methoxy)pyridin-3-yl]hex-4-ynoic acid was prepared from ethyl 3-[6-([3-[2-methyl-4-(oxan-4-yloxy)phenyl]-1-benzothiophen-5-yl]methoxy)pyridin-3-yl]hex-4-ynoate following General Procedure C, using LiOH as base, EtOH in place of MeOH, a rt reaction temperature overnight and 1N HCl for reaction acidification. The product precipitated directly upon acidification and was isolated by filtration. LC/MS: mass calcd for $C_{32}H_{31}NO_5S$: 541.66, found 542.2 [M+H]$^+$.

(E) Enantiomeric resolution of 3-[6-([3-[2-methyl-4-(oxan-4-yloxy)phenyl]-1-benzothiophen-5-yl]methoxy)pyridin-3-yl]hex-4-ynoic acid was carried out by chiral chromatography on a ChiralPak AS-H 5μ column (2×25 cm) using an isocratic mobile phase [hexane (0.1% HOAc)/EtOH (70:30); 20 mL/min] to afford (3S)-3-[6-([3-[2-methyl-4-(oxan-4-yloxy)phenyl]-1-benzothiophen-5-yl]methoxy)pyridin-3-yl]hex-4-ynoic acid (Cpd 72) (RT=6 min) and (3R)-3-[6-([3-[2-methyl-4-(oxan-4-yloxy)phenyl]-1-benzothiophen-5-yl]methoxy)pyridin-3-yl]hex-4-ynoic acid (Cpd 73) (RT=9 min).

(Cpd 72): $^1$H NMR (DMSO-d$_6$) δ 12.20-12.60 (br. m, 1H), 8.09 (s, 1H), 8.03 (d, J=8.4 Hz, 1H), 7.71 (dd, J=8.4, 2.4 Hz, 1H), 7.64 (s, 1H), 7.43-7.48 (m, 2H), 7.16 (d, J=8.4 Hz, 1H), 6.99 (d, J=2.4 Hz, 1H), 6.92 (dd, J=8.4, 2.7 Hz, 1H), 6.79 (d, J=8.4 Hz, 1H), 5.41 (s, 2H), 4.55-4.65 (m, 1H), 3.95-4.04 (m, 1H), 3.85-3.89 (m, 2H), 3.48-3.54 (m, 2H), 2.60 (t, J=6.8 Hz, 2H),1.95-2.05 (m, 5H), 1.77 (d, J=2.4 Hz, 3H), 1.55-1.65 (m, 2H). LC/MS: mass calcd. for $C_{32}H_{31}NO_5S$: 541.66, found: 542.1 [M+H]$^+$.

(Cpd 73): $^1$H NMR (DMSO-d$_6$) δ 12.20-12.60 (br. m, 1H), 8.09 (s, 1H), 8.03 (d, J=8.4 Hz, 1H), 7.71 (dd, J=8.4, 2.4 Hz, 1H), 7.64 (s, 1H), 7.43-7.48 (m, 2H), 7.16 (d, J=8.4 Hz, 1H), 6.99 (d, J=2.4 Hz, 1H), 6.92 (dd, J=8.4, 2.7 Hz, 1H), 6.79 (d, J=8.4 Hz, 1H), 5.41 (s, 2H), 4.55-4.65 (m, 1H), 3.95-4.04 (m, 1H), 3.85-3.89 (m, 2H), 3.48-3.54 (m, 2H), 2.60 (t, J=6.8 Hz, 2H),1.95-2.05 (m, 5H), 1.77 (d, J=2.4 Hz, 3H), 1.55-1.65 (m, 2H). LC/MS: mass calcd. for $C_{32}H_{31}NO_5S$: 541.66, found: 540.1 [M−H]$^−$.

Examples 74 and 75

(3S)-3-(6-((3-(4-((1,1-Dioxidotetrahydro-2H-thiopyran-4-yl)methoxy)-2-methylphenyl)benzo[b]thiophen-5-yl)methoxy)pyridin-3-yl)hex-4-ynoic acid (Cpd 74) and (3R)-3-(6-((3-(4-((1,1-Dioxidotetrahydro-2H-thiopyran-4-yl)methoxy)-2-methylphenyl)benzo[b]thiophen-5-yl)methoxy)pyridin-3-yl)hex-4-ynoic acid (Cpd 75)

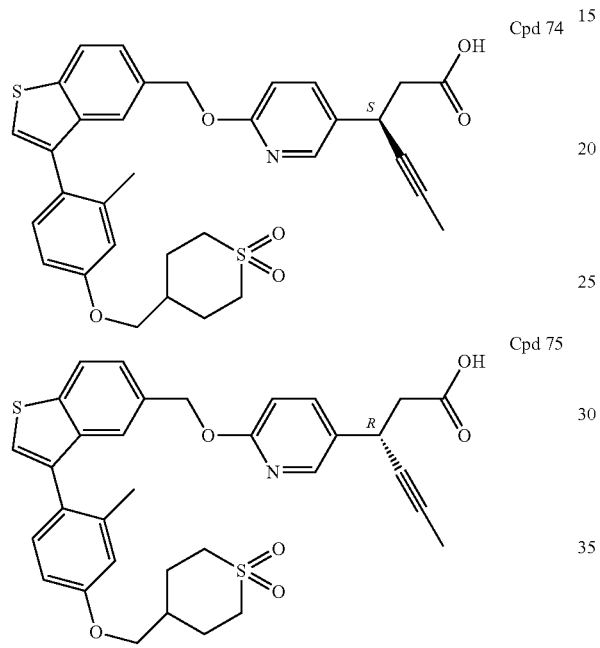

Enantiomeric resolution of 3-(6-((3-(4-((1,1-dioxidotetrahydro-2H-thiopyran-4-yl)methoxy)-2-methylphenyl)benzo[b]thiophen-5-yl)methoxy)pyridin-3-yl)hex-4-ynoic acid (Cpd 63) was carried out by chiral chromatography on a ChiralPak AS-H 5μ column (2×25 cm) using an isocratic mobile phase [hexane (0.1% HOAc)/EtOH (50:50); 18 mL/min] to afford (3S)-3-(6-((3-(4-((1,1-dioxidotetrahydro-2H-thiopyran-4-yl)methoxy)-2-methylphenyl)benzo[b]thiophen-5-yl)methoxy)pyridin-3-yl)hex-4-ynoic acid (Cpd 74) (RT=16 min) and (3R)-3-(6-((3-(4-((1,1-dioxidotetrahydro-2H-thiopyran-4-yl)methoxy)-2-methylphenyl)benzo[b]thiophen-5-yl)methoxy)pyridin-3-yl)hex-4-ynoic acid (Cpd 75) (RT=22 min).

(Cpd 74): $^1$H NMR (DMSO-d$_6$) δ 8.10 (s, 1H), 8.04 (d, J=8.4 Hz, 1H), 7.71 (dd, J=2.4, 8.4 Hz, 1H), 7.64 (s, 1H), 7.43-7.51(m, 2H), 7.17 (d, J=8.4 Hz, 1H), 6.96 (d, J=2.4 Hz, 1H), 6.89 (dd, J=2.7, 8.4 Hz, 1H), 6.80 (d, J=8.8 Hz, 1H), 5.40 (s, 2H), 3.95-4.00 (m, 3H), 3.19-3.33 (m, 2H), 3.08-3.12 (m, 2H), 2.59-2.69 (m, 2H), 2.16-2.20 (m, 3H), 2.06 (s, 3H), 1.78-1.85 (m, 5H). LC/MS: mass calcd. for C$_{33}$H$_{33}$NO$_6$S$_2$: 603.75, found: 604.1 [M+H]$^+$.

(Cpd 75): $^1$H NMR (DMSO-d$_6$) δ 8.10 (s, 1H), 8.04 (d, J=8.4 Hz, 1H), 7.71 (dd, J=2.4, 8.4 Hz, 1H), 7.64 (s, 1H), 7.43-7.51(m, 2H), 7.17 (d, J=8.4 Hz, 1H), 6.96 (d, J=2.4 Hz, 1H), 6.89 (dd, J=2.7, 8.4 Hz, 1H), 6.80 (d, J=8.8 Hz, 1H), 5.39 (s, 2H), 3.95-4.00 (m, 3H), 3.05-3.33 (m, 4H), 2.59-2.69 (m, 2H), 2.16-2.20 (m, 3H), 2.06 (s, 3H), 1.78-1.85 (m, 5H). LC/MS: mass calcd. for C$_{33}$H$_{33}$NO$_6$S$_2$: 603.75, found: 604.1 [M+H]$^-$.

Examples 76 and 77

(3S)-3-(6-((3-(4-(2-Methoxyethoxy)-2-methylphenyl)benzo[b]thiophen-5-yl)methoxy)pyridin-3-yl)hex-4-ynoic acid (Cpd 76) and (3R)-3-(6-((3-(4-(2-Methoxyethoxy)-2-methylphenyl)benzo[b]thiophen-5-yl)methoxy)pyridin-3-yl)hex-4-ynoic acid (Cpd 77)

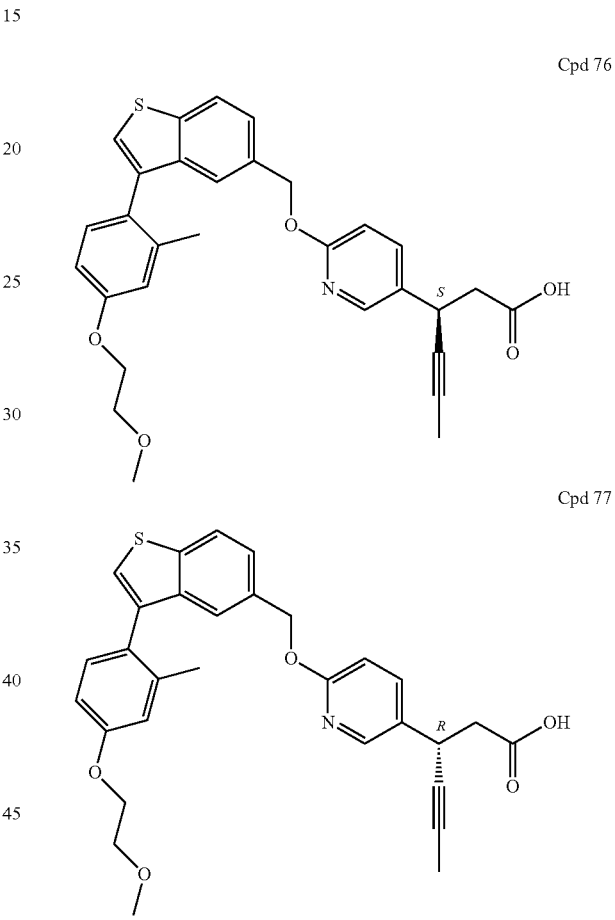

Enantiomeric resolution of 3-(6-((3-(4-(2-methoxyethoxy)-2-methylphenyl)benzo[b]-thiophen-5-yl)methoxy)pyridin-3-yl)hex-4-ynoic acid (Cpd 47) was carried out by chiral chromatography on a ChiralPak AS-H 5μ column (2×25 cm) using an isocratic mobile phase [hexane (0.1% HOAc)/EtOH (85:15); 20 mL/min] to afford (3S)-3-(6-((3-(4-(2-methoxyethoxy)-2-methylphenyl)benzo[b]thiophen-5-yl)methoxy)pyridin-3-yl)hex-4-ynoic acid (Cpd 76) (RT=8 min) and (3R)-3-(6-((3-(4-(2-methoxyethoxy)-2-methylphenyl)benzo[b]thiophen-5-yl)methoxy)pyridin-3-yl)hex-4-ynoic acid (Cpd 77) (RT=13.5 min).

(Cpd 76): $^1$H NMR (DMSO-d$_6$) δ 8.10 (d, J=2.4 Hz, 1H), 8.04 (d, J=8.4 Hz, 1H), 7.71 (dd, J=2.4, 8.4 Hz, 1H), 7.64 (s, 1H), 7.42-7.48 (m, 2H), 7.16 (d, J=8.4 Hz, 1H), 6.96 (d, J=2.4 Hz, 1H), 6.85 (dd, J=2.7, 8.4 Hz, 1H), 6.80 (d, J=8.4 Hz, 1H), 5.40 (s, 2H), 4.14-4.17 (m, 2H), 3.96-4.02 (m, 2H), 3.68-3.71 (m, 2H), 3.33 (d, J=6.0 Hz, 3H), 2.64 (dd, J=2.1, 7.8 Hz, 2H), 2.01 (s, 3H), 1.77 (d, J=2.4 Hz, 3H). LC/MS: mass calcd. for $C_{30}H_{29}NO_5S$: 515.62, found: 514.1 [M−H]−.

(Cpd 77): $^1$H NMR (DMSO-$d_6$) δ 8.10 (d, J=2.4 Hz, 1H), 8.04 (d, J=8.4 Hz, 1H), 7.71 (dd, J=2.4, 8.4 Hz, 1H), 7.64 (s, 1H), 7.42-7.48 (m, 2H), 7.16 (d, J=8.4 Hz, 1H), 6.96 (d, J=2.4 Hz, 1H), 6.85 (dd, J=2.7, 8.4 Hz, 1H), 6.80 (d, J=8.4 Hz, 1H), 5.40 (s, 2H), 4.14-4.17 (m, 2H), 3.96-4.02 (m, 2H), 3.68-3.71 (m, 2H), 3.33 (d, J=6.0 Hz, 3H), 2.64 (dd, J=2.1, 7.8 Hz, 2H), 2.01 (s, 3H), 1.77 (d, J=2.4 Hz, 3H). LC/MS: mass calcd.

for $C_{30}H_{29}NO_5S$: 515.62, found: 514.1 [M−H]−.

Example 78

(3S)-3-(4-((3-(2-Methoxypyridin-3-yl)benzo[b]thiophen-5-yl)methoxy)phenyl)hex-4-ynoic acid (Cpd 78)

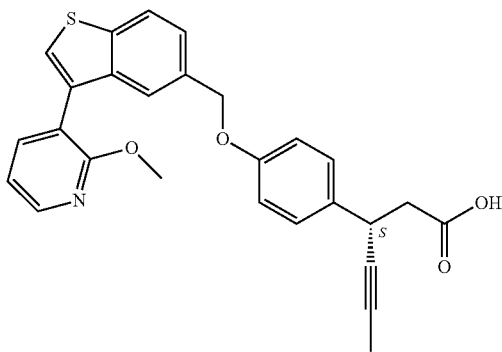

(A) (3S)-Ethyl 3-(4-((3-(2-methoxypyridin-3-yl)benzo[b]thiophen-5-yl)methoxy)phenyl)hex-4-ynoate was prepared from (3S)-ethyl 3-(4-((3-bromobenzo[b]thiophen-5-yl)methoxy)phenyl)hex-4-ynoate (from Example 11E) and 2-methoxypyridin-3-ylboronic acid following General Procedure A using PdCl$_2$(dppf).CH$_2$Cl$_2$ as the palladium catalyst and Cs$_2$CO$_3$ in place of K$_2$CO$_3$. LC/MS: mass calcd. for $C_{29}H_{27}NO_4S$: 485.59, found: 486.2 [M+H]+.

(B) (3S)-3-(4-((3-(2-Methoxypyridin-3-yl)benzo[b]thiophen-5-yl)methoxy)phenyl)hex-4-ynoic acid (Cpd 78) was prepared from (3S)-ethyl 3-(4-((3-(2-methoxypyridin-3-yl)benzo[b]thiophen-5-yl)methoxy)phenyl)hex-4-ynoate following General Procedure C, using LiOH as base, EtOH in place of MeOH, a rt reaction temperature overnight and 1N HCl for reaction acidification. $^1$H NMR (DMSO-$d_6$) δ 12.22 (br. s, 1H), 8.27-8.29 (m, 1H), 8.06 (d, J=8.4 Hz, 1H), 7.83 (s, 1H), 7.77-7.79 (m, 1H), 7.58 (s, 1H), 7.48 (d, J=8.4 Hz, 1H), 7.26 (d, J=8.8 Hz, 2H), 7.13-7.16 (m, 1H), 6.94 (d, J=8.8 Hz, 2H), 5.21 (s, 2H), 3.90-3.95 (m, 1H), 3.78 (s, 3H), 2.59 (d, J=7.2 Hz, 2H), 1.77 (d, J=2.4 Hz, 3H). LC/MS: mass calcd. for $C_{27}H_{23}NO_4S$: 457.54, found: 458.1 [M+H]+.

Example 79

(3S)-3-(4-((3-(2-Methoxyphenyl)benzo[b]thiophen-5-yl)methoxy)phenyl)hex-4-ynoic acid (Cpd 79)

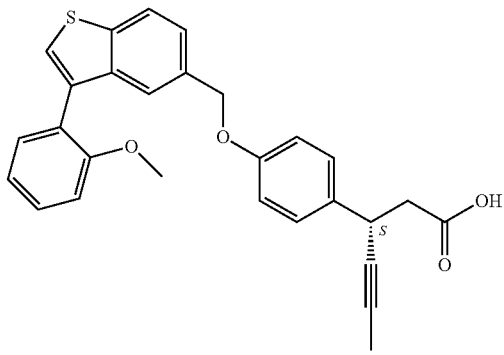

(A) (3S)-Ethyl 3-(4-((3-(2-methoxyphenyl)benzo[b]thiophen-5-yl)methoxy)phenyl)hex-4-ynoate was prepared from (3S)-ethyl 3-(4-((3-bromobenzo[b]thiophen-5-yl)methoxy)phenyl)hex-4-ynoate (from Example 11E) and 2-methoxyphenylboronic acid following General Procedure A using PdCl$_2$(dppf).CH$_2$Cl$_2$ as the palladium catalyst and Cs$_2$CO$_3$ in place of K$_2$CO$_3$. LC/MS: mass calcd. for $C_{30}H_{28}O_4S$: 484.61, found: 502.1 [M+NH$_4$]+.

(B) (3S)-3-(4-((3-(2-Methoxyphenyl)benzo[b]thiophen-5-yl)methoxy)phenyl)hex-4-ynoic acid (Cpd 79) was prepared from (3S)-ethyl 3-(4-((3-(2-methoxyphenyl)-benzo[b]thiophen-5-yl)methoxy)phenyl)hex-4-ynoate following General Procedure C, using LiOH as base, EtOH in place of MeOH, a rt reaction temperature overnight and 1N HCl for reaction acidification. $^1$H NMR (DMSO-$d_6$) δ 8.00 (d, J=8.4 Hz, 1H), 7.69 (s, 1H), 7.51 (s, 1H), 7.44 (t, J=7.2 Hz, 2H), 7.31-7.33 (m, 1H), 7.24 (d, J=8.4 Hz, 2H), 7.17 (d, J=7.8 Hz, 1H), 7.06 (t, J=6.9 Hz, 1H), 6.90 (d, J=8.1 Hz, 2H), 5.18 (s, 2H), 3.90-3.95 (m, 1H), 3.68 (s, 3H), 2.51 (s, 2H), 1.75 (d, J=1.8 Hz, 3H). LC/MS: mass calcd. for $C_{28}H_{24}O_4S$: 456.55, found: 479.2 [M+Na]+.

Example 80

(3S)-3-(4-((3-(6-Methoxy-2-methylpyridin-3-yl)benzo[b]thiophen-5-yl)methoxy)phenyl)hex-4-ynoic acid (Cpd 80)

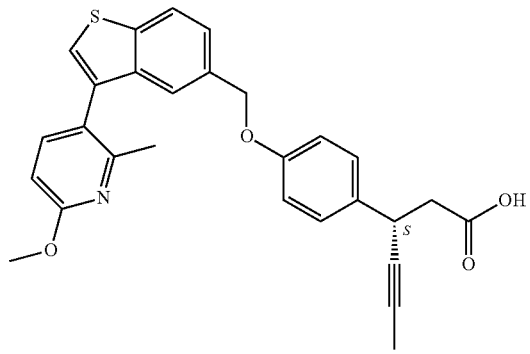

(A) (3S)-Ethyl 3-(4-((3-(6-methoxy-2-methylpyridin-3-yl)benzo[b]thiophen-5-yl)methoxy)phenyl)hex-4-ynoate was prepared from (3S)-ethyl 3-(4-((3-bromobenzo[b]thiophen-5-yl)methoxy)phenyl)hex-4-ynoate (from Example 11E) and 6-methoxy-2-methylpyridin-3-ylboronic acid following General Procedure A using PdCl$_2$(dppf).CH$_2$Cl$_2$ as the palladium catalyst and Cs$_2$CO$_3$ in place of K$_2$CO$_3$. LC/MS: mass calcd. for C$_{30}$H$_{29}$NO$_4$S: 499.62, found: 522.2 [M+Na]$^+$.

(B) (3S)-3-(4-((3-(6-Methoxy-2-methylpyridin-3-yl)benzo[b]thiophen-5-yl)methoxy)phenyl)hex-4-ynoic acid (Cpd 80) was prepared from (3S)-ethyl 3-(4-((3-(6-methoxy-2-methylpyridin-3-yl)benzo[b]thiophen-5-yl)methoxy)phenyl)hex-4-ynoate following General Procedure C, using LiOH as base, EtOH in place of MeOH, a rt reaction temperature overnight and 1N HCl for reaction acidification. $^1$H NMR (DMSO-d$_6$) δ 12.22 (br. s, 1H), 8.09 (d, J=8.0 Hz, 1H), 7.76 (s, 1H), 7.58 (d, J=8.4 Hz, 1H), 7.50 (d, J=8.4 Hz, 1H), 7.46 (s, 1H), 7.25 (d, J=8.4 Hz, 2H), 6.93 (d, J=8.8 Hz, 2H), 6.77 (d, J=8.0 Hz, 1H), 5.18 (s, 2H), 3.90-3.94 (m, 4H), 2.55-2.68 (m, 2H), 2.23 (s, 3H), 1.77 (d, J=2.0 Hz, 2H). LC/MS: mass calcd. for C$_{28}$H$_{25}$NO$_4$S: 471.57, found: 472.2 [M+H]$^+$.

Example 81

(3S)-3-(4-((3-(4-Methoxypyridin-3-yl)benzo[b]thiophen-5-yl)methoxy)phenyl)hex-4-ynoic acid (Cpd 81)

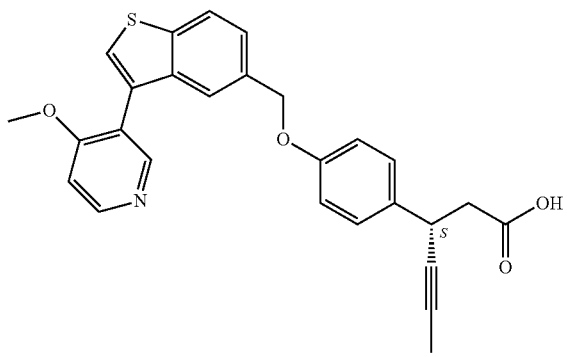

(A) (3S)-Ethyl 3-(4-((3-(4-methoxypyridin-3-yl)benzo[b]thiophen-5-yl)methoxy)phenyl)hex-4-ynoate was prepared from (3S)-ethyl 3-(4-((3-bromobenzo[b]thiophen-5-yl)methoxy)phenyl)hex-4-ynoate (from Example 11E) and 4-methoxypyridin-3-ylboronic acid following General Procedure A using PdCl$_2$(dppf).CH$_2$Cl$_2$ as the palladium catalyst and Cs$_2$CO$_3$ in place of K$_2$CO$_3$. LC/MS: mass calcd. for C$_{29}$H$_{27}$NO$_4$S: 485.59, found: 486.4 [M+H]$^+$.

(B) (3S)-3-(4-((3-(4-Methoxypyridin-3-yl)benzo[b]thiophen-5-yl)methoxy)phenyl)hex-4-ynoic acid (Cpd 81) was prepared from (3S)-ethyl 3-(4-((3-(4-methoxypyridin-3-yl)benzo[b]thiophen-5-yl)methoxy)phenyl)hex-4-ynoate following General Procedure C, using LiOH as base, EtOH in place of MeOH, a rt reaction temperature overnight and 1N HCl for reaction acidification. $^1$H NMR (DMSO-d$_6$) δ 12.23 (br. s, 1H), 8.63 (d, J=6.0 Hz, 1H), 8.50 (s, 1H), 8.07 (d, J=8.4 Hz, 1H), 7.87 (s, 1H), 7.56 (s, 1H), 7.49 (dd, J=1.2, 8.1 Hz, 1H), 7.36 (d, J=6.3 Hz, 1H), 7.25 (d, J=8.7 Hz, 2H), 6.93 (d, J=8.7 Hz, 2H), 5.75 (s, 2H), 3.89-3.95 (m, 1H), 3.80 (s, 3H), 2.51-2.59 (m, 2H), 1.76 (d, J=2.4 Hz, 2H). LC/MS: mass calcd. for C$_{27}$H$_{23}$NO$_4$S: 457.54, found: 456.1 [M−H]$^-$.

Example 82

(3S)-3-(4-((3-(6-Methoxy-4-methylpyridin-3-yl)benzo[b]thiophen-5-yl)methoxy)phenyl)hex-4-ynoic acid (Cpd 82)

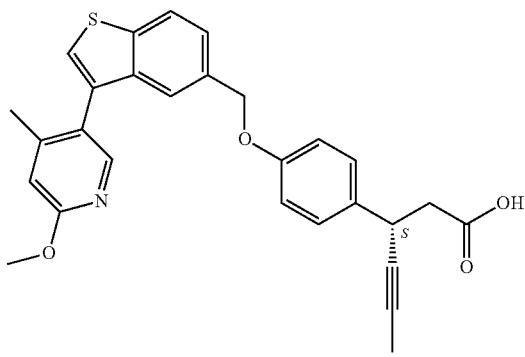

(A) (3S)-Ethyl 3-(4-((3-(6-methoxy-4-methylpyridin-3-yl)benzo[b]thiophen-5-yl)methoxy)phenyl)hex-4-ynoate was prepared from (3S)-ethyl 3-(4-((3-bromobenzo[b]thiophen-5-yl)methoxy)phenyl)hex-4-ynoate (from Example 11E) and 6-methoxy-4-methylpyridin-3-ylboronic acid following General Procedure A using PdCl$_2$(dppf).CH$_2$Cl$_2$ as the palladium catalyst and Cs$_2$CO$_3$ in place of K$_2$CO$_3$. LC/MS: mass calcd. for C$_{30}$H$_{29}$NO$_4$S: 499.62, found: 500.1 [M+H]$^+$.

(B) (3S)-3-(4-((3-(6-Methoxy-4-methylpyridin-3-yl)benzo[b]thiophen-5-yl)methoxy)phenyl)hex-4-ynoic acid (Cpd 82) was prepared from (3S)-ethyl 3-(4-((3-(6-methoxy-4-methylpyridin-3-yl)benzo[b]thiophen-5-yl)methoxy)phenyl)hex-4-ynoate following General Procedure C, using LiOH as base, EtOH in place of MeOH, at 40° C. overnight and 1N HCl for reaction acidification. $^1$H NMR (DMSO-d$_6$) δ 8.80 (d, J=8.1 Hz, 1H), 8.04 (s, 1H), 7.77 (s, 1H), 7.49 (d, J=9.6 Hz, 1H), 7.45 (s, 1H), 7.24 (d, J=8.7 Hz, 2H), 6.91 (d, J=8.7 Hz, 2H), 6.86 (s, 1H), 5.18 (s, 2H), 3.92-3.96 (m, 1H), 3.90 (s, 3H), 2.56 (d, J=8.1 Hz, 2H), 2.05 (s, 3H), 1.77 (s, 3H). LC/MS: mass calcd. for C$_{28}$H$_{25}$NO$_4$S: 471.57, found: 472.1 [M+H]$^+$.

Example 83

(3S)-3-(4-((3-(3-Methoxypyridin-4-yl)benzo[b]thiophen-5-yl)methoxy)phenyl)hex-4-ynoic acid (Cpd 83)

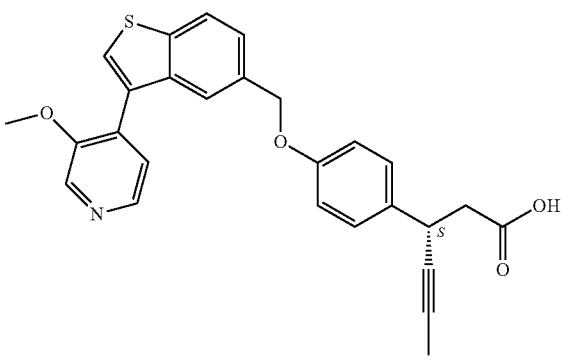

(A) (3S)-Ethyl 3-(4-((3-(3-methoxypyridin-4-yl)benzo[b]thiophen-5-yl)methoxy)phenyl)hex-4-ynoate was prepared from (3S)-ethyl 3-(4-((3-bromobenzo[b]thiophen-5-yl)methoxy)phenyl)hex-4-ynoate (from Example 11E) and 3-methoxypyridin-4-ylboronic acid following General Procedure A using $PdCl_2(dppf).CH_2Cl_2$ as the palladium catalyst and $Cs_2CO_3$ in place of $K_2CO_3$. LC/MS: mass calcd. for $C_{29}H_{27}NO_4S$: 485.59, found: 486.4 $[M+H]^+$.

(B) (3S)-3-(4-((3-(3-Methoxypyridin-4-yl)benzo[b]thiophen-5-yl)methoxy)phenyl)hex-4-ynoic acid (Cpd 83) was prepared from (3S)-ethyl 3-(4-((3-(3-methoxypyridin-4-yl)benzo[b]thiophen-5-yl)methoxy)phenyl)hex-4-ynoate following General Procedure C, using LiOH as base, EtOH in place of MeOH, a rt reaction temperature overnight and 1N HCl for reaction acidification. $^1$H NMR (DMSO-$d_6$) δ 8.71 (s, 1H), 8.55 (d, J=5.4 Hz, 1H), 8.10-8.13 (m, 2H), 7.81-7.83 (m, 1H), 7.70 (s, 1H), 7.53 (d, J=8.4 Hz, 1H), 7.26 (d, J=8.7 Hz, 2H), 6.94 (d, J=8.7 Hz, 2H), 5.20 (s, 2H), 3.93-3.96 (m, 1H), 3.89 (s, 3H), 2.58 (d, J=7.5 Hz, 2H), 1.77 (d, J=2.4 Hz, 3H). LC/MS: mass calcd. for $C_{27}H_{23}NO_4S$: 457.54, found: 458.3 $[M+H]^+$.

Example 84

(3S)-3-(4-((3-(5-Methoxy-3-methylpyridin-2-yl)benzo[b]thiophen-5-yl)methoxy)phenyl)hex-4-ynoic acid (Cpd 84)

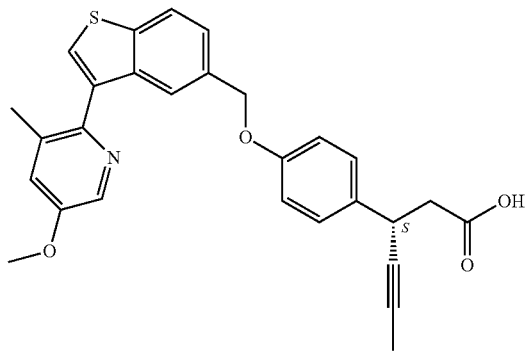

(A) To an ice-cooled solution of 6-bromo-5-methylpyridin-3-ol (500 mg, 2.66 mmol) in DMF (10 mL) was added NaH (60% wt; 160 mg, 4.0 mmol) in a portionwise fashion and the resultant mixture was allowed to stir at rt for 1 h. The mixture was then cooled to 0° C. and $CH_3I$ (755 mg, 5.32 mmol) was added in dropwise fashion. After stirring for 1 h at rt, the reaction was quenched with water (20 mL) and the mixture was extracted with EtOAc (3×30 mL). The combined extracts were dried ($Na_2SO_4$), concentrated under reduced pressure and purified by silica gel chromatography (0-10% EtOAc/petroleum ether) to afford 2-bromo-5-methoxy-3-methylpyridine (400 mg, 74% yield) as a white solid. LC/MS: mass calcd. for $C_7H_8BrNO$: 202.05, found: 202.0, 204.0 $[M, M+2]^+$.

(B) (3-(5-Methoxy-3-methylpyridin-2-yl)benzo[b]thiophen-5-yl)methanol was prepared from 2-bromo-5-methoxy-3-methylpyridine and (3-(4,4,5,5-tetramethyl-1,3,2-dioxaborolan-2-yl)benzo[b]thiophen-5-yl)methanol (from Example 41A) following General Procedure A using $PdCl_2(dppf).CH_2Cl_2$ as the palladium catalyst and $Cs_2CO_3$ in place of $K_2CO_3$. LC/MS: mass calcd. for $C_{16}H_{15}NO_2S$: 285.36, found: 286.1 $[M+H]^+$.

(C) 2-(5-(Chloromethyl)benzo[b]thiophen-3-yl)-5-methoxy-3-methylpyridine was prepared from (3-(5-methoxy-3-methylpyridin-2-yl)benzo[b]thiophen-5-yl)methanol following General Procedure D. LC/MS: mass calcd. for $C_{16}H_{14}ClNOS$: 303.81, found: 304.1 $[M]^+$.

(D) (3S)-Ethyl 3-(4-((3-(5-methoxy-3-methylpyridin-2-yl)benzo[b]thiophen-5-yl)methoxy)phenyl)hex-4-ynoate was prepared from 2-(5-(chloromethyl)benzo[b]thiophen-3-yl)-5-methoxy-3-methylpyridine and (3S)-ethyl 3-(4-hydroxyphenyl)hex-4-ynoate (available from Synnovator, Inc., Research Triangle Park, N.C.; Cat. #PB05708) following General Procedure E. LC/MS: mass calcd. for $C_{30}H_{29}NO_4S$: 499.62, found: 500.1 $[M+H]^+$.

(E) (3S)-3-(4-((3-(5-Methoxy-3-methylpyridin-2-yl)benzo[b]thiophen-5-yl)methoxy)phenyl)hex-4-ynoic acid (Cpd 84) was prepared from (3S)-ethyl 3-(4-((3-(5-methoxy-3-methylpyridin-2-yl)benzo[b]thiophen-5-yl)methoxy)phenyl)hex-4-ynoate following General Procedure C, using LiOH as base, EtOH in place of MeOH, at 40° C. overnight and 1N HCl for reaction acidification. $^1$H NMR (DMSO-$d_6$) δ 12.23 (br. s, 1H), 8.27 (d, J=2.7 Hz, 1H), 8.06 (d, J=8.1 Hz, 1H), 7.85 (s, 1H), 7.69 (s, 1H), 7.48 (d, J=8.4 Hz, 1H), 7.42 (s, 1H), 7.25 (d, J=8.7 Hz, 2H), 6.93 (d, J=8.7 Hz, 2H), 5.15 (s, 2H), 3.90-3.97 (m, 1H), 3.89 (s, 3H), 2.58 (d, J=7.5 Hz, 2H), 2.24 (s, 3H), 1.77 (s, 3H). LC/MS: mass calcd. for $C_{28}H_{25}NO_4S$: 471.57, found: 472.0 $[M+H]^+$.

Example 85

(3R)-3-[6-[[3-(2-Methylphenyl)benzo[b]thiophen-5-yl]methoxy]pyridin-3-yl]hex-4-ynoic acid (Cpd 85)

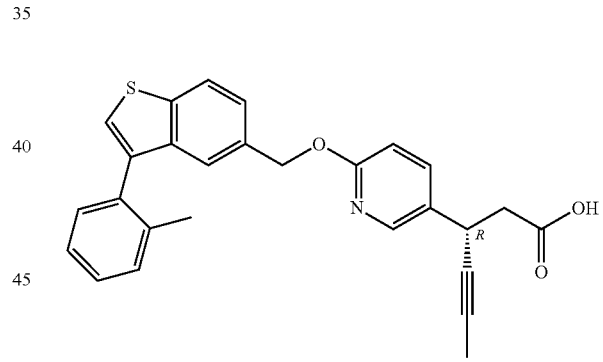

(A) Enantiomeric resolution of ethyl 3-(6-hydroxypyridin-3-yl)hex-4-ynoate (from Example 45E) was carried out by chiral super critical fluid chromatography on a ChiralPak AS-H 5μ column (2×25 cm) using an isocratic mobile phase [EtOH (0.2% DEA)/$CO_2$ (50:50); 170 g/min] to afford (3R)-ethyl 3-(6-hydroxypyridin-3-yl)hex-4-ynoate (RT=4.15 min) $^1$H NMR (CDCl$_3$) δ 7.47-7.55 (m, 2H), 6.59 (d J=9.3 Hz, 1H), 4.09-4.19 (m, 2H), 3.89-3.95 (m, 1H), 2.70 (dd, J=7.5, 15.3 Hz, 1H), 2.59 (dd, J=7.5, 15.6 Hz, 1H), 1.82 (s, 3H), 1.25-1.27 (m, 3H) and (3S)-ethyl 3-(6-hydroxypyridin-3-yl)hex-4-ynoate (RT=5.97 min).

(B) To an ice-cooled solution of 5-hydroxymethyl-3-(2-methylphenyl)benzo[b]-thiophene (from Example 1B) (200 mg, 0.79 mmol) in DCM (20 mL) and DMF (2 mL) was added phosphorous tribromide (148 μL, 1.57 mmol) in dropwise fashion. After stirring for 1 h, the mixture was neutralized to pH 6-7 with the addition of 1M aq. $NaHCO_3$, and the resulting mixture was extracted with DCM (3×10 mL). The combined organic extracts were dried (Na$_2$SO$_4$) and concentrated under reduced pressure to afford crude 5-bromomethyl-3-(2-methylphenyl)benzo[b]-thiophene, which was used directly without purification.

(C) To a solution of 5-bromomethyl-3-(2-methylphenyl)benzo[b]-thiophene from the above step in toluene (10 mL) was added (3R)-ethyl 3-(6-hydroxypyridin-3-yl)hex-4-ynoate (170 mg, 0.73 mmol) and Ag$_2$CO$_3$ (434 mg, 1.57 mmol) and the resulting mixture was stirred at 60° C. overnight. Water (20 mL) was then added and the mixture was extracted with EtOAc (3×20 mL). The combined organic extracts were concentrated under reduced pressure and the resultant residue was purified by silica gel chromatography (0-20% EtOAc/petroleum ether) to afford (3R)-ethyl 3-(6-((3-(2-methylphenyl)benzo[b]thiophen-5-yl)methoxy)pyridin-3-yl)hex-4-ynoate (80 mg, 19% yield) as colorless oil. LC/MS: mass calcd. for C$_{29}$H$_{27}$NO$_3$S: 469.60, found: 470.3 [M+H]$^+$.

(D) (3R)-3-(6-((3-(2-Methylphenyl)benzo[b]thiophen-5-yl)methoxy)pyridin-3-yl)hex-4-ynoic acid (Cpd 85) was prepared from (3R)-ethyl 3-(6-((3-(2-methylphenyl)benzo[b]thiophen-5-yl)methoxy)pyridin-3-yl)hex-4-ynoate following General Procedure C, using LiOH as base, EtOH in place of MeOH, a rt reaction temperature overnight and 1N HCl for reaction acidification. $^1$H NMR (DMSO-d$_6$) δ 8.01-8.09 (m, 2H), 7.62-7.69 (m, 2H), 7.46 (dd, J=1.5, 8.4 Hz, 1H), 7.20-7.42 (m, 5H), 6.75 (d, J=8.4 Hz, 1H), 5.38 (s, 2H), 3.95-4.05 (m, 1H), 2.40-2.50 (m, 2H), 2.06 (s, 3H), 1.75 (d, J=2.4 Hz, 3H). LC/MS: mass calcd. for C$_{27}$H$_{23}$NO$_3$S: 441.54, found: 442.0 [M+H]$^+$.

Example 86

(3S)-3-[4-[([3-[2-Methyl-4-(tetrahydrofuran-3-yloxy)phenyl]-1-benzothiophen-5-yl]oxy)methyl]phenyl]hex-4-ynoic acid (Cpd 86)

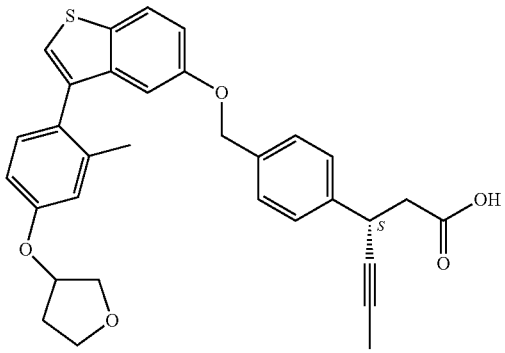

(A) 3-(4-Bromo-3-methylphenoxy)tetrahydrofuran was prepared from 4-bromo-3-methylphenol and 3-hydroxytetrahydrofuran following General Procedure B using PPh$_3$ and DEAD. LC/MS: mass calcd. for C$_{11}$H$_{13}$BrO$_2$: 257.12, found 257.1, 259.1 [M, M+2]$^-$.

(B) (3-(2-Methyl-4-(tetrahydrofuran-3-yloxy)phenyl)benzo[b]thiophen-5-yl)methanol was prepared from 3-(4-bromo-3-methylphenoxy)tetrahydrofuran and (3-(4,4,5,5-tetramethyl-1,3,2-dioxaborolan-2-yl)benzo[b]thiophen-5-yl)methanol (from Example 41A) following General Procedure A using PdCl$_2$(dppf).CH$_2$Cl$_2$ as the palladium catalyst and Cs$_2$CO$_3$ in place of K$_2$CO$_3$. LC/MS: mass calcd. for C$_{20}$H$_{20}$O$_3$S: 340.44, found: 323.1 [M−OH]$^+$.

(C) 3-(4-(5-(Chloromethyl)benzo[b]thiophen-3-yl)-3-methylphenoxy)tetrahydrofuran was prepared from (3-(2-methyl-4-(tetrahydrofuran-3-yloxy)phenyl)benzo[b]-thiophen-5-yl)methanol following General Procedure D. LC/MS: mass calcd. for C$_{20}$H$_{19}$ClO$_2$S: 358.88, found: 359.1 [M]$^+$.

(D) (3S)-Ethyl 3-(4-((3-(2-methyl-4-(tetrahydrofuran-3-yloxy)phenyl)benzo[b]-thiophen-5-yl)methoxy)phenyl)hex-4-ynoate was prepared from 3-(4-(5-(chloromethyl)benzo[b]thiophen-3-yl)-3-methylphenoxy)tetrahydrofuran and (3S)-ethyl 3-(4-hydroxyphenyl)hex-4-ynoate (available from Synnovator, Inc., Research Triangle Park, N.C.; Cat. #PB05708) following General Procedure E. LC/MS: mass calcd. for C$_{34}$H$_{34}$O$_5$S: 554.70, found: 572.1 [M+NH$_4$]$^+$.

(E) (3S)-3-(4-((3-(2-Methyl-4-(tetrahydrofuran-3-yloxy)phenyl)benzo[b]thiophen-5-yl)methoxy)phenyl)hex-4-ynoic acid (Cpd 86) was prepared from (3S)-ethyl 3-(4-((3-(2-methyl-4-(tetrahydrofuran-3-yloxy)phenyl)benzo[b]-thiophen-5-yl)methoxy)phenyl)hex-4-ynoate following General Procedure C, using LiOH as base, EtOH in place of MeOH, a 35° C. reaction temperature overnight and 1N HCl for reaction acidification. $^1$H NMR (DMSO-d$_6$) δ 12.23 (br. m, 1H), 8.05 (d, J=8.1 Hz, 1H), 7.65 (s, 1H), 7.47 (d, J=8.1 Hz, 1H), 7.42 (s, 1H), 7.24 (d, J=8.7 Hz, 2H), 7.17 (d, J=8.4 Hz, 1H), 6.84-6.93 (m, 4H), 5.17 (s, 2H), 5.06-5.10 (m, 1H), 3.74-3.96 (m, 5H), 2.57 (d, J=7.5 Hz, 2H), 2.19-2.29 (m, 1H), 2.09 (s, 3H), 1.97-2.05 (m, 1H) 1.77 (s, 3H). LC/MS: mass calcd. for C$_{32}$H$_{30}$O$_5$S: 526.64, found: 527.1 [M+H]$^+$.

Example 87

(3R)-3-(6-((3-(5-(2-Methoxyethoxy)-2-methylphenyl)benzo[b]thiophen-5-yl)methoxy)pyridin-3-yl)hex-4-ynoic acid (Cpd 87)

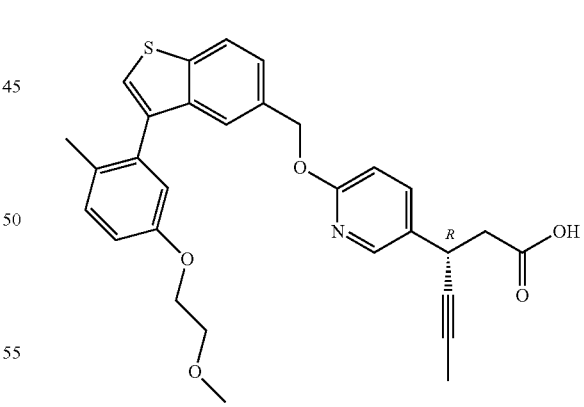

(A) 3-(5-(2-Methoxyethoxy)-2-methylphenyl)benzo[b]thiophene-5-carbaldehyde was prepared from 2-bromo-4-(2-methoxyethoxy)-1-methylbenzene (from Example 65A) and (3-(4,4,5,5-tetramethyl-1,3,2-dioxaborolan-2-yl)benzo[b]thiophen-5-yl)methanol (from Example 41A) following General Procedure A using PdCl$_2$(dppf). CH$_2$Cl$_2$ as the palladium catalyst and Cs$_2$CO$_3$ in place of K$_2$CO$_3$. LC/MS: mass calcd. for C$_{19}$H$_{18}$O$_3$S: 326.41, found: 327.0 [M+H]$^+$.

(B) (3-(5-(2-Methoxyethoxy)-2-methylphenyl)benzo[b]thiophen-5-yl)methanol was prepared from 3-(5-(2-methoxyethoxy)-2-methylphenyl)benzo[b]thiophene-5-carbaldehyde following General Procedure F. LC/MS: mass calcd. for $C_{19}H_{20}O_3S$: 428.43, found: 311.1 [M−OH]⁺.

(C) 5-(Bromomethyl)-3-(5-(2-methoxyethoxy)-2-methylphenyl)benzo[b]thiophene was prepared from (3-(5-(2-methoxyethoxy)-2-methylphenyl)benzo[b]thiophen-5-yl)methanol following the procedure described in Example 85B and used directly in the following reaction.

(E) (3R)-Ethyl 3-(6-((3-(5-(2-methoxyethoxy)-2-methylphenyl)benzo[b]thiophen-5-yl)methoxy)pyridin-3-yl)hex-4-ynoate was prepared from 5-(bromomethyl)-3-(5-(2-methoxyethoxy)-2-methylphenyl)benzo[b]thiophene and (3R)-ethyl 3-(6-hydroxypyridin-3-yl)hex-4-ynoate (from Example 85A) following the procedure described in Example 85C. LC/MS: mass calcd. for $C_{32}H_{33}NO_5S$: 543.67, found: 544.1 [M+H]⁺.

(D) (3R)-3-(6-((3-(5-(2-methoxyethoxy)-2-methylphenyl)benzo[b]thiophen-5-yl)methoxy)pyridin-3-yl)hex-4-ynoic acid was prepared from (3R)-ethyl 3-(6-((3-(5-(2-methoxyethoxy)-2-methylphenyl)benzo[b]thiophen-5-yl)methoxy)pyridin-3-yl)hex-4-ynoate following General Procedure C, using LiOH as base, EtOH in place of MeOH, a rt reaction temperature overnight and 2N HCl for reaction acidification. ¹H NMR (DMSO-$d_6$) δ 8.10 (d, J=2.4 Hz, 1H), 8.05 (d, J=8.1 Hz, 1H), 7.68-7.73 (m, 2H), 7.45-7.49 (m, 2H), 7.26 (d, J=8.4 Hz, 1H), 6.93-6.97 (m, 1H), 6.77-6.82 (m, 2H), 5.41 (s, 2H), 4.07-4.10 (m, 2H), 3.96-4.02 (m, 1H), 3.63-3.66 (m, 2H), 3.30 (s, 3H), 2.59-2.65 (m, 2H), 1.98 (s, 3H), 1.77 (d, J=2.1 Hz, 3H). LC/MS: mass calcd. for $C_{30}H_{29}NO_5S$: 515.62, found: 516.3 [M+H]⁺.

Example 88

(3R)-3-(6-((3-(3-(2-Methoxyethoxy)-2-methylphenyl)benzo[b]thiophen-5-yl)methoxy)pyridin-3-yl)hex-4-ynoic acid (Cpd 88)

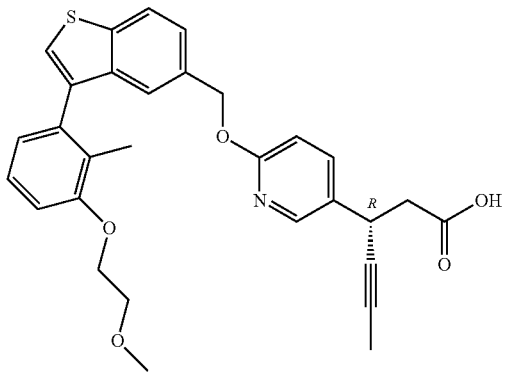

(A) (3-(3-(2-Methoxyethoxy)-2-methylphenyl)benzo[b]thiophen-5-yl)methanol was prepared from 2-bromo-3-(2-methoxyethoxy)-1-methylbenzene (from Example 67A) and (3-(4,4,5,5-tetramethyl-1,3,2-dioxaborolan-2-yl)benzo[b]thiophen-5-yl)methanol (from Example 41A) following General Procedure A using PdCl₂(dppf)·CH₂Cl₂ as the palladium catalyst and Cs₂CO₃ in place of K₂CO₃. LC/MS: mass calcd. for $C_{19}H_{20}O_3S$: 428.43, found: 311.1 [M−OH]⁺.

(B) 5-(Bromomethyl)-3-(3-(2-methoxyethoxy)-2-methylphenyl)benzo[b]thiophene was prepared from (3-(3-(2-methoxyethoxy)-2-methylphenyl)benzo[b]thiophen-5-yl)methanol following the procedure described in Example 85B and used directly in the following reaction.

(C) (3R)-Ethyl 3-(6-((3-(3-(2-methoxyethoxy)-2-methylphenyl)benzo[b]thiophen-5-yl)methoxy)pyridin-3-yl)hex-4-ynoate was prepared from 5-(bromomethyl)-3-(3-(2-methoxyethoxy)-2-methylphenyl)benzo[b]thiophene and (3R)-ethyl 3-(6-hydroxypyridin-3-yl)hex-4-ynoate (from Example 85A) following the procedure described in Example 85C. LC/MS: mass calcd. for $C_{32}H_{33}NO_5S$: 543.67, found: 544.1 [M+H]⁺.

(D) (3R)-3-(6-((3-(3-(2-methoxyethoxy)-2-methylphenyl)benzo[b]thiophen-5-yl)methoxy)pyridin-3-yl)hex-4-ynoic acid was prepared from (3R)-ethyl 3-(6-((3-(3-(2-methoxyethoxy)-2-methylphenyl)benzo[b]thiophen-5-yl)methoxy)pyridin-3-yl)hex-4-ynoate following General Procedure C, using LiOH as base, EtOH in place of MeOH, a rt reaction temperature overnight and 2N HCl for reaction acidification. ¹H NMR (DMSO-$d_6$) δ 8.09 (d, J=2.1 Hz, 1H), 8.04 (d, J=8.4 Hz, 1H), 7.66-7.71 (m, 2H), 7.47 (dd, J=1.5, 8.4 Hz, 1H), 7.41 (s, 1H), 7.26 (t, J=8.1 Hz, 1H), 7.06 (d, J=8.1 Hz, 1H), 6.86 (d, J=7.5 Hz, 1H), 6.77 (d, J=8.7 Hz, 1H), 5.39 (s, 2H), 4.15-4.19 (m, 2H), 3.96-4.01 (m, 1H), 3.71-3.74 (m, 2H), 3.35 (s, 3H), 2.54-2.61 (m, 2H), 1.92 (s, 3H), 1.76 (d, J=2.1 Hz, 3H). LC/MS: mass calcd. for $C_{30}H_{29}NO_5S$: 515.62, found: 514.1 [M−H]⁻.

Example 89

(3R)-3-(6-((3-(5-(2-Methoxyethoxy)-3-methylpyridin-2-yl)benzo[b]thiophen-5-yl)methoxy)pyridin-3-yl)hex-4-ynoic acid (Cpd 89)

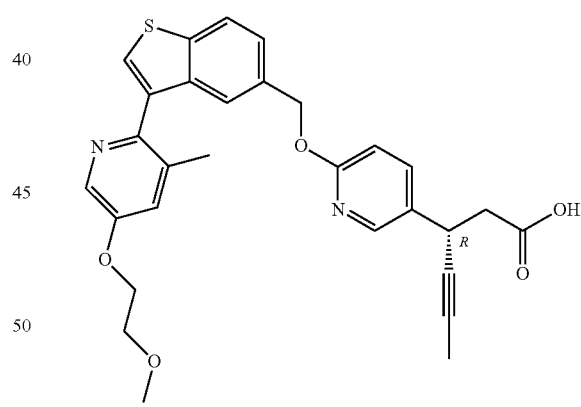

(A) 2-(5-(Bromomethyl)benzo[b]thiophen-3-yl)-5-(2-methoxyethoxy)-3-methylpyridine was prepared from (3-(5-(2-methoxyethoxy)-3-methylpyridin-2-yl)benzo[b]thiophen-5-yl)methanol (from Example 48B) following the procedure described in Example 85B and used directly in the following reaction. LC/MS: mass calcd. for $C_{18}H_{18}BrNO_2S$: 392.31, found: 392.2, 394.2 [M, M+2]⁺.

(B) (3R)-Ethyl 3-(6-((3-(5-(2-methoxyethoxy)-3-methylpyridin-2-yl)benzo[b]thiophen-5-yl)methoxy)pyridin-3-yl)hex-4-ynoate was prepared from 2-(5-(bromomethyl)benzo[b]thiophen-3-yl)-5-(2-methoxyethoxy)-3-methylpyridine and (3R)-ethyl 3-(6-hydroxypyridin-3-yl)hex-4-ynoate (from Example 85A) following the procedure described in Example 85C. LC/MS: mass calcd. for $C_{32}H_{33}NO_5S$: 544.66, found: 545.3 $[M+H]^-$.

(C) (3R)-3-(6-((3-(5-(2-methoxyethoxy)-3-methylpyridin-2-yl)benzo[b]thiophen-5-yl)methoxy)pyridin-3-yl)hex-4-ynoic acid was prepared from (3R)-ethyl 3-(6-((3-(5-(2-methoxyethoxy)-3-methylpyridin-2-yl)benzo[b]thiophen-5-yl)methoxy)pyridin-3-yl)hex-4-ynoate following General Procedure C, using LiOH as base, EtOH in place of MeOH, a rt reaction temperature overnight and 1N HCl for reaction acidification. $^1$H NMR (DMSO-d$_6$) δ 12.25 (br. m, 1H), 8.28 (d, J=2.4 Hz, 1H), 8.12 (s, 1H), 8.04 (d, J=8.4 Hz, 1H), 7.86 (s, 1H), 7.70-7.74 (m, 2H), 7.44-7.49 (m, 2H), 6.81 (d, J=8.8 Hz, 1H), 5.40 (s, 2H), 4.25 (t, J=4.0 Hz, 2H), 3.99-4.00 (m, 1H), 3.72 (t, J=4.4 Hz, 2H), 3.32 (s, 3H), 2.65-2.67 (m, 2H), 2.24 (s, 3H), 1.78 (s, 3H). LC/MS: mass calcd. for $C_{30}H_{29}NO_5S$: 516.61, found: 517.1 $[M+H]^+$.

Example 90

(3R)-3-(6-((3-(2-Chloro-5-methylpyridin-4-yl)benzo[b]thiophen-5-yl)methoxy)pyridin-3-yl)hex-4-ynoic acid (Cpd 90)

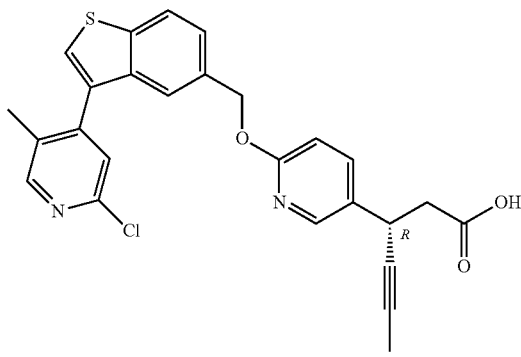

(A) (3-(2-chloro-5-methylpyridin-4-yl)benzo[b]thiophen-5-yl)methanol was prepared from 4-bromo-2-chloro-5-methylpyridine and (3-(4,4,5,5-tetramethyl-1,3,2-dioxaborolan-2-yl)benzo[b]thiophen-5-yl)methanol (from Example 41A) following General Procedure A using PdCl$_2$(dppf).CH$_2$Cl$_2$ as the palladium catalyst and Cs$_2$CO$_3$ in place of K$_2$CO$_3$. LC/MS: mass calcd. for $C_{15}H_{12}ClNOS$: 289.78, found: 290.0, 292.0 $[M, M+2]^+$.

(B) 2-Chloro-4-(5-(bromomethyl)benzo[b]thiophen-3-yl)-5-methylpyridine was prepared from (3-(2-chloro-5-methylpyridin-4-yl)benzo[b]thiophen-5-yl)methanol following the procedure described in Example 85B and used directly in the following reaction.

(C) (3R)-Ethyl 3-(6-((3-(2-chloro-5-methylpyridin-4-yl)benzo[b]thiophen-5-yl)methoxy)pyridin-3-yl)hex-4-ynoate was prepared from 2-chloro-4-(5-(bromomethyl)benzo[b]thiophen-3-yl)-5-methylpyridine and (3R)-ethyl 3-(6-hydroxypyridin-3-yl)hex-4-ynoate (from Example 85A) following the procedure described in Example 85C. LC/MS: mass calcd. for $C_{28}H_{25}ClN_2O_3S$: 505.03, found: 505.2, 507.2 $[M, M+2]^+$.

(D) (3R)-3-(6-((3-(2-chloro-5-methylpyridin-4-yl)benzo[b]thiophen-5-yl)methoxy)pyridin-3-yl)hex-4-ynoic acid was prepared from (3R)-ethyl 3-(6-((3-(2-chloro-5-methylpyridin-4-yl)benzo[b]thiophen-5-yl)methoxy)pyridin-3-yl)hex-4-ynoate following General Procedure C, using LiOH as base, EtOH in place of MeOH, a rt reaction temperature overnight and 1N HCl for reaction acidification. $^1$H NMR (DMSO-d$_6$) δ 12.28 (br. s, 1H), 8.44 (s, 1H), 8.07-8.14 (m, 2H), 7.97 (s, 1H), 7.73 (dd, J=2.7, 8.7 Hz, 1H), 7.53 (d, J=7.8 Hz, 2H), 7.44 (s, 1H), 6.81 (d, J=8.7 Hz, 1H), 5.43 (s, 2H), 4.00 (q, J=6.3 Hz, 1H), 2.65 (dd, J=1.8, 7.8 Hz, 2H), 2.07 (s, 3H), 1.78 (d, J=2.4 Hz, 3H). LC/MS: mass calcd. for $C_{26}H_{21}ClN_2O_3S$: 476.98, found: 477.1, 479.1 $[M, M+2]^+$.

Example 91

(3S)-3-(4-((3-(3-Methoxypyridin-2-yl)benzo[b]thiophen-5-yl)methoxy)phenyl)hex-4-ynoic acid (Cpd 91)

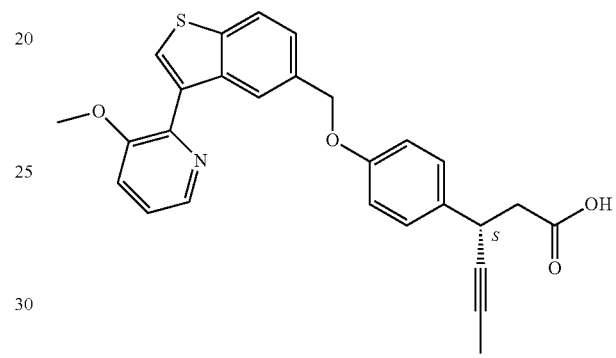

(A) (3-(3-Methoxypyridin-2-yl)benzo[b]thiophen-5-yl)methanol was prepared from 2-bromo-3-methoxypyridine and (3-(4,4,5,5-tetramethyl-1,3,2-dioxaborolan-2-yl)benzo[b]thiophen-5-yl)methanol (from Example 41A) following General Procedure A using PdCl$_2$(dppf).CH$_2$Cl$_2$ as the palladium catalyst and Cs$_2$CO$_3$ in place of K$_2$CO$_3$ at a reaction temperature of 80° C. overnight. LC/MS: mass calcd. for $C_{15}H_{13}NO_2S$: 271.33, found: 272.1 $[M+H]^+$.

(B) 2-(5-(Chloromethyl)benzo[b]thiophen-3-yl)-3-methoxypyridine was prepared from (3-(3-methoxypyridin-2-yl)benzo[b]thiophen-5-yl)methanol following General Procedure D. LC/MS: mass calcd. for $C_{15}H_{12}ClNOS$: 289.78, found: 290.0 $[M]^+$.

(C) (3S)-Ethyl 3-(4-((3-(3-methoxypyridin-2-yl)benzo[b]thiophen-5-yl)methoxy)phenyl)hex-4-ynoate was prepared from 2-(5-(chloromethyl)benzo[b]thiophen-3-yl)-3-methoxypyridine and (3S)-ethyl 3-(4-hydroxyphenyl)hex-4-ynoate (available from Synnovator, Inc., Research Triangle Park, N.C.; Cat. #PB05708) following General Procedure E. LC/MS: mass calcd. for $C_{29}H_{27}NO_4S$: 485.59, found: 486.1 $[M+H]^+$.

(D) (3S)-3-(4-((3-(3-Methoxypyridin-2-yl)benzo[b]thiophen-5-yl)methoxy)phenyl)hex-4-ynoic acid (Cpd 91) was prepared from (3S)-ethyl 3-(4-((3-(3-methoxypyridin-2-yl)benzo[b]thiophen-5-yl)methoxy)phenyl)hex-4-ynoate following General Procedure C, using LiOH as base, EtOH in place of MeOH, a 30° C. reaction temperature overnight and 1N HCl for reaction acidification. Further purification was carried out by preparative HPLC on a Waters SunFire™ Prep C18, 5µ column (19×100 mm) using an acetonitrile/water (0.5% NH$_4$HCO$_3$) gradient (55-75%). $^1$H NMR (DMSO-d$_6$) δ 8.30 (d, J=8.7 Hz, 1H), 8.20 (s, 1H), 8.15 (s, 1H), 8.04 (d, J=8.4 Hz, 1H), 7.61 (d, J=9.9 Hz, 1H), 7.39-7.48 (m, 2H), 7.12 (d, J=8.7 Hz, 2H), 6.92 (d, J=8.7 Hz, 2H), 5.17 (s, 2H), 3.91-3.96 (m, 2H), 3.81 (s, 3H), 2.37-2.44 (m, 2H), 1.74 (s, 3H). LC/MS: mass calcd. for $C_{27}H_{23}NO_4S$: 457.54, found: 458.2 $[M+H]^+$.

Example 92

(3R)-3-(6-((3-(5-(2-Methoxyethoxy)-2-methylpyridin-3-yl)benzo[b]thiophen-5-yl)methoxy)pyridine-3-yl)hex-4-ynoic acid (Cpd 92)

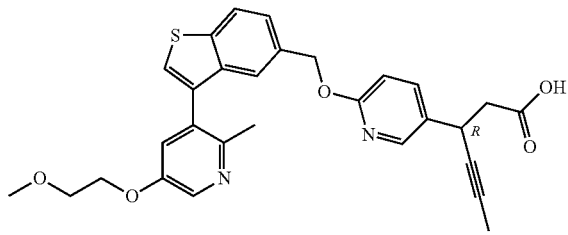

(A) (3-(5-(2-Methoxyethoxy)-2-methylpyridin-3-yl)benzo[b]thiophen-5-yl)methanol was prepared from 3-bromo-5-(2-methoxyethoxy)-2-methylpyridine (from Example 49A) and (3-(4,4,5,5-tetramethyl-1,3,2-dioxaborolan-2-yl)benzo[b]thiophen-5-yl)methanol (from Example 41A) following General Procedure A using PdCl$_2$(dppf).CH$_2$Cl$_2$ as the palladium catalyst and Cs$_2$CO$_3$ in place of K$_2$CO$_3$. LC/MS: mass calcd. for $C_{18}H_{19}NO_3S$: 329.41, found: 330.0 $[M+H]^+$.

(B) 3-(5-(Bromomethyl)benzo[b]thiophen-3-yl)-5-(2-methoxyethoxy)-2-methylpyridine was prepared from (3-(5-(2-methoxyethoxy)-2-methylpyridin-3-yl)benzo[b]thiophen-5-yl)methanol following the procedure described in Example 85B and used directly in the following reaction. LC/MS: mass calcd. for $C_{18}H_{18}BrNO_2S$: 392.41, found: 391.9, 393.9 $[M, M+2]^+$.

(C) (3R)-Ethyl 3-(6-((3-(5-(2-methoxyethoxy)-2-methylpyridin-3-yl)benzo[b]thiophen-5-yl)methoxy)pyridin-3-yl)hex-4-ynoate was prepared from 3-(5-(bromomethyl)benzo[b]thiophen-3-yl)-5-(2-methoxyethoxy)-2-methylpyridine and (3R)-ethyl 3-(6-hydroxypyridin-3-yl)hex-4-ynoate (from Example 85A) following the procedure described in Example 85C. LC/MS: mass calcd. for $C_{31}H_{32}N_2O_5S$: 544.66, found: 545.1 $[M+H]^-$.

(D) (3R)-3-(6-((3-(5-(2-Methoxyethoxy)-2-methylpyridin-3-yl)benzo[b]thiophen-5-yl)methoxy)pyridin-3-yl)hex-4-ynoic acid (Cpd 92) was prepared from (3R)-ethyl 3-(6-((3-(5-(2-methoxyethoxy)-2-methylpyridin-3-yl)benzo[b]thiophen-5-yl)methoxy)pyridin-3-yl)hex-4-ynoate following General Procedure C, using LiOH as base, EtOH in place of MeOH, a 35° C. reaction temperature overnight and 2N HCl for reaction acidification. $^1$H NMR (DMSO-d$_6$) δ 8.28 (d, J=3.0 Hz, 1H), 8.09-8.11 (m, 2H), 7.83 (s, 1H), 7.71 (dd, J=2.4, 8.4 Hz, 1H), 7.48-7.53 (m, 2H), 7.29 (d, J=3.0 Hz, 1H), 6.80 (d, J=8.7 Hz, 1H), 5.42 (s, 2H), 4.17-4.20 (m, 2H), 3.95-4.00 (m, 1H), 3.65-3.68 (m, 2H), 3.30 (s, 3H), 2.63-2.66 (m, 2H), 2.19 (s, 3H), 1.77 (d, J=2.4 Hz, 3H). LC/MS: mass calcd. for $C_{29}H_{28}N_2O_5S$: 516.61, found: 517.3 $[M+H]^+$.

Example 93

(3S)-3-(4-((3-(6-Chloro-3-methylpyridin-2-yl)benzo[b]thiophen-5-yl)methoxy)phenyl)hex-4-ynoic acid (Cpd 93)

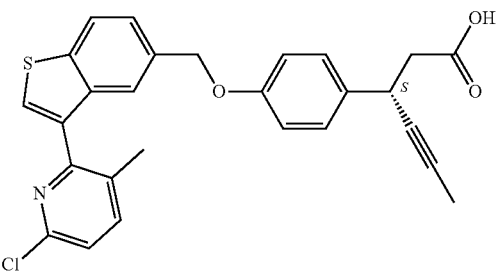

(A) (3-(6-Chloro-3-methylpyridin-2-yl)benzo[b]thiophen-5-yl)methanol was prepared from 2-bromo-6-chloro-3-methylpyridine and (3-(4,4,5,5-tetramethyl-1,3,2-dioxaborolan-2-yl)benzo[b]thiophen-5-yl)methanol (from Example 41A) following General Procedure A using PdCl$_2$(dppf).CH$_2$Cl$_2$ as the palladium catalyst and Cs$_2$CO$_3$ in place of K$_2$CO$_3$. LC/MS: mass calcd. for $C_{15}H_{12}ClNOS$: 289.78, found: 290.0, 292.0 $[M, M+2]^+$.

(B) 6-Chloro-2-(5-(chloromethyl)benzo[b]thiophen-3-yl)-3-methylpyridine was prepared from (3-(6-chloro-3-methylpyridin-2-yl)benzo[b]thiophen-5-yl)methanol following General Procedure D and used directly in the following step.

(C) (3S)-Ethyl 3-(4-((3-(6-chloro-3-methylpyridin-2-yl)benzo[b]thiophen-5-yl)methoxy)phenyl)hex-4-ynoate was prepared from 6-chloro-2-(5-(chloromethyl)benzo[b]thiophen-3-yl)-3-methylpyridine and (3S)-ethyl 3-(4-hydroxyphenyl)hex-4-ynoate (available from Synnovator, Inc., Research Triangle Park, N.C.; Cat. #PB05708) following General Procedure E, using K$_2$CO$_3$ in place of Cs$_2$CO$_3$, DMF as solvent in place of MeCN and a reaction temperature of 60° C. overnight. LC/MS: mass calcd. for $C_{29}H_{26}ClNO_3S$: 504.04, found: 504.1 $[M]^+$.

(D) 3-(4-((3-(6-Chloro-3-methylpyridin-2-yl)benzo[b]thiophen-5-yl)methoxy)phenyl)hex-4-ynoic acid (Cpd 93) was prepared from (3S)-ethyl 3-(4-((3-(6-chloro-3-methylpyridin-2-yl)benzo[b]thiophen-5-yl)methoxy)phenyl)hex-4-ynoate following General Procedure C, using LiOH as base, EtOH in place of MeOH, a rt reaction temperature overnight and 1N HCl for reaction acidification. Further purification was carried out by reversed phase flash chromatography on an Agela Technologies C18 cartridge, (120 g, 20-35µ, 100 Å) using an acetonitrile/water gradient (35-90%). $^1$H NMR (DMSO-d$_6$) δ 12.22 (br. s, 1H), 8.10 (d, J=8.3 Hz, 1H), 8.05 (s, 1H), 7.89 (dd, J=0.8, 8.7 Hz, 1H), 7.73 (d, J=1.6 Hz, 1H), 7.48-7.54 (m, 2H), 7.22-7.29 (m, 2H), 6.92-6.98 (m, 2H), 5.19 (s, 2H), 3.89-3.96 (m, 1H), 2.58 (d, J=7.6 Hz, 2H), 2.24 (s, 3H), 1.77 (d, J=2.4 Hz, 3H). LC/MS: mass calcd. for $C_{27}H_{22}ClNO_3S$: 475.99, found: 475.9 $[M]^+$.

Example 94

(3S)-3-(4-((3-(6-Methoxy-3-methylpyridin-2-yl)benzo[b]thiophen-5-yl)methoxy)phenyl)hex-4-ynoic acid (Cpd 94)

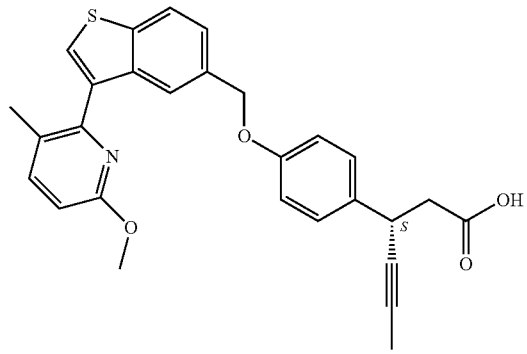

(A) A mixture of (3-(6-chloro-3-methylpyridin-2-yl)benzo[b]thiophen-5-yl)methanol (300 mg, 1.04 mmol, from Example 93A), DMSO (10 mL) and sodium methoxide in methanol (4 ml) was heated for 30 min in a microwave reactor at 100° C. After cooling to rt, the reaction was quenched with water (50 mL) and the mixture was extracted with EtOAc (3×50 mL). The combined extracts were concentrated under reduced pressure to afford crude 6-(5-(hydroxymethyl)benzo[b]thiophen-3-yl)-5-methylpyridin-2-ol as black oil, which was used directly without further purification. LC/MS: mass calcd. for $C_{15}H_{13}NO_2S$: 271.33, found: 272.0 $[M+H]^+$.

(B) To a mixture of 6-(5-(hydroxymethyl)benzo[b]thiophen-3-yl)-5-methylpyridin-2-ol (340 mg, 1.25 mmol) and $Ag_2CO_3$ (1.04 g, 3.76 mmol), in toluene (10 ml), was added iodomethane (0.53 g, 3.76 mmol). After stirring overnight at 45° C., the mixture was filtered and the filtrate was concentrated under reduced pressure. The residue thus obtained was purified by silica gel chromatography eluting with EtOAc/petroleum ether (0-30%) to afford (3-(6-methoxy-3-methylpyridin-2-yl)benzo[b]thiophen-5-yl)methanol (121 mg, 28%), as a colorless oil. LC/MS: mass calcd. for $C_{16}H_{15}NO_2S$: 285.36, found: 286.0 $[M+H]^+$.

(C) 2-(5-(Chloromethyl)benzo[b]thiophen-3-yl)-6-methoxy-3-methylpyridine was prepared from (3-(6-methoxy-3-methylpyridin-2-yl)benzo[b]thiophen-5-yl)methanol following General Procedure D, and used directly.

(D) (3S)-Ethyl 3-(4-((3-(6-methoxy-3-methylpyridin-2-yl)benzo[b]thiophen-5-yl)methoxy)phenyl)hex-4-ynoate was prepared from 2-(5-(chloromethyl)benzo[b]thiophen-3-yl)-6-methoxy-3-methylpyridine and (3S)-ethyl 3-(4-hydroxyphenyl)hex-4-ynoate (available from Synnovator, Inc., Research Triangle Park, N.C.; Cat. #PB05708) following General Procedure E. LC/MS: mass calcd. for $C_{30}H_{29}NO_4S$: 499.62, found: 500.3 $[M+H]^+$.

(F) (3S)-3-(4-((3-(6-Methoxy-3-methylpyridin-2-yl)benzo[b]thiophen-5-yl)methoxy)phenyl)hex-4-ynoic acid (Cpd 94) was prepared from (3S)-ethyl 3-(4-((3-(6-methoxy-3-methylpyridin-2-yl)benzo[b]thiophen-5-yl)methoxy)phenyl)hex-4-ynoate following General Procedure C, using LiOH as base, EtOH in place of MeOH, a rt reaction temperature overnight and 1N HCl for reaction acidification. $^1H$ NMR (DMSO-$d_6$) δ 8.07 (d, J=8.4 Hz, 1H), 7.78 (s, 1H), 7.95 (d, J=7.6 Hz, 1H), 7.71 (d, J=8.4 Hz, 1H), 7.49 (dd, J=8.4,1.6 Hz, 1H), 7.20-7.28 (m, 2H), 6.88-6.96 (m, 2H), 6.80 (d, J=8.3 Hz, 1H), 5.20 (s, 2H), 3.90-3.95 (m, 1H), 3.77 (s, 3H), 2.57 (dd, J=7.6, 1.2 Hz, 2H), 2.22 (s, 3H), 1.76 (d, J=2.4 Hz, 3H). LC/MS: mass calcd. for $C_{28}H_{25}NO_4S$: 471.57, found: 472.2 $[M+H]^+$.

Example 95

(3S)-3-(4-((3-(2-Methyl-4-(piperidin-4-ylmethyl)phenyl)benzo[b]thiophen-5-yl)methoxy)phenyl)hex-4-ynoic acid (Cpd 95)

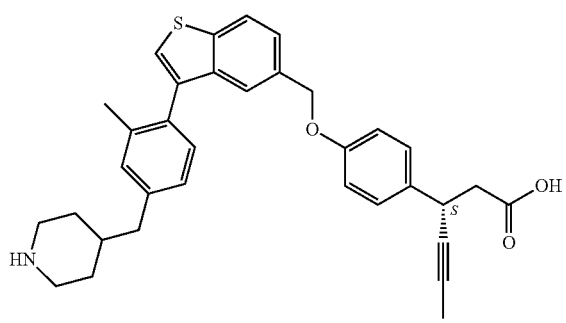

(A) Methyl 3-(4-hydroxy-2-methylphenyl)benzo[b]thiophene-5-carboxylate was prepared from methyl 3-bromobenzo[b]thiophene-5-carboxylate and 4-hydroxy-2-methylphenylboronic acid following General Procedure A using $PdCl_2(dppf).CH_2Cl_2$ as the palladium catalyst and TEA in place of $K_2CO_3$ and EtOH as solvent at a temperature of 80° C. overnight. LC/MS: mass calcd. for $C_{17}H_{14}O_3S$: 298.36, found: 299.0, $[M+H]^+$.

(B) To a solution of methyl 3-(4-hydroxy-2-methylphenyl)benzo[b]thiophene-5-carboxylate (3.9 g, 13.1 mmol) and pyridine (3.10 g, 39.2 mmol) in DCM (50 ml), was added $Tf_2O$ (5.53 g, 19.6 mmol) in dropwise fashion. After stirring overnight at rt, the mixture was diluted with water (40 mL) and extracted with EtOAc (3×100 mL). The combined organic extracts were washed with brine, dried ($Na_2SO_4$) and concentrated under reduced pressure. The residue thus obtained was purified by silica gel chromatography eluting with EtOAc/petroleum ether (0-15%) to afford methyl 3-(2-methyl-4-(trifluoromethylsulfonyloxy)phenyl)benzo[b]thiophene-5-carboxylate (5.0 g, 80%), as a colorless oil. LC/MS: mass calcd. for $C_{18}H_{13}F_3O_5S_2$: 430.42, found: 431.1 $[M+H]^+$.

(C) 9-Borabicyclo[3.3.1]nonane (0.5 M solution in THF; 20.5 ml, 10.25 mmol) was added to tert-butyl 4-methylenepiperidine-1-carboxylate (2.02 g, 10.24 mmol) under an inert atmosphere of nitrogen and the resultant solution was stirred at 60° C. for 1 h. Methyl 3-(2-methyl-4-(trifluoromethylsulfonyloxy)phenyl)benzo[b]thiophene-5-carboxylate (4 g, 9.29 mmol), Pd(dppf)Cl$_2$.CH$_2$Cl$_2$ (22.7 mg, 0.028 mmol), $K_2CO_3$ (12.8 g, 92.75 mmol), DMF (40 ml) and $H_2O$ (4 ml) were added, and the resulting solution was stirred at 60° C. for an additional 3 h. The mixture was then extracted with EtOAc (3×100 mL) and the combined organic extracts were washed with brine, dried ($Na_2SO_4$) and concentrated under reduced pressure. The residue thus obtained was purified by silica gel chromatography eluting with EtOAc/petroleum ether (0-15%) to afford tert-butyl 4-(4-(5-(methoxycarbonyl) benzo[b]thiophen-3-yl)-3-methylphenyl)piperidine-1-carboxylate (3.51g, 70.8%) as colorless oil. LC/MS: mass calcd. for $C_{28}H_{33}NO_4S$: 479.63, found: 480.3 $[M+H]^+$.

(D) To a cooled (−60° C.) solution of tert-butyl 4-(4-(5-(methoxycarbonyl)benzo[b]thiophen-3-yl)-3-methylphenyl)piperidine-1-carboxylate (3.51g, 7.32 mmol) in toluene (35 mL) was added DIBAL-H (1M in toluene; 14.6 mL, 14.6 mmol) and the resultant solution was stirred at rt for 2 h. The mixture was quenched by the addition of MeOH (20 mL), diluted with $H_2O$ (100 mL) then extracted with EtOAc (3×100 mL) and the combined organic extracts were washed with brine, dried ($Na_2SO_4$) and concentrated under reduced pressure. The residue thus obtained was purified by silica gel chromatography eluting with EtOAc/petroleum ether (0-15%) to afford tert-butyl 4-(4-(5-(hydroxymethyl)benzo[b]thiophen-3-yl)-3-methylbenzyl)piperidine-1-carboxylate (1.91 g, 57.8%) as colorless oil. LC/MS: mass calcd. for $C_{27}H_{33}NO_3S$: 451.62, found: 452.2 $[M+H]^+$.

(E) (3S)-tert-Butyl 4-(4-(5-((4-(1-ethoxy-1-oxohex-4-yn-3-yl)phenoxy)methyl)benzo-[b]thiophen-3-yl)-3-methylbenzyl)piperidine-1-carboxylate was prepared from tert-butyl 4-(4-(5-(hydroxymethyl)benzo[b]thiophen-3-yl)-3-methylbenzyl)piperidine-1-carboxylate and (3S)-ethyl 3-(4-hydroxyphenyl)hex-4-ynoate (available from Synnovator, Inc., Research Triangle Park, N.C.; Cat. #PB05708) following General Procedure B using $(Bu)_3P$ and ADDP at a reaction temperature of 70° C. overnight. LC/MS: mass calcd. for $C_{41}H_{47}NO_5S$: 665.88, found: 666.3 $[M+H]^+$.

(F) To a solution of (3S)-tert-butyl 4-(4-(5-((4-(1-ethoxy-1-oxohex-4-yn-3-yl)phenoxy)methyl)benzo-[b]thiophen-3-yl)-3-methylbenzyl)piperidine-1-carboxylate (900 mg, 1.35 mmol) in dioxane (15 mL) was added 4N HCl/dioxane (4 mL, 16 mmol) and the resulting solution was stirred overnight. The solution pH was adjusted to 6 with aq. $NaHCO_3$ and the mixture was extracted with EtOAc (3×100 mL). The combined extracts were concentrated under reduced pressure and the resultant residue was purified by preparative HPLC on a Waters SunFire™ Prep C18, 5μ column (19×100 mm) using a gradient of acetonitrile/water (0.05% TFA) (25-70%) as eluent to afford (3S)-ethyl 3-(4-((3-(2-methyl-4-(piperidin-4-ylmethyl)phenyl)benzo[b]thiophen-5-yl)methoxy)phenyl)hex-4-ynoate (TFA salt) (134 mg, 14.4%) as an off white solid. LC/MS: mass calcd. for $C_{36}H_{39}NO_3S$: 565.76, found: 566.3 $[M+H]^-$.

(G) (3S)-3-(4-((3-(2-Methyl-4-(piperidin-4-ylmethyl)phenyl)benzo[b]thiophen-5-yl)methoxy)phenyl)hex-4-ynoic acid (Cpd 95) was prepared from (3S)-ethyl 3-(4-((3-(2-methyl-4-(piperidin-4-ylmethyl)phenyl)benzo[b]thiophen-5-yl)methoxy)phenyl)hex-4-ynoate (TFA salt) following General Procedure C, using LiOH as base, THF/water (1:1) as solvent, a rt reaction temperature overnight and 2N HCl for reaction acidification. The residue obtained was purified by preparative HPLC on a Waters SunFire™ Prep C18, 5μ column (19×100 mm) using a gradient of acetonitrile/water (0.05% TFA) (25-70%) as eluent. $^1H$ NMR ($CD_3OD$) δ 7.88 (d, J=8.0 Hz, 1H), 7.35-7.39 (m, 2H), 7.17-7.27 (m, 3H), 7.03-7.12 (m, 3H), 6.78-6.80 (m, 2H), 5.07 (s, 2H), 3.96-3.97 (m, 1H), 3.27 (m, 2H), 2.81-2.89 (m, 2H), 2.51-2.62 (m, 3H), 2.37-2.45 (m, 1H), 2.01 (s, 3H), 1.81-1.86 (m, 3H), 1.76 (s, 3H), 1.26-1.45 (m, 2H). LC/MS: mass calcd. for $C_{34}H_{35}NO_3S$: 537.71, found: 536.1$[M-H]^-$.

Example 96

(3S)-3-(4-((3-(2-Methyl-4-(piperidin-4-yl)phenyl) benzo[b]thiophen-5-yl)methoxy)phenyl)hex-4-ynoic acid (Cpd 96)

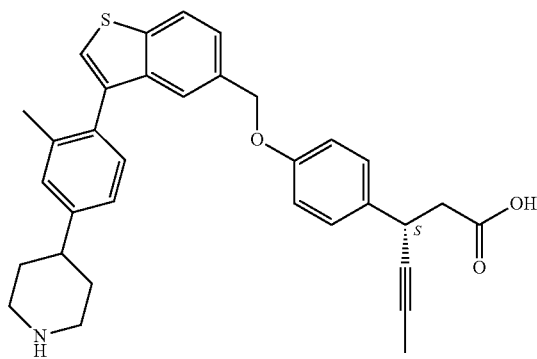

(A) tert-Butyl 4-(4-(5-(methoxycarbonyl)benzo[b]thiophen-3-yl)-3-methylphenyl)-5,6-dihydropyridine-1(2H)-carboxylate was prepared from methyl 3-(2-methyl-4-(trifluoromethylsulfonyloxy)phenyl)benzo[b]thiophene-5-carboxylate (from Example 95B) and tert-butyl 4-(4,4,5,5-tetramethyl-1,3,2-dioxaborolan-2-yl)-5,6-dihydropyridine-1(2H)-carboxylate following General Procedure A using $Pd(PPh_3)_4$ as the palladium catalyst and $Na_2CO_3$ in place of $K_2CO_3$ at a temperature of 80° C. overnight. LC/MS: mass calcd. for $C_{27}H_{29}NO_4S$: 463.59, found: 486.2 $[M+Na]^+$.

(B) A mixture of tert-butyl 4-(4-(5-(methoxycarbonyl)benzo[b]thiophen-3-yl)-3-methylphenyl)-5,6-dihydropyridine-1(2H)-carboxylate (4.5 g, 9.71 mmol) and Pd/C (10%, 500 mg) in MeOH (100 mL) was hydrogenated overnight at rt. The mixture was then filtered and the filtrate was concentrated under reduced pressure to afford tert-butyl 4-(4-(5-(methoxycarbonyl)benzo[b]thiophen-3-yl)-3-methylphenyl)piperidine-1-carboxylate (4.3 g, 94%) as light-yellow oil. LC/MS: mass calcd. for $C_{27}H_{31}NO_4S$: 465.60, found: 488.2 $[M+Na]^-$.

(C) tert-Butyl 4-(4-(5-(hydroxymethyl)benzo[b]thiophen-3-yl)-3-methylphenyl)piperidine-1-carboxylate was prepared from tert-butyl 4-(4-(5-(methoxycarbonyl)benzo[b]thiophen-3-yl)-3-methylphenyl)piperidine-1-carboxylate following the procedure described in Example 95D. EtOAc/petroleum ether (0-20%) was used as eluent for the silica gel chromatographic purification. LC/MS: mass calcd. for $C_{26}H_{31}NO_3S$: 437.59, found: 460.15 $[M+Na]^+$.

(D) tert-Butyl 4-(4-(5-((4-((3S)-1-ethoxy-1-oxohex-4-yn-3-yl)phenoxy)methyl)benzo[b]thiophen-3-yl)-3-methylphenyl)piperidine-1-carboxylate was prepared from tert-butyl 4-(4-(5-(hydroxymethyl)benzo[b]thiophen-3-yl)-3-methylphenyl)piperidine-1-carboxylate and (3S)-ethyl 3-(4-hydroxyphenyl)hex-4-ynoate (available from Synnovator, Inc., Research Triangle Park, N.C.; Cat. #PB05708) following General Procedure B using $(Bu)_3P$ and ADDP at a reaction temperature of 60° C. overnight. LC/MS: mass calcd. for $C_{40}H_{45}NO_5S$: 651.85, found: 652.4 $[M+H]^+$.

189

(E) (3S)-Ethyl 3-(4-((3-(2-methyl-4-(piperidin-4-yl)phenyl)benzo[b]thiophen-5-yl)methoxy)phenyl)hex-4-ynoate was prepared from tert-Butyl 4-(4-(5-((4-((3S)-1-ethoxy-1-oxohex-4-yn-3-yl)phenoxy)methyl)benzo[b]thiophen-3-yl)-3-methylphenyl)piperidine-1-carboxylate following the procedure described in Example 95F. LC/MS: mass calcd. for $C_{35}H_{37}NO_3S$: 551.74, found: 552.25 $[M+H]^+$.

(F) (3S)-3-(4-((3-(2-Methyl-4-(piperidin-4-yl)phenyl)benzo[b]thiophen-5-yl)methoxy)phenyl)hex-4-ynoic acid (Cpd 96) was prepared from (3S)-ethyl 3-(4-((3-(2-methyl-4-(piperidin-4-yl)phenyl)benzo[b]thiophen-5-yl)methoxy)phenyl)hex-4-ynoate following General Procedure C, using NaOH as base, THF/water (1:1) as solvent, a rt reaction temperature overnight and 1N HCl for reaction acidification. Product purification was carried out by silica gel chromatography using MeOH/DCM (0-25%) as eluent. $^1$H NMR (DMSO-$d_6$) δ 8.01 (s, 1H), 7.68 (s, 1H), 7.39-7.41 (m, 1H), 7.15-7.29 (m, 4H), 7.04-7.06 (m, 2H), 6.81-6.87 (m, 2H), 5.20 (s, 2H), 3.98-4.01 (m, 1H), 3.10-3.18 (m, 2H), 2.67-2.70 (m, 3H), 2.31-2.46 (m, 2H), 2.00 (s, 3H), 1.72-1.75 (m, 7H). LC/MS: mass calcd. for $C_{33}H_{33}NO_3S$: 523.68, found: 524.2 $[M+H]^+$.

Example 97

3-(4-((3-(2-Methylphenyl)benzo[b]thiophen-5-yl)methoxy)phenyl)hex-4-ynoic acid (Cpd 97)

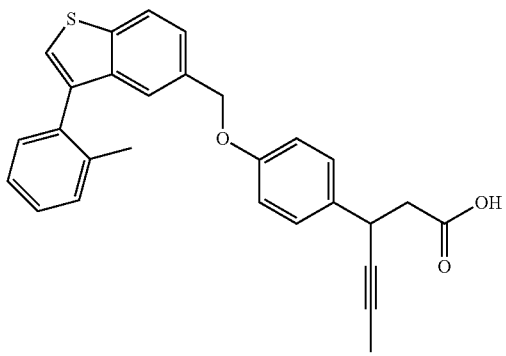 [SMILES: CC#CC(CC(=O)O)c1ccc(OCc2ccc3scc(-c4ccccc4C)c3c2)cc1]

(A) Methyl 3-(4-((3-(2-methylphenyl)benzo[b]thiophen-5-yl)methoxy)phenyl)hex-4-ynoate was prepared from 5-(chloromethyl)-3-(2-methylphenyl)benzo[b]thiophene (Example 2a, Step F) and methyl 3-(4-hydroxyphenyl)hex-4-ynoate (available from Oxchem Corporation, Irwindale, Calif.; Cat. #AX8267763) following General Procedure E, at a reaction temperature of 40° C. LC/MS: mass calcd. for $C_{29}H_{26}O_3S$ : 454.16, found: 477.1 $[M+Na]^+$.

(B) 3-(4-((3-(2-Methylphenyl)benzo[b]thiophen-5-yl)methoxy)phenyl)hex-4-ynoic acid (Cpd 97) was prepared from methyl 3-(4-((3-(2-methylphenyl)benzo[b]thiophen-5-yl)methoxy)phenyl)hex-4-ynoate following General Procedure C, using NaOH as a base, at a 35° C. reaction temperature for 2 h and 2M citric acid for reaction acidification. $^1$H NMR (CDCl$_3$) δ 7.92 (d, J=9.1 Hz, 1H), 7.39-7.51 (m, 2H), 7.24-7.36 (m, 7H), 6.89 (d, J=8.6 Hz, 2H), 5.08 (s, 2H), 4.03 (m, 1H), 2.78 (dd, J=15.7, 8.6 Hz, 1H), 2.68 (dd, J=15.9, 6.8 Hz, 1H), 2.15 (s, 3H), 1.82 (d, J=2.0 Hz, 3H). LC/MS: mass calcd. for $C_{28}H_{24}O_3S$: 440.14, found: 463.2 $[M+Na]^+$.

190

BIOLOGICAL EXAMPLES

In Vitro Assays

Example 1

GPR40 Calcium Flux Assay

Compounds were tested in a calcium flux assay using transfected HEK293 cells stably expressing either human GPR40 or rat GPR40. Human GPR40 expressing cells were cultured in DMEM-High Glucose media supplemented with 10% fetal bovine serum, 1×L-Glutamine, 1×Penicillin/Streptomycin and 500 μg/mL G418. Rat GPR40 expressing cells were cultured in DMEM-High Glucose media supplemented with 10% fetal bovine serum and 1 μg/mL puromycin. Cells were plated into poly-D-lysine coated 384-well plates and cultured overnight in a 37° C. humidified tissue culture incubator under 5% $CO_2$/90% $O_2$ atmosphere. On the day of the experiment, the culture media was replaced with assay buffer (HBSS, 20 mM HEPES, 0.1% BSA) and the cells incubated at 37° C. for 1 h. Calcium-sensitive fluorescent dye (Fluo 8 No-Wash Calcium Dye, ABD Bioquest) was then added and the cells incubated for another 30 min at 37° C. followed by 15 min at room temperature while protected from the light. The cell plate and a plate of diluted compounds of Formula (I) were loaded into a fluorescent plate reader that added compounds onto the cells while measuring the fluorescence intensity of each well. The plate reader recorded fluorescence intensity at 1 second intervals for 8 min and provided the data for analysis in an Excel format. $EC_{50}$ values were calculated using Prism (GraphPad) software. Resultant mean data are shown in Table 2.

TABLE 2

| | $Ca^{2+}$ Mobilization Data |
|---|---|
| Cpd No | hGPR40 $Ca^{2+}$ Assay EC50 (μM) |
| 1 | 0.007 |
| 2 | 0.005 |
| 3 | 0.005 |
| 4 | 0.003 |
| 5 | 0.023 |
| 6 | 0.015 |
| 7 | 0.007 |
| 8 | 0.02 |
| 9 | 0.017 |
| 10 | 0.041 |
| 11 | 0.016 |
| 12 | 0.009 |
| 13 | 0.007 |
| 14 | 0.009 |
| 15 | 0.002 |
| 16 | 0.005 |
| 17 | 0.006 |
| 18 | 0.011 |
| 19 | 0.008 |
| 20 | 0.005 |
| 21 | 0.008 |
| 22 | 0.008 |
| 23 | 0.01 |
| 24 | 0.009 |
| 25 | 0.024 |
| 26 | 0.018 |
| 27 | 0.02 |
| 28 | 0.012 |
| 29 | 0.034 |
| 30 | 0.006 |
| 31 | 0.014, 0.048 |

TABLE 2-continued

Ca$^{2+}$ Mobilization Data

| Cpd No | hGPR40 Ca$^{2+}$ Assay EC50 (μM) |
|---|---|
| 32 | 0.036 |
| 33 | 0.015 |
| 34 | 0.025 |
| 35 | 0.026 |
| 36 | 0.043 |
| 37 | 0.017 |
| 38 | 0.019 |
| 39 | 0.046 |
| 40 | 0.015 |
| 41 | 0.021 |
| 42 | 0.012 |
| 43 | 0.031 |
| 44 | 0.022 |
| 45 | 0.013 |
| 46 | 0.018 |
| 47 | 0.02 |
| 48 | 0.01 |
| 49 | 0.009 |
| 50 | 0.012 |
| 51 | 0.006 |
| 52 | 0.019 |
| 53 | 0.89 |
| 54 | 0.044 |
| 55 | 0.033 |
| 56 | 0.034 |
| 57 | 0.017 |
| 58 | 0.014 |
| 59 | 0.014 |
| 60 | 0.070 |
| 61 | 0.016 |
| 62 | 0.010 |
| 63 | 0.010 |
| 64 | 0.021 |
| 65 | 0.011 |
| 66 | 0.014 |
| 67 | 0.009 |
| 68 | 0.019 |
| 69 | 0.015 |
| 70 | 0.5 |
| 71 | 0.012 |
| 72 | 1.33 |
| 73 | 0.013 |
| 74 | 0.18 |
| 75 | 0.007 |
| 76 | 0.83 |
| 77 | 0.016; 0.006; 0.005 |
| 78 | 0.009 |
| 79 | 0.028 |
| 80 | 0.02 |
| 81 | 0.011 |
| 82 | 0.037 |
| 83 | 0.010 |
| 84 | 0.052 |
| 85 | 0.007; 0.006 |
| 86 | 0.008 |
| 87 | 0.011 |
| 88 | 0.008 |
| 89 | 0.02 |
| 90 | 0.015 |
| 91 | 0.017 |
| 92 | 0.013 |
| 93 | 0.015 |
| 94 | 0.015 |
| 95 | 0.004 |
| 96 | 0.008 |
| 97 | 0.002 |
| 98 | 0.16 |

In-vivo Assay

Oral Glucose Tolerance Test

Male SD rats (200-250 g) were housed 2 per cage in a temperature-controlled room with a 12-hour light/dark cycle. They were allowed ad libitum access to water and fed with normal rodent chow. The night before the oral glucose tolerance test (oGTT), the rats were transferred to clean cages and fasted overnight. On the morning of the oGTT, the rats were weighed and randomized into groups based on fasted blood glucose and body weight. Rats were dosed with vehicle (0.5% methocel) or compounds (10 mg/kg, po) thirty to forty min prior to the oGTT (glucose, 2 g/kg, po). Blood was collected from the tail vein at 0, 10, 30, 60 and 120 minutes after glucose challenge to measure blood glucose; plasma was used to determine insulin levels. The area under the curve for blood glucose excursion was calculated from t=0 to t=120 minutes. Percent lowering of glucose was calculated from the AUC data with respect to the vehicle-treated group. Resultant data are shown in Table 3.

TABLE 3

| Cpd No. | Percent Lowering of Glucose (AUC compound vs. AUC Vehicle) |
|---|---|
| 2 | 72% |
| 16 | 76% |

Note:
AUC = Integrated area under the glucose excursion curve from t = 0 to t = 120 minutes.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

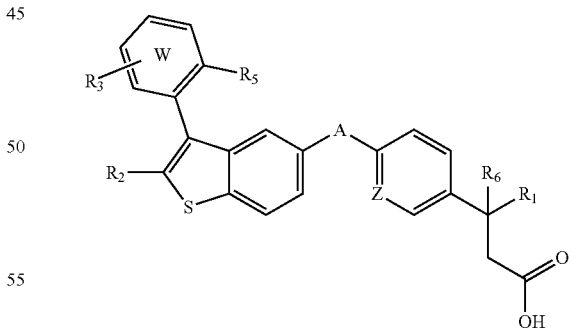

Formula (I)

wherein
ring W is phenyl;
A is —CH$_2$O— or —OCH$_2$—;
Z is CH;
R$_6$ is hydrogen;
R$_1$ is selected from hydrogen or methylacetylenyl; or R$_1$ and R$_6$ are taken together to form a spirofused 3-hydroxycyclobutyl or a spirofused 3-oxocyclobutyl;
R$_2$ is selected from hydrogen or methyl;

R$_3$ is a substituent selected from the group consisting of piperidin-4-yl, and piperidin-4-ylmethyl;

R$_5$ is methyl, methoxy, bromo, chloro, C$_{1-6}$alkoxy-C$_{1-6}$alkoxyl, C$_{1-6}$alkylsulfonyl, or trifluoromethyl;

or an enantiomer, diastereomer, or pharmaceutically acceptable salt forms thereof.

2. The compound of claim 1 wherein A is —CH$_2$O—.

3. The compound of claim 1 wherein A is —OCH$_2$—.

4. The compound of claim 1 wherein Z is CH, R$_6$ is hydrogen and R$_1$ is (S)-methylacetylenyl; or R$_1$ and R$_6$ are taken together to form a spirofused 3-hydroxycyclobutyl or a spirofused 3-oxocyclobutyl.

5. The compound of claim 1 wherein R$_2$ is hydrogen.

6. The compound of claim 1 wherein R$_3$ is piperidin-4-yl.

7. A compound of Formula (I)

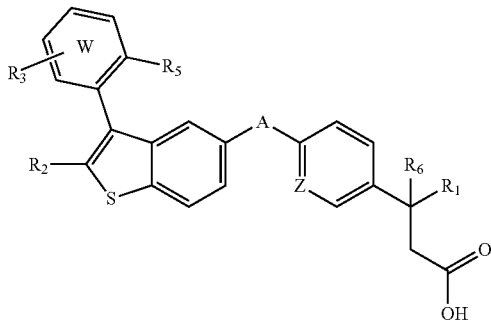

Formula (I)

wherein
ring W is phenyl;
A is —CH$_2$O— or —OCH$_2$—;
Z is CH;
R$_6$ is hydrogen;
R$_1$ is selected from hydrogen or methylacetylenyl; or R$_1$ and R$_6$ are taken together to form a spirofused 3-hydroxycyclobutyl or a spirofused 3-oxocyclobutyl;
R$_2$ is hydrogen;
R$_3$ is a substituent selected from the group consisting of piperidin-4-yl, and piperidin-4-ylmethyl;
R$_5$ is methyl, methoxy, 2-methoxyethoxy, methanesulfonyl, chloro, or trifluoromethyl;
or an enantiomer, diastereomer, or pharmaceutically acceptable salt form thereof.

8. The compound of claim 7 wherein when Z is CH, R$_6$ is hydrogen and R$_1$ is (S)-methylacetylenyl; or R$_1$ and R$_6$ are taken together to form a spirofused 3-hydroxycyclobutyl or a spirofused 3-oxocyclobutyl or R$_1$ and R$_6$ are taken together to form a spirofused 3-hydroxycyclobutyl or a spirofused cyclobut-3-one-yl.

9. A compound of Formula (I)

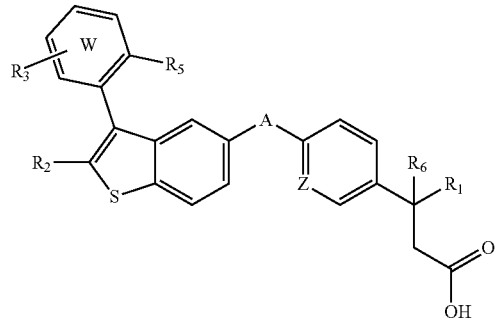

Formula (I)

wherein
ring W is phenyl;
A is —CH$_2$O— or —OCH$_2$—;
Z is CH, R$_6$ is hydrogen and R$_1$ is (S)-methylacetylenyl; or R$_1$ and R$_6$ are taken together to form a spirofused 3-hydroxycyclobutyl or a spirofused 3-oxocyclobutyl;
R$_2$ is hydrogen;
R$_3$ is piperidin-4-yl, or piperidin-4-ylmethyl;
R$_5$ is methyl, methoxy, 2-methoxyethoxy, methanesulfonyl, chloro, or trifluoromethyl;
or an enantiomer, diastereomer, or pharmaceutically acceptable salt form thereof.

10. A compound selected from the group consisting of
Cpd 95, (3S)-3-(4-((3-(2-Methyl-4-(piperidin-4-ylmethyl)phenyl)benzo[b]-thiophen-5-yl)methoxy)phenyl)hex-4-ynoic acid; and
Cpd 96, (3S)-3-(4-((3-(2-Methyl-4-(piperidin-4-yl)phenyl)benzo[b]thiophen-5-yl)methoxy)phenyl)hex-4-ynoic acid;
or a pharmaceutically acceptable salt forms thereof.

11. A pharmaceutical composition comprising a compound of claim 1 and at least one of a pharmaceutically acceptable carrier, a pharmaceutically acceptable excipient, and a pharmaceutically acceptable diluent.

12. The pharmaceutical composition of claim 11, wherein the composition is a solid oral dosage form.

13. The pharmaceutical composition of claim 11, wherein the composition is a syrup, an elixir or a suspension.

14. A pharmaceutical composition comprising the compound of claim 10 and at least one of a pharmaceutically acceptable carrier, a pharmaceutically acceptable excipient, and a pharmaceutically acceptable diluent.

* * * * *